United States Patent
Conte-Mayweg et al.

(10) Patent No.: US 7,259,183 B2
(45) Date of Patent: Aug. 21, 2007

(54) INDOLE, INDAZOLE AND INDOLINE DERIVATIVES AS CETP INHIBITORS

(75) Inventors: Aurelia Conte-Mayweg, Loerrach (DE); Holger Kuehne, Grenzach-Wyhlen (DE); Thomas Luebbers, Loerrach (DE); Cyrille Maugeais, Mulhouse (FR); Werner Mueller, Aesch (CH); Philippe Pflieger, Schwoben (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 98 days.

(21) Appl. No.: 11/197,688

(22) Filed: Aug. 4, 2005

(65) Prior Publication Data

US 2006/0030613 A1    Feb. 9, 2006

(30) Foreign Application Priority Data

Aug. 5, 2004   (EP) .................. 04103762

(51) Int. Cl.
*A61K 31/4045*   (2006.01)
*A61K 31/416*    (2006.01)
*C07D 231/56*    (2006.01)
*C07D 209/08*    (2006.01)

(52) U.S. Cl. .............. 514/419; 514/405; 548/361.1; 548/490

(58) Field of Classification Search ......... 548/361.1, 548/490; 514/405, 419
See application file for complete search history.

(56) References Cited

U.S. PATENT DOCUMENTS

2003/0229120 A1* 12/2003 Olsen et al. ............ 514/314

FOREIGN PATENT DOCUMENTS

WO   WO 2004/020393    3/2004
WO   WO 2004/022523    3/2004

OTHER PUBLICATIONS

Le Goff et al., Pharmacology & Therapeutics 101:17-38 (2004).
Okamoto et al., Nature 406:203-207 2000).
Archiv der Pharmazie, vol. 325, p. 433-437 (Jul. 1992).

* cited by examiner

*Primary Examiner*—Rebecca Anderson
*Assistant Examiner*—Michael P. Barker
(74) *Attorney, Agent, or Firm*—George W. Johnston; Dennis P. Tramaloni; Samuel H. Megerditchian

(57) ABSTRACT

The present invention relates to compounds of formula (I):

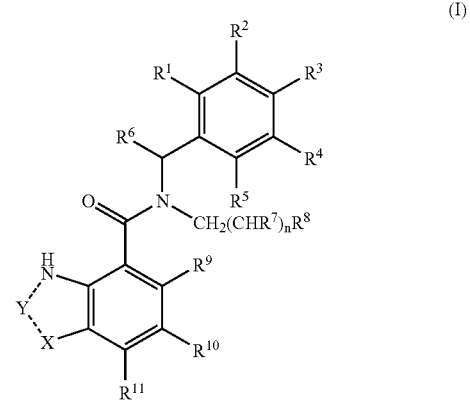

wherein —X—Y—, $R^1$ to $R^{11}$ and n are as defined in the description and claims, and pharmaceutically acceptable salts thereof. The compounds are useful for the treatment and/or prevention of diseases which are mediated by CETP inhibitors.

5 Claims, No Drawings

INDOLE, INDAZOLE AND INDOLINE DERIVATIVES AS CETP INHIBITORS

FIELD OF THE INVENTION

The present invention is directed to novel 1H-indole-7-carboxamido, 1H-indazole-7-carboxamido and 1H-indoline-7-carboxamido derivatives, their manufacture, pharmaceutical compositions containing them and their use as medicaments.

In particular, the present invention relates to compounds of the general formula I:

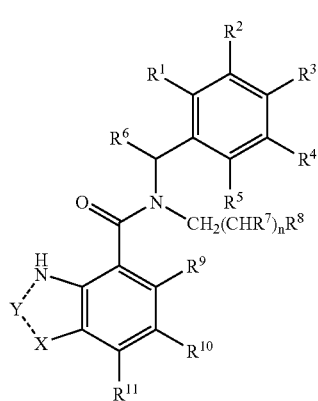

and all pharmaceutically acceptable salts thereof.

The compounds of formula I are cholesteryl ester transfer protein (CETP) inhibitors.

All documents cited or relied upon below are expressly incorporated herein by reference.

BACKGROUND OF THE INVENTION

Atherosclerosis and its associated coronary heart disease are the leading causes of death in the industrialized world. Risk for development of coronary heart disease has been shown to be strongly correlated with certain plasma lipid levels. Lipids are transported in the blood by lipoproteins.

The general structure of lipoproteins is a core of neutral lipids (triglyceride and cholesterol ester) and an envelop of polar lipids (phospholipids and non esterified cholesterol). There are 3 different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

Plasma lipoprotein metabolism can be described as a flux of cholesterol between liver and the other tissues. The LDL pathway corresponds to the secretion of VLDL from the liver to deliver cholesterol by LDL to tissues. Any alteration in LDL catabolism could lead to uptake of excess cholesterol in the vessel wall forming foam cells and atherosclerosis. The opposite pathway is the mobilization of free cholesterol from peripheral tissues by HDL to deliver cholesterol to the liver to be eventually excreted with bile. In humans a significant part of cholesteryl ester (CE) is transferred from HDL to the VLDL, LDL pathway. This transfer is mediated by a 70,000 dalton plasma glycoprotein, the cholesteryl ester transfer protein (CETP).

Mutations in the CETP gene associated with CETP deficiency are characterized by high HDL-cholesterol levels (>60 mg/dL) and reduced cardiovascular risk. Such findings are consistent with studies of pharmacologically mediated inhibition of CETP in the rabbit, which argue strongly in favor of CETP inhibition as a valid therapeutic approach [Le Goff et al., Pharmacology & Therapeutics 101:17-38 (2004); Okamoto et al., Nature 406:203-207 2000)].

No entirely satisfactory HDL-elevating therapy exists. For example, niacin can significantly increase HDL, but it also has serious toleration issues which reduce compliance. Fibrates and the HMG CoA reductase inhibitors raise HDL-cholesterol only modestly (~10-12%).

Thus, there is a significant unmet medical need for a well tolerated agent which can significantly elevate plasma HDL levels. The net result of CETP activity is a lowering of HDL-C and an increase in LDL-C. This effect on lipoprotein profile is believed to be pro-atherogenic, especially in subjects whose lipid profile constitutes an increased risk for coronary heart disease. By inhibiting CETP activity there is the potential to inverse this relationship towards a lower risk and ultimately to protect against coronary heart diseases and associated mortality.

CETP inhibitors, therefore, are useful as medicaments for the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In addition, CETP inhibitors may be used in combination with another compound such as, for example, an HMG-CoA reductase inhibitor, a microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

SUMMARY OF THE INVENTION

In one embodiment of the present invention, provided is a compound of the formula (I):

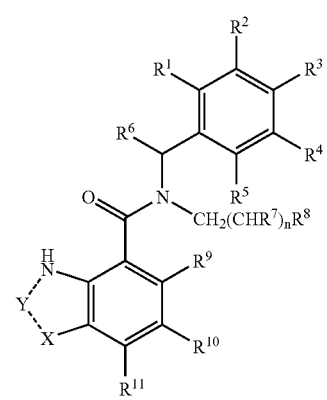

wherein:

—X—Y— is —$CR^a$=$CR^c$— or —$CR^a$=N— or —$CR^aR^b$—$CR^cR^d$—, $R^a$, $R^b$, $R^c$ and $R^d$ are independently from each other selected from the group consisting of hydrogen and lower alkyl;

$R^1$, $R^2$, $R^4$ and $R^5$ are independently from each other selected from the group consisting of hydrogen, lower alkyl, lower alkoxy, halogen and lower halogenalkyl;

$R^3$ is selected from the group consisting of lower alkyl, cycloalkyl being unsubstituted or substituted by lower alkyl, cyano or lower alkoxy, lower halogenalkyl, lower alkoxyalkyl, lower alkoxy-halogenalkyl, halogenalkoxy and pentafluorosulphuranyl; or $R^2$ and $R^3$ taken together with the carbon atoms to which they are attached form a 5- or 6-membered carbocyclic ring or a 5- or 6-membered heterocyclic ring containing one or two heteroatoms selected from the group consisting of N, O and S, said carbocyclic or heterocyclic ring being unsubstituted or substituted by one, two, three or four groups independently selected from lower alkyl, cycloalkyl, lower alkoxy, halogen, and lower halogenalkyl;

$R^6$ is selected from the group consisting of hydrogen and lower alkyl;

$R^7$ is selected from the group consisting of hydrogen, lower alkyl, hydroxy and halogen;

$R^8$ is selected from the group consisting of lower alkyl, lower alkenyl, lower halogenalkyl, heterocyclyl, heteroaryl which is unsubstituted or substituted by one or two groups independently selected from lower alkyl, lower alkoxy, lower halogenalkyl, lower halogenalkoxy and halogen, phenyl which is unsubstituted or substituted by one or two groups independently selected from lower alkyl, lower alkoxy, lower halogenalkyl, lower halogenalkoxy and halogen, —$OR^{12}$, wherein $R^{12}$ is lower alkyl or phenyl which is unsubstituted or substituted by one or two groups independently selected from lower alkyl, lower alkoxy, lower halogenalkyl, lower halogenalkoxy and halogen, —$NR^{13}R^{14}$, wherein $R^{13}$ and $R^{14}$ independently from each other are selected from hydrogen, lower alkyl, and phenyl which is unsubstituted or substituted by one or two groups independently selected from lower alkyl, lower alkoxy, lower halogenalkyl, lower halogenalkoxy and halogen, and —$C(O)$—$OR^{15}$, wherein $R^{15}$ is hydrogen or lower alkyl;

$R^9$, $R^{10}$ and $R^{11}$ independently from each other are selected from the group consisting of hydrogen, lower alkyl, cycloalkyl, lower alkoxy, lower halogenalkyl, and halogen;

n is 1 or 2;

and all pharmaceutically acceptable salts thereof.

In another embodiment of the present invention, provided is A process for the manufacture of a compound of formula I according to claim 1, comprising the steps of:

reacting an acid of the formula II

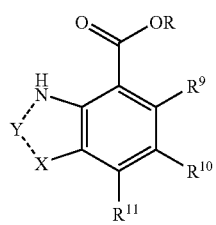

(II)

wherein —X—Y—, $R^9$, $R^{10}$ and $R^{11}$ are as defined in claim 1 and R is hydrogen or lower alkyl, with an amine of formula III

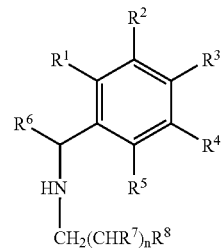

(III)

wherein $R^1$ to $R^8$ and n are as defined in claim 1, in the presence of a coupling agent; or, alternatively, reacting a halogen derivative of formula IV

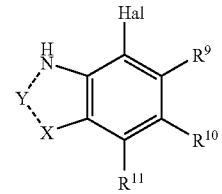

(IV)

wherein —X—Y—, $R^9$, $R^{10}$ and $R^{11}$ are as defined in claim 1 and Hal means halogen, with an amine of formula III in the presence of a suitable catalyst and carbon monoxide, and if desired, converting the compound obtained into a pharmaceutically acceptable acid addition salt.

In a further embodiment of the present invention, provided is a pharmaceutical composition comprising a therapeutically effective amount of a compound of claim 1 as well as a pharmaceutically acceptable carrier and/or adjuvant.

In a still another embodiment of the present invention, provided is a method for the treatment and/or prophylaxis of diseases which are mediated by CETP inhibitors, comprising the step of administering a therapeutically effective amount of a compound according to claim 1 to a human being or animal in need thereof.

DETAILED DESCRIPTION

The compounds of formula I and their pharmaceutically acceptable salts possess valuable pharmacological properties. For example, it has been found that the compounds of the present invention are inhibitors of the cholesteryl ester transfer protein (CETP).

Unless otherwise indicated the following definitions are set forth to illustrate and define the meaning and scope of the various terms used to describe the invention herein.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms, e.g. a straight or branched-chain alkyl group with 1 to 6 carbon atoms, e.g. a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, e.g. methyl, ethyl and tert.-butyl.

The term "lower alkenyl" or "$C_{2-8}$-alkenyl", alone or in combination, means a straight-chain or branched hydrocarbon radical comprising an olefinic bond and up to 8, e.g., up to 6, e.g., up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl.

Especially preferred are cyclopropyl, cyclobutyl and cyclopentyl.

The term "alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec.butoxy and tert.butoxy, preferably methoxy and ethoxy and most preferred methoxy.

The term "lower alkoxyalkyl" or "$C_{1-8}$-alkoxy-$C_{1-8}$-alkyl" refers to lower alkyl groups as defined above wherein at least one of the hydrogen atoms of the lower alkyl groups is replaced by an alkoxy group, preferably methoxy or ethoxy. Among the preferred lower alkoxyalkyl groups are 2-methoxyethyl, 3-methoxypropyl or 1-methoxy-1-methylethyl.

The term "halogen" refers to fluorine, chlorine, bromine and iodine, with fluorine, chlorine and bromine being preferred, and fluorine and chlorine being especially preferred. The term "lower halogenalkyl" or "halogen-$C_{1-8}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with trifluoromethyl being especially preferred.

The term "lower halogenalkoxy" or "halogen-$C_{1-8}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluoromethoxy and chloromethoxy, with difluoromethoxy and trifluoromethoxy being especially preferred.

The term "lower alkoxy-halogenalkyl" or "$C_{1-8}$-alkoxy-halogen-$C_{1-8}$-alkyl" refers to lower halogenalkyl groups as defined above wherein at least one of the hydrogen atoms of the lower halogenalkyl group is replaced by an alkoxy group. An example of a lower alkoxy-halogenalkyl group is 2,2,2-trifluoro-1-methoxy-1-trifluoromethyl-ethyl.

The term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, or pyrrolyl. Especially preferred are furyl, thienyl, thiazolyl and pyridyl.

The term "heterocyclyl" refers to a saturated or partly unsaturated 5- or 6-membered ring comprising one, two or three atoms selected from nitrogen, oxygen and sulphur. Examples of heterocyclyl include piperidinyl, piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, tetrahydrothiopyranyl and thiamorpholinyl. A preferred heterocylcyl group is tetrahydrothiopyranyl.

The term "form a 5- or 6-membered carbocyclic ring or a 5- or 6-membered heterocyclic ring containing one or two heteroatoms selected from the group consisting of N, O or S, said carbocyclic or heterocyclic ring being unsubstituted or substituted by one, two, three or four groups independently selected from lower alkyl, cycloalkyl, lower alkoxy, halogen, and lower halogenalkyl" refers to a saturated 5- or 6-membered carbocyclic ring (cyclopentyl or cyclohexyl) or a 5- or 6-membered heterocyclic ring, which contains one or two nitrogen, oxygen or sulfur atoms, such as pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl or pyranyl. Such ring may be unsubstituted or substituted by one, two, three or four groups independently selected from lower alkyl, cycloalkyl, lower alkoxy, halogen, and lower halogenalkyl. The 5- or 6-membered carbocyclic ring or 5- or 6-membered heterocyclic ring is condensed with the phenyl ring $R^2$ and $R^3$ are attached to. Examples for the condensed rings are indanyl, chromanyl or 2,3-dihydrospiro(cyclopropane-1,1'-[1H]inden)-5-yl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have the identical molecular formula but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

Preferred compounds of formula I of the present invention are compounds of formula I, wherein —X—Y— signifies —$CR^a$=$CR^c$— and $R^a$ and $R^c$ are independently from each other selected from the group consisting of hydrogen and lower alkyl. More preferably, $R^a$ and $R^c$ are hydrogen.

In one embodiment the present invention provides compounds of formula I having the formula

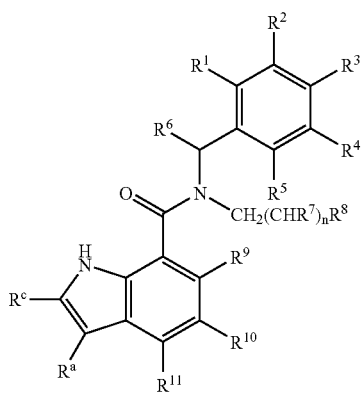

(I-A)

wherein $R^a$ and $R^c$ are independently from each other selected from the group consisting of hydrogen and lower alkyl;

$R^1$, $R^2$, $R^4$ and $R^5$ are independently from each other selected from the group consisting of hydrogen, lower alkyl, lower alkoxy, halogen and lower halogenalkyl;

$R^3$ is selected from the group consisting of lower alkyl, cycloalkyl being unsubstituted or substituted by lower alkyl, cyano or lower alkoxy, lower halogenalkyl, lower alkoxyalkyl, lower alkoxy-halogenalkyl, halogenalkoxy and pentafluorosulphuranyl; or $R^2$ and $R^3$ taken together with the carbon atoms they are attached to form a 5- or 6-membered carbocyclic ring or a 5- or 6-membered heterocyclic ring containing one or two heteroatoms selected from the group consisting of N, O or S, said carbocyclic or heterocyclic ring being unsubstituted or substituted by one, two, three or four groups independently selected from lower alkyl, cycloalkyl, lower alkoxy, halogen, and lower halogenalkyl;

$R^6$ is selected from the group consisting of hydrogen and lower alkyl;

$R^7$ is selected from the group consisting of hydrogen, lower alkyl, hydroxy and halogen;

$R^8$ is selected from the group consisting of lower alkyl, lower alkenyl, lower halogenalkyl, heterocyclyl, heteroaryl which is unsubstituted or substituted by one or two groups independently selected from lower alkyl, lower alkoxy, lower halogenalkyl, lower halogenalkoxy and halogen, phenyl which is unsubstituted or substituted by one or two groups independently selected from lower alkyl, lower alkoxy, lower halogenalkyl, lower halogenalkoxy and halogen, —$OR^{12}$, wherein $R^{12}$ is lower alkyl or phenyl which is unsubstituted or substituted by one or two groups independently selected from lower alkyl, lower alkoxy, lower halogenalkyl, lower halogenalkoxy and halogen, —$NR^{13}R^{14}$, wherein $R^{13}$ and $R^{14}$ independently from each other are selected from hydrogen, lower alkyl, and phenyl which is unsubstituted or substituted by one or two groups independently selected from lower alkyl, lower alkoxy, lower halogenalkyl, lower halogenalkoxy and halogen, and —C(O)—$OR^5$, wherein $R^{15}$ is hydrogen or lower alkyl;

$R^9$, $R^{10}$ and $R^{11}$ independently from each other are selected from the group consisting of hydrogen, lower alkyl, cycloalkyl, lower alkoxy, lower halogenalkyl, and halogen;

n is 1 or 2;

and all pharmaceutically acceptable salts thereof.

In another embodiment the invention further provides compounds of formula I, wherein —X—Y— is —$CR^a$=N— and $R^a$ is hydrogen or lower alkyl; thus meaning compounds of formula I having the formula

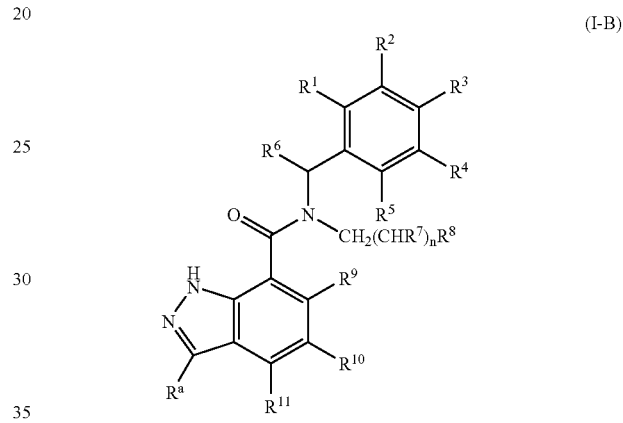

(I-B)

wherein $R^a$ is hydrogen and lower alkyl;

$R^1$, $R^2$, $R^4$ and $R^5$ are independently from each other selected from the group consisting of hydrogen, lower alkyl, lower alkoxy, halogen and lower halogenalkyl;

$R^3$ is selected from the group consisting of lower alkyl, cycloalkyl being unsubstituted or substituted by lower alkyl, cyano or lower alkoxy, lower halogenalkyl, lower alkoxyalkyl, lower alkoxy-halogenalkyl, halogenalkoxy and pentafluorosulphuranyl; or $R^2$ and $R^3$ taken together with the carbon atoms they are attached to form a 5- or 6-membered carbocyclic ring or a 5- or 6-membered heterocyclic ring containing one or two heteroatoms selected from the group consisting of N, O or S, said carbocyclic or heterocyclic ring being unsubstituted or substituted by one, two, three or four groups independently selected from lower alkyl, cycloalkyl, lower alkoxy, halogen, and lower halogenalkyl;

$R^6$ is selected from the group consisting of hydrogen and lower alkyl;

$R^7$ is selected from the group consisting of hydrogen, lower alkyl hydroxy and halogen;

$R^8$ is selected from the group consisting of lower alkyl, lower alkenyl, lower halogenalkyl, heterocyclyl, heteroaryl which is unsubstituted or substituted by one or two groups independently selected from lower alkyl, lower alkoxy, lower halogenalkyl, lower halogenalkoxy and halogen, phenyl which is unsubstituted or substituted by one or two groups independently selected from lower alkyl, lower alkoxy, lower halogenalkyl, lower halogenalkoxy and halogen, —OR$^{12}$, wherein R$^{12}$ is lower alkyl or phenyl which is unsubstituted or substituted by one or two groups independently selected from lower alkyl, lower alkoxy, lower halogenalkyl, lower halogenalkoxy and halogen, —NR$^{13}$R$^{14}$, wherein R$^{13}$ and R$^{14}$ independently from each other are selected from hydrogen, lower alkyl, and phenyl which is unsubstituted or substituted by one or two groups independently selected from lower alkyl, lower alkoxy, lower halogenalkyl, lower halogenalkoxy and halogen, and —C(O)—OR$^{15}$, wherein R$^{15}$ is hydrogen or lower alkyl;

R$^9$, R$^{10}$ and R$^{11}$ independently from each other are selected from the group consisting of hydrogen, lower alkyl, cycloalkyl, lower alkoxy, lower halogenalkyl, and halogen;

n is 1 or 2;

and all pharmaceutically acceptable salts thereof.

Preferred are compounds of formula I-B, wherein R$^a$ is hydrogen.

Furthermore, the invention relates to compounds of formula I, wherein —X—Y— signifies —CR$^a$R$^b$—CR$^c$R$^d$— and R$^a$, R$^b$, R$^c$ and R$^d$ are independently from each other selected from the group consisting of hydrogen and lower alkyl; thus meaning compounds of formula I having the formula

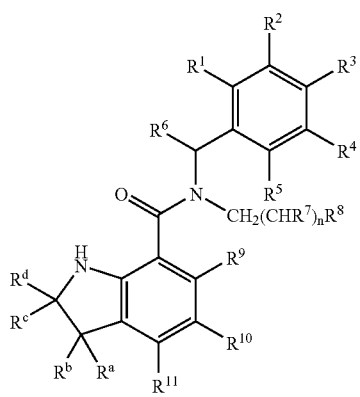

(I-C)

wherein

R$^a$, R$^b$, R$^c$ and R$^d$ are independently from each other selected from the group consisting of hydrogen and lower alkyl;

R$^1$, R$^2$, R$^4$ and R$^5$ are independently from each other selected from the group consisting of hydrogen, lower alkyl, lower alkoxy, halogen and lower halogenalkyl;

R$^3$ is selected from the group consisting of lower alkyl, cycloalkyl being unsubstituted or substituted by lower alkyl, cyano or lower alkoxy, lower halogenalkyl, lower alkoxyalkyl, lower alkoxy-halogenalkyl, halogenalkoxy and pentafluorosulphuranyl; or R$^2$ and R$^3$ taken together with the carbon atoms they are attached to form a 5- or 6-membered carbocyclic ring or a 5- or 6-membered heterocyclic ring containing one or two heteroatoms selected from the group consisting of N, O or S, said carbocyclic or heterocyclic ring being unsubstituted or substituted by one, two, three or four groups independently selected from lower alkyl, cycloalkyl, lower alkoxy, halogen, and lower halogenalkyl;

R$^6$ is selected from the group consisting of hydrogen and lower alkyl;

R$^7$ is selected from the group consisting of hydrogen, lower alkyl, hydroxy and halogen;

R$^8$ is selected from the group consisting of lower alkyl, lower alkenyl, lower halogenalkyl, heterocyclyl, heteroaryl which is unsubstituted or substituted by one or two groups independently selected from lower alkyl, lower alkoxy, lower halogenalkyl, lower halogenalkoxy and halogen, phenyl which is unsubstituted or substituted by one or two groups independently selected from lower alkyl, lower alkoxy, lower halogenalkyl, lower halogenalkoxy and halogen, —OR$^{12}$, wherein R$^{12}$ is lower alkyl or phenyl which is unsubstituted or substituted by one or two groups independently selected from lower alkyl, lower alkoxy, lower halogenalkyl, lower halogenalkoxy and halogen, —NR$^{13}$R$^{14}$, wherein R$^{13}$ and R$^{14}$ independently from each other are selected from hydrogen, lower alkyl, and phenyl which is unsubstituted or substituted by one or two groups independently selected from lower alkyl, lower alkoxy, lower halogenalkyl, lower halogenalkoxy and halogen, and —C(O)—OR$^{15}$, wherein R$^{15}$ is hydrogen or lower alkyl;

R$^9$, R$^{10}$ and R$^{11}$ independently from each other are selected from the group consisting of hydrogen, lower alkyl, cycloalkyl, lower alkoxy, lower halogenalkyl, and halogen;

n is 1 or 2;

and all pharmaceutically acceptable salts thereof.

In one embodiment the present invention provides compounds of formula I-C, wherein R$^a$, R$^b$, R$^c$ and R$^d$ are hydrogen.

In another embodiment the present invention provides compounds of formula I of the present invention are preferred, wherein R$^1$, R$^2$, R$^4$ and R$^5$ are hydrogen.

In still another embodiment the present invention provides compounds of formula I wherein R$^1$ is lower alkoxy or halogen and R$^2$, R$^4$ and R$^5$ are hydrogen. In still another embodiment the present invention provides compounds of formula I, wherein R$^2$ is halogen and R$^1$, R$^4$ and R$^5$ are hydrogen.

In another embodiment the present invention provides compounds of formula I, wherein R$^3$ is selected from the group consisting of lower alkyl, cycloalkyl being unsubstituted or substituted by lower alkyl, cyano or lower alkoxy, halogenalkoxy and lower halogenalkyl. In still another embodiment the present invention provides compounds of formula I, wherein R$^3$ is lower alkyl, e.g. compounds wherein R$^3$ is tert-butyl.

The invention further relates to compounds of formula I, wherein R$^2$ and R$^3$ taken together with the carbon atoms they are attached to form a 5- or 6-membered carbocyclic ring or a 5- or 6-membered heterocyclic ring containing one or two heteroatoms selected from the group consisting of N, O or S, said carbocyclic or heterocyclic ring being unsubstituted or substituted by one, two, three or four groups independently selected from lower alkyl, cycloalkyl, lower alkoxy, halogen, and lower halogenalkyl. In another embodiment the present invention provides compounds of formula I, wherein R$^2$ and R$^3$ together with the phenyl ring they are attached to, form 1,1-dimethyl-indan-5-yl, 2,2-dimethyl-chroman-6-yl or 2,3-dihydrospiro(cyclopropane-1,1'-[1H]inden)-5-yl.

In one embodiment the present invention provides compounds wherein R$^6$ is hydrogen. In one embodiment the present invention provides compounds of formula I, wherein R$^7$ is hydrogen.

In another embodiment the present invention provides compounds of formula I wherein $R^8$ is selected from the group consisting of lower alkyl, lower alkenyl, and lower halogenalkyl.

In still another embodiment the present invention provides compounds of formula I wherein $R^8$ is heterocyclyl or heteroaryl which is unsubstituted or substituted by one or two groups independently selected from lower alkyl, lower alkoxy, lower halogenalkyl, lower halogenalkoxy and halogen. In still another embodiment the present invention provides compounds of formula I wherein heterocyclyl is tetrahydrothiopyranyl and heteroaryl is selected from furanyl, pyridyl, thiazolyl or thienyl.

In one embodiment the present invention provides compounds of formula I wherein $R^8$ is —$OR^{12}$, and $R^{12}$ is lower alkyl or phenyl which is unsubstituted or substituted by one or two groups independently selected from lower alkyl, lower alkoxy, lower halogenalkyl, lower halogenalkoxy and halogen.

In one embodiment the present invention provides compounds of formula I, wherein $R^8$ is —$NR^{13}R^{14}$, wherein $R^{13}$ and $R^{14}$ independently from each other are selected from hydrogen, lower alkyl, and phenyl which is unsubstituted or substituted by one or two groups independently selected from lower alkyl, lower alkoxy, lower halogenalkyl, lower halogenalkoxy and halogen.

In one embodiment the present invention provides compounds of formula I wherein $R^8$ is —C(O)—$OR^{15}$, wherein $R^{15}$ is hydrogen or lower alkyl.

In another embodiment the present invention provides compounds of formula I wherein $R^8$ is phenyl which is unsubstituted or substituted by one or two groups independently selected from lower alkyl, lower alkoxy, lower halogenalkyl, lower halogenalkoxy and halogen. In still another embodiment the present invention provides compounds of formula I-A, wherein $R^8$ is phenyl which is substituted by one or two groups independently selected from lower halogenalkyl, lower halogenalkoxy and halogen. In still another embodiment the present invention provides compounds of formula I-A wherein $R^8$ is selected from 3-trifluoromethoxyphenyl, 3-trifluoromethyl, 3-chloro-4-fluoromethyl, 4-fluoro-3-trifluoromethylphenyl, 3-difluoromethoxyphenyl, or 3,4-dichlorophenyl. In still another embodiment the present invention provides compounds of formula I wherein $R^8$ is selected from 3-trifluoromethoxyphenyl, 3-trifluoromethyl, 3-chloro-4-fluoromethyl, 4-fluoro-3-trifluoromethylphenyl, 3-difluoromethoxyphenyl, 3-trifluoromethylphenyl and 3,4-dichlorophenyl. In still another embodiment the present invention provides compounds of formula I wherein $R^8$ is 3-trifluoromethylphenyl.

In another embodiment the present invention provides compounds of formula I, wherein at least one of $R^9$, $R^{10}$ and $R^{11}$ is selected from the group consisting of lower alkyl, lower halogenalkyl or halogen. In still another embodiment the present invention provides compounds of formula I wherein one of $R^9$, $R^{10}$ and $R^{11}$ is selected from lower halogenalkyl or halogen.

In another embodiment the present invention provides compounds of formula I, wherein $R^{10}$ is halogen. In still another embodiment the present invention provides compounds of formula I wherein halogen means chloro.

In one embodiment the present invention provides compounds of formula I, wherein two of $R^9$, $R^{10}$ and $R^{11}$ are halogen and the other is hydrogen. In another embodiment the present invention provides compounds of formula I, wherein $R^9$ and $R^{10}$ are halogen and $R^{11}$ is hydrogen. In still another embodiment the present invention provides compounds of formula I, wherein $R^9$ is fluorine, $R^{10}$ is chlorine and $R^{11}$ is hydrogen.

The integer n is 1 or 2. In one embodiment the present invention provides compounds of formula I, wherein n is 1.

In one embodiment the present invention provides a compound of formula I selected from 1H-indole-7-carboxylic acid (4-tert-butyl-benzyl)-(3-methyl-butyl)-amide, 1H-indole-7-carboxylic acid (4-tert-butyl-benzyl)-pent-4-enyl-amide, 1H-indole-7-carboxylic acid (4-tert-butyl-benzyl)-(4,4,4-trifluoro-butyl)-amide, 1H-indole-7-carboxylic acid (4-tert-butyl-benzyl)-[2-(tetrahydro-thiopyran-4-yl)-ethyl]-amide, 1H-indole-7-carboxylic acid (4-tert-butyl-benzyl)-[3-(5-methyl-furan-2-yl)-butyl]-amide, 1H-indole-7-carboxylic acid (4-tert-butyl-benzyl)-[2-(4-fluoro-phenyl)-ethyl]-amide, 1H-indole-7-carboxylic acid (4-tert-butyl-benzyl)-[2-(4-methoxy-phenyl)-ethyl]-amide, 1H-indole-7-carboxylic acid (4-tert-butyl-benzyl)-(2-p-tolyl-ethyl)-amide, 5-bromo-1H-indole-7-carboxylic acid (4-tert-butyl-benzyl)-[2-(3-trifluoromethyl-phenyl)-ethyl]-amide, 1H-indole-7-carboxylic acid (4-tert-butyl-benzyl)-[2-(3-fluoro-phenyl)-ethyl]-amide, 5-chloro-1H-indole-7-carboxylic acid (4-tert-butyl-benzyl)-[2-(3-cyclopropyl-methoxy-phenyl)-ethyl]-amide, 1H-indole-7-carboxylic acid (4-tert-butyl-benzyl)-[2-(2-fluoro-phenyl)-ethyl]-amide, 1H-indole-7-carboxylic acid (4-tert-butyl-benzyl)-[2-(4-chloro-phenyl)-ethyl]-amide, 5-chloro-6-fluoro-1H-indole-7-carboxylic acid [4-(1-cyano-cyclopropyl)-benzyl]-[2-(3-trifluoromethyl-phenyl)-ethyl]-amide, 1H-indole-7-carboxylic acid (4-tert-butyl-benzyl)-[2-(3-chloro-phenyl)-ethyl]-amide, 1H-indole-7-carboxylic acid (4-tert-butyl-benzyl)-[2-(3-trifluoromethyl-phenyl)-ethyl]-amide, 1H-indole-7-carboxylic acid (4-tert-butyl-benzyl)-[2-(2-chloro-phenyl)-ethyl]-amide, 1H-indole-7-carboxylic acid (4-tert-butyl-benzyl)-[2-(3,4-dichloro-phenyl)-ethyl]-amide, 1H-indole-7-carboxylic acid (4-tert-butyl-benzyl)-[2-(2,6-dichloro-phenyl)-ethyl]-amide, 1H-indole-7-carboxylic acid (4-tert-butyl-benzyl)-[2-(3,5-difluoro-phenyl)-ethyl]-amide, 1H-indole-7-carboxylic acid (4-tert-butyl-benzyl)-[2-(4-trifluoromethyl-phenyl)-ethyl]-amide, 1H-indole-7-carboxylic acid (4-tert-butyl-benzyl)-[2-(3,4-difluoro-phenyl)-ethyl]-amide, 1H-indole-7-carboxylic acid (4-tert-butyl-benzyl)-phenethyl-amide, 1H-indole-7-carboxylic acid (4-tert-butyl-benzyl)-[2-(3-fluoro-4-trifluoromethyl-phenyl)-ethyl]-amide, 1H-indole-7-carboxylic acid (4-tert-butyl-benzyl)-[2-(3-trifluoromethoxy-phenyl)-ethyl]-amide, 1H-indole-7-carboxylic acid (4-tert-butyl-benzyl)-[2-(4-fluoro-3-trifluoromethyl-phenyl)-ethyl]-amide, 1H-indole-7-carboxylic acid (4-tert-butyl-benzyl)-[2-(2-fluoro-3-trifluoromethyl-phenyl)-ethyl]-amide, 1H-indole-7-carboxylic acid (4-tert-butyl-benzyl)-[2-(4-difluoromethoxy-phenyl)-ethyl]-amide, 5,6-difluoro-1H-indole-7-carboxylic acid (4-tert-butyl-benzyl)-[2-(4-fluoro-3-trifluoromethyl-phenyl)-ethyl]-amide, 5-chloro-1H-indole-7-carboxylic acid (4-tert-butyl-benzyl)-[2-(4-chloro-phenyl)-ethyl]-amide,
1H-indole-7-carboxylic acid (4-tert-butyl-benzyl)-[(R)-2-(4-chloro-phenyl)-2-hydroxy-ethyl]-amide,
5-chloro-1H-indole-7-carboxylic acid (4-tert-butyl-benzyl)-[(R)-2-(4-chloro-phenyl)-2-hydroxy-ethyl]-amide,
1H-indole-7-carboxylic acid (4-tert-butyl-benzyl)-(3-phenyl-propyl)-amide,
1H-indole-7-carboxylic acid (4-tert-butyl-benzyl)-[2-(3-ethoxy-phenyl)-ethyl]-amide,
1H-indole-7-carboxylic acid (4-tert-butyl-benzyl)-(2-hydroxy-2-phenyl-ethyl)-amide,
6-fluoro-1H-indole-7-carboxylic acid (4-tert-butyl-benzyl)-[2-(3,5-difluoro-phenyl)-ethyl]-amide,
6-fluoro-1H-indole-7-carboxylic acid (4-tert-butyl-benzyl)-[2-(3,4-difluoro-phenyl)-ethyl]-amide,
5-chloro-1H-indole-7-carboxylic acid (4-tert-butyl-benzyl)-[2-(3-trifluoromethoxy-phenyl)-ethyl]-amide,
5-chloro-1H-indole-7-carboxylic acid (4-tert-butyl-benzyl)-[2-(4-fluoro-3-trifluoromethyl-phenyl)-ethyl]-amide,
1H-indole-7-carboxylic acid (4-tert-butyl-benzyl)-[2-(3,4-dichloro-phenyl)-2-hydroxy-ethyl]-amide,
5,6-difluoro-1H-indole-7-carboxylic acid (4-tert-butyl-benzyl)-[2-(3-trifluoromethoxy-phenyl)-ethyl]-amide,
1H-indole-7-carboxylic acid (4-tert-butyl-benzyl)-[2-(4-fluoro-phenyl)-2-hydroxy-ethyl]-amide,
5-chloro-1H-indole-7-carboxylic acid (4-tert-butyl-benzyl)-[2-(3,4-dichloro-phenyl)-2-hydroxy-ethyl]-amide,
5-Chloro-1H-indole-7-carboxylic acid (4-tert-butyl-benzyl)-[2-(4-fluoro-phenyl)-2-hydroxy-ethyl]-amide,
5,6-difluoro-1H-indole-7-carboxylic acid (4-tert-butyl-benzyl)-[2-(4-fluoro-phenyl)-2-hydroxy-ethyl]-amide,
1H-indole-7-carboxylic acid (4-tert-butyl-benzyl)-[2-(4-chloro-phenyl)-2-hydroxy-ethyl]-amide,
5-chloro-1H-indole-7-carboxylic acid (4-tert-butyl-benzyl)-[2-(4-chloro-phenyl)-2-hydroxy-ethyl]-amide,
5-chloro-1H-indole-7-carboxylic acid (4-tert-butyl-benzyl)-[2-(4-chloro-phenyl)-2-fluoro-ethyl]-amide,
5-chloro-6-fluoro-1H-indole-7-carboxylic acid (4-tert-butyl-benzyl)-[2-(3-trifluoromethoxy-phenyl)-ethyl]-amide,
5-chloro-6-fluoro-1H-indole-7-carboxylic acid (4-tert-butyl-benzyl)-[2-(3-trifluoromethyl-phenyl)-ethyl]-amide,
5-chloro-6-fluoro-1H-indole-7-carboxylic acid (4-tert-butyl-benzyl)-[2-(3-chloro-4-fluoro-phenyl)-ethyl]-amide,
5-chloro-6-fluoro-1H-indole-7-carboxylic acid (4-tert-butyl-benzyl)-[2-(4-chloro-phenyl)-ethyl]-amide,
5-chloro-6-fluoro-1H-indole-7-carboxylic acid (4-cyclopropyl-benzyl)-[2-(3-trifluoromethyl-phenyl)-ethyl]-amide,
5-chloro-1H-indole-7-carboxylic acid (4-tert-butyl-benzyl)-(4,4,4-trifluoro-3-trifluoromethyl-butyl)-amide,
1H-indole-7-carboxylic acid (4-tert-butyl-benzyl)-[2-(3-chloro-4-fluoro-phenyl)-ethyl]-amide,
5-chloro-1H-indole-7-carboxylic acid (4-tert-butyl-benzyl)-[2-(3-chloro-4-fluoro-phenyl)-ethyl]-amide,
1H-indole-7-carboxylic acid (4-tert-butyl-benzyl)-[2-(2-fluoro-5-trifluoromethyl-phenyl)-ethyl]-amide,
5-chloro-1H-indole-7-carboxylic acid (4-tert-butyl-benzyl)-[2-(2-fluoro-5-trifluoromethyl-phenyl)-ethyl]-amide,
5-chloro-6-fluoro-1H-indole-7-carboxylic acid (4-tert-butyl-benzyl)-[2-(4-fluoro-3-trifluoromethyl-phenyl)-ethyl]-amide,
5-chloro-1H-indole-7-carboxylic acid (4-tert-butyl-benzyl)-[2-(4-chloro-3-trifluoromethyl-phenyl)-ethyl]-amide,
5-chloro-1H-indole-7-carboxylic acid (4-cyclopropyl-benzyl)-[2-(4-fluoro-3-trifluoromethyl-phenyl)-ethyl]-amide,
5-chloro-6-fluoro-1H-indole-7-carboxylic acid (4-tert-butyl-benzyl)-[2-(4-chloro-3-trifluoromethyl-phenyl)-ethyl]-amide,
5-chloro-1H-indole-7-carboxylic acid (4-cyclopropyl-benzyl)-[2-(3-trifluoromethoxy-phenyl)-ethyl]-amide,
5-chloro-1H-indole-7-carboxylic acid (4-tert-butyl-benzyl)-[2-(3-fluoro-5-trifluoromethyl-phenyl)-ethyl]-amide,
5-chloro-1H-indole-7-carboxylic acid (4-cyclopropyl-benzyl)-[2-(3,4-dichloro-phenyl)-ethyl]-amide,
5-chloro-6-fluoro-1H-indole-7-carboxylic acid (4-tert-butyl-benzyl)-[2-(3-fluoro-5-trifluoromethyl-phenyl)-ethyl]-amide,
5-chloro-1H-indole-7-carboxylic acid [2-(4-chloro-phenyl)-ethyl]-(4-cyclopropyl-benzyl)-amide,
1H-indole-7-carboxylic acid (4-tert-butyl-benzyl)-[2-(3-difluoromethoxy-phenyl)-ethyl]-amide,
1H-indole-7-carboxylic acid (4-tert-butyl-benzyl)-[2-(3-chloro-2-fluoro-phenyl)-ethyl]-amide,
5-chloro-1H-indole-7-carboxylic acid (4-tert-butyl-benzyl)-[2-(3-chloro-2-fluoro-phenyl)-ethyl]-amide,
5,6-difluoro-1H-indole-7-carboxylic acid (4-tert-butyl-benzyl)-[2-(3-chloro-2-fluoro-phenyl)-ethyl]-amide,
5-chloro-1H-indole-7-carboxylic acid (4-tert-butyl-benzyl)-[2-(3-difluoromethoxy-phenyl)-ethyl]-amide,
5-chloro-6-fluoro-1H-indole-7-carboxylic acid (4-tert-butyl-benzyl)-[2-(3-difluoromethoxy-phenyl)-ethyl]-amide,
5-chloro-6-fluoro-1H-indole-7-carboxylic acid (4-tert-butyl-benzyl)-[2-(2-fluoro-5-trifluoromethyl-phenyl)-ethyl]-amide,
1H-indole-7-carboxylic acid (4-tert-butyl-benzyl)-(3,3,3-trifluoro-2-hydroxy-propyl)-amide,
2,3-dihydro-1H-indole-7-carboxylic acid (4-tert-butyl-benzyl)-[2-(4-fluoro-phenyl)-ethyl]-amide,
1H-indole-7-carboxylic acid butyl-(4-tert-butyl-benzyl)-amide,
1H-indole-7-carboxylic acid (4-tert-butyl-benzyl)-[2-(3-methoxy-phenyl)-ethyl]-amide,
1H-indole-7-carboxylic acid (4-tert-butyl-benzyl)-[2-(4-chloro-phenyl)-propyl]-amide,
1H-indole-7-carboxylic acid (4-tert-butyl-benzyl)-[2-(2,4-dichloro-phenyl)-ethyl]-amide,
4-chloro-1H-indole-7-carboxylic acid (4-tert-butyl-benzyl)-[2-(4-fluoro-phenyl)-ethyl]-amide,
4-chloro-1H-indole-7-carboxylic acid (4-tert-butyl-benzyl)-[2-(4-chloro-phenyl)-ethyl]-amide,
4-fluoro-1H-indole-7-carboxylic acid (4-tert-butyl-benzyl)-phenethyl-amide,
4-fluoro-1H-indole-7-carboxylic acid (4-tert-butyl-benzyl)-[2-(4-fluoro-phenyl)-ethyl]-amide,
4-fluoro-1H-indole-7-carboxylic acid (4-tert-butyl-benzyl)-[2-(4-chloro-phenyl)-ethyl]-amide,
6-fluoro-1H-indole-7-carboxylic acid (4-tert-butyl-benzyl)-[2-(4-chloro-phenyl)-ethyl]-amide,
6-fluoro-1H-indole-7-carboxylic acid (4-tert-butyl-benzyl)-[2-(4-fluoro-phenyl)-ethyl]-amide,
2,3-dihydro-1H-indole-7-carboxylic acid (4-tert-butyl-benzyl)-phenethyl-amide,
6-fluoro-1H-indole-7-carboxylic acid (4-tert-butyl-benzyl)-phenethyl-amide,
1H-indole-7-carboxylic acid (4-tert-butyl-benzyl)-[2-(4-fluoro-phenoxy)-ethyl]-amide,
1H-indole-7-carboxylic acid (4-tert-butyl-benzyl)-[2-(2-chloro-phenoxy)-ethyl]-amide,
1H-indole-7-carboxylic acid [2-(3-bromo-phenoxy)-ethyl]-(4-tert-butyl-benzyl)-amide,
1H-indole-7-carboxylic acid (4-tert-butyl-benzyl)-[2-(3-fluoro-phenoxy)-ethyl]-amide, 1H-indole-7-carboxylic acid (4-tert-butyl-benzyl)-{2-[(4-chloro-phenyl)-methyl-amino]-ethyl}-amide,
1H-indole-7-carboxylic acid (4-tert-butyl-benzyl)-(2-phenylamino-ethyl)-amide,
H-indole-7-carboxylic acid (4-tert-butyl-benzyl)-(2-pyridin-3-yl-ethyl)-amide,
1H-indole-7-carboxylic acid (4-tert-butyl-benzyl)-(2-pyridin-4-yl-ethyl)-amide,
3-[(4-tert-butyl-benzyl)-(1H-indole-7-carbonyl)-amino]-propionic acid tert-butyl ester,
5-chloro-1H-indole-7-carboxylic acid (4-tert-butyl-benzyl)-(2-pyridin-4-yl-ethyl)-amide,
5-chloro-1H-indole-7-carboxylic acid (4-tert-butyl-benzyl)-{2-[(4-chloro-phenyl)-methyl-amino]-ethyl}-amide,
1H-indole-7-carboxylic acid (4-tert-butyl-benzyl)-[2-(ethyl-m-tolyl-amino)-ethyl]-amide,
5-chloro-1H-indole-7-carboxylic acid (4-tert-butyl-benzyl)-[2-(ethyl-m-tolyl-amino)-ethyl]-amide,
5-chloro-1H-indole-7-carboxylic acid (4-tert-butyl-benzyl)-(2-phenylamino-ethyl)-amide,
5-chloro-1H-indazole-7-carboxylic acid (4-tert-butyl-benzyl)-[2-(3,4-dichloro-phenyl)-ethyl]-amide,
5-fluoro-1H-indole-7-carboxylic acid (4-tert-butyl-benzyl)-phenethyl-amide,
5-fluoro-1H-indole-7-carboxylic acid (4-tert-butyl-benzyl)-[2-(4-fluoro-phenyl)-ethyl]-amide,
5-fluoro-1H-indole-7-carboxylic acid (4-tert-butyl-benzyl)-[2-(4-chloro-phenyl)-ethyl]-amide,
5-fluoro-1H-indole-7-carboxylic acid (4-tert-butyl-benzyl)-[2-(3-trifluoromethyl-phenyl)-ethyl]-amide,
5-chloro-1H-indole-7-carboxylic acid (4-tert-butyl-benzyl)-[3-(5-methyl-furan-2-yl)-butyl]-amide,
6-fluoro-1H-indole-7-carboxylic acid (4-tert-butyl-benzyl)-[2-(3,4-dichloro-phenyl)-ethyl]-amide,
4-fluoro-1H-indole-7-carboxylic acid (4-tert-butyl-benzyl)-[2-(3-trifluoromethyl-phenyl)-ethyl]-amide,
4-fluoro-1H-indole-7-carboxylic acid (4-tert-butyl-benzyl)-[2-(3,4-dichloro-phenyl)-ethyl]-amide,
1H-indole-7-carboxylic acid (4-tert-butyl-benzyl)-[2-(3-trifluoromethyl-phenoxy)-ethyl]-amide,
5-fluoro-1H-indole-7-carboxylic acid (4-tert-butyl-benzyl)-[2-(3,4-dichloro-phenyl)-ethyl]-amide,
1H-indole-7-carboxylic acid (4-tert-butyl-benzyl)-[2-(2-trifluoromethyl-phenoxy)-ethyl]-amide,
5,6-difluoro-1H-indole-7-carboxylic acid (4-tert-butyl-benzyl)-[2-(4-chloro-phenyl)-ethyl]-amide,
5,6-difluoro-1H-indole-7-carboxylic acid (4-tert-butyl-benzyl)-[2-(3,4-dichloro-phenyl)-ethyl]-amide,
5,6-difluoro-1H-indole-7-carboxylic acid (4-tert-butyl-benzyl)-phenethyl-amide,
5,6-difluoro-1H-indole-7-carboxylic acid (4-tert-butyl-benzyl)-[2-(3-trifluoromethyl-phenyl)-ethyl]-amide,
5,6-difluoro-1H-indole-7-carboxylic acid (4-tert-butyl-benzyl)-(2-p-tolyl-ethyl)-amide,
5,6-difluoro-1H-indole-7-carboxylic acid (4-tert-butyl-benzyl)-[2-(3-chloro-phenyl)-ethyl]-amide,
5-chloro-6-fluoro-1H-indole-7-carboxylic acid (4-tert-butyl-benzyl)-[2-(3,4-dichloro-phenyl)-ethyl]-amide,
1H-indole-7-carboxylic acid (4-tert-butyl-2-methoxy-benzyl)-[2-(4-fluoro-phenyl)-ethyl]-amide,
5-chloro-1H-indole-7-carboxylic acid [2-(4-fluoro-phenyl)-ethyl]-(4-trifluoromethyl-benzyl)-amide,
5-chloro-1H-indole-7-carboxylic acid (4-tert-butyl-2-chloro-benzyl)-[2-(4-fluoro-phenyl)-ethyl]-amide,
5-chloro-1H-indole-7-carboxylic acid (4-tert-butyl-2-chloro-benzyl)-[2-(3-trifluoromethyl-phenyl)-ethyl]-amide,
5-chloro-6-fluoro-1H-indole-7-carboxylic acid (4-tert-butyl-2-chloro-benzyl)-[2-(3-trifluoromethyl-phenyl)-ethyl]-amide,
5-chloro-1H-indole-7-carboxylic acid (4-tert-butyl-2-chloro-benzyl)-[2-(3-trifluoromethoxy-phenyl)-ethyl]-amide,
5-chloro-6-fluoro-1H-indole-7-carboxylic acid (4-tert-butyl-2-chloro-benzyl)-[2-(3,4-dichloro-phenyl)-ethyl]-amide,
5-chloro-1H-indole-7-carboxylic acid (4-tert-butyl-2-chloro-benzyl)-[2-(3,4-dichloro-phenyl)-ethyl]-amide,
5-chloro-1H-indole-7-carboxylic acid (4-tert-butyl-2-fluoro-benzyl)-[2-(3-trifluoromethyl-phenyl)-ethyl]-amide,
5-chloro-6-fluoro-1H-indole-7-carboxylic acid (4-tert-butyl-2-fluoro-benzyl)-[2-(3-trifluoromethyl-phenyl)-ethyl]-amide,
5-chloro-1H-indole-7-carboxylic acid (4-tert-butyl-benzyl)-phenethyl-amide,
5-chloro-1H-indole-7-carboxylic acid (4-tert-butyl-benzyl)-[2-(4-fluoro-phenyl)-ethyl]-amide,
5-chloro-1H-indole-7-carboxylic acid (4-tert-butyl-benzyl)-[2-(3,4-dichloro-phenyl)-ethyl]-amide,
5-chloro-1H-indole-7-carboxylic acid (4-tert-butyl-benzyl)-[2-(3-trifluoromethyl-phenyl)-ethyl]-amide,
5-chloro-1H-indole-7-carboxylic acid (4-tert-butyl-benzyl)-(2-p-tolyl-ethyl)-amide,
5-chloro-1H-indole-7-carboxylic acid (4-tert-butyl-benzyl)-[2-(3-chloro-phenyl)-ethyl]-amide,
5-chloro-1H-indazole-7-carboxylic acid (4-tert-butyl-benzyl)-[2-(4-fluoro-phenyl)-ethyl]-amide,
5-chloro-1H-indazole-7-carboxylic acid (4-tert-butyl-benzyl)-[2-(3-trifluoromethyl-phenyl)-ethyl]-amide,
5-chloro-1H-indazole-7-carboxylic acid (4-tert-butyl-benzyl)-(2-p-tolyl-ethyl)-amide,
5-chloro-1H-indazole-7-carboxylic acid (4-tert-butyl-benzyl)-[2-(4-chloro-phenyl)-ethyl]-amide,
5-chloro-2-methyl-1H-indole-7-carboxylic acid (4-tert-butyl-benzyl)-[2-(4-fluoro-phenyl)-ethyl]-amide,
5-chloro-2-ethyl-1H-indole-7-carboxylic acid (4-tert-butyl-benzyl)-[2-(4-fluoro-phenyl)-ethyl]-amide,
5-chloro-2-ethyl-1H-indole-7-carboxylic acid (4-tert-butyl-benzyl)-[2-(3,4-dichloro-phenyl)-ethyl]-amide,
5-chloro-1H-indole-7-carboxylic acid (4-cyclopropyl-benzyl)-[2-(3-trifluoromethyl-phenyl)-ethyl]-amide,
5-chloro-1H-indole-7-carboxylic acid [4-(1-methyl-cyclopropyl)-benzyl]-[2-(3-trifluoromethyl-phenyl)-ethyl]-amide,
5-chloro-1H-indole-7-carboxylic acid [1-(4-tert-butyl-phenyl)-ethyl]-[2-(3-trifluoromethyl-phenyl)-ethyl]-amide,
5-chloro-1H-indole-7-carboxylic acid [4-(1-methoxy-cyclopropyl)-benzyl]-[2-(3-trifluoromethyl-phenyl)-ethyl]-amide,
5-chloro-1H-indole-7-carboxylic acid [4-(1-ethyl-cyclopropyl)-benzyl]-[2-(3-trifluoromethyl-phenyl)-ethyl]-amide,
5-methyl-1H-indole-7-carboxylic acid (4-tert-butyl-benzyl)-[2-(4-chloro-phenyl)-ethyl]-amide,
5-methyl-1H-indole-7-carboxylic acid (4-tert-butyl-benzyl)-[2-(3-trifluoromethyl-phenyl)-ethyl]-amide,
5-methyl-1H-indole-7-carboxylic acid (4-tert-butyl-benzyl)-[2-(4-fluoro-phenyl)-ethyl]-amide,
5-trifluoromethyl-1H-indole-7-carboxylic acid (4-tert-butyl-benzyl)-[2-(3,4-dichloro-phenyl)-ethyl]-amide,
5-methyl-1H-indole-7-carboxylic acid (4-pentafluoro-sulphuranyl-benzyl)-[2-(4-fluoro-phenyl)-ethyl]-amide,
2-methyl-1H-indole-7-carboxylic acid (4-pentafluoro-sulphuranyl-benzyl)-[2-(3,4-dichloro-phenyl)-ethyl]-amide, 2-methyl-1H-indole-7-carboxylic acid (4-tert-butyl-benzyl)-[2-(3-trifluoromethoxy-phenyl)-ethyl]-amide,
2-methyl-1H-indole-7-carboxylic acid (4-tert-butyl-benzyl)-[2-(4-fluoro-3-trifluoromethyl-phenyl)-ethyl]-amide,
5-methyl-1H-indole-7-carboxylic acid (4-tert-butyl-benzyl)-[2-(3-trifluoromethoxy-phenyl)-ethyl]-amide,
5-methyl-1H-indole-7-carboxylic acid (4-tert-butyl-benzyl)-[2-(4-fluoro-3-trifluoromethyl-phenyl)-ethyl]-amide,
5,6-difluoro-1H-indole-7-carboxylic acid (4-tert-butyl-benzyl)-[2-(4-methyl-thiazol-2-yl)-ethyl]-amide,
5-chloro-1H-indole-7-carboxylic acid (4-tert-butyl-benzyl)-[2-(4-methyl-thiazol-2-yl)-ethyl]-amide,
5-trifluoromethyl-1H-indole-7-carboxylic acid (4-tert-butyl-benzyl)-[2-(3-trifluoromethyl-phenyl)-ethyl]-amide,
5-trifluoromethyl-1H-indole-7-carboxylic acid (4-tert-butyl-benzyl)-[2-(4-fluoro-3-trifluoromethyl-phenyl)-ethyl]-amide,
5-trifluoromethyl-1H-indole-7-carboxylic acid (4-tert-butyl-benzyl)-[2-(3-trifluoromethoxy-phenyl)-ethyl]-amide,
5-trifluoromethyl-1H-indole-7-carboxylic acid (4-tert-butyl-benzyl)-[2-(4-chloro-phenyl)-ethyl]-amide,
5-trifluoromethyl-1H-indole-7-carboxylic acid (4-cyclopropyl-benzyl)-[2-(3-trifluoromethyl-phenyl)-ethyl]-amide,
5-chloro-1H-indole-7-carboxylic acid [4-(1-methoxy-cyclobutyl)-benzyl]-[2-(3-trifluoromethyl-phenyl)-ethyl]-amide,
2-methyl-1H-indole-7-carboxylic acid (4-tert-butyl-benzyl)-[2-(3,4-dichloro-phenyl)-ethyl]-amide,
2-methyl-1H-indole-7-carboxylic acid (4-tert-butyl-benzyl)-[2-(4-chloro-phenyl)-ethyl]-amide,
2-methyl-1H-indole-7-carboxylic acid (4-tert-butyl-benzyl)-(2-p-tolyl-ethyl)-amide,
2-methyl-1H-indole-7-carboxylic acid (4-tert-butyl-benzyl)-[2-(3-trifluoromethyl-phenyl)-ethyl]-amide,
5-methyl-1H-indole-7-carboxylic acid (4-tert-butyl-benzyl)-[2-(3,4-dichloro-phenyl)-ethyl]-amide,
1H-indole-7-carboxylic acid (4-pentafluoro-sulphuranyl-benzyl)-[2-(4-fluoro-phenyl)-ethyl]-amide,
2-methyl-1H-indole-7-carboxylic acid (4-tert-butyl-benzyl)-[2-(4-fluoro-phenyl)-ethyl]-amide,
2-methyl-1H-indole-7-carboxylic acid (4-tert-butyl-benzyl)-[2-(3,4-difluoro-phenyl)-ethyl]-amide,
5-methyl-1H-indole-7-carboxylic acid (4-pentafluoro-sulphuranyl-benzyl)-[2-(3,4-dichloro-phenyl)-ethyl]-amide,
5-methyl-1H-indole-7-carboxylic acid [2-(3,4-dichloro-phenyl)-ethyl]-[4-(2,2,2-trifluoro-1-methoxy-1-trifluoromethyl-ethyl)-benzyl]-amide,
5-chloro-1H-indole-7-carboxylic acid [2-(3,4-dichloro-phenyl)-ethyl]-[4-(1,2,2,2-tetrafluoro-1-trifluoromethyl-ethyl)-benzyl]-amide,
5-chloro-1H-indole-7-carboxylic acid [4-(1,2,2,2-tetrafluoro-1-trifluoromethyl-ethyl)-benzyl]-[2-(3-trifluoromethyl-phenyl)-ethyl]-amide,
5-chloro-1H-indole-7-carboxylic acid [2-(4-fluoro-3-trifluoromethyl-phenyl)-ethyl]-[4-(1,2,2,2-tetrafluoro-1-trifluoromethyl-ethyl)-benzyl]-amide,
5-chloro-1H-indole-7-carboxylic acid [4-(1,2,2,2-tetrafluoro-1-trifluoromethyl-ethyl)-benzyl]-[2-(3-trifluoromethoxy-phenyl)-ethyl]-amide,
5-chloro-1H-indole-7-carboxylic acid [2-(4-chloro-phenyl)-ethyl]-[4-(1,2,2,2-tetrafluoro-1-trifluoromethyl-ethyl)-benzyl]-amide,
1H-indole-7-carboxylic acid (4-tert-butyl-benzyl)-(2-thiophen-2-yl-ethyl)-amide,
5-chloro-1H-indole-7-carboxylic acid (1,1-dimethyl-indan-5-ylmethyl)-[2-(3-trifluoromethyl-phenyl)-ethyl]-amide,
5-chloro-1H-indole-7-carboxylic acid (1,1-dimethyl-indan-5-ylmethyl)-phenethyl-amide,
5-chloro-1H-indole-7-carboxylic acid [4-(1-methoxy-1-methyl-ethyl)-benzyl]-[2-(3-trifluoromethyl-phenyl)-ethyl]-amide,
5-chloro-1H-indole-7-carboxylic acid [2-(3,4-dichloro-phenyl)-ethyl]-[4-(1,1-dimethyl-propyl)-benzyl]-amide,
5-chloro-1H-indole-7-carboxylic acid [4-(1,1-dimethyl-propyl)-benzyl]-[2-(3-trifluoromethyl-phenyl)-ethyl]-amide,
5-chloro-1H-indole-7-carboxylic acid [3-chloro-4-(1-methyl-cyclopropyl)-benzyl]-[2-(3-trifluoromethyl-phenyl)-ethyl]-amide,
5-chloro-1H-indole-7-carboxylic acid [3-chloro-4-(1-methyl-cyclopropyl)-benzyl]-[2-(3,4-dichloro-phenyl)-ethyl]-amide,
6-fluoro-5-trifluoromethyl-1H-indole-7-carboxylic acid (4-tert-butyl-benzyl)-[2-(3-trifluoromethyl-phenyl)-ethyl]-amide,
6-fluoro-5-trifluoromethyl-1H-indole-7-carboxylic acid (4-tert-butyl-benzyl)-[2-(3,4-dichloro-phenyl)-ethyl]-amide,
6-fluoro-5-trifluoromethyl-1H-indole-7-carboxylic acid (4-tert-butyl-benzyl)-[2-(4-fluoro-3-trifluoromethyl-phenyl)-ethyl]-amide,
6-fluoro-5-trifluoromethyl-1H-indole-7-carboxylic acid (4-tert-butyl-benzyl)-[2-(3-chloro-4-fluoro-phenyl)-ethyl]-amide,
5-chloro-1H-indole-7-carboxylic acid (2,2-dimethyl-chroman-6-ylmethyl)-[2-(3-trifluoromethyl-phenyl)-ethyl]-amide,
5-chloro-1H-indole-7-carboxylic acid (2,2-dimethyl-chroman-6-ylmethyl)-phenethyl-amide,
5-chloro-1H-indole-7-carboxylic acid [4-(1-ethyl-1-methoxy-propyl)-benzyl]-[2-(3-trifluoromethyl-phenyl)-ethyl]-amide,
5-chloro-N-[2-(3,4-dichlorophenyl)ethyl]-N-[(2',3'-dihydrospiro [cyclopropane-1,1'-[1H]inden]-5'-yl)methyl]-1H-indole-7-carboxamide,
5-chloro-N-[(2',3'-dihydrospiro[cyclopropane-1,1'-[1H]inden]-5'-yl)methyl]-N-[2-[3-(trifluoromethyl)phenyl]ethyl]-1H-indole-7-carboxamide,
5-chloro-1H-indole-7-carboxylic acid (4-tert-butyl-3-chloro-benzyl)-[2-(3-trifluoromethyl-phenyl)-ethyl]-amide,
5-chloro-1H-indole-7-carboxylic acid (4-tert-butyl-3-chloro-benzyl)-[2-(3,4-dichloro-phenyl)-ethyl]-amide,
5-chloro-1H-indole-7-carboxylic acid [4-(1,1-dimethyl-butyl)-benzyl]-[2-(3-trifluoromethyl-phenyl)-ethyl]-amide,
5-chloro-6-fluoro-1H-indole-7-carboxylic acid [4-(1,1-dimethyl-butyl)-benzyl]-[2-(3-trifluoromethyl-phenyl)-ethyl]-amide,
5-chloro-1H-indole-7-carboxylic acid (4-cyclobutyl-benzyl)-[2-(3,4-dichloro-phenyl)-ethyl]-amide,
5-chloro-6-fluoro-1H-indole-7-carboxylic acid (4-cyclobutyl-benzyl)-[2-(3,4-dichloro-phenyl)-ethyl]-amide,
5-chloro-6-fluoro-1H-indole-7-carboxylic acid (4-cyclobutyl-benzyl)-[2-(3-trifluoromethyl-phenyl)-ethyl]-amide,
5-chloro-1H-indole-7-carboxylic acid (4-cyclobutyl-benzyl)-[2-(3-trifluoromethyl-phenyl)-ethyl]-amide,
5-chloro-1H-indole-7-carboxylic acid (4-cyclopentyl-benzyl)-[2-(3,4-dichloro-phenyl)-ethyl]-amide, and pharmaceutically acceptable salts thereof.

In still another embodiment the present invention provides a compound of formula I selected from
5-chloro-1H-indole-7-carboxylic acid (4-tert-butyl-benzyl)-[2-(3-trifluoromethoxy-phenyl)-ethyl]-amide, 5-chloro-6-fluoro-1H-indole-7-carboxylic acid (4-tert-butyl-benzyl)-[2-(3-trifluoromethoxy-phenyl)-ethyl]-amide,
5-chloro-6-fluoro-1H-indole-7-carboxylic acid (4-tert-butyl-benzyl)-[2-(3-trifluoromethyl-phenyl)-ethyl]-amide,
5-chloro-6-fluoro-1H-indole-7-carboxylic acid (4-tert-butyl-benzyl)-[2-(3-difluoromethoxy-phenyl)-ethyl]-amide,
5-chloro-6-fluoro-1H-indole-7-carboxylic acid (4-tert-butyl-benzyl)-[2-(3-chloro-4-fluoro-phenyl)-ethyl]-amide,
5-chloro-6-fluoro-1H-indole-7-carboxylic acid (4-tert-butyl-benzyl)-[2-(4-fluoro-3-trifluoromethyl-phenyl)-ethyl]-amide,
5-chloro-6-fluoro-1H-indole-7-carboxylic acid (4-tert-butyl-benzyl)-[2-(4-chloro-3-trifluoromethyl-phenyl)-ethyl]-amide,
5-chloro-6-fluoro-1H-indole-7-carboxylic acid (4-tert-butyl-benzyl)-[2-(3,4-dichloro-phenyl)-ethyl]-amide,
5-chloro-6-fluoro-1H-indole-7-carboxylic acid (4-tert-butyl-2-chloro-benzyl)-[2-(3,4-dichloro-phenyl)-ethyl]-amide,
5-chloro-6-fluoro-1H-indole-7-carboxylic acid (4-tert-butyl-2-fluoro-benzyl)-[2-(3-trifluoromethyl-phenyl)-ethyl]-amide,
5-chloro-1H-indole-7-carboxylic acid (4-tert-butyl-benzyl)-[2-(3,4-dichloro-phenyl)-ethyl]-amide,
5-chloro-1H-indole-7-carboxylic acid (4-tert-butyl-benzyl)-[2-(3-trifluoromethyl-phenyl)-ethyl]-amide,
5-chloro-1H-indole-7-carboxylic acid [4-(1-methyl-cyclopropyl)-benzyl]-[2-(3-trifluoromethyl-phenyl)-ethyl]-amide and
5-chloro-1H-indole-7-carboxylic acid [2-(3,4-dichloro-phenyl)-ethyl]-[4-(1,2,2,2-tetra-fluoro-1-trifluoromethyl-ethyl)-benzyl]-amide, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, e.g., hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, e.g., racemates, optically pure diastereoisomers, mixtures of diastereoisomers, diastereoisomeric racemates or mixtures of diastereoisomeric racemates. The optically active forms can be obtained, e.g., by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises
reacting an acid of the formula II

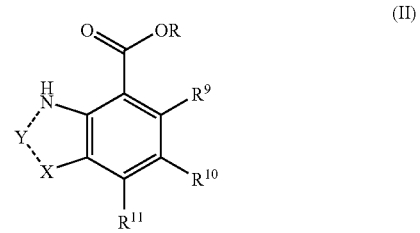

wherein —X—Y—, $R^9$, $R^{10}$ and $R^{11}$ are as defined herein before and R is hydrogen or lower alkyl, with an amine of formula III

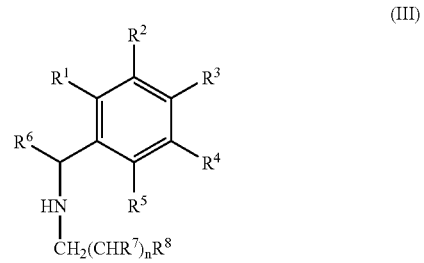

wherein $R^1$ to $R^8$ and n are as defined herein before, in the presence of a coupling agent; or, alternatively,
reacting a halogen derivative of formula IV

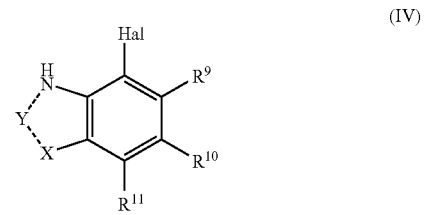

wherein —X—Y—, $R^9$, $R^{10}$ and $R^{11}$ are as defined herein before and Hal means halogen,
with an amine of formula III in the presence of a suitable catalyst and carbon monoxide, and if desired,
converting the compound obtained into a pharmaceutically acceptable acid addition salt.

Preferred coupling reagents are 1-ethyl-3-(3-dimethyl-aminopropyl)-carbodiimide (EDC) or its hydrochloride (EDC.HCl), N,N'-dicyclohexyl-carbodiimide (DCC) or O-(benzotriazol-1-yl)-N,N,N',N'-tetramethyl-uronium-tetrafluoroborate (TBTU).

In more detail, the compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

According to reaction scheme 1 formula I compounds may be prepared by coupling of an acid derivative II with an appropriate secondary amine derivative III.

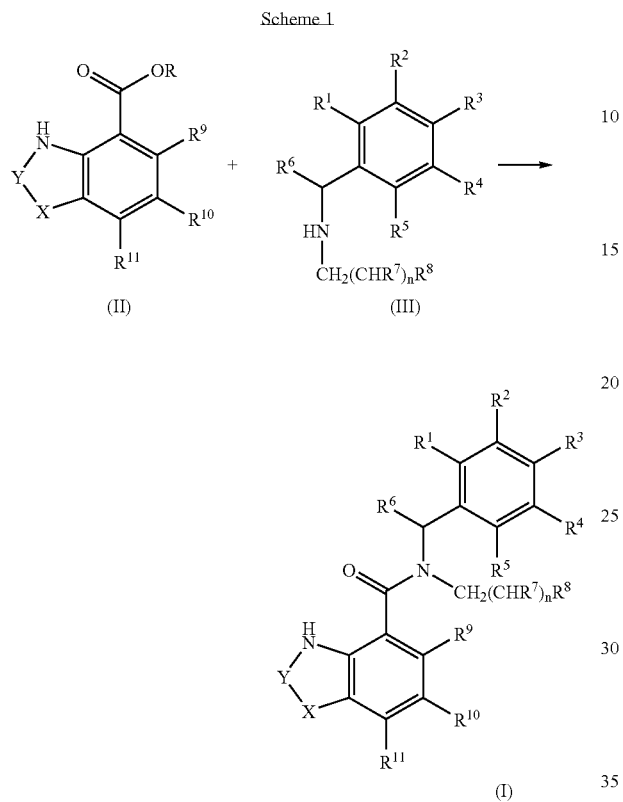

If acids (R=H) of formula II are used in this process, standard peptide coupling reagents can be applied to activate the acid prior to the coupling reaction. Typically, the acid derivative II (R=H) is mixed with a coupling reagent such as EDC or EDC.HCl, DCC or TBTU in an inert solvent such as dimethylformamide (DMF), dimethylacetamide (DMA) or dichloromethane (DCM) together with the appropriate secondary amine derivative III. Optionally a base (e.g. N,N-diisopropylethyl amine, triethylamine, N-methyl morpholine) and/or 1-hydroxybenzotriazole (HOBT) can be added. The reaction mixture is stirred for 1 to 24 h at a temperature of about −30° C. to about 70° C. (preferably ambient temperature).

Alternatively, esters of formula II (R=CH$_3$ or C$_2$H$_5$) may be used in the coupling process. In that case, the amine derivative III is treated with trimethylaluminum in an inert solvent such as DCM or toluene at ambient temperature prior to the addition of the ester derivative II.

Acid derivatives of formula II are commercially available or can be prepared following a standard indole, indoline or indazole synthesis as, e.g., described in the general schemes 4 to 7.

Possible routes to synthesize secondary amine derivatives III are outlined in the general schemes 8 to 11 or are given within the example section.

According to scheme 2, compounds of the general formula I may also be prepared by coupling of a halogen derivative IV with an appropriate secondary amine derivative III in the presence of a suitable catalyst (e.g. Pd(dppf)Cl$_2$) and carbon monoxide (e.g. 1 to 100 atmospheres) in an inert solvent (preferably a mixture of methanol and toluene) at a temperature of about 50° C. to about 150° C. Possible routes for the synthesis of the necessary halogen derivatives IV are outlined in the general schemes 4, 5 and 9.

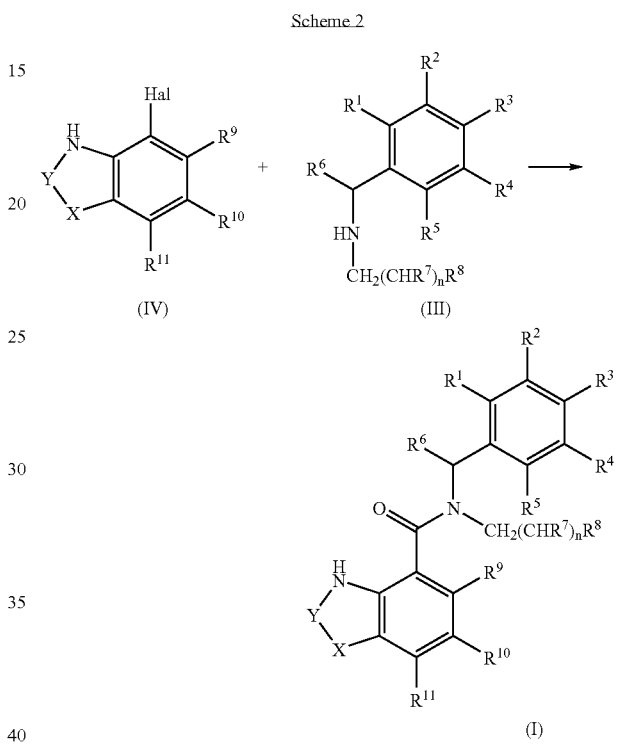

A possible synthesis of compounds of the general formula I wherein R$^8$ represent a group OR$^{12}$ is described in the general scheme 3. In a first step an acid derivative II is coupled with an amine derivative V applying standard peptide coupling conditions (as described for scheme 1). Etherification of the hydroxy group of the intermediate VI to prepare the final compounds can be accomplished using standard methods (e.g. Mitsunobu conditions).

If the appropriate substituents R$^a$ and R$^c$ in compounds of formula I wherein —X—Y— represents —CR$^a$=CR$^c$— are not already present in the acid derivative II or halogen derivative IV that is used in the coupling reaction, they can also be introduced by transformation of a group —CH=CR$^c$—, —CR$^a$=CH— or —CH=CH— into —CR$^a$=CR$^c$— using standard chemistry.

Formula I compounds wherein —X—Y— represents —CR$^a$R$^b$—CR$^c$R$^d$— can be prepared either by using the appropriate acid derivative II or halogen derivative IV in the coupling reaction with the amine III or by transformation of a group —CR$^a$=CR$^c$— into —CR$^a$R$^b$—CR$^c$R$^d$— at any stage of the synthesis. For example, this can be accomplished by sodium borohydride in acetic acid.

Scheme 3
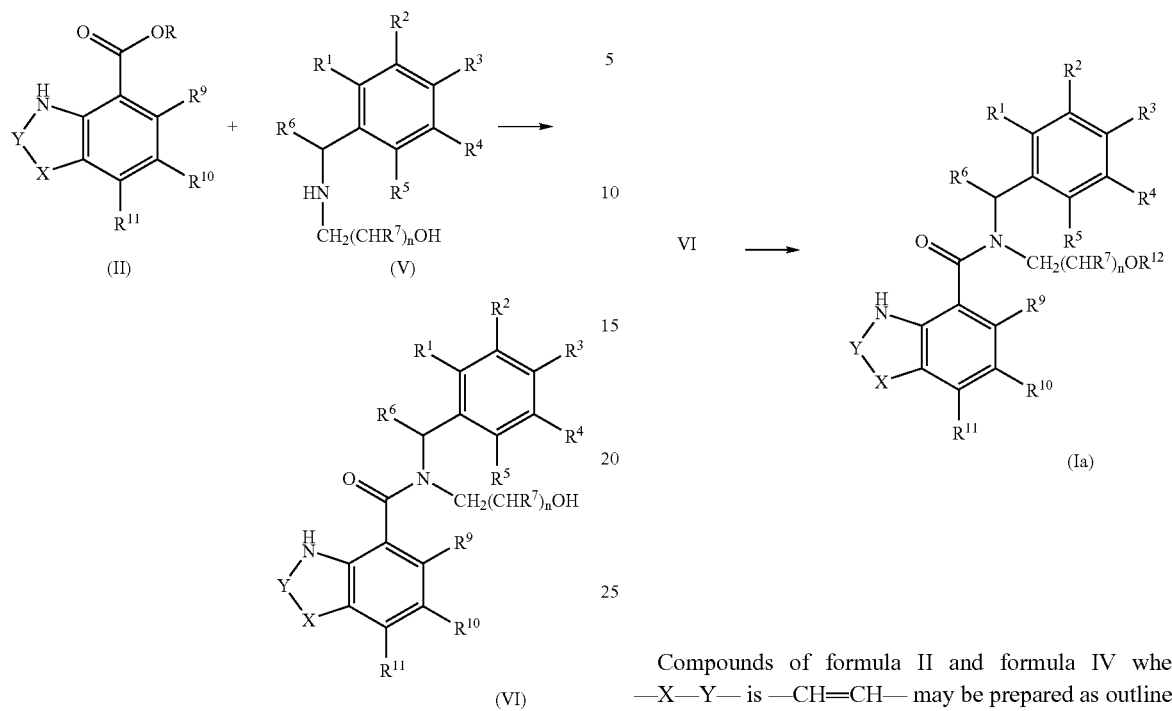
Compounds of formula II and formula IV wherein —X—Y— is —CH=CH— may be prepared as outlined in schemes 4 and 5.
Scheme 4
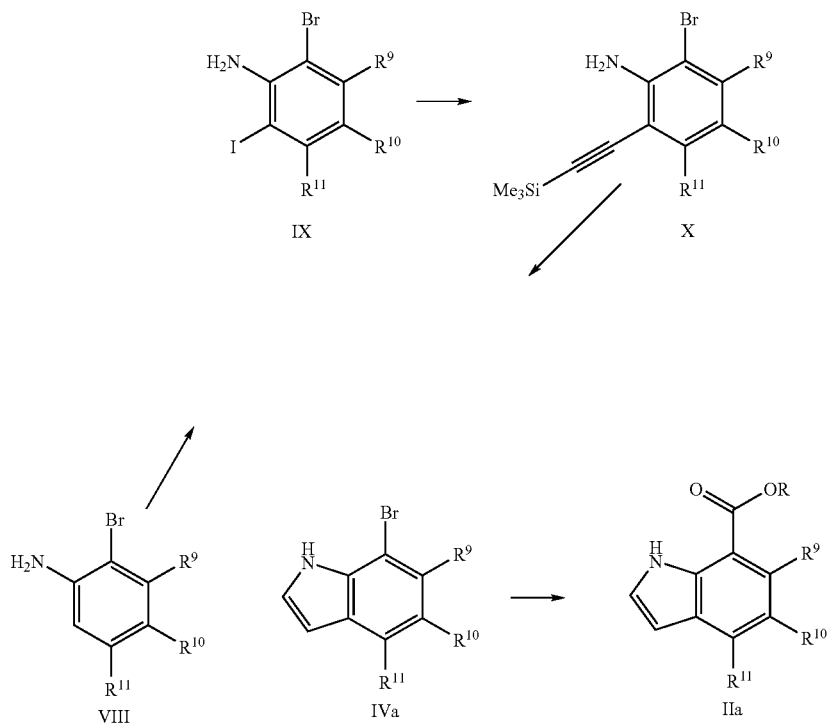

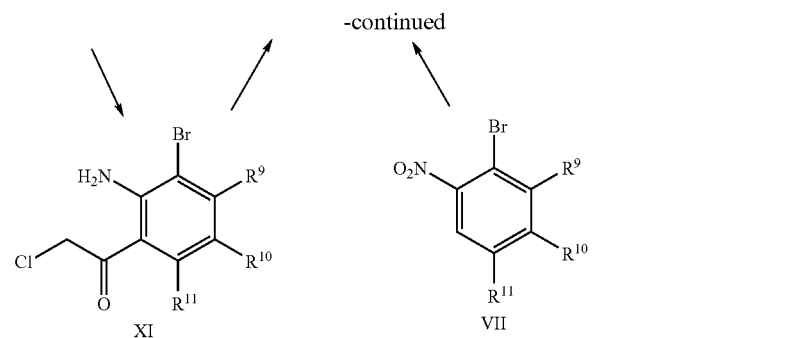

According to scheme 4, compounds of the general formula VII can be converted into indoles of formula IVa in one step. Thus, compounds of formula VII are subjected to an excess of a vinyl Grignard reagent (preferably 3 equivalents) at low temperature (preferably at or below −40° C.) in tetrahydrofuran (THF) to prepare bromo-indole compounds of the general structure IVa. Bromo-indoles IVa can be converted into acid derivatives IIa by halogen-metal exchange reaction (preferably using alkyllithium reagents) and trapping of the organometallic intermediate with a suitable electrophile such as carbon dioxide or an alkyl chloroformate. Bromo-indoles IVa can also be reacted with carbon monoxide (e.g. 1 to 100 atmospheres) and an alcohol in the presence of a palladium catalyst (e.g. Pd(dppf)Cl$_2$) to obtain compounds of formula IIa.

Alternatively, compounds of formula IVa and IIa may be prepared starting from anilines with the general structure VIII. Iodination of formula VIII compounds (e.g. with iodine or N-iodosuccinimide) can provide iodo-anilines IX that can be converted into formula X compounds using a Sonogashira coupling reaction. Thus, compounds of formula IX are reacted with ethinyltrimethylsilane in the presence of a palladium catalyst (e.g. Pd(PPh$_3$)$_2$Cl$_2$), copper(I)iodide and an amine base such as triethylamine. The trimethylsilyl protected acetylenes X can either be first deprotected (e.g. with tetrabutyl-ammonium fluoride in THF) and then cyclized to compounds of formula IVa or they can be directly cyclized to compounds of formula IVa using a base such as potassium tert-butoxide in a polar solvent such as N-methylpyrrolidone (NMP).

Compounds of formula IIa and IVa may also be prepared from chloroacetophenone derivatives XI. Thus, aniline derivatives VIII are treated with chloroacetonitrile in the presence of a mixture of boron trichloride and aluminum trichloride in an inert solvent to obtain compounds of formula XI which are then cyclized to indoles IVa by the action of sodium borohydride in dioxane.

Scheme 5

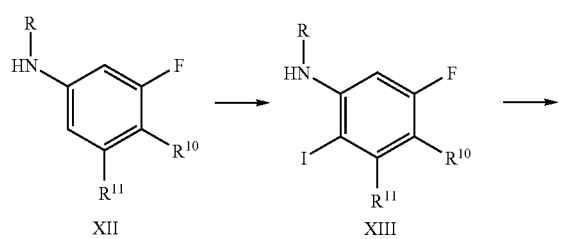

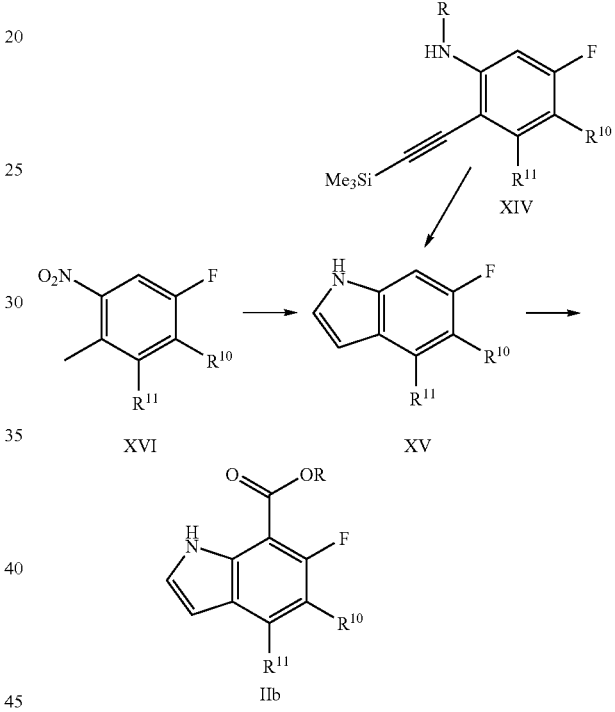

An alternative route for the synthesis of formula II and formula IV compounds wherein —X—Y— is —CH═CH— and R$^9$ is fluorine is outlined in scheme 5. Fluoro-anilines XII can be converted into iodo compounds XIII (R=H) using an iodination reagent such as N-iodosuccinimide. Alternatively a suitable protecting group R such as an alkoxycarbonyl group can be introduced at the aniline nitrogen prior to the iodination step. The protecting group R may be introduced by treatment of a formula XII compound wherein R=H with an appropriate alkyl chloroformate (e.g. methyl or ethyl chloroformate) in an inert solvent in the presence of a base (e.g. sodium bicarbonate). Sonogashira reaction of compounds of formula XIII with ethinyltrimethylsilane results in the formation of acetylenes XIV. Compounds of formula XIV wherein the protecting group R is an alkoxycarbonyl group can be cyclized to indole derivatives XV by treatment with a base (e.g. NaOEt in ethanol) or a fluoride reagent such as tetrabutylammonium fluoride in a solvent such as THF. For compounds of formula XIV wherein R is hydrogen the cyclization to indoles of formula XV can be accomplished using a base such as potassium tert-butoxide in NMP. Alternatively the trimethylsilyl protecting group of the acetylene moiety can be cleaved prior to the cyclization (e.g. with tetrabutylammonium fluoride in THF).

Indoles of formula XV may also be synthesized starting from compounds of formula XVI. Thus, derivatives XVI are treated first with N,N-dimethylformamide dimethylacetal in the presence of a base (e.g. pyrrolidine) and in a second step with hydrogen in the presence of a suitable catalyst (e.g. palladium on charcoal) in a protic solvent such as methanol.

In addition, indoles of formula XV may be prepared from aniline derivatives XII (R=H) by reaction with chloroacetonitrile in the presence of a mixture of boron trichloride and aluminum trichloride and subsequent cyclization using sodium borohydride in dioxane in analogy to the conversion of aniline derivatives VIII into formula IVa compounds as described in scheme 4.

Treatment of indoles of formula XV with an excess of n-butyllithium and potassium tert-butoxide at low temperature (preferably below −70° C.) results in the formation of an organometallic intermediate that can be reacted with electrophiles such as carbon dioxide or an alkyl chloroformate to form acid derivatives IIb.

Scheme 6

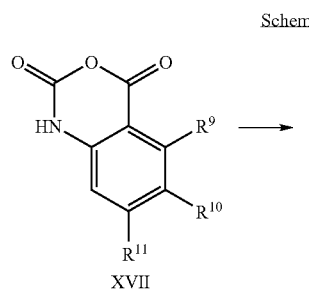

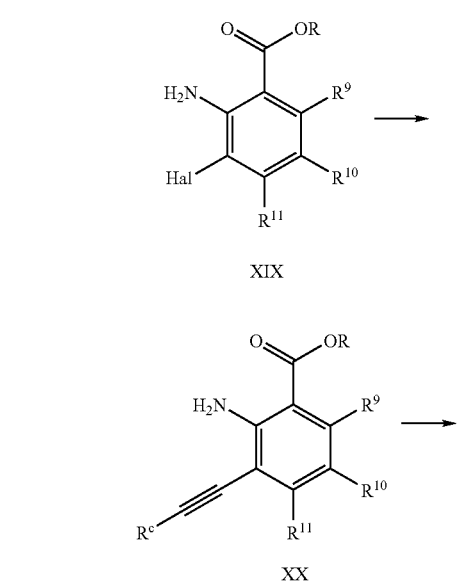

-continued

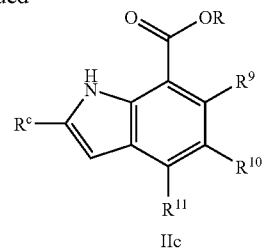

According to scheme 6 indole derivatives of formula II wherein —X—Y— is —CH=CR$^c$— may be prepared starting from isatoic anhydride derivatives of the general formula XVII. For example compounds of formula XVII can be first converted into anthranilic acid esters XVIII (e.g. with sodium methoxide or with methanol in the presence of DMAP) and then into the halogenated derivatives XIX by treatment with a halogenating agent such as iodine or N-iodosuccinimide. Compounds XIX can then be reacted with the appropriate substituted acetylenes (Sonogashira conditions) to provide compounds of formula XX that are subsequently cyclized to indole derivatives IIc. The cyclisation step can be accomplished either using a base such as potassium tert-butoxide in a solvent such as NMP or by using palladium(II)chloride in a solvent such as acetonitrile. Compounds of formula IIc with R=alkyl can be converted to the corresponding acids (R=H) by treatment with aqueous hydroxide (e.g. lithium or sodium hydroxide) in a polar solvent (preferably methanol and/or THF).

Scheme 7

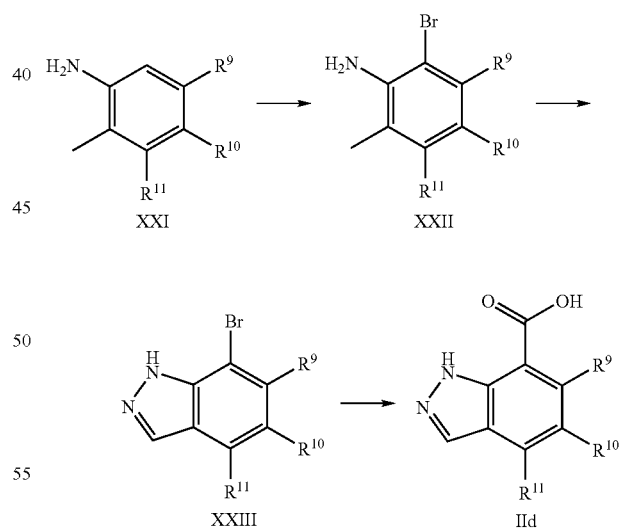

Acid derivatives of formula II wherein —X—Y— is —CR$^{12}$=N— may be synthesized as described in scheme 7. Anilines XXI can be brominated to obtain compounds of formula XXII that can be cyclized to indazole derivatives XXIII by treatment with sodium nitrite in acetic acid.

Secondary amines of the general formula III can be synthesized by standard methods. They may be synthesized as outlined in schemes 8 to 11.

Scheme 8

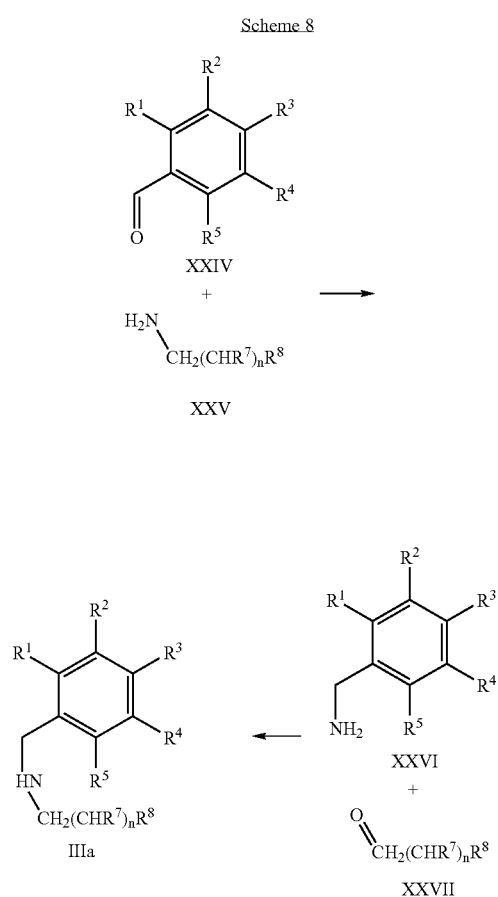

Scheme 8 illustrates a possible synthesis of compounds IIIa ($R^6$=H) either by reductive amination of benzaldehyde derivatives XXIV with amines XXV or by reductive amination of aldehydes XXVII with benzylic amine derivatives XXVI. The necessary starting amines and aldehydes are commercially available or are synthesized using standard methods as e.g. described in the example section.

Secondary amines IIIa may alternatively be synthesized from amide derivatives XXIX or XXXII as outlined in scheme 9.

Scheme 9

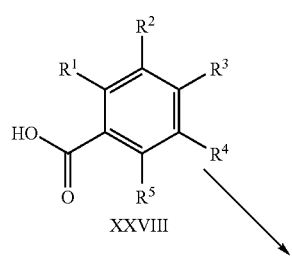

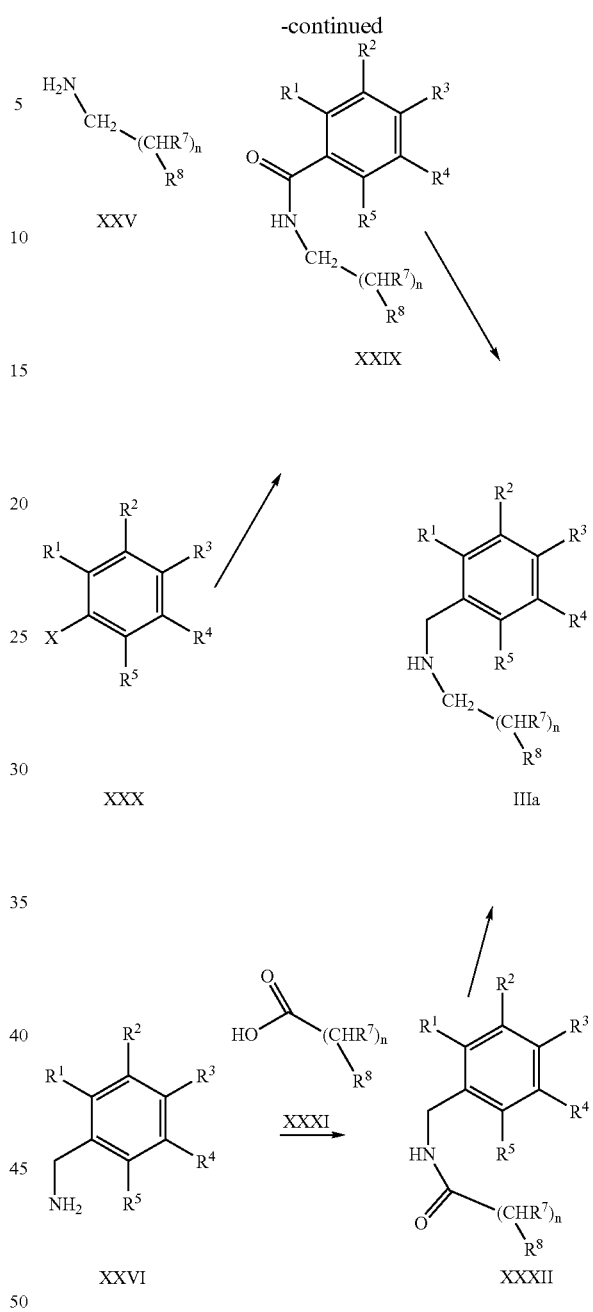

Whereas amide derivatives of formula XXIX are available by the coupling of benzoic acid derivatives XXVIII with amines XXV, amides of formula XXXII can be synthesized by coupling benzylic amines XXVI with acids XXXI. These amide couplings can be accomplished using standard coupling reagents and conditions (as described for scheme 1). The necessary starting amines and acids are commercially available or are synthesized using standard conditions as e.g. described in the example section. Alternatively, amide derivatives of formula XXIX can be obtained from compounds of formula XXX wherein X is a halogen atom or a triflate. Thus, compounds of formula XXX are treated with carbon monoxide in the presence of an amine derivative XXV and a suitable catalyst (e.g. Pd(OAc)$_2$ and dppf).

Scheme 10

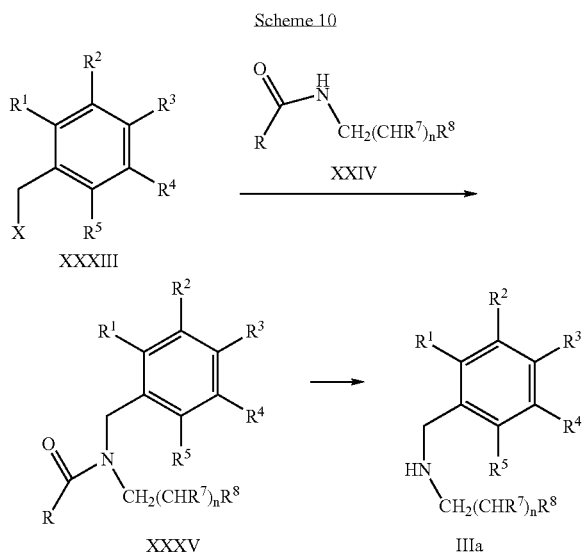

Amines of formula IIIa may also be prepared by alkylation of amide derivatives XXXIV with benzylic halides XXXIII (X=Cl, Br, I) and subsequent cleavage of the amide bond of the intermediates XXXV as described in scheme 10. For example, trifluoroacetamide derivatives XXXIV (R=CF$_3$) can be reacted with a base such as sodium hydride and then with a benzylic halide XXXIII in an inert solvent such as DMF to obtain compounds of formula XXXV (R=CF$_3$). A possible way to cleave the trifluoroacetyl group of the compounds of formula XXXV (R=CF$_3$) is the reaction with sodium borohydride in ethanol.

Scheme 11

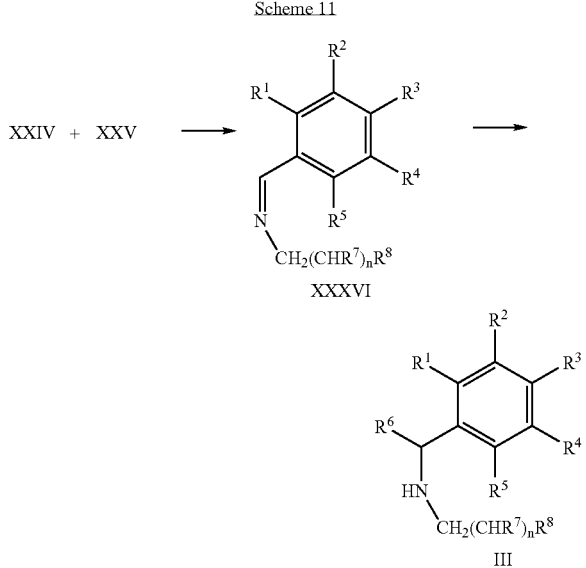

Secondary amines III may also be synthesized from imines XXXVI by the reaction with an alkyllithium reagent R$^6$Li (e.g. methyllithium) in the presence of a Lewis acid such as boron trifluoride ethyl etherate. Imines XXXVI are accessible from aldehydes XXIV and amines XXV by standard methods.

As described above, the compounds of formula I of the present invention can be used as medicaments for the treatment and/or prophylaxis of diseases which are mediated by CETP inhibitors. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use as medicament for the treatment and/or prevention of dyslipidemia is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prophylaxis of diseases which are mediated by CETP inhibitors. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In another embodiment, the invention relates to a method for the treatment and/or prophylaxis of diseases which are mediated by CETP inhibitors. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. A method for the treatment and/or prophylaxis of dyslipidemia is preferred.

The invention further relates to the use of compounds of formula I as defined above for the treatment and/or prophylaxis of diseases are mediated by CETP inhibitors. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the treatment and/or prophylaxis of dyslipidemia is preferred.

In addition, the invention relates to the use of compounds of formula I as defined above for the preparation of medicaments for the treatment and/or prophylaxis of diseases are mediated by CETP inhibitors. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the preparation of medicaments for the treatment and/or prophylaxis of dyslipidemia is preferred.

In addition, CETP inhibitors are useful in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

The invention therefore also relates to pharmaceutical compositions comprising a compound of formula I as defined above in combination with an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant, as well as a pharmaceutically acceptable carrier and/or adjuvant.

The invention further relates to the use of compounds of formula I as defined above in combination with an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant for the treatment and/or prophylaxis of diseases such as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia, as well as to the use of such a combination for the preparation of corresponding medicaments.

The compounds of formula I and their pharmaceutically acceptable salts and esters can be used as medicaments, e.g. in the form of pharmaceutical preparations for enteral, parenteral or topical administration. They can be administered, e.g., perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, e.g., lactose, corn starch or derivatives thereof, talc, stearic acid or its salts can be used as carrier materials for tablets, coated tablets, dragées and hard gelatine capsules. Suitable carrier materials for soft gelatine capsules are, e.g., vegetable oils, waxes, fats and semi-solid and liquid polyols (depending on the nature of the active ingredient no carriers are, however, required in the case of soft gelatine capsules). Suitable carrier materials for the production of solutions and syrups are, e.g., water, polyols, sucrose, invert sugar and the like. Suitable carrier materials for injection solutions are, e.g., water, alcohols, polyols, glycerol and vegetable oils. Suitable carrier materials for suppositories are, e.g., natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The following examples serve to illustrate the present invention in more detail. They are, however, not intended to limit its scope in any manner.

EXAMPLES

Abbreviations:

EtOAc=ethyl acetate, n-BuLi=n-butyllithium, DAST=(diethylamino)sulfur trifluoride, DCM=dichloromethane, DMF=N,N-dimethylformamide, dppp=1,3-bis(diphenylphosphino)propane, EDC=N-(3-dimethylaminopropyl)-N'-ethylcarbodiimide, eq.=equivalents, h=hour(s), DMSO=dimethyl sulfoxide, HPLC=high performance liquid chromatography, HCl=hydrochloric acid, HBTU=O-Benzotriazol-1-yl-N,N,N',N'-tetra-methyluronium hexafluorophosphate, HOBT=1-Hydroxybenzotriazole, LiMH$_4$=Lithium aluminum hydride, min=minute(s), NMP=N-Methyl-2-pyrrolidinone, Pd(Ph$_3$P)$_2$Cl$_2$=dichlorobis(triphenylphosphine)palladium(II), rt=room temperature, TBTU=O-Benzotriazol-1-yl-N,N,N',N'-tetramethylisouronium tetrafluoroborate, THF=tetrahydrofuran.

Preparation of Starting Compounds

Example S1

Preparation of (4-tert-butyl-benzyl)-(3-methyl-butyl)-amine 0.44 ml of 4-tert-butylbenzylamine (2.5 mmol) and 0.414 ml of 3-methylbutyraldehyde (3.75 mmol) were dissolved in 7.5 ml methanol at rt and then refluxed for 1.5 h. After cooling down to rt, 114 mg (3 mmol) of sodium borohydride were added and the reaction mixture was then refluxed for 1.5 h. After cooling down to rt, the reaction mixture was treated with 5 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:1) to give 458 mg light yellow oil (78%). MS (ISP) 234.3 (M+H)$^+$.

Example S2

Preparation of (4-tert-butyl-benzyl)-pent-4-enyl-amine 0.44 ml of 4-tert-butylbenzylamine (2.5 mmol) and 0.414 ml of pent-4-enal (3.75 mmol) were dissolved in 7.5 ml methanol at rt and then refluxed for 1.5 h. After cooling down to rt, 114 mg (3 mmol) of sodium borohydride were added and after stirring for 15 min at rt, the reaction mixture was then refluxed for 2¼ h. After cooling down to rt again 114 mg of sodium borohydride were added and the mixture was again refluxed for additional 1¼ h. After cooling down to rt, the reaction mixture was treated with 5 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:1) to give 172 mg light yellow oil (29%). MS (ISP) 232.3 (M+H)$^+$.

Example S3

Preparation of (4-tert-butyl-benzyl)-(4,4,4-trifluoro-butyl)-amine 0.097 ml of 4-tert-butylbenzylamine (0.55 mmol) and 110 mg 4,4,4-trifluoro-butyraldehyde (0.83 mmol) were dissolved in 2 ml methanol and stirred 30 min at rt and then refluxed for 2.5 h. After cooling down to rt, 25 mg (0.66 mmol) of sodium borohydride were added and after stirring for 5 min at rt, the reaction mixture was refluxed for 2¾ h. After cooling down to rt, the reaction mixture was treated with 1 drop 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (8 g silica gel; EtOAc/heptane 1:2) to give 110 mg colorless viscous oil (73%). MS (ISP) 274.2 (M+H)$^+$.

Example S4

Preparation of (4-tert-butyl-benzyl)-[2-(tetrahydro-thiopyran-4-yl)-ethyl]-amine 0.44 ml of 4-tert-butylbenzylamine (2.5 mmol) and 541 mg (tetrahydro-thiopyran-4-yl)-acetaldehyde (3.75 mmol) were dissolved in 7.5 ml methanol and stirred for 30 min at rt and then refluxed for 2.5 h. After cooling down to rt, 114 mg (3 mmol) of sodium borohydride were added and after stirring for 15 min at rt, the reaction mixture was refluxed for 2¾ h. After cooling down to rt, the reaction mixture was treated with 5 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (90 g silica gel; EtOAc/heptane 1:2 then EtOAc) to give 632 mg light yellow viscous oil (87%). MS (ISP) 292.3 (M+H)$^+$.

Example S5

Preparation of [rac]-(4-tert-butyl-benzyl)-[3-(5-methyl-furan-2-yl)-butyl]-amine 0.26 ml of 4-tert-butylbenzylamine (1.5 mmol) and 346 mg of [rac]-3-(5-methyl-furan-2-yl)-butyraldehyde (2.25 mmol) were dissolved in 4.5 ml methanol at rt, and after stirring for 30 min at rt, were refluxed for 2.5 h. After cooling down to rt, 68 mg (1.8 mmol) of sodium borohydride were added and after stirring for 15 min at rt, the reaction mixture was then refluxed for 2¼ h. After cooling down to rt again 68 mg of sodium borohydride were added and the mixture was again refluxed for additional 18 h. After cooling down to rt, the reaction mixture was treated with 3 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 328 mg light yellow oil (73%). MS (ISP) 300.4 (M+H)$^+$.

Example S6

Preparation of (4-tert-butyl-benzyl)-[2-(4-fluoro-phenyl)-ethyl]-amine and (4-tert-butyl-benzyl)-(2-thiophen-2-yl-ethyl)-amine 0.38 ml of 4-tert-butylbenzaldehyde (2.25 mmol) and 0.200 ml 2-(4-fluoro-phenyl)-ethyl-amine (1.5 mmol) were dissolved in 4.5 ml methanol and after stirring for 30 min at rt, were refluxed for 4 h. After cooling down to rt, 85 mg (2.25 mmol) sodium borohydride were added and after stirring for 5 min at rt, the reaction mixture was then refluxed for 2 h. After cooling down to rt, the reaction mixture was treated with 4 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 450 mg colorless viscous oil (100%). MS (ISP) 286.2 (M+H)$^+$.

(4-tert-butyl-benzyl)-(2-thiophen-2-yl-ethyl)-amine was prepared in analogy to the above procedure starting from 4-tert-butylbenzaldehyde and (2-thiophen-2-yl-ethyl)-amine.

Example S7

Preparation of (4-tert-butyl-benzyl)-[2-(4-methoxy-phenyl)-ethyl]-amine 0.39 ml of 4-tert-butylbenzaldehyde (2.25 mmol) and 0.230 ml 2-(4-methoxy-phenyl)-ethylamine (1.5 mmol) were dissolved in 4.5 ml methanol and after stirring for 30 min at rt, were refluxed for 2.5 h. After cooling down to rt, 85 mg (2.25 mmol) sodium borohydride were added and after stirring for 5 min at rt, the reaction mixture was then refluxed for 2.5 h. After cooling down to rt, the reaction mixture was treated with 4 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:1) to give 430 mg colorless viscous oil (96%). MS (ISP) 298.4 (M+H)$^+$.

Example S8

Preparation of (4-tert-butyl-benzyl)-(2-p-tolyl-ethyl)-amine 0.39 ml of 4-tert-butylbenzaldehyde (2.25 mmol) and 0.22 ml 2-p-tolyl-ethylamine (1.5 mmol) were dissolved in 4.5 ml methanol and after stirring for 30 min at rt, were refluxed for 2.5 h. After cooling down to rt, 85 mg (2.25 mmol) sodium borohydride were added and after stirring for 5 min at rt, the reaction mixture was then refluxed for 2.5 h. After cooling down to rt, the reaction mixture was treated with 4 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:1) to give 480 mg light yellow viscous oil (100%). MS (ISP) 282.2 (M+H)$^+$.

Example S9

Preparation of 5-bromo-1H-indole-7-carboxylic acid 371 mg of 2-amino-5-bromo-benzoic acid methyl ester (2 mmol) was dissolved in 2 ml conc acetic acid and treated with 495 mg of N-iodosuccinimide (2.2 mmol) at rt for 17 h. The reaction mixture was then poured on 5 ml saturated sodium bicarbonate solution and ice, extracted twice with EtOAc. The combined organic phases were then washed with brine, dried over magnesium sulfate, filtered and concentrated in vacuo, leading to 585 mg 2-amino-5-bromo-3-iodo-benzoic acid methyl ester (82%) as a light brown solid. MS (EI) 354.9 (M)$^+$.

580 mg of 2-amino-5-bromo-3-iodo-benzoic acid methyl ester were dissolved in 6 ml triethylamine. 65 mg of Pd(PPh$_3$)Cl$_2$ (0.09 mmol), 18 mg of CuI (0.09 mmol) and 0.285 ml of ethinyltrimethylsilane (2.05 mmol) were added and the mixture was stirred at rt under argon for 1.5 h. The reaction mixture was then diluted with DCM and extracted twice with water followed by brine. The organic phase was finally dried over magnesium sulfate, filtered and concentrated in vacuo, leading to 574 mg of 2-amino-5-bromo-3-trimethylsilanylethynyl-benzoic acid methyl ester as a brown powder (100%). MS (EI) 325 (M)$^+$.

550 mg (ca 1.58 mmol) of 2-amino-5-bromo-3-trimethylsilanylethynyl-benzoic acid methyl ester were dissolved in 5 ml NMP and added dropwise at 0° C. to a solution of 371 mg of potassium tert-butylate (3.31 mmol) in 5 ml NMP. After 1 h stirring at 0° C., the reaction mixture was stirred 1.5 h at rt. The reaction mixture was then treated with 20 ml water and extracted twice with diethylether. The combined organic phases were washed with brine and dried over magnesium sulfate, filtered and concentrated in vacuo. The residue was purified by column chromatography (40 g silicagel, heptane/EtOAc 100:0 the 90:10) leading to 99 mg 5-bromo-1H-indole-7-carboxylic acid methyl ester as a light brown solid (25%). MS (EI) 253.1 (M)$^+$.

409 mg of 5-bromo-1H-indole-7-carboxylic acid methyl ester (1.61 mmol) were suspended in a mixture of 1.6 ml 2N NaOH and 1.6 ml ethanol and stirred at 40° C. for 2 h. After cooling down, the mixture was treated with 2N aqueous HCl, and extracted twice with EtOAc. The organic phase was the washed with brine, dried over magnesium sulfate, filtered and concentrated in vacuo, leading to 353 mg of 5-bromo-1H-indole-7-carboxylic acid as a light brown solid (85%). MS (ISP) 237.9 (M−H)$^-$.

Example S10

Preparation of (4-tert-butyl-benzyl)-[2-(3-fluoro-phenyl)-ethyl]-amine 0.38 ml of 4-tert-butylbenzaldehyde (2.25 mmol) and 0.20 ml 2-(3-fluoro-phenyl)-ethyl-amine (1.5 mmol) were dissolved in 4.5 ml methanol at rt, and after stirring for 30 min at rt, were refluxed for 2 h. After cooling down to rt, 85 mg (2.25 mmol) sodium borohydride were added and after stirring for 5 min at rt, the reaction mixture was then refluxed for 3 h. After cooling down to rt, the reaction mixture was treated with 4 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 2:1) to give 478 mg colorless viscous oil (100%). MS (ISP) 286.2 (M+H)$^+$.

Example S11

Preparation of [2-(3-benzyloxy-phenyl)-ethyl]-(4-tert-butyl-benzyl)-amine 8.49 g of 3-benzyloxy-benzaldehyde (40 mmol) and 7.3 g ammonium acetate (92 mmol) were dissolved in 70 ml acetic acid and treated with 6.2 ml nitromethane (114 mmol). The mixture was refluxed for 2 h and after cooling down to rt, diluted with 70 ml water, leading to the formation of a precipitate. The mixture was extracted 3 times with DCM and the organic phases were then washed twice with water, once with brine and dried over magnesium sulfate. After filtration the solvent was removed in vacuo. The solid residue was stirred with 200 ml heptane for 30 min, filtered off, washed with heptane and dried in high vacuo, leading to 9 g 1-benzyloxy-3-(2-nitro-vinyl)-benzene (88%) as a green solid. MS (EI) 255.2 (M)$^+$.

1.62 g lithium borohydride (70.5 mmol) were suspended under stirring in 30 ml THF and treated dropwise with 18 ml trimethylchlorosilane (141 mmol). After 5 min stirring at rt, a solution of 4.5 g 1-benzyloxy-3-(2-nitro-vinyl)-benzene (17.63 mmol) in 20 ml THF was added dropwise over a period of 30 min (Due to exothermic reaction the reaction is cooled with a water bath). The reaction mixture was subsequently stirred at rt for additional 72 h at rt. Under cooling with cold water, the reaction mixture was then treated with 60 ml methanol during 1 h. After evaporation of the solvent in vacuo, the residue was dissolved in DCM/1 N HCl the precipitate was removed by filtration. The solid was dissolved in EtOAc, treated with aqueous sodium bicarbonate and the organic phase separated. The aqueous phase was extracted with EtOAc and the combined organic phases washed with water and brine, dried over magnesium sulfate, filtered and concentrated in vacuo. The oily residue was dissolved in 100 ml diethylether and treated with 3 N HCl in diethylether. The suspension was stirred for 30 min and filtered. The resulting solid was dried in high vacuo, leading to 1.7 g 2-(3-benzyloxy-phenyl)-ethylamine hydrochloride as a white solid. MS (ISP) 228.2 (M+H)+.

1.52 ml of 4-tert-butylbenzaldehyde (9.1 mmol) and 1.6 g 2-(3-benzyloxy-phenyl)-ethylamine hydrochloride (6.07 mmol) and 838 mg potassium carbonate (6.07 mmol) were suspended in 18 ml methanol at rt, and after stirring for 30 min at rt, were refluxed for 2 h. After cooling down to rt, 344 mg (9.1 mmol) sodium borohydride were added and after stirring for 5 min at rt, the reaction mixture was then refluxed for 2.5 h. After cooling down to rt, the reaction mixture was treated with 2 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:1) to give 2.13 g [2-(3-benzyloxy-phenyl)-ethyl]-(4-tert-butyl-benzyl)-amine as a light yellow viscous oil (94%). MS (ISP) 374.5 (M+H)+.

Example S12

Preparation of (4-tert-butyl-benzyl)-[2-(2-fluoro-phenyl)-ethyl]-amine 0.38 ml of 4-tert-butylbenzaldehyde (2.25 mmol) and 0.200 ml 2-(2-fluoro-phenyl)-ethyl-amine (1.5 mmol) were dissolved in 4.5 ml methanol at rt, and after stirring for 30 min at rt, were refluxed for 2.5 h. After cooling down to rt, 85 mg (2.25 mmol) sodium borohydride were added and after stirring for 5 min at rt, the reaction mixture was then refluxed for 3 h. After cooling down to rt, the reaction mixture was treated with 4 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 280 mg light yellow oil (65%). MS (ISP) 286.2 (M+H)+.

Example S13

Preparation of (4-tert-butyl-benzyl)-[2-(4-chloro-phenyl)-ethyl]-amine 0.38 ml of 4-tert-butylbenzaldehyde (2.25 mmol) and 0.200 ml 2-(4-chloro-phenyl)-ethylamine (1.5 mmol) were dissolved in 4.5 ml methanol at rt, and after stirring for 30 min at rt, were refluxed for 2.5 h. After cooling down to rt, 85 mg (2.25 mmol) sodium borohydride were added and after stirring for 5 min at rt, the reaction mixture was then refluxed for 2 h. After cooling down to rt, the reaction mixture was treated with 4 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 437 mg light yellow oil (96%). MS (ISP) 302.3 (M+H)+.

Example S14

Preparation of 1-(4-{[2-(3-trifluoromethyl-phenyl)-ethylamino]-methyl}-phenyl)-cyclopropanecarbonitrile 303 mg (3 mmol) of triethyl amine were added at 0° C. under nitrogen to 386 mg (2 mmol) of 2-(3-trifluoromethylphenyl)ethyl amine dissolved in 15 ml DCM. Then a solution of 525 mg (2.5 mmol) of trifluoro acetic acid anhydride in 5 ml DCM was added dropwise within 5 min. The reaction mixture was stirred at 0° C. for 30 min than for 3 h at rt. The solution was diluted with DCM, washed twice with water, dried over sodium sulfate, filtered and the solvent was evaporated to yield 620 mg (98%) of 2,2,2-trifluoro-N-[2-(3-trifluoromethyl-phenyl)-ethyl]-acetamide as the product contaminated with 10% diacetylated byproduct as a light yellow solid. $^{1H}$ NMR (DMSO-$d_6$, 300 MHz): δ 9.48 (br m, 1H), 7.68-7.43 (m, 4H), 3.46 (q, 2H), 2.91 (t, 2H).

20 mg (0.51 mmol) of a sodium hydride suspension in mineral oil (60%) were suspended in 4.2 ml DMF. At 0° C. 134 mg (0.42 mmol) of 2,2,2-trifluoro-N-[2-(3-trifluoromethyl-phenyl)-ethyl]-acetamide dissolved in 1 ml DMF were added dropwise and the reaction mixture was stirred for 30 min at 0° C. Then 100 mg (0.42 mmol) of 1-(4-bromomethyl-phenyl)-cyclopropanecarbonitrile dissolved in 1 ml DMF were added and the reaction mixture was stirred at 0° C. for 3 h. Water was added and the mixture was extracted twice with EtOAc. The combined organic layers were washed with saturated aqueous sodium chloride solution, dried over sodium sulfate, filtered and the solvent was evaporated. The residue was purified by column chromatography (45 g silica gel; heptane/diethyl ether=1:1) to yield 135 mg (72%) of N-[4-(1-cyano-cyclopropyl)-benzyl]-2,2,2-trifluoro-N-[2-(3-trifluoromethyl-phenyl)-ethyl]-acetamide as a yellow viscous oil. MS (ISP) 458.4 (M+NH$_4$)+. MS (ISP). 499.1 (M+OAc)−.

46 mg (1.23 mmol) of sodium borohydride were added to 135 mg (0.31 mg) of N-[4-(1-cyano-cyclopropyl)-benzyl]-2,2,2-trifluoro-N-[2-(3-trifluoromethyl-phenyl)-ethyl]-acetamide dissolved in 3.1 ml ethanol under nitrogen. The reaction mixture was stirred at rt for 3 h. Under ice bath cooling water was added and the reaction mixture was extracted twice with EtOAc. The combined organic layers were washed with saturated aqueous sodium chloride solution, dried over sodium sulfate, filtered and the solvent was evaporated. The residue was purified by column chromatography (25 g silica gel; methylene chloride/methanol=19:1) to yield 81 mg (77%) of 1-(4-{[2-(3-trifluoromethyl-phenyl)-ethylamino]-methyl}-phenyl)-cyclopropanecarbonitrile as a colorless oil. $^{1H}$NMR (DMSO-$d_6$, 300 MHz): δ 7.61-7.47 (m, 4H), 7.30 (d, 2H), 7.24 (d, 2H), 3.69 (s, 2H), 2.81 (t, 2H), 2.73 (t, 2H), 1.72 (m, 2H), 1.44 (m, 2H).

Example S15

Preparation of (4-tert-butyl-benzyl)-[2-(3-chloro-phenyl)-ethyl]-amine 0.38 ml of 4-tert-butylbenzaldehyde (2.25 mmol) and 0.215 ml 2-(3-chloro-phenyl)-ethylamine (1.5 mmol) were dissolved in 4.5 ml methanol at rt, and after stirring for 30 min at rt, were refluxed for 2.5 h. After cooling down to rt, 85 mg (2.25 mmol) sodium borohydride were added and after stirring for 5 min at rt, the reaction mixture was then refluxed for 4 h. After cooling down to rt, the reaction mixture was treated with 4 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 465 mg light yellow oil (100%). MS (ISP) 302.3 (M+H)$^+$.

Example S16

Preparation of (4-tert-butyl-benzyl)-[2-(3-trifluoromethyl-phenyl)-ethyl]-amine, (4-tert-butyl-benzyl)-[2-(2-trifluoromethyl-phenyl)-ethyl]-amine; hydrochloride and (4-trifluoromethoxy-benzyl)-[2-(3-trifluoromethyl-phenyl)-ethyl]-amine 0.38 ml of 4-tert-butylbenzaldehyde (2.25 mmol) and 0.24 ml 2-(3-trifluoromethyl-phenyl)-ethylamine (1.5 mmol) were dissolved in 4.5 ml methanol at rt, and after stirring for 30 min at rt, were refluxed for 4 h. After cooling down to rt, 85 mg (2.25 mmol) sodium borohydride were added and after stirring for 5 min at rt, the reaction mixture was then refluxed for 4 h. After cooling down to rt, the reaction mixture was treated with 4 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 450 mg colorless viscous oil (89%). MS (ISP) 336.3 (M+H)$^+$.

(4-tert-butyl-benzyl)-[2-(2-trifluoromethyl-phenyl)-ethyl]-amine; hydrochloride was synthesized in analogy to the above procedure using 7.463 g 4-tert-butylbenzaldehyde (45.54 mmol) and 7.463 g of 2-(2-trifluoromethyl-phenyl)-ethylamine (30.36 mmol) and 1.776 g of sodium borohydride (45.54 mmol). The hydrochloride was formed in DCM and crystallized from a mixture of ethanol and DCM, leading to 4.8 g white crystals (42.3%). MS (ISP) 336.3 (M+H)$^+$.

(4-trifluoromethoxy-benzyl)-[2-(3-trifluoromethyl-phenyl)-ethyl]-amine was synthesized in analogy to the above procedure using 1.232 g 4-(trifluoromethoxy)benzaldehyde (6.48 mmol) and 0.817 g 2-(3-trifluoromethyl-phenyl)-ethylamine (4.32 mmol), 1.31 g (83%) of a light yellow liquid were obtained. MS: 364 (M+H)$^+$.

Example S17

Preparation of (4-tert-butyl-benzyl)-[2-(2-chlorophenyl)-ethyl]-amine 0.38 ml of 4-tert-butylbenzaldehyde (2.25 mmol) and 0.215 ml 2-(2-chloro-phenyl)-ethylamine (1.5 mmol) were dissolved in 4.5 ml methanol at rt, and after stirring for 30 min at rt, were refluxed for 2.5 h. After cooling down to rt, 85 mg (2.25 mmol) sodium borohydride were added and after stirring for 5 min at rt, the reaction mixture was then refluxed for 3 h. After cooling down to rt, the reaction mixture was treated with 4 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 465 mg light yellow oil (97%). MS (ISP) 302.3 (M+H)$^+$.

Example S18

Preparation of (4-tert-butyl-benzyl)-[2-(3,4-dichloro-phenyl)-ethyl]-amine 0.38 ml of 4-tert-butylbenzaldehyde (2.25 mmol) and 0.227 ml 2-(3,4-dichloro-phenyl)-ethylamine (1.5 mmol) were dissolved in 4.5 ml methanol at rt, and after stirring for 30 min at rt, were refluxed for 2 h. After cooling down to rt, 85 mg (2.25 mmol) sodium borohydride were added and after stirring for 5 min at rt, the reaction mixture was then refluxed for 2 h. After cooling down to rt, the reaction mixture was treated with 4 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 515 mg colorless viscous oil (97%). MS (ISP) 336.2 (M+H)$^+$.

Example S19

Preparation of (4-tert-butyl-benzyl)-[2-(2,6-dichloro-phenyl)-ethyl]-amine 0.38 ml of 4-tert-butylbenzaldehyde (2.25 mmol) and 288 mg 2-(2,6-dichloro-phenyl)-ethylamine (1.5 mmol) were dissolved in 4.5 ml methanol at rt, and after stirring for 30 min at rt, were refluxed for 2 h. After cooling down to rt, 85 mg (2.25 mmol) sodium borohydride were added and after stirring for 5 min at rt, the reaction mixture was then refluxed for 3 h. After cooling down to rt, the reaction mixture was treated with 4 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 533 mg colorless viscous oil (95%). MS (ISP) 336.2 (M+H)$^+$.

Example S20

Preparation of (4-tert-butyl-benzyl)-[2-(3,5-difluoro-phenyl)-ethyl]-amine 0.67 ml of 4-tert-butylbenzaldehyde (3.87 mmol) and 500 mg 2-(3,5-difluoro-phenyl)-ethylamine (2.58 mmol) were dissolved in 7.5 ml methanol at rt, and after stirring for 30 min at rt, were refluxed for 4 h. After cooling down to rt, 147 mg (3.87 mmol) sodium borohydride were added and after stirring for 5 min at rt, the reaction mixture was then refluxed for 2.5 h. After cooling down to rt, the reaction mixture was treated with 10 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 653 mg light yellow oil (83%). MS (ISP) 304.2 (M+H)$^+$.

Example S21

Preparation of (4-tert-butyl-benzyl)-[2-(4-trifluoromethyl-phenyl)-ethyl]-amine 0.67 ml of 4-tert-butylbenzaldehyde (3.99 mmol) and 600 mg 2-(4-trifluoromethyl-phenyl)-ethylamine (2.66 mmol) were dissolved in 9 ml methanol at rt, and after stirring for 30 min at rt, were refluxed for 2.5 h. After cooling down to rt, 151 mg (3.99 mmol) sodium borohydride were added and after stirring for 5 min at rt, the reaction mixture was then refluxed for 3 h. After cooling down to rt, the reaction mixture was treated with 1 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 2:1) to give 673 mg dark red oil (75%). MS (ISP) 336.2 (M+H)$^+$.

Example S22

Preparation of (4-tert-butyl-benzyl)-[2-(3,4-difluoro-phenyl)-ethyl]-amine 1.3 ml of 4-tert-butylbenzaldehyde (7.75 mmol) and 1 g of 2-(3,4-difluoro-phenyl)-ethyl-amine hydrochloride (5.16 mmol) and 714 mg of potassium carbonate (5.16 mmol) were suspended in 15 ml methanol at rt, and after stirring for 30 min at rt, were refluxed for 2 h. After cooling down to rt, 293 mg (7.75 mmol) sodium borohydride were added and after stirring for 5 min at rt, the reaction mixture was then refluxed for 4 h. After cooling down to rt, the reaction mixture was treated with 1 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:4) to give 584 mg yellow oil (37%). MS (ISP) 304.2 (M+H)$^+$.

Example S23

Preparation of 2-(3,4-difluoro-phenyl)-ethylamine hydrochloride

To 3.71 g of LiAlH$_4$ (98 mmol) in 30 ml of dry diethyl-ether were added dropwise at 0° C. under nitrogen 5 g of 3,4-difluoroacetonitrile (33 mmol) in 30 ml THF. After the addition and additional 15 min of stirring at 0° C., the ice bath was removed and the reaction was allowed to warm to ambient temperature. The flask was then immersed in an oil bath, heated to 55° C. and the reaction was refluxed overnight. The oil bath was then removed and the reaction mixture cooled to 0° C. The LiAlH$_4$ was then quenched by the slow and sequential addition of saturated aqueous sodium sulfate solution. After the initial exothermic reaction had subsided, the flask was allowed to warm to ambient temperature and further sodium sulfate solution was added until the color was light grey. Then more solid sodium sulfate (dry) was added to dry the mixture, which was subsequently filtered through a short bed of sodium sulfate in a sinter funnel. To the filtrate was added a 5 N HCl solution in dioxane. The HCl-salt precipitated out and was filtered. The collected yellow solid (4.2 g; 82% yield) was found to be of good purity by NMR and was taken into the next step without further purification. MS (ISP) 158.1 (M+H)$^+$.

Example S24

Preparation of (4-tert-butyl-benzyl)-phenethyl-amine 0.65 ml of 4-tert-butylbenzaldehyde (3.7 mmol) and 0.32 ml of phenethylamine (2.5 mmol) were dissolved in 7.5 ml methanol at rt, and after stirring for 30 min at rt, were refluxed for 2¼ h. After cooling down to rt, 142 mg (3.7 mmol) of sodium borohydride were added and after stirring for 15 min at rt, the reaction mixture was then refluxed for 3.5 h. After cooling down to rt, the reaction mixture was treated with 6 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 609 mg of colorless oil (91%). MS (ISP) 268.3 (M+H)$^+$.

Example S25

Preparation of (4-tert-butyl-benzyl)-[2-(3-fluoro-4-trifluoromethyl-phenyl)-ethyl]-amine 1 ml of 4-tert-butylbenzaldehyde (6.16 mmol), 1 g of 2-(3-fluoro-4-trifluoromethyl-phenyl)-ethylamine hydrochloride (4.1 mmol) and 567 mg of potassium carbonate (4.1 mmol) were suspended in 12 ml methanol at rt, and after stirring for 30 min at rt, were refluxed for 3.5 h. After cooling down to rt, 233 mg (6.16 mmol) sodium borohydride were added and after stirring for 5 min at rt, the reaction mixture was then refluxed for 2.5 h. After cooling down to rt, the reaction mixture was treated with 0.8 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:6 then 1:4) to give 1.156 g light yellow oil (79%). MS (ISP) 354.3 (M+H)$^+$.

Example S26

Preparation of 2-(3-fluoro-4-trifluoromethyl-phenyl)-ethylamine hydrochloride 3 g of (3-fluoro-4-trifluoromethyl-phenyl)-acetonitrile (14.5 mmol) were dissolved in 23 ml THF and cooled down to 0° C. under nitrogen. 77 ml of a 1M borane-THF complex solution in THF were then added dropwise over 35 min by keeping the temperature between 0-2° C. After addition the reaction mixture was stirred at rt for additional 45 min, and refluxed for 21 h. The reaction mixture was then cooled down to 0° C. and treated between 2 and 5° C. with 17 ml methanol over a period of 30 min. After 1 h refluxing the reaction mixture was concentrated, the residue dissolved in DCM and the amine extracted twice with 1N aqueous HCl. The combined aqueous phases were then treated with concentrated NaOH to adjust the pH to 12, and then extracted twice with DCM. The combined organic phases were then washed with water, dried over magnesium sulfate, filtered and concentrated in vacuo leading to 2.1 g yellow oily residue. This was dissolved in 50 ml diethylether, treated with 5 ml 2.6N HCl in diethylether, stirred at rt for additional 15 min, evaporated to dryness and dried under vacuo, leading to 2.34 g white solid (66%). MS (ISP) 208.2 $(M+H)^+$.

Example S27

Preparation of (4-tert-butyl-benzyl)-[2-(3-trifluoromethoxy-phenyl)-ethyl]-amine and (4-cyclopropyl-benzyl)-[2-(3-trifluoromethoxy-phenyl)-ethyl]-amine 1.04 ml of 4-tert-butylbenzaldehyde (6.21 mmol), 1 g of 2-(3-trifluoromethoxy-phenyl)-ethylamine hydrochloride (4.1 mmol) and 572 mg of potassium carbonate (4.1 mmol) were suspended in 12 ml methanol at rt, and after stirring for 30 min at rt, were refluxed for 2 h. After cooling down to rt, 235 mg (6.21 mmol) of sodium borohydride were added and after stirring for 5 min at rt, the reaction mixture was then refluxed for 3 h. After cooling down to rt, the reaction mixture was treated with 0.8 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (90 g silica gel; EtOAc/heptane 1:4 then 1:2) to give 1.33 g light yellow oil (91%). MS (ISP) 352.3 $(M+H)^+$.

(4-cyclopropyl-benzyl)-[2-(3-trifluoromethoxy-phenyl)-ethyl]-amine was synthesized in analogy to the above procedure starting from 1.45 g 2-(3-trifluoromethoxy-phenyl) ethylamine hydrochloride (6 mmol) and 1.316 g 4-cyclopropyl-benzaldehyde (9 mmol) leading to 1.65 g (82%) product as a light yellow oil. MS (ISP) 336.5 $(M+H)^+$.

Example S28

Preparation of 2-(3-trifluoromethoxy-phenyl)-ethylamine hydrochloride 3 g of (3-trifluoromethoxy-phenyl)-acetonitrile (14.9 mmol) were dissolved in 24 ml THF and cooled down to 0° C. under nitrogen. 79 ml borane-THF complex 1M were then added dropwise over 20 min by keeping the temperature between 0-2° C. After addition the reaction mixture was stirred at rt for additional 45 min and then refluxed for 17 h. The reaction mixture was then cooled down to 0° C. and treated between 2 and 5° C. with 18 ml methanol over a period of 30 min. After 1 h refluxing the reaction mixture was concentrated, the residue dissolved in DCM and the amine extracted twice with 1N aqueous HCl. The combined aqueous phases were then treated with concentrated NaOH to adjust the pH to 12, and then extracted twice with DCM. The combined organic phases were then washed with water, dried over magnesium sulfate, filtered and concentrated in vacuo leading to 2.1 g yellow oily residue. This was dissolved in 50 ml diethylether, treated with 5 ml 2.6N HCl in diethylether, stirred at rt for additional 1 h, filtered off, washed with diethylether and dried under high vacuo, leading to 2.25 g white solid (62%). MS (ISP) 206.2 $(M+H)^+$.

Example S29

Preparation of (4-tert-butyl-benzyl)-[2-(4-fluoro-3-trifluoromethyl-phenyl)-ethyl]-amine 0.62 ml of 4-tert-butylbenzaldehyde (3.69 mmol), 600 mg of 2-(4-fluoro-3-trifluoromethyl-phenyl)-ethylamine hydrochloride (2.46 mmol) and 340 mg of potassium carbonate (2.46 mmol) were suspended in 7 ml methanol at rt, and after stirring for 30 min at rt, were refluxed for 2 h. After cooling down to rt, 140 mg (3.69 mmol) of sodium borohydride were added and after stirring for 5 min at rt, the reaction mixture was then refluxed for 3 h. After cooling down to rt, the reaction mixture was treated with 0.5 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:4 then 1:2) to give 784 mg light yellow oil (90%). MS (ISP) 354.3 $(M+H)^+$.

Example S30

Preparation of 2-(4-fluoro-3-trifluoromethyl-phenyl)-ethylamine hydrochloride

To 1.61 g of $LiAlH_4$ (42.45 mmol) in 20 ml of dry diethylether were added dropwise at 0-5° C. under nitrogen 4 g of (4-fluoro-3-trifluoromethyl-phenyl)-acetonitrile (19.3 mmol) in 20 ml THF over 35 min. After addition the ice bad was removed and the reaction was allowed to warm to ambient temperature. The flask was then immersed in an oil bath, heated to 60° C. and the reaction was refluxed overnight. The oil bath was then removed and the reaction mixture cooled to 0° C. The $LiAlH_4$ was then quenched by the slow and sequential addition of saturated aqueous sodium sulfate solution. After the initial exothermic reaction had subsided, the flask was allowed to warm to ambient temperature and solid magnesium sulfate (dry) was added to dry the suspension, which was subsequently filtered and washed with diethylether. After removal of the solvent, the residue was dissolved in 50 ml diethylether, treated with 8 ml 2.6N HCl in diethylether, and evaporated to dryness, leading to a solid orange foam. This residue was dissolved in 200 ml DCM, and treated with 100 ml water, followed by 50 ml 1N aqueous HCl, and stirred for 15 min. After this time the DCM was separated and extracted a second time with 50 ml 1N HCl. The combined aqueous phases were then washed with 50 ml DCM, treated with concentrated NaOH to adjust the pH to 12, and extracted twice with DCM. The organic phases were combined, washed with water and dried over magnesium sulfate. After filtration and evaporation of the solvent, the residue was dissolved in 5 ml diethylether, treated with 2 ml 2.6N HCl in diethylether, and stirred for 10 min. The precipitated HCl-salt was filtered and dried under high-vacuo leading to 632 mg white solid (13%). MS (ISP) 208.2 $(M+H)^+$.

Example S31

Preparation of (4-tert-butyl-benzyl)-[2-(2-fluoro-3-trifluoromethyl-phenyl)-ethyl]-amine 1 ml of 4-tert-butylbenzaldehyde (6.16 mmol), 1 g of 2-(2-fluoro-3-trifluoromethyl-phenyl)-ethylamine hydrochloride (4.1 mmol) and 567 mg of potassium carbonate (4.1 mmol) were suspended in 12 ml methanol at rt, and after stirring for 30 min at rt, were refluxed for 2.5 h. After cooling down to rt, 233 mg (6.16 mmol) of sodium borohydride were added and after stirring for 5 min at rt, the reaction mixture was then refluxed for 2.5 h. After cooling down to rt, the reaction mixture was treated with 1 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:4) to give 1.09 g yellow oil (75%). MS (ISP) 354.3 (M+H)$^+$.

Example S32

Preparation of 2-(2-fluoro-3-trifluoromethyl-phenyl)-ethylamine hydrochloride

To 2.8 g of LiAlH$_4$ (74 mmol) in 30 ml of dry diethylether were added dropwise at 0° C. under nitrogen 5 g of (2-fluoro-3-trifluoromethyl-phenyl)-acetonitrile (25 mmol) in 30 ml THF. After addition and additional 15 min stirring at 0° C., the ice bad was removed and the reaction was allowed to warm to ambient temperature. The flask was then immersed in an oil bath, heated to 55° C. and the reaction was refluxed overnight. The oil bath was then removed and the reaction mixture cooled to 0° C. The LiAlH$_4$ was then quenched by the slow and sequential addition of saturated aqueous sodium sulfate solution. After the initial exothermic reaction had subsided, the flask was allowed to warm to ambient temperature and further sodium sulfate solution was added until the color was light grey. Then more solid sodium sulfate (dry) was added to dry the mixture, which was subsequently filtered through a short bed of sodium sulfate in a sinter funnel. To the filtrate was added 5 N HCl solution in dioxane. The HCl-salt precipitated out and was filtered. The collected off-white solid (3.0 g; 59% yield) was found to be of good purity by NMR and was taken into the next reaction without further purification. MS (ISP) 208.1 (M+H)$^+$.

Example S33

Preparation of (4-tert-butyl-benzyl)-[2-(4-difluoromethoxy-phenyl)-ethyl]-amine 1.12 ml of 4-tert-butylbenzaldehyde (6.71 mmol), 1 g of 2-(4-difluoromethoxy-phenyl)-ethylamine hydrochloride (4.47 mmol) and 618 mg of potassium carbonate (4.47 mmol) were suspended in 13 ml methanol at rt, and after stirring for 30 min at rt, were refluxed for 2 h. After cooling down to rt, 254 mg (6.71 mmol) sodium borohydride were added and after stirring for 5 min at rt, the reaction mixture was then refluxed for 2.5 h. After cooling down to rt, the reaction mixture was treated with 1.2 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:4) to give 1.19 g light yellow oil (80%). MS (ISP) 334.3 (M+H)$^+$.

Example S34

Preparation of 2-(4-difluoromethoxy-phenyl)-ethylamine hydrochloride 2 g of (4-difluoromethoxy-phenyl)-acetonitrile (10.9 mmol) were dissolved in 18 ml THF and cooled down to 0° C. under nitrogen. 58 ml borane-THF complex 1M were then added dropwise over 30 min by keeping the temperature between 0-2° C. After addition the reaction mixture was stirred at rt for additional 15 min, and refluxed for 21 h. The reaction mixture was then cooled down to 0° C. and treated between 2 and 5° C. with 13 ml methanol over a period of 25 min. After 1 h refluxing the reaction mixture was concentrated, the residue dissolved in DCM and the amine extracted twice with 1N aqueous HCl. The combined aqueous phases are then treated with concentrated NaOH to adjust the pH to 12, and then extracted twice with DCM. The combined organic phases were then washed with water, dried over magnesium sulfate, filtered and concentrated in vacuo leading to 2.1 g yellow oily residue. This was dissolved in 45 ml diethylether, treated with 4 ml 2.6N HCl in diethylether, stirred at rt for additional 1 h, filtered, washed with diethylether and dried under high vacuo, leading to 1.42 g white solid (58%). MS (ISP) 188.3 (M+H)$^+$.

Example S35

Preparation of (4-tert-butyl-benzyl)-[(R)-2-(4-chloro-phenyl)-2-hydroxy-ethyl]-amine and [(R)-2-(4-chloro-phenyl)-2-hydroxy-ethyl]-(4-cyclopropyl-benzyl)-amine 1.2 ml of 4-tert-butylbenzaldehyde (7.21 mmol), 1 g of (R)-2-(4-chloro-phenyl)-2-hydroxy-ethylamine hydrochloride (4.81 mmol) and 664 mg of potassium carbonate (4.81 mmol) were suspended in 14 ml methanol at rt, and after stirring for 30 min at rt, were refluxed for 2 h. After cooling down to rt, 273 mg (7.21 mmol) of sodium borohydride were added and after stirring for 5 min at rt, the reaction mixture was then refluxed for 2.5 h. After cooling down to rt, the reaction mixture was treated with 1.2 ml 1 N HCl and concentrated in vacuo. The residue was diluted with water/EtOAc, and saturated with sodium chloride (solid). After separation of the organic phase, the aqueous phase was extracted three times with EtOAc and the combined organic phases were washed with brine, dried with magnesium sulfate, filtered off and concentrated in vacuo. The residue was treated with 80 ml diethylether/heptane 1:1, stirred 15 min and filtered, leading to 345 mg white solid (22%). MS (ISP) 318.2 (M+H)$^+$.

[(R)-2-(4-chloro-phenyl)-2-hydroxy-ethyl]-(4-cyclopropyl-benzyl)-amine was synthesized in analogy to the above procedure starting from 1.15 g 4-cyclopropyl-benzaldehyd (7.21 mmol) and 1 g (R)-2-(4-chloro-phenyl)-2-hydroxy-ethylamine hydrochloride leading to 1.28 g (88%) product as a white solid. MS (ISP) 302.2 (M+H)$^+$.

Example S36

Preparation of (R)-2-(4-chloro-phenyl)-2-hydroxy-ethylamine hydrochloride 1.9 g of (R)-(+)-4-chloromandelonitrile (11 mmol) were dissolved in 18 ml THF and cooled down to 0° C. under nitrogen. 58 ml of a 1M borane-THF complex solution in THF were then added dropwise over 30 min, keeping the temperature between 0-2° C. After addition the reaction mixture was stirred at rt for additional 45 min and then refluxed for 16 h. The reaction mixture is then cooled down to 0° C. and treated between 2 and 5° C. with 13 ml methanol over a period of 35 min. After 1 h refluxing the reaction mixture is concentrated, the residue dissolved in DCM and the amine extracted twice with 1N aqueous HCl. The combined aqueous phases are then treated with concentrated NaOH to adjust the pH to 12, and then extracted twice with DCM. The combined organic phases were then washed with water, dried over magnesium sulfate, filtered and concentrated in vacuo leading to a colorless solid which was dissolved in 100 ml diethylether, treated with 4 ml 2.6N HCl in diethylether, stirred at rt for additional 1 h, filtered and dried under high vacuo, leading to 1.24 g white solid (54%). MS (ISP) 172.1 (M+H)$^+$.

Example S37

Preparation of (4-tert-butyl-benzyl)-(3-phenyl-propyl)-amine 0.38 ml of 4-tert-butylbenzaldehyde (2.25 mmol) and 0.213 ml of 3-phenylpropylamine (1.5 mmol) were dissolved in 5 ml methanol at rt, and after stirring for 30 min at rt, were refluxed for 2 h. After cooling down to rt, 85 mg (2.25 mmol) of sodium borohydride were added and after 10 min stirring at rt, the reaction mixture was then refluxed for 3 h. After cooling down to rt, the reaction mixture was treated with 0.15 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue, 558 mg of a light brown oil, was not further purified and used directly in the next step.

Example S38

Preparation of (4-tert-butyl-benzyl)-[2-(3-ethoxy-phenyl)-ethyl]-amine 0.38 ml of 4-tert-butylbenzaldehyde (2.25 mmol) and 0.245 ml of 3-ethoxyphenethyl-amine (1.5 mmol) were dissolved in 5 ml methanol at rt, and after stirring for 30 min at rt, were refluxed for 2 h. After cooling down to rt, 85 mg (2.25 mmol) of sodium borohydride were added and after 10 min stirring at rt, the reaction mixture was then refluxed for 3 h. After cooling down to rt, the reaction mixture was treated with 0.15 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue, 461 mg of a light yellow oil, was not further purified and used directly in the next step.

Example S39

Preparation of [rac]-(4-tert-butyl-benzyl)-(2-hydroxy-2-phenyl-ethyl)-amide 0.38 ml of 4-tert-butylbenzaldehyde (2.25 mmol) and 206 mg of [rac]-2-amino-1-phenyl-ethanol (1.5 mmol) were dissolved in 4.5 ml methanol at rt, and after stirring for 30 min at rt, were refluxed for 3 h. After cooling down to rt, 85 mg (2.25 mmol) of sodium borohydride were added and after 10 min stirring at rt, the reaction mixture was then refluxed overnight. After cooling down to rt, the reaction mixture was treated with 5 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by silicagel chromatography (40 g, DCM/methanol 9:1) leading to 275 mg residue which was directly used in the next step.

Example S40

Preparation of 6-fluoro-1H-indole-7-carboxylic acid

A solution of 70.3 g of 4-fluoro-1-methyl-2-nitro-benzene (453 mmol) in 330 ml DMF was treated at rt with 87.5 ml of N,N-dimethylformamide dimethylacetal (DMFDMA, 589 mmol) and 50 ml of pyrrolidine (544 mmol) and then heated in an oil bath at 115° C. under argon. The dark red solution was then cooled down to rt, and poured into 1500 ml brine, extracted twice with diethylether. The combined organic phases were washed with brine, dried over magnesium sulfate, filtered and concentrated in vacuo, leading to 106 g residue. About half of this residue (51.5 g) were dissolved in 800 ml methanol, treated with 12.5 g 10% Pd/C and hydrogenated at 50° C. After removal of the catalyst by filtration, the residue was purified by silicagel chromatography (800 g silicagel, heptane/EtOAc 9:1) leading to 3.5 g of 6-fluoro-1H-indole as a light green solid (5.7%).

60 ml THF were cooled down to −60° C. under argon and 27 ml of a 1.6M n-BuLi solution (42.9 mmol) in hexane were added followed by 2.9 g of 6-fluoro-1H-indole (21 mmol) in 12 ml THF (addition over 25 min, temperature between −72 and −70° C.). After 5 min additional stirring at this temperature, a solution of 4.8 g of potassium tert-butylate (42.9 mmol) in 18 ml THF were added at the same temperature over 30 min. The reaction mixture was then stirred for 2 h at −72° C. and then treated with a large excess of solid $CO_2$ over 1.5 h (temperature raised by 15° C.). To the brown/orange suspension, 40 ml of water were added, and after addition of diethylether the phases were separated, the aqueous phase extracted with 2× diethylether. Finally the aqueous phase was treated with conc HCl until pH 1 and extracted twice with diethylether. The combined organic phases were then washed with brine, dried over magnesium sulfate, filtered and concentrated in vacuo, and crystallized from diethylether/hexane, leading to 1.9 g 6-fluoro-1H-indole-7-carboxylic acid, as a light brown solid (51%). MS: 177.9 (M−H)$^−$

Example S41

Preparation of [rac]-(4-tert-butyl-benzyl)-[2-(3,4-dichloro-phenyl)-2-hydroxy-ethyl]-amine 804 mg of 2-bromo-1-(3,4-dichloro-phenyl)-ethanone (3 mmol) were dissolved in 15 ml acetonitrile and treated with 342 mg of sodium diformylamide (3.6 mmol) at rt. After 2.5 h additional stirring at rt, the reaction mixture was heated to 70° C., filtered and concentrated under vacuo. The residue was purified by silicagel chromatography (90 g silicagel, EtOAc/heptane 1:1), leading to 437 mg off-white solid. MS: 259.0 (M).

340 mg of the solid described above were then suspended in 2.5 ml 6N—HCl and heated to 125° C. (bath) for 1 h. The suspension was then evaporated to dryness and dried in high vacuo for 17 h, leading to a light green solid.

The crude material (approximately 1.2 mmol) was dissolved in 10 ml methanol, treated with 166 mg of potassium carbonate (1.21 mmol) and stirred 5 min at rt. The reaction mixture was then cooled to 0° C. and treated with 91 mg sodium borohydride (2.41 mmol) in small portions. After additional 30 min at 0° C., the reaction mixture was concentrated, diluted with water and extracted with EtOAc (4×). The combined organic phases were then washed with brine, dried over magnesium sulfate, filtered and evaporated, leading to 255 mg of [rac]-2-amino-1-(3,4-dichloro-phenyl)-ethanol as light brown amorphous solid, which was directly used in the next step.

0.32 ml of 4-tert-butylbenzaldehyde (1.8 mmol) and 250 mg of [rac]-2-amino-1-(3,4-dichloro-phenyl)-ethanol (1.2 mmol) were dissolved in 10 ml methanol at rt, and after stirring for 5 min at rt, were refluxed for 2 h. After cooling down to rt, 68 mg (1.8 mmol) of sodium borohydride were added and after stirring for 15 min at rt, the reaction mixture was then refluxed for 2 h. After cooling down to rt, the residue was diluted with water/EtOAc. After separation of the organic phase, the aqueous phase was extracted with EtOAc and the combined organic phases were washed with brine, dried with magnesium sulfate, filtered off and concentrated in vacuo. The residue was stirred with diethylether/heptane, filtered and the solid dried under high vacuo, leading to 147 mg of [rac]-(4-tert-butyl-benzyl)-[2-(3,4-dichloro-phenyl)-2-hydroxy-ethyl]-amine as a light yellow solid (35%). MS (ISP) 352.3 (M+H)$^+$.

Example S42

Preparation of [rac]-(4-tert-butyl-benzyl)-[2-(4-fluoro-phenyl)-2-hydroxy-ethyl]-amine 0.868 g of 2-bromo-1-(4-fluoro-phenyl)-ethanone (4 mmol) were dissolved in 20 ml acetonitrile and treated with 0.456 g of sodium diformylamide (4.8 mmol) at rt. After 17 h additional stirring at rt, the reaction mixture was heated to 70° C., filtered and concentrated under vacuo. The residue was stirred with a small amount of diethylether and filtered, leading to 0.533 g light brown solid.

The crude material was then suspended in 6 ml 6N HCl and refluxed for 1 h. The suspension was then evaporated to dryness and dried in high vacuo, leading to a light brown solid which was dissolved in 15 ml methanol, treated with 349 mg potassium carbonate (2.5 mmol) and stirred 5 min at rt. The reaction mixture was then cooled to 0° C. and treated with 192 mg sodium borohydride (5.06 mmol) in small portions. After additional 30 min stirring at 0° C. and 2 h at rt, the reaction mixture was concentrated, diluted with water and extracted with 5× EtOAc. The combined organic phases were then washed with brine, dried over magnesium sulfate, filtered and evaporated, leading to 327 mg of [rac]-2-amino-1-(4-fluoro-phenyl)-ethanol as light brown waxy solid, which was directly used in the next step. MS (ISP) 155.9 (M+H)$^+$.

0.52 ml of 4-tert-butylbenzaldehyde (3.1 mmol) and 320 mg of [rac]-2-amino-1-(4-fluoro-phenyl)-ethanol (2.06 mmol) were dissolved in 15 ml methanol at rt, and after stirring for 5 min at rt, were refluxed for 2 h. After cooling down to rt, 117 mg (3.1 mmol) of sodium borohydride were added and after stirring for 15 min at rt, the reaction mixture was then refluxed for 2 h. After cooling down to rt, the residue was diluted with water/EtOAc. After separation of the organic phase, the aqueous phase was extracted with EtOAc and the combined organic phases were washed with brine, dried with magnesium sulfate, filtered off and concentrated in vacuo. The residue was stirred with diethylether/heptane, filtered and the solid dried under high vacuo, leading to 410 mg of [rac]-(4-tert-butyl-benzyl)-[2-(4-fluoro-phenyl)-2-hydroxy-ethyl]-amine as a white solid (66%). MS (ISP) 302.2 (M+H)$^+$.

Example S43

Preparation of [rac]-(4-tert-butyl-benzyl)-[2-(4-chloro-phenyl)-2-hydroxy-ethyl]-amine 2.33 g of 2-bromo-1-(4-chloro-phenyl)-ethanone (10 mmol) were dissolved in 60 ml acetonitrile and treated with 1.14 g sodium diformylamide (12 mmol) at rt. After 17 h additional stirring at rt, the reaction mixture was heated to 70° C., filtered and concentrated under vacuo. The residue was stirred with a small amount of diethylether and filtered, leading to 1.63 g light brown solid. MS (EI) 225.1 (M)$^+$.

1 g of the solid described above was then suspended in 18.5 ml 6N HCl and refluxed for 1 h. The suspension was then evaporated to dryness and dried in high vacuo, leading to 0.86 g (94%) of a light brown solid. MS (ISP) 170.1 (M+H)$^+$.

The solid was dissolved in 40 ml methanol, treated with 569 mg of potassium carbonate (4.12 mmol) and stirred 5 min at rt. The reaction mixture was then cooled to 0° C. and treated with 312 mg of sodium borohydride (8.25 mmol) in small portions. After additional 30 min stirring at 0° C. and 2 h at rt, the reaction mixture was concentrated, diluted with water and extracted with 6× EtOAc. The combined organic phases were then washed with brine, dried over magnesium sulfate, filtered and evaporated, leading to 923 mg of [rac]-2-amino-1-(4-chloro-phenyl)-ethanol (>100%) as light yellow waxy solid, which was directly used in the next step. MS (ISP) 172.1 (M+H)$^+$.

1 ml of 4-tert-butylbenzaldehyde (6.15 mmol) and 960 mg of [rac]-2-amino-1-(4-chloro-phenyl)-ethanol (estimated 4.1 mmol) were dissolved in 40 ml methanol at rt, and after stirring for 5 min at rt, were refluxed for 2 h. After cooling down to rt, 310 mg (8.2 mmol) of sodium borohydride were added and after stirring for 15 min at rt, the reaction mixture was then refluxed for 2 h. After cooling down to rt, the residue was diluted with water/EtOAc. After separation of the organic phase, the aqueous phase was extracted with EtOAc and the combined organic phases were washed with brine, dried with magnesium sulfate, filtered off and concentrated in vacuo. The residue was stirred with a small quantity of diethylether/heptane, filtered and the solid dried under high vacuo, leading to 723 g of

[rac]-(4-tert-butyl-benzyl)-[2-(4-chloro-phenyl)-2-hydroxy-ethyl]-amine as a white solid (55%). MS (ISP) 318.2 (M+H)+.

Example S44

Preparation of [rac]-(4-tert-butyl-benzyl)-[2-(4-chloro-phenyl)-2-fluoro-ethyl]-amine 159 mg of [rac]-(4-tert-butyl-benzyl)-[2-(4-chloro-phenyl)-2-hydroxy-ethyl]-amine (0.5 mmol, described in example S43) in 5 ml DCM was cooled to 2° C. and treated with 0.2 ml of DAST (1.5 mmol) for 2 min. After 2 h stirring at 0° C. followed by 1 h at rt, the reaction mixture was again cooled down to 0° C. and treated with 5 ml saturated aqueous sodium bicarbonate. The reaction mixture was stirred until $CO_2$ evolution stopped, then the organic phase was separated, washed with brine, dried over magnesium sulfate, filtered and concentrated in vacuo. The residue was Purified by silicagel chromatography (40 g silica gel; heptane/EtOAc 2:1) leading to 27 mg of a light yellow semisolid (17%). M(ISP) 320.3 (M+H)+.

Example S45

Preparation of 5-chloro-6-fluoro-1H-indole-7-carboxylic acid 10 g of 4-chloro-3-fluoro-phenylamine (68.7 mmol) were dissolved in 38 ml DCM and treated with 6.82 g of sodium bicarbonate (72.1 mmol) in 110 ml water. At rt 8 ml of methyl chloroformate (103 mmol) were added dropwise over a period of 25 min (temperature raises from 22 to 28° C.). After 1.5 h stirring at rt, the reaction mixture was diluted with 100 ml DCM. After separation, the organic phase was washed with 45 ml brine, dried over magnesium sulfate, filtered and diluted with 140 ml hexane. The DCM was then removed under vacuo and the resulting suspension filtered leading to 13 g (4-chloro-3-fluoro-phenyl)-carbamic acid methyl ester as a white powder (92%). MS (EI) 203.1 (M)+.

5.34 g of (4-chloro-3-fluoro-phenyl)-carbamic acid methyl ester (26.2 mmol) were dissolved in 50 ml acetonitrile and treated with 6.49 g of N-iodosuccinimide (28.85 mmol) and 0.23 ml of trifluoromethanesulfonic acid (2.62 mmol) under nitrogen and stirred at rt for 3 h. The reaction mixture was then poured on 50 ml saturated sodium bicarbonate solution, extracted twice with EtOAc. The combined organic phases were then washed with brine, dried over magnesium sulfate, filtered and concentrated in vacuo, leading to 8.2 g of (4-chloro-5-fluoro-2-iodo-phenyl)-carbamic acid methyl ester (95%) as a dark blue powder. MS (EI) 328.9 (M)+.

153 mg of $Pd(PPh_3)_2Cl_2$ (0.22 mmol) and 42 mg of Cu(I) (0.22 mmol) were dissolved in 40 ml triethylamine and refluxed under argon for 20 min. The reaction mixture was then cooled down to 0° C. and 7.2 g of (4-chloro-5-fluoro-2-iodo-phenyl)-carbamic acid methyl ester (21 mmol) were added. After 10 min stirring at rt, 3.45 ml ethinyltrimethylsilane (24.9 mmol) was added dropwise (exothermic, temperature raises from 18 to 33° C.) and the reaction mixture was stirred for 1 h at rt. The reaction mixture was then poured on 180 ml aqueous 1N HCl and ice and extracted with twice 180 ml EtOAc. The organic phases were washed with water and brine, dried over magnesium sulfate, filtered and concentrated in vacuo.

The crude material (ca 21 mmol) was dissolved in 200 ml THF and treated with 43.3 ml of tetrabutylammonium fluoride (1M in THF) (43.3 mmol) at rt. After 5 min stirring at rt, the reaction mixture was refluxed for 1 h under argon. The reaction mixture was then cooled down to rt and concentrated in vacuo. The resulting oil was treated with 55 ml water, stirred for 10 min and finally extracted with 2×100 ml EtOAc. The combined organic phases were sequentially washed with 50 ml 1M HCl, 50 ml saturated sodium bicarbonate, 50 ml brine and finally dried over magnesium sulfate, filtered and concentrated in vacuo. The residue was stirred with 200 ml hexane under reflux, cooled to 5° C. and filtered leading to 3.15 g 5-chloro-6-fluoro-1H-indole as a light brown solid (85%). MS (EI) 169.1 (M)+.

35 ml THF was cooled down to −75° C. under argon and 19.05 ml of a 1.6M solution of n-BuLi in hexane (30.5 mmol) were added. Then a solution of 2.35 g of 5-chloro-6-fluoro-1H-indole (13.7 mmol) in 9 ml THF was added dropwise (temperature kept between −70 and −75° C.) over 15 min. After 5 additional min stirring at this temperature a solution of 3.7 g potassium tert-butylate in 15 ml THF was added over 10 min (temperature kept between −70 and −75° C.). The brown solution was stirred 2 h at the same temperature and then treated with a large excess of solid $CO_2$. The temperature was then raised to 10° C. over a period of 75 min, and treated with 30 ml water. After separation of the organic phase, the aqueous phase was extracted with 2×20 ml diethylether, treated with concentrated HCl until pH 1. The suspension was then filtered, the solid washed with water and dried in high vacuo. The residue was stirred with 10 ml hexane/diethylether 9:1 for 15 min and filtered, washed with 5 ml of the same mixture and the collected solid dried in high vacuo, leading to 2.2 g of 5-chloro-6-fluoro-1H-indole-7-carboxylic acid as a light brown solid (75%). MS: 212.2 (M−H)−.

Example S46

Preparation of (4-tert-butyl-benzyl)-(4,4,4-trifluoro-3-trifluoromethyl-butyl)-amine hydrochloride A solution of 5 g of 4,4,4-trifluoro-3-trifluoromethyl-butyric acid ethyl ester (21 mmol) in 20 ml ethanol was treated with 21 ml of 2N-NaOH and stirred at rt for 17 h and then refluxed for 1 h. After cooling down to rt the ethanol was removed in vacuo and the pH adjusted to 1 by addition of 2N HCl. Finally the reaction mixture was extracted twice with diethylether, washed with brine, dried over magnesium sulfate and concentrated in vacuo, leading to 4.02 g of 4,4,4-trifluoro-3-trifluoromethyl-butyric acid as a light yellow liquid (91%).

A solution of 2.1 g of 4,4,4-trifluoro-3-trifluoromethyl-butyric acid (10 mmol) in 80 ml DMF was treated with 3.12 g of TBTU (10 mmol) and 8.55 ml of N,N-diisopropylethyl amine and stirred for 5 min at rt under argon. Then 1.93 ml of 4-tert-butylbenzylamine (11 mmol) were added and the reaction mixture was stirred 17 h at rt. The reaction mixture was then diluted with 400 ml water and extracted twice with EtOAc, the combined organic phases washed with brine, dried over magnesium sulfate filtered and concentrated in vacuo. The residue was purified by column chromatography (40 g silica gel; heptane/EtOAc 4:1) to give 2.14 g of N-(4-tert-butyl-benzyl)-4,4,4-trifluoro-3-trifluoromethyl-butyramide as a light yellow solid (60%).

0.355 g of N-(4-tert-butyl-benzyl)-4,4,4-trifluoro-3-trifluoromethyl-butyramide (1 mmol) were dissolved in 5 ml THF and treated at rt with 8 ml of a 1M borane-THF complex solution in THF over 20 min. After addition the reaction mixture was refluxed for 4 h. The reaction mixture was then cooled down to rt and treated dropwise with 1.5 ml methanol and refluxed for 1 h. Then the reaction mixture was concentrated, the residue dissolved in DCM and extracted twice with 1N aqueous HCl. Since the acidic aqueous phases did not contain the product, the DCM phase was washed with brine, dried over magnesium sulfate, filtered and concentrated in vacuo leading to a white solid which was stirred with DCM, filtered off and dried under high vacuo, leading to 216 mg of (4-tert-butyl-benzyl)-(4,4,4-trifluoro-3-trifluoromethyl-butyl)-amine hydrochloride as a white solid (63%). MS (ISP) 342.2 $(M+H)^+$.

Example S47

Preparation of (4-tert-butyl-benzyl)-[2-(3-chloro-4-fluoro-phenyl)-ethyl]-amine 4.54 ml of 4-tert-butylbenzaldehyde (27.13 mmol), 3.8 g 2-(3-chloro-4-fluoro-phenyl)-ethylamine hydrochloride (18.1 mmol) and 2.5 g potassium carbonate (18.1 mmol) were suspended in 55 ml methanol at rt, and after stirring for 30 min at rt, were refluxed for 2 h. After cooling down to rt, 1.03 (27.13 mmol) sodium borohydride were added and after stirring for 5 min at rt, the reaction mixture was then refluxed for 2.5 h. After cooling down to rt, the reaction mixture was treated with 5 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (90 g silica gel; EtOAc/heptane 1:4) to give 4.66 g light yellow oil (80%). MS (ISP) 320.3 $(M+H)^+$.

Example S48

Preparation of 2-(3-chloro-4-fluoro-phenyl)-ethylamine hydrochloride 4.37 g of 3-chloro-4-fluoro-phenylacetonitrile (25 mmol) were dissolved in 40 ml THF and cooled down to 0° C. under nitrogen. 132 ml of a 1M borane-THF complex solution in THF were then added dropwise over 30 min keeping the temperature between 0-5° C. After addition the reaction mixture was stirred at rt for additional 20 min, and refluxed for 21 h. The reaction mixture was then cooled down to 0° C. and treated between 2 and 5° C. with 30 ml methanol over a period of 45 min. After 1 h refluxing the reaction mixture was concentrated, the residue dissolved in DCM and the amine extracted twice with 1N aqueous HCl. The combined aqueous phases were then treated with concentrated NaOH to adjust the pH to 12, and then extracted twice with DCM. The combined organic phases were then washed with water, dried over magnesium sulfate, filtered and concentrated in vacuo leading to 4.3 g colorless oil. This was dissolved in 125 ml diethylether, treated with 15 ml 2.6N HCl in diethylether, stirred at rt for additional 1 h, filtered and dried under high vacuo, leading to 3.93 g white solid (75%). MS (ISP) 174.1 $(M+H)^+$.

Example S49

Preparation of (4-tert-butyl-benzyl)-[2-(2-fluoro-5-trifluoromethyl-phenyl)-ethyl]-amine 4 ml of 4-tert-butylbenzaldehyde (24 mmol), 3.9 g of 2-(2-fluoro-5-trifluoromethyl-phenyl)-ethylamine hydrochloride (16 mmol) and 2.2 g of potassium carbonate (18.1 mmol) were suspended in 55 ml methanol at rt, and after stirring for 30 min at rt, were refluxed for 2.5 h. After cooling down to rt, 0.91 (24 mmol) of sodium borohydride were added and after stirring for 5 min at rt, the reaction mixture was refluxed for 2.5 h. After cooling down to rt, the reaction mixture was treated with 5 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (90 g silica gel; EtOAc/heptane 1:4) to give 6.28 g light yellow oil (100%). MS (ISP) 354.3 $(M+H)^+$.

Example S50

Preparation of 2-(2-fluoro-5-trifluoromethyl-phenyl)-ethylamine hydrochloride 4.98 g of 2-fluoro-5-trifluoromethyl-phenylacetonitrile (24 mmol) were dissolved in 40 ml THF and cooled down to 0° C. under nitrogen. 127 ml of a 1M borane-THF complex solution in THF were then added dropwise over 25 min by keeping the temperature between 0 to 2° C. After addition the reaction mixture was stirred at rt for additional 15 min, and refluxed for 22 h. The reaction mixture is then cooled down to 0° C. and treated between 2 and 5° C. with 30 ml methanol over a period of 45 min. After 1 h refluxing the reaction mixture was concentrated, the residue dissolved in DCM and the amine extracted twice with 1N aqueous HCl. The combined aqueous phases were then treated with concentrated NaOH to adjust the pH to 12, and then extracted twice with DCM. The combined organic phases were then washed with water, dried over magnesium sulfate, filtered and concentrated in vacuo leading to 3.6 g colorless oil. This was dissolved in 100 ml diethylether, treated with 10 ml 2.6N HCl in diethylether, stirred at rt for an additional 1 h, filtered and dried under high vacuo, leading to 4 g white solid (68%). MS (ISP) 206.2 $(M+H)^+$.

Example S51

Preparation of (4-tert-butyl-benzyl)-[2-(4-chloro-3-trifluoromethyl-phenyl)-ethyl]-amine 1.54 ml of 4-tert-butylbenzaldehyde (9.23 mmol), 1.6 g of 2-(4-chloro-3-trifluoromethyl-phenyl)-ethylamine hydrochloride (6.15 mmol) and 850 mg of potassium carbonate (6.15 mmol) were suspended in 18 ml methanol at rt, and after stirring for 30 min at rt, were refluxed for 2 h. After cooling down to rt, 349 mg (9.23 mmol) of sodium borohydride were added and after stirring for 5 min at rt, the reaction mixture was refluxed for 2.5 h. After cooling down to rt, the reaction mixture was treated with 1.2 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 2.01 g light yellow oil (88%). MS (ISP) 370.2 (M+H)+.

Example S52

Preparation of 2-(4-chloro-3-trifluoromethyl-phenyl)-ethylamine hydrochloride 3.94 g of 4-bromomethyl-1-chloro-2-trifluoromethyl-benzene (14.4 mmol) and 1.06 g sodium cyanide (21.6 mmol) were suspended in 12 ml DMSO under argon and stirring and heated to 50° C. for 1 h. The reaction mixture was then poured on water/ice and extracted four times with DCM. The combined organic phases were washed with water, dried over magnesium sulfate, filtered and concentrated in vacuo, leading to 3.188 g of (4-chloro-3-trifluoromethyl-phenyl)-acetonitrile as a dark red oil, which was directly used in the next step.

3.188 g of crude (4-chloro-3-trifluoromethyl-phenyl)-acetonitrile (14.5 mmol) were dissolved in 25 ml THF and cooled down to 0° C. under nitrogen. 76 ml of a 1M borane-THF complex solution in THF (76 mmol) were then added dropwise over 20 min by keeping the temperature between 0 to 2° C. After addition the reaction mixture was stirred at rt for additional 45 min, and refluxed for 17 h. The reaction mixture was then cooled down to 0° C. and treated between 2 and 5° C. with 18 ml methanol over a period of 45 min. After 1 h refluxing the reaction mixture was concentrated, the residue dissolved in DCM and the amine extracted twice with 1N aqueous HCl. The combined aqueous phases were then treated with concentrated NaOH to adjust the pH to 12, and then extracted twice with DCM. The combined organic phases were then washed with water, dried over magnesium sulfate, filtered and concentrated in vacuo leading to 1.54 g colorless oil. This was dissolved in 50 ml diethylether, treated with 4 ml 2.6N HCl in diethylether, stirred at rt for additional 30 min, filtered and dried under high vacuo, leading to 1.52 g white solid (40%). MS (ISP) 224.1 (M+H)+.

Example S53

Preparation of (4-cyclopropylbenzyl)-[2-(4-fluoro-3-trifluoromethylphenyl)-ethyl]-amine, (4-cyclopropylbenzyl)-[2-(3-trifluoromethoxypheyl)-ethyl]-amine, (4-cyclopropylbenzyl)-[2-(3,4-dichlorophenyl)-ethyl]-amine, [2-(4-chlorophenyl)-ethyl]-(4-cyclopropylbenzyl)-amine, (4-cyclopropylbenzyl)-[2-(3-trifluoromethylphenyl)-ethyl]-amine, (2,2-dimethylchroman-6-ylmethyl)-[2-(3-trifluoromethylphenyl)-ethyl]-amine, (2,2-dimethylchroman-6-ylmethyl)-phenethylamine, (2,2-difluoro-benzo[1,3]dioxol-5-ylmethyl)-[2-(3-trifluoromethyl-phenyl)-ethyl]-amine and [2-(3,4-dichloro-phenyl)-ethyl]-(2,2-difluoro-benzo[1,3]dioxol-5-ylmethyl)-amine Preparation of 4-cyclopropyl benzaldehyde To a solution of 1-bromo-4-cyclopropylbenzene [synthesized in analogy to a procedure described in J. Org. Chem. 41:2262-2266 (1976)] (1.58 g, 8.04 mmol) in THF at −78° C. was added n-BuLi (5.08 ml, 1.6M solution in hexane, 8.11 mmol) and the reaction mixture was stirred at −78° C. for 10 min. DMF (1.25 ml, 16.08 mmol) was then added and the reaction mixture was stirred at −78° C. for 15 min. The reaction mixture was then warmed to 0° C. slowly (over 2 h) and stirred at 0° C. for 1 h. The reaction was quenched with sat. NH$_4$Cl (aq) solution and the aqueous phase was extracted with ether. The organic layer was washed with brine, dried (MgSO$_4$), filtered and concentrated in vacuo to give a residue which was purified by flash column chromatography (1:9 diethylether:pentane) to give 4-cyclopropyl benzaldehyde (1.10 g, 94%) as a colorless oil. $^1H$ NMR (CDCl$_3$, 300 MHz): δ 9.94 (s, 1H), 7.76 (d, J=8.5 Hz, 2H), 7.19 (d, J=8.5 Hz, 2H), 1.97 (m, 1H), 1.13-1.06 (m, 2H), 0.84-0.78 (m, 2H).

Preparation of (4-cyclopropylbenzyl)-[2-(4-fluoro-3-trifluoromethylphenyl)-ethyl]-amine A mixture of 4-cyclopropyl benzaldehyde (103 mg, 0.71 mmol), 2-(4-fluoro-3-trifluoromethylphenyl) -ethylamine (prepared as described in example S30) (172 mg, 0.71 mmol) and molecular sieves (500 mg, 4 Å) in diethyl ether (4 ml) was stirred at rt overnight. The mixture was filtered through celite® and concentrated in vacuo to give the corresponding imine which was dissolved in methanol. Sodium borohydride (40 mg, 1.06 mmol) was added and the reaction mixture was stirred at rt for 4 h. The reaction mixture was then quenched with 0.1N NaOH$_{(aq)}$ and the mixture was diluted with EtOAc and washed with brine. The organic phase was dried (MgSO$_4$), filtered and concentrated in vacuo to give a residue which was purified by flash column chromatography to give the desired (4-cyclopropylbenzyl)-[2-(4-fluoro-3-trifluoromethylphenyl)-ethyl]-amine (108 mg, 82%) as a colorless oil. MS (ISP) 338.3 (M+H)+.

(4-cyclopropylbenzyl)-[2-(3-trifluoromethoxyphenyl)-ethyl]-amine was synthesized in analogy to the above procedure using 4-cyclopropyl benzaldehyde (106 mg, 0.73 mmol), 2-(3-trifluoromethoxy-phenyl)-ethylamine (prepared as described in Example S28) (175 mg, 0.73 mmol) and sodium borohydride (41 mg, 1.09 mmol). The desired product (92 mg, 70%) was isolated without further purification as a colorless oil. MS (ISP) 336.1 (M+H)+.

(4-cyclopropylbenzyl)-[2-(3,4-dichlorophenyl)-ethyl]-amine was synthesized in analogy to the above procedure using 4-cyclopropyl benzaldehyde (219 mg, 1.50 mmol), 2-(3,4-dichloro-phenyl)-ethylamine (284 mg, 1.50 mmol) and sodium borohydride (85 mg, 1.09 mmol). The desired product (95 mg, 75%) was isolated without further purification as a colorless oil. MS (ISP) 320.2 (M+H)+.

[2-(4-chlorophenyl)-ethyl]-(4-cyclopropylbenzyl)-amine was synthesized in analogy to the above procedure using 4-cyclopropyl benzaldehyde (204 mg, 1.40 mmol), 2-(4-chlorophenyl)-ethylamine (217 mg, 1.40 mmol) and sodium borohydride (79 mg, 2.09 mmol). The desired product (317 mg, 79%) was isolated without further purification as a colorless oil. MS (ISP) 285.9 (M+H)+.

(4-cyclopropylbenzyl)-[2-(3-trifluoromethylphenyl)-ethyl]-amine was synthesized in analogy to the above procedure using 4-cyclopropyl benzaldehyde (197 mg, 1.35 mmol), 2-(3-trifluoromethylphenyl)-ethylamine (255 mg, 1.35 mmol) and sodium borohydride (76 mg, 2.02 mmol). The desired product was isolated without further purification as a colorless oil. MS (ISP) 320.4 (M+H)+.

(2,2-dimethylchroman-6-ylmethyl)-[2-(3-trifluoromethylphenyl)-ethyl]-amine was synthesized in analogy to the above procedure using 2,2-dimethylchroman-6-carbaldehyde (99 mg, 0.52 mmol), 2-(3-trifluoromethylphenyl)-ethylamine (98 mg, 0.52 mmol) and sodium borohydride (30 mg, 0.78 mmol). The desired product (185 mg, 98%) was isolated without further purification as a colorless oil. MS (ISP) 364.2 (M+H)$^+$.

(2,2-dimethylchroman-6-ylmethyl)-phenethylamine was synthesized in analogy to the above procedure using 2,2-dimethylchroman-6-carbaldehyde (95 mg, 0.50 mmol), phenyl-ethylamine (63 mg, 0.50 mmol) and sodium borohydride (28 mg, 0.75 mmol). The desired product (142 mg, 96%) was isolated without further purification as a colorless oil. MS (ISP) 296.3 (M+H)$^+$.

(2,2-difluoro-benzo[1,3]dioxol-5-ylmethyl)-[2-(3-trifluoromethyl-phenyl)-ethyl]-amine was synthesized in analogy to the above procedure using 100 mg of 2,2-difluoro-1,3-benzodioxole-5-carbaldehyde (0.54 mmol), 102 mg of 2-(3-trifluoromethylphenyl)-ethylamine (0.54 mmol) and 31 mg of sodium borohydride (0.81 mmol). The isolated colorless semisolid (110 mg, 57%) was used in the following step without further purification. MS (ISP) 360.0 (M+H)$^+$.

[2-(3,4-dichloro-phenyl)-ethyl]-(2,2-difluoro-benzo[1,3]dioxol-5-ylmethyl)-amine was synthesized in analogy to the above procedure using 100 mg of 2,2-difluoro-1,3-benzodioxole-5-carbaldehyde (0.54 mmol), 102 mg of 2-(3,4-dichloro-phenyl)-ethylamine (0.54 mmol) and 31 mg of sodium borohydride (0.81 mmol). The isolated colorless semisolid (98 mg, 51%) was used in the following step without further purification. MS (ISP) 360.0 (M+H)$^+$.

Example S54

Preparation of (4-tert-butyl-benzyl)-[2-(3-fluoro-5-trifluoromethyl-phenyl)-ethyl]-amine 3.1 ml of 4-tert-butylbenzaldehyde (18.47 mmol), 3 g of 2-(3-fluoro-5-trifluoromethyl -phenyl)-ethylamine hydrochloride (12.3 mmol) and 1.7 g of potassium carbonate (12.3 mmol) were suspended in 36 ml methanol at rt, and after stirring for 30 min at rt, were refluxed for 2 h. After cooling down to rt, 700 mg (18.47 mmol) of sodium borohydride were added and after stirring for 5 min at rt, the reaction mixture was refluxed for 2.5 h. After cooling down to rt, the reaction mixture was treated with 2.4 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (90 g silica gel; EtOAc/heptane 1:2) to give 4.35 g light yellow oil (90%). MS (ISP) 354.3 (M+H)$^+$.

Example S55

Preparation of 2-(3-fluoro-5-trifluoromethyl-phenyl)-ethylamine hydrochloride 5.45 g of (3-fluoro-5-trifluoromethyl-phenyl)-acetonitrile (26.3 mmol) were dissolved in 45 ml THF and cooled down to 0° C. under nitrogen. 138 ml of a 1M borane-THF complex solution in THF (138 mmol) were then added dropwise over 20 min by keeping the temperature between 0-2° C. After addition the reaction mixture was stirred at rt for additional 45 min, and refluxed for 17 h. The reaction mixture was then cooled down to 0° C. and treated between 2 and 5° C. with 33 ml methanol over a period of 45 min. After 1 h refluxing the reaction mixture was concentrated, the residue dissolved in DCM and the amine extracted twice with 1N aqueous HCl. The combined aqueous phases are then treated with concentrated NaOH to adjust the pH to 12, and then extracted twice with DCM. The combined organic phases were then washed with water, dried over magnesium sulfate, filtered and concentrated in vacuo leading to 4.44 g colorless oil. This was dissolved in 100 ml diethylether, treated with 9 ml 2.6N HCl in diethylether, stirred at rt for additional 30 min, filtered and dried under high vacuo, leading to 4.6 g white solid (72%). MS (ISP) 207.1 (M+H)$^+$.

Example S56

Preparation of (4-tert-butyl-benzyl)-[2-(3-difluoromethoxy-phenyl)-ethyl]-amine 0.55 ml of 4-tert-butylbenzaldehyde (9.19 mmol), 1.37 g of 2-(3-trifluoromethoxy-phenyl)-ethylamine hydrochloride (6.13 mmol) and 0.304 g of potassium carbonate (6.13 mmol) were suspended in 18 ml methanol at rt, and after stirring for 30 min at rt, were refluxed for 2.5 h. After cooling down to rt, 348 mg (9.19 mmol) of sodium borohydride were added and after stirring for 5 min at rt, the reaction mixture was refluxed for 22 h. After cooling down to rt, the reaction mixture was treated with 0.4 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo to give 1.82 g off-white oil (89%). MS (ISP) 334.3 (M+H)$^+$.

Example S57

Preparation of 2-(3-trifluoromethoxy-phenyl)-ethylamine hydrochloride 2 g of (3-difluoromethoxy-phenyl)-acetonitrile (11 mmol) were dissolved in 18 ml THF and cooled down to 0° C. under nitrogen. 58 ml of a 1M borane-THF complex solution in THF (58 mmol) were then added dropwise over 30 min by keeping the temperature between 0 to 2° C. After addition the reaction mixture was stirred at rt for additional 20 min, and refluxed for 21 h. The reaction mixture was then cooled down to 0° C. and treated between 2 and 5° C. with 13 ml methanol over a period of 45 min. After 1 h refluxing the reaction mixture was concentrated, the residue dissolved in DCM and the amine extracted twice with 1N aqueous HCl. The combined aqueous phases were then treated with concentrated NaOH to adjust the pH to 12, and then extracted twice with DCM. The combined organic phases were then washed with water, dried over magnesium sulfate, filtered and concentrated in vacuo leading to 1.5 g colorless oil. This was dissolved in 30 ml diethylether, treated with 4 ml 2.6N HCl in diethylether, stirred at rt for additional 60 min, filtered and dried under high vacuo, leading to 1.56 g white solid (63%). MS (ISP) 188.3 (M+H)$^+$.

Example S58

Preparation of (4-tert-butyl-benzyl)-[2-(3-chloro-2-fluoro-phenyl)-ethyl]-amine 1.2 ml of 4-tert-butylbenzaldehyde (7.14 mmol), 1 g of 2-(3-chloro-2-fluoro-phenyl)-ethylamine hydrochloride (4.76 mmol) and 658 mg of potassium carbonate (4.76 mmol) were suspended in 14 ml methanol at rt, and after stirring for 30 min at rt, were refluxed for 2 h. After cooling down to rt, 270 mg (7.14 mmol) of sodium borohydride were added and after stirring for 5 min at rt, the reaction mixture was refluxed for 2.5 h. After cooling down to rt, the reaction mixture was treated with 1.2 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:4) to give 860 mg light yellow oil (56%). MS (ISP) 320.3 (M+H)$^+$.

Example S59

Preparation of 2-(3-chloro-2-fluoro-phenyl)-ethylamine hydrochloride 1.87 g of (3-chloro-2-fluoro-phenyl)-acetonitrile (11 mmol) were dissolved in 18 ml THF and cooled down to 0° C. under nitrogen. 58 ml of a 1M borane-THF complex solution in THF (58 mmol) were then added dropwise over 20 min by keeping the temperature between 0 to 2° C. After addition the reaction mixture was stirred at rt for additional 20 min, and refluxed for 21 h. The reaction mixture was then cooled down to 0° C. and treated between 2 and 5° C. with 13 ml methanol over a period of 35 min. After 1 h refluxing the reaction mixture was concentrated, the residue dissolved in DCM and the amine extracted twice with 1N aqueous HCl. The combined aqueous phases were then treated with concentrated NaOH to adjust the pH to 12, and then extracted twice with DCM. The combined organic phases were then washed with water, dried over magnesium sulfate, filtered and concentrated in vacuo leading to 1.6 g colorless oil. This was dissolved in 50 ml diethylether, treated with 5 ml 2.6N HCl in diethylether, stirred at rt for additional 60 min, filtered and dried under high vacuo, leading to 1.6 g white solid (69%). MS (ISP) 174.2 (M+H)$^+$.

Example S60

Preparation of [rac]-(4-tert-butyl-benzyl)-(3,3,3-trifluoro-2-hydroxy-propyl)-amine To a solution of 0.88 ml of tert-butylbenzylamine (5 mmol) and 0.77 ml of triethylamine (5.5 mmol) in 5 ml DCM, were added dropwise 0.7 ml of trifluoroacetic acid anhydride (5 mmol) in 1 ml DCM keeping the temperature between 2 and 5° C. The reaction mixture was stirred at this temperature for one additional h and at rt for 17 h. The reaction mixture was then diluted with 5 ml DCM, washed with water and brine, dried over magnesium sulfate, filtered and concentrated in vacuo. The residue was purified by column chromatography (90 g silica gel; EtOAc/heptane 1:9) to give 805 mg N-(4-tert-butyl-benzyl)-2,2,2-trifluoro-acetamide as a white solid (62%). MS (EI) 259.1 (M)$^+$.

260 mg of N-(4-tert-butyl-benzyl)-2,2,2-trifluoro-acetamide (1 mmol) were dissolved in 10 ml acetonitrile and treated with 169 mg of potassium tert-butylate (1.5 mmol). After 5 min stirring at rt, 0.125 ml of [rac]-3-bromo-1,1,1-trifluoro-propan-2-ol (1.2 mmol) were added and the reaction mixture stirred at 75° C. bath temperature for 22 h. After cooling down to rt, the reaction mixture was concentrated in vacuo, dissolved in EtOAc/water and the phases separated. The organic phase was then washed with brine, dried over magnesium sulfate, filtered and concentrated in vacuo. The residue was purified by column chromatography (90 g silica gel; EtOAc/heptane 1:4) to give 111 mg of N-(4-tert-butyl-benzyl)-2,2,2-trifluoro-N-(3,3,3-trifluoro-2-hydroxy-propyl)-acetamide as a white solid (30%). MS (ISP) 301.2 (M+H)$^+$.

99 mg of [rac]-N-(4-tert-butyl-benzyl)-2,2,2-trifluoro-N-(3,3,3-trifluoro-2-hydroxy-propyl)-acetamide (0.27 mmol) were dissolved in 0.5 ml ethanol, treated with 0.4 ml 2N NaOH (0.8 mmol) and heated to 75° C. (bath temperature) for 4 h. After this period a second portion of 0.4 ml 2N NaOH (0.8 mmol) was added and the reaction mixture stirred at 7° C. (bath temperature) for additional 24 h. Then the reaction mixture was cooled down to rt, diluted with diethylether, treated with 1.6 ml 1N HCl and extracted with EtOAc. The organic phase was washed with brine, dried over magnesium sulfate, filtered and concentrated in vacuo, leading to 87 mg of [rac]-(4-tert-butyl-benzyl)-(3,3,3-trifluoro-2-hydroxy-propyl)-amine as an off-white solid (>100%). The crude material was used without further purification in the next step.

Example S61

Preparation of butyl-(4-tert-butyl-benzyl)-amine 0.5 ml of 4-tert-butylbenzaldehyde (3 mmol) and 0.20 ml of butylamine (2 mmol) were dissolved in 5 ml methanol at rt and then refluxed for 17 h. After cooling down to rt, 113 mg (3 mmol) of sodium borohydride were added and the reaction mixture was then refluxed for 3 h. After cooling down to rt, the reaction mixture was treated with 4 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (8 g silica gel; EtOAc/heptane 1:1) to give 334 mg colorless oil (51%). MS (ISP) 220.4 (M+H)$^+$.

Example S62

Preparation of (4-tert-butyl-benzyl)-[2-(3-methoxy-phenyl)-ethyl]-amine 0.38 ml of 4-tert-butylbenzaldehyde (2.25 mmol) and 0.22 ml of 2-(3-methoxy-phenyl)-ethylamine (1.5 mmol) were dissolved in 5 ml methanol at rt and then refluxed for 2 h. After cooling down to rt, 85 mg (2.25 mmol) of sodium borohydride were added in portions and the reaction mixture was then refluxed for 3 h. After cooling down to rt, the reaction mixture was treated with 0.15 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (90 g silica gel; EtOAc/heptane 1:1) to give 520 mg light yellow oil (>100%).

Example S63

Preparation of [rac]-(4-tert-butyl-benzyl)-[2-(4-chloro-phenyl)-propyl]-amine 618 mg of [rac]-2-(4-chloro-phenyl)-propylamine hydrochloride (3 mmol) were dissolved in 8 ml methanol at rt and treated with 415 mg of potassium carbonate (3 mmol) and after 5 min stirring treated with 0.755 ml of 4-tert-butyl-benzaldehyde (4.5 mmol). After 30 min stirring at rt, the reaction mixture was refluxed for 3 h, and After cooling down to rt, treated with 170 mg (4.5 mmol) sodium borohydride in portions. After 10 min at rt, the reaction mixture was refluxed for 20 h. After cooling down to rt, the reaction mixture was treated with 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 753 mg light brown oil (79%). MS(ISP) 316.3 $(M+H)^+$.

Example S64

Preparation of (4-tert-butyl-benzyl)-[2-(2,4-dichloro-phenyl)-ethyl]-amine 0.753 ml of 4-tert-butylbenzaldehyde (4.5 mmol) and 0.436 ml of 2-(2,4-dichloro-phenyl)-ethylamine (3 mmol) were dissolved in 8 ml methanol at rt and after 30 min at rt refluxed for 3.5 h. After cooling down to rt, 170 mg (4.5 mmol) of sodium borohydride were added in portions and the reaction mixture was then refluxed overnight. After cooling down to rt, the reaction mixture was treated with 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 691 mg colorless oil (68%). MS(ISP) 336.3 $(M+H)^+$.

Example S65

Preparation of 4-chloro-1H-indole-7-carboxylic acid 1.19 g (5 mmol) of 2-bromo-5-chloro-nitrobenzene were dissolved in 50 ml THF. At a temperature of −45° C. 15 ml of a 1M vinyl magnesium bromide solution in THF were added under nitrogen in such a way that the temperature did not exceed −40° C. After complete addition the dark solution was stirred for 30 min at −40° C. The reaction mixture was quenched with 10 ml aqueous saturated ammonium chloride solution and extracted twice with diethyl ether. The combined organic layers were washed once with saturated aqueous sodium chloride solution, dried over sodium sulfate, filtered and the solvent was evaporated. The residue was purified by column chromatography (100 g silica gel; heptane/EtOAc 19:1) to yield 562 mg (49%) of 7-bromo-4-chloro-1H-indole as an orange oil. MS (EI) 229.0 (80), 231.0 (100), 233.0 (30) $(M)^+$.

560 mg (2.43 mmol) of 7-bromo-4-chloro-1H-indole were dissolved in 15 ml THF. The reaction mixture was cooled to −78° C. and 4.55 ml of a 1.6 M butyl lithium solution in hexane were added under nitrogen in such a way, that the temperature did not exceed a maximum of −70° C. The yellow solution was stirred at 0 to 5° C. after complete addition for 30 min. The reaction mixture was cooled to −78° C. and dry ice was added. The reaction mixture was warmed to rt, stirred for 15 min and poured onto 100 ml water. The aqueous layer was washed twice with diethyl ether, acidified with 1N aqueous HCl solution and extracted twice with diethyl ether. The combined organic layers were washed with saturated aqueous sodium chloride solution, dried over sodium sulfate, filtered and the solvent was evaporated. The crude residue was stirred with hexane for 15 min, filtered and dried to yield 319 mg (67%) of 4-chloro-1H-indole-7-carboxylic acid as an off-white solid. MS (ISP) 194.1 $(M-H)^-$.

Example S66

Preparation of 4-fluoro-1H-indole-7-carboxylic acid 1.12 g (5 mmol) of 2-bromo-5-fluoro-nitrobenzene were dissolved in 50 ml THF. At a temperature of −45° C. 15 ml of a 1M vinyl magnesium bromide solution in THF were added under nitrogen in such a way that the temperature did not exceed −40° C. After complete addition the dark solution was stirred for 30 min at −40° C. The reaction mixture was quenched with 10 ml aqueous saturated ammonium chloride solution and extracted twice with diethyl ether. The combined organic layers were washed once with saturated aqueous sodium chloride solution, dried over sodium sulfate, filtered and the solvent was evaporated. The residue was dissolved in DCM and purified by column chromatography (100 g silica gel; heptane/EtOAc 9:1) to yield 501 mg (47%) 7-bromo-4-fluoro-1H-indole as an orange oil. MS (EI) 213.0 (100), 215.0 (100) $(M)^+$.

492 mg (2.30 mmol) of 7-bromo-4-fluoro-1H-indole were dissolved in 14 ml THF. The reaction mixture was cooled to −78° C. and 4.31 ml of a 1.6 M butyl lithium solution in hexane were added under nitrogen in such a way, that the temperature did not exceed a maximum of −70° C. The yellow solution was stirred at 0 to 5° C. after complete addition for 30 min. The reaction mixture was cooled to −78° C. and dry ice was added. The reaction mixture was warmed to rt, stirred for 15 min and poured onto 100 ml water. The aqueous layer was washed twice with diethyl ether, acidified with 1N aqueous HCl solution and extracted twice with DCM. The combined organic layers were washed with saturated aqueous sodium chloride solution, dried over sodium sulfate, filtered and the solvent was evaporated. The crude residue was stirred with hexane for 15 min, filtered and dried to yield 328 mg (80%) of 4-fluoro-1H-indole-7-carboxylic acid as an off-white solid. MS (ISP) 177.9 $(M-H)^-$.

Example S67

Preparation of 1H-indole-7-carboxylic acid (4-tert-butyl-benzyl)-(2-hydroxy-ethyl)-amide 3.24 g (20 mmol) of 4-tert-butyl benzaldehyde and 1.22 g (20 mmol) of ethanol amine were dissolved in 20 ml methanol and stirred at rt for 30 min. 740 mg (20 mmol) of sodium borohydride were added in portions under nitrogen and the reaction mixture was stirred for 1 h at rt after complete addition. The solvent was evaporated and the residue was dissolved in diethyl ether. The organic layer was washed twice with water, dried over sodium sulfate, filtered and the solvent was evaporated. The residue was dissolved in 20 ml DCM and 3.22 g (20 mol) of 1H-indole-7-carboxylic acid and 3.82 g (20 mmol) of EDC.HCl were added. The reaction mixture was stirred at rt over night. The solvent was evaporated and the residue was dissolved in EtOAc. The organic layer was washed twice with 1N aqueous HCl solution, once with 2N aqueous NaOH solution and once with saturated aqueous NaCl solution, dried over sodium sulfate, filtered and the solvent was evaporated to leave a colorless oil, which on treatment with diethyl ether yielded 2.54 g (36%) product as a white solid after filtration and drying. MS (ISP) 351.3 (M+H)$^+$.

Example S68

Preparation of 3-(4-tert-butyl-benzylamino)-propionic acid tert-butyl ester 3.24 g (20 mmol) of 4-tert-butyl benzaldehyde, 3.63 g (20 mmol) of beta-alanine tert-butylester hydrochloride and 2.22 g (22 mmol) of triethyl amine were dissolved in 20 ml methanol and stirred at rt for 1 h. 1.11 g (30 mmol) of sodium borohydride were added in portions under nitrogen and the reaction mixture was stirred for 2 h at rt after complete addition. Water was added and the solvent was evaporated. The residue was extracted twice with diethyl ether. The combined organic layers were washed twice with saturated aqueous sodium chloride solution, dried over sodium sulfate, filtered and the solvent was evaporated. The residue was purified by column chromatography (silica gel, diethyl ether) to yield 4.62 g (79%) product as a colorless oil. $^{1H}$ NMR (DMSO-d$_6$, 300 MHz): δ 7.34 (d, 2H), 7.25 (d, 2H), 3.76 (s, 2H), 2.86 (t, 2H), 2.45 (t, 2H), 1.44 (s, 9H), 1.31 (s, 9H).

Example S69

Preparation of (4-tert-butyl-benzyl)-(2-pyridin-4-yl-ethyl)-amine 1.22 g (10 mmol) of 2-(4-pyridyl)-ethyl amine and 1.62 g (10 mmol) of 4-tert-butyl benzaldehyde were dissolved in 20 ml methanol and stirred at rt over night. 555 mg (15 mmol) of sodium borohydride were added in portions under cooling. After complete addition the reaction mixture was stirred for 1 h at rt. Water was added and methanol was evaporated. The reaction mixture was extracted twice with diethyl ether. The combined organic layers were washed with water, dried over sodium sulfate, filtered and the solvent was evaporated to yield 2.45 g (91%) product as a light yellow oil. $^{1H}$ NMR (DMSO-d$_6$, 300 MHz): δ 8.49 (d, 2H), 7.34 (d, 2H) 7.21 (d, 2H), 7.13 (d, 2H), 3.77 (s, 2H), 2.93 (t, 2H), 2.81 (t, 2H), 1.31 (s, 9H).

Example S70

Preparation of 5-chloro-1H-indole-7-carboxylic acid 8.26 g (40 mmol) of 2-bromo-4-chloro-aniline were added dropwise at 0° C. to 44 ml (44 mmol) of a 1M solution of boron trichloride in DCM under nitrogen. After complete addition 25 ml of 1,2-dichloroethane were added. After stirring for 30 min at rt 3 ml (48 mmol) of chloro acetonitrile, 5.9 g (44 mmol) of aluminium trichloride and 55 ml 1,2-dichloroethane were added. At 75° C. DCM was distilled off and the reaction mixture was heated to reflux over night. After cooling to rt 80 ml of 2N aqueous solution of HCl solution was added dropwise and the reaction mixture was heated to 80° C. for 1 h. The reaction mixture was cooled to rt and filtered. The solid was washed with methylene chloride. The combined organic layers were washed with water and saturated aqueous NaCl solution, dried over sodium sulfate, filtered and the solvent was evaporated to yield a mixture of starting material and of 1-(2-amino-3-bromo-5-chloro-phenyl)-2-chloro-ethanone.

The crude reaction mixture was dissolved in 90% aqueous dioxane and 0.75 g (20 mmol) of sodium borohydride were added in portions. The reaction mixture was heated to reflux over night. The solvent was evaporated, the residue dissolved in DCM. The organic layer was washed once with 1N aqueous HCl solution, once with saturated aqueous NaHCO$_3$ solution and once with saturated aqueous sodium chloride solution, dried over sodium sulfate, filtered and the solvent was evaporated. The residue was purified by column chromatography (100 g silica gel, heptane/DCM 4:1) to yield 3.37 g (37%) of 7-bromo-5-chloro-1H-indole as yellow crystals. MS (EI) 229.0 (80), 230.9 (100), 233.0 (25) (M)$^+$.

1.15 g (5 mmol) of 7-bromo-5-chloro-1H-indole were dissolved in 30 ml THF. At a temperature of –75° C. under argon 9.4 ml (15 mmol) of a 1.6 M n-butyl lithium solution in hexane were added dropwise. After complete addition the reaction mixture was stirred at 5° C. for 30 min, cooled to –75° C. and 10 g dry ice was added. The reaction mixture was warmed to rt and stirred for 15 min. It was poured onto 100 ml of water and extracted twice with EtOAc. The aqueous layer was acidified with 1N aqueous HCl solution and extracted twice with DCM. The combined organic layers were dried over sodium sulfate, filtered and the solvent was evaporated. The residue was treated with hexane and stirred for 10 min. The precipitate was filtered, washed with hexane and dried to yield 700 mg (72%) of 5-chloro-1H-indole-7-carboxylic acid as a white solid. MS (ISP) 194.0 (M–H)$^-$.

Example S71

Preparation of N'-(4-tert-butyl-benzyl)-N-(4-chloro-phenyl)-N-methyl-ethane-1,2-diamine 1.62 g (10 mmol) of 4-tert-butyl benzaldehyde and 1.85 g (10 mmol) of N-(4-chloro-phenyl)-N-methyl-ethane-1,2-diamine were dissolved in 20 ml methanol and the solution was stirred for 2 h at rt. 567 mg (15 mmol) of sodium borohydride were added in portions under nitrogen. The reaction mixture was stirred at rt over night. Water was added and the solvent was evaporated. The reaction mixture was extracted with diethyl ether and the organic layer was washed with saturated aqueous NaCl solution, dried over sodium sulfate, filtered and the solvent was evaporated to leave the 2.97 g (90%) product as a yellow oil. $^{1H}$ NMR (DMSO-d$_6$, 300 MHz): δ 7.34 (d, 2H), 7.24 (d, 2H), 7.13 (d, 2H), 6.64 (d, 2H), 3.77 (s, 2H), 3.42 (t, 2H), 2.91 (s, 3H), 2.83 (t, 2H), 1.30 (s, 9H).

Example S72

Preparation of N'-(4-tert-butyl-benzyl)-N-ethyl-N-m-tolyl-ethane-1,2-diamine 1.62 g (10 mmol) of 4-tert-butyl benzaldehyde and 1.78 g (10 mmol) of N*1*-ethyl-N*1* -m-tolyl-ethane-1,2-diamine were dissolved in 20 ml methanol and the solution was stirred for 2 h at rt. 567 mg (15 mmol) of sodium borohydride were added in portions under nitrogen. The reaction mixture was stirred at rt over night. Water was added and the solvent was evaporated. The reaction mixture was extracted with diethyl ether and the organic layer was washed with saturated aqueous NaCl solution, dried over sodium sulfate, filtered and the solvent was evaporated to leave the 3.08 g (95%) product as a light yellow oil. $^{1H}$ NMR (DMSO-d$_6$, 300 MHz): δ 7.33 (d, 2H), 7.24 (d, 2H), 7.09 (dd, 1H), 6.51 (m, 3H), 3.78 (s, 2H), 3.42 (t, 2H), 3.34 (q, 2H), 2.85 (t, 2H), 2.29 (s, 3H), 1.31 (s, 9H), 1.11 (t, 3H).

Example S73

Preparation of N-(4-tert-butyl-benzyl)-N'-phenyl-ethane-1,2-diamine 1.62 g (10 mmol) of 4-tert-butyl benzaldehyde and 1.36 g (10 mmol) of N-phenyl ethylene-1,2-diamine were dissolved in 20 ml methanol and the solution was stirred for 2 h at rt. 567 mg (15 mmol) of sodium borohydride were added in portions under nitrogen. The reaction mixture was stirred at rt over night. Water was added and the solvent was evaporated. The reaction mixture was extracted with diethyl ether and the organic layer was washed with saturated aqueous NaCl solution, dried over sodium sulfate, filtered and the solvent was evaporated to leave 2.75 g (97%) product as a light yellow oil. $^{1H}$ NMR (DMSO-d$_6$, 300 MHz): δ 7.35 (d, 2H), 7.24 (d, 2H), 7.17 (t, 2H), 6.70 (t, 1H), 6.62 (d, 2H), 4.15 (br s, 1H), 3.78 (s, 2H), 3.22 (m, 2H), 2.91 (t, 2H), 1.31 (s, 9H).

Example S74

Preparation of 5-chloro-1H-indazole-7-carboxylic acid 2.83 g (20 mmol) of 4-chloro-2-methyl aniline and 1.74 g (22 mmol) of pyridine were dissolved in 20 ml DCM. 3.20 g (20 mmol) of bromine were added dropwise under cooling. The reaction mixture was stirred for 2 h at rt. The solvent was removed and the residue was dissolved in diethyl ether. The organic layer was washed with water, dried over sodium sulfate, filtered and the solvent was evaporated. The crude product was purified by column chromatography (silica gel; diethyl ether/heptane 1:1) to yield 3.91 g (89%) of 2-bromo-4-chloro-6-methyl aniline as a light green solid. $^{1H}$ NMR (CDCl$_3$, 300 MHz): δ 7.30 (s, 1H), 6.99 (s, 1H), 4.04 (br s, 2H), 2.19 (s, 3H).

2.20 g (10 mmol) of 2-bromo-4-chloro-6-methyl aniline were dissolved in 125 ml acetic acid. 0.69 g (10 mmol) of sodium nitrite dissolved in 2 ml water were added dropwise. The reaction mixture was stirred at rt for 4 h. Acetic acid was evaporated and the residue dissolved in EtOAc. The organic layer was washed with water, dried over sodium sulfate, filtered and the solvent was evaporated. The residue was several times evaporated with heptane to yield 2.04 g (88%) of 7-bromo-5-chloro-1H-indazol as a light brown solid. $^{1H}$ NMR (DMSO-d$_6$, 300 MHz): δ 8.23 (s, 1H), 7.91 (s, 1H), 7.67 (s, 1H).

463 mg (2 mmol) of 7-bromo-5-chloro-1H-indazol were dissolved in 12 ml THF. The so-lution was cooled to −78° C. under argon. 3.75 ml (6 mmol) of a 1.6 M butyl lithium solution in hexane were added slowly within 10 min. The reaction mixture was warmed to 5° C. and stirred for 30 min at this temperature. A suspension was obtained, which was cooled to −78° C. Solid carbon dioxide was added and the reaction mixture was warmed to rt. At 10° C. the suspension became a clear solution. The solvent was evaporated and the residue was treated with water and diethyl ether. The aqueous layer was extracted once with diethyl ether, acidified with 1N aqueous HCl solution. A white solid precipitated, which was filtered off and washed with water. The solid was suspended in diethyl ether/heptane in order to remove pentanoic acid. 130 mg (33%) of 5-chloro-1H-indazole-7-carboxylic acid were obtained as a white solid after filtration and drying. MS (ISP) 195.1 (M−H)$^−$.

Example S75

Preparation of 5-fluoro-1H-indol-7-carboxylic acid 1.22 g (5.0 mmol) of 1-bromo-5-fluoro-2-nitrobenzene were dissolved in 50 ml THF. At a temperature of −45° C. under nitrogen 15 ml (15.0 mmol) of a 1M vinyl magnesium bromide solution in THF were added in such a way, that the temperature was kept below −40° C. The resulting dark solution was stirred for 30 min at −40° C. 10 ml of saturated aqueous NH$_4$Cl solution were added and the reaction mixture was warmed to rt. It was extracted twice with diethyl ether. The organic layer was washed with saturated aqueous NaCl solution, dried over sodium sulfate, filtered and the solvent was evaporated. The residue was purified by column chromatography (100 g silica gel, heptane/EtOAc 9:1) to yield 553 mg (52%) 7-bromo-5-fluoro-indol as a light brown oil. $^{1H}$ NMR (CDCl$_3$, 300 MHz): δ 8.30 (br s, 1H), 7.29 (m, 1H), 7.25 (m, 1H), 7.16 (m, 1H), 6.60 (m, 1H).

550 mg (2.57 mmol) of 7-bromo-5-chloro-1H-indol were dissolved in 15.6 ml THF. The solution was cooled to −78° C. under argon. 4.82 ml (7.71 mmol) of a 1.6 M butyl lithium solution in hexane were added slowly within 10 min to keep the temperature below −70° C. The reaction mixture was warmed to 5° C., stirred for 30 min at this temperature and cooled to −78° C. Solid carbon dioxide was added and the reaction mixture was warmed to rt. 100 ml of water was added and the reaction mixture was extracted twice with diethyl ether. The aqueous layer was acidified with 1N aqueous HCl solution and extracted twice with DCM. The organic layer was washed with saturated aqueous NaCl solution, dried over sodium sulfate, filtered and the solvent was evaporated. The residue was stirred with hexane for 15 min and the product was filtered to yield 382 mg (75%) of 5-fluoro-1H-indol-7-carboxylic acid as an off-white solid. MS (EI) 179.0 (M)$^+$.

Example S76

Preparation of 5,6-difluoro-1H-indol-7-carboxylic acid 1.25 ml (2 mmol) of a 1.6 M butyl lithium solution in hexane were diluted with 4 ml THF at −78° C. under nitrogen. 224 mg (2 mmol) of potassium-tert-butylate and then 156 mg (1 mmol) of 5,6-difluoro-1H-indol were added. The reaction was exothermal and an orange solution was obtained, which was stirred for 2 h at −75° C. Solid carbon dioxide was added at that temperature and the reaction mixture was allowed to warm to rt within 30 min. Water was added and the reaction mixture was extracted three times with diethyl ether. The aqueous layer was acidified with 1N aqueous HCl solution and extracted three times with diethyl ether. The combined organic layers were washed with saturated aqueous NaCl solution, dried over sodium sulfate, filtered and the solvent was evaporated. The residue was stirred with n-hexane and a trace of diethyl ether for 15 min and filtered to yield 100 mg (51%) product as a yellow solid. $^{1H}$ NMR (DMSO-d$_6$, 300 MHz): 13.6 (br, 1H), 11.2 (br, 1H), 7.85 (dd, 1H), 7.42 (s, 1H), 6.53 (s, 1H).

Example S77

Preparation of
5-chloro-6-fluoro-1H-indole-7-carboxylic acid 1.46 g (10 mmol) of 4-chloro-3-fluoro-aniline in 3.5 ml 1,2-dichloro ethane were added dropwise at 0° C. within 5 min to 11 ml (11 mmol) of a 1M solution of boron trichloride in DCM under nitrogen. After stirring for 30 min at rt a suspension was obtained to which 0.78 ml (12 mmol) of chloro acetonitrile, 1.47 g (11 mmol) of aluminium trichloride and 15 ml 1,2-dichloroethane were added. At 75° C. DCM was distilled off and the reaction mixture was heated to reflux over night. Additional 0.78 ml (12 mmol) of chloro acetonitrile and 1.47 g (11 mmol) of aluminium trichloride were added and the reaction mixture was heated to reflux for 15 h. After cooling to rt 40 ml of 2N aqueous solution of HCl solution was added dropwise and the reaction mixture was heated to 80° C. for 1 h. The reaction mixture was cooled to rt and extracted three times with methylene chloride. The combined organic layers were washed twice with water, dried over sodium sulfate, filtered and the solvent was evaporated. The residue was purified by column chromatography (100 g silica gel; heptane/diethyl ether 1:1) to yield 1.10 g (50%) of 1-(2-amino-5-chloro-4-fluoro-phenyl)-2-chloro-ethanone as a 3:1 mixture of regioisomers as a yellow solid. $^{1H}$ NMR (CDCl$_3$, 300 MHz): δ 7.69 (d, 1H), 6.47 (br s & d, 3H), 4.59 (s, 2H).

382 mg (1.72 mmol) of 1-(2-amino-5-chloro-4-fluoro-phenyl)-2-chloro-ethanone as a 3:1 mixture of regioisomers were dissolved in 9.5 ml 90% aqueous dioxane and 72 mg (1.89 mmol) of sodium borohydride were added in portions. The reaction mixture was heated to reflux for 1 h, additional 72 mg (1.89 mmol) of sodium borohydride were added and the reaction mixture was heated to reflux over night. The solvent was evaporated, the residue dissolved in DCM. The organic layer was washed once with 1N aqueous HCl solution, once with saturated aqueous NaHCO$_3$ solution and once with saturated aqueous sodium chloride solution, dried over sodium sulfate, filtered and the solvent was evaporated. The residue was purified by column chromatography (25 g silica gel; heptane/DCM 4:1) to yield 153 mg (52%) 5-chloro-6-fluoro-1H-indole as light yellow crystals as a 3:1 mixture of regioisomers (predominantly the wanted one). $^{1H}$ NMR (CDCl$_3$, 300 MHz): δ 8.16 (br, 1H), 7.62 (d, 1H), 7.20 (s, 1H), 7.13 (d, 1H), 6.50 (s, 1H).

1.56 ml (2.49 mmol) of a 1.6 M butyl lithium solution in hexane were diluted with 3.2 ml THF at −78° C. under nitrogen. 211 mg (1.24 mmol) of 5-chloro-6-fluoro-1H-indole as a 3:1 mixture of regioisomers dissolved in 0.8 ml THF were added within 15 min keeping the temperature below −70° C. After 5 min 279 mg (2.49 mmol) of potassium-tert-butylate dissolved in 1 ml THF were added within 15 min. The reaction mixture was stirred for 2 h at −75° C. to give a clear orange solution. Solid carbon dioxide was added at that temperature and the reaction mixture was allowed to warm to rt within 30 min. Water was added and the reaction mixture was extracted twice with diethyl ether. The aqueous layer was acidified with 1N aqueous HCl solution and extracted twice with diethyl ether. The combined organic layers were washed with saturated aqueous NaCl solution, dried over sodium sulfate, filtered and the solvent was evaporated. The residue was stirred with n-hexane and a trace of diethyl ether for 2 h and filtered to yield 121 mg (46 of 5-chloro-6-fluoro-1H-indole-7-carboxylic acid as a light brown solid. $^{1H}$ NMR (DMSO-d$_6$, 300 MHz): δ 13.6 (br, 1H), 11.3 (br, 1H), 8.00 (d, 1H), 7.42 (s, 1H), 6.52 (s, 1H).

Example S78

Preparation of 1H-indole-7-carboxylic acid (4-tert-butyl-2-hydroxy-benzyl)-[2-(4-fluoro-phenyl)-ethyl]-amide A solution of 5.69 g (30 mmol) of titan tetrachloride in 15 ml DCM were added dropwise at 0° C. under nitrogen to 3.76 g (25 mmol) of 3-tert-butylphenol dissolved in 75 ml DCM. After stirring for 30 min 3.16 g (27.5 mmol) of dichloromethyl methyl ether was added. The reaction mixture was stirred for 2 h at 0° C. Carefully 30 ml of 1N aqueous HCl solution and then 90 ml water were added. The reaction mixture was extracted twice with DCM. The combined organic layers were washed with saturated aqueous NaCl solution, dried over sodium sulfate, filtered and the solvent was evaporated. The residue was purified by column chromatography (250 g silica gel, DCM) to yield 2.32 g (52%) 4-tert-butyl-2-hydroxy benzaldehyde as a light yellow oil. $^{1H}$ NMR (DMSO-d$_6$, 300 MHz): δ 10.62 (br s, 1H), 10.18 (s, 1H), 7.61 (d, 1H), 7.04 (d, 1H), 6.98 (s, 1H).

1.83 g (13 mmol) of 2-(4-fluoro-phenyl) ethyl amine were added to 2.32 g (13 mmol) of 4-tert-butyl-2-hydroxy benzaldehyde dissolved in 130 ml methanol. The reaction mixture was stirred at rt over night under nitrogen. 492 mg (13 mmol) of sodium borohydride were added in portions and the reaction mixture was stirred for 2 h at rt. The solvent was evaporated and the residue was dissolved in DCM. The organic layer was washed with water and with saturated aqueous NaCl solution, dried over sodium sulfate, filtered and the solvent was evaporated. The residue was purified by column chromatography (250 g silica gel; DCM, then DCM/methanol 19:1) to yield 3.26 g (83%) of 5-tert-butyl-2-{[2-(4-fluoro-phenyl)-ethylamino]-methyl}-phenol as a yellow viscous oil. $^{1H}$ NMR (DMSO-d$_6$, 300 MHz): δ 7.24 (t, 2H), 7.09 (t, 2H), 6.95 (d, 1H), 6.71 (d, 1H), 6.68 (s, 1H), 3.76 (s, 2H), 1.23 (s, 9H).

1.69 g (8.8 mmol) of EDC.HCl were added to 1.46 g (8.8 mmol) of 1H-indol-7-carboxylic acid and 2.41 g (8.8 mmol) of 5-tert-butyl-2-{[2-(4-fluoro-phenyl)-ethylamino]-methyl}-phenol dissolved in 80 ml DCM. The reaction mixture was stirred at rt over night, diluted with DCM and washed once with water and once with saturated aqueous NaCl solution, dried over sodium sulfate, filtered and the solvent was evaporated. The residue was purified by column chromatography (250 g silica gel; heptane/EtOAc 7:3) to yield 2.9 g (82%) 1H-indole-7-carboxylic acid (4-tert-butyl-2-hydroxy-benzyl)-[2-(4-fluoro-phenyl)-ethyl]-amide as a colorless foam. MS (ISP) 445.3 (M+H)$^+$.

Example S79

Preparation of [2-(4-fluoro-phenyl)-ethyl]-(4-trifluoromethyl-benzyl)-amine 562 mg (4 mmol) of 2-(4-fluoro-phenyl) ethyl amine were added to 733 mg (4 mmol) of 4-trifluoromethyl benzaldehyde dissolved in 40 ml methanol. The reaction mixture was stirred at rt over night under nitrogen. 151 mg (4 mmol) of sodium borohydride were added in portions and the reaction mixture was stirred for 2 h at rt. The solvent was evaporated and the residue was dissolved in DCM. The organic layer was washed with water and with saturated aqueous NaCl solution, dried over sodium sulfate, filtered and the solvent was evaporated. The residue was purified by column chromatography (60 g silica gel; DCM/methanol 19:1) to yield 1.16 g (98%) of [2-(4-fluoro-phenyl)-ethyl]-(4-trifluoromethyl-benzyl)-amine as a light yellow oil. $^{1H}$ NMR (DMSO-$d_6$, 300 MHz): δ 7.65 (d, 2H), 7.52 (d, 2H), 7.21 (dd, 2H), 7.06 (dd, 2H), 3.79 (s, 2H), 2.70 (s, 4H).

Example S80

Preparation of (4-tert-butyl-2-chloro-benzyl)-[2-(4-fluoro-phenyl)-ethyl]-amine 1.50 g (10 mmol) of 4-tert.-butyl phenol were dissolved in 40 ml acetonitrile. 1.34 g (10 mmol) of NCS were added and the reaction mixture was stirred at rt over night. The reaction mixture was heated for 1.5 h to reflux. Then additional 134 mg (1 mmol) of NCS were added and the reaction mixture was heated to reflux for 2 h. The solvent was evaporated and the residue was stirred with diethyl ether for 15 min. The solid was filtered off and the filtrate was evaporated. The residue was purified by column chromatography (100 silica gel, DCM) to yield 1.49 g (81%) of 4-tert.-butyl-2-chloro-phenol as a colorless viscous oil. $^{1H}$ NMR (DMSO-$d_6$, 300 MHz): δ 9.85 (s, 1H), 7.26 (s, 1H), 7.14 (d, 2H), 6.88 (d, 2H), 1.22 (s, 9H).

To a solution of 1.49 g (8.05 mmol) of 4-tert-butyl-2-chloro-phenol and 1.22 g (12.1 mmol) of triethyl amine in 15 ml DCM was added under nitrogen at 0° C. slowly a solution of 2.90 g (10.1 mmol) of trifluoro-methansulfonic acid anhydride in 1.7 ml DCM. The dark red solution was stirred for 1 h at 0° C. and at rt over night. The reaction mixture was diluted with DCM, washed with water, once with 1N aqueous HCl solution and once with saturated aqueous NaCl solution, dried over sodium sulfate, filtered and the solvent was evaporated to yield 2.0 g (78%) of trifluoro-methanesulfonic acid 4-tert-butyl-2-chloro-phenyl ester as a light yellow oil. $^{1H}$ NMR (DMSO-$d_6$, 300 MHz): δ 7.75 (s, 1H), 7.55 (s, 2H), 1.30 (s, 9H).

317 mg (1 mmol) of trifluoro-methanesulfonic acid 4-tert-butyl-2-chloro-phenyl ester and 281 mg (2 mmol) of 2-(4-fluoro-phenyl) ethyl amine were dissolved in 5 ml DMF. Under argon at rt 6.7 mg (0.03 mmol) of palladium acetate and 12.4 mg (0.03 mmol) of dppp were added. The reaction mixture was evacuated and charged with carbon monoxide gas three times. The reaction mixture was heated to 70° C. under a carbon monoxide atmosphere for 1 h. Water was added and the reaction mixture was extracted twice with EtOAc. The combined organic layers were washed with 1N aqueous HCl solution, once with saturated aqueous NaCl solution, dried over sodium sulfate, filtered and the solvent was evaporated. The residue was purified by column chromatography (45 g silica gel; heptane/EtOAc 7:3) to yield 198 mg (59%) of 4-tert-butyl-2-chloro-N-[2-(4-fluoro-phenyl)-ethyl]-benzamide as a white solid. $^{1H}$ NMR (DMSO-$d_6$, 300 MHz): δ 8.41 (t, 1H), 7.42 (s, 1H), 7.39 (d, 1H), 7.30 (d, 1H), 7.28 (t, 2H), 7.12 (t, 2H), 3.43 (q, 2H), 2.81 (t, 2H), 1.27 (s, 1H).

1.78 ml (1.78 mmol) of a 1M borane-THF complex solution in THF were added under nitrogen at rt to 198 mg (0.59 mmol) of 4-tert-butyl-2-chloro-N-[2-(4-fluoro-phenyl)-ethyl]-benzamide dissolved in 3 ml THF. The reaction mixture was heated to reflux over night. At rt 5 ml 2N aqueous HCl solution were added and the reaction mixture was heated to reflux for 3 h. The reaction mixture was basified with 7 ml 2N aqueous NaOH solution and extracted twice with diethyl ether. The combined organic layers were washed with saturated aqueous NaCl solution, dried over sodium sulfate, filtered and the solvent was evaporated. The residue was purified by column chromatography (5 g silica gel; DCM/methanol 19:1) to yield 141 mg (67%) of (4-tert-butyl-2-chloro-benzyl)-[2-(4-fluoro-phenyl)-ethyl]-amine as a yellow oil. $^{1H}$ NMR (DMSO-$d_6$, 300 MHz): δ 7.40-7.22 (m, 5H), 7.09 (t, 2H), 3.74 (s, 2H), 2.73 (s, 4H), 1.26 (s, 9H).

Example S81

Preparation of (4-tert-butyl-2-chloro-benzyl)-[2-(3-trifluoromethyl-phenyl)-ethyl]-amine 633 mg (2 mmol) of trifluoro-methanesulfonic acid 4-tert-butyl-2-chloro-phenyl ester (prepared as described in example S80) and 416 mg (2.2 mmol) of 2-(3-trifluoromethyl-phenyl) ethyl amine were dissolved in 10 ml DMF. Under argon at rt 13.4 mg (0.06 mmol) of palladium acetate and 24.8 mg (0.06 mmol) of dppp were added. The reaction mixture was evacuated and charged with carbon monoxide gas three times. The reaction mixture was heated to 70° C. under a carbon monoxide atmosphere for 1 h. Water was added and the reaction mixture was extracted twice with EtOAc. The combined organic layers were washed with 1N aqueous HCl solution, once with saturated aqueous NaCl solution, dried over sodium sulfate, filtered and the solvent was evaporated. The residue was purified by column chromatography (45 g silica gel, heptane/EtOAc 7:3) to yield 298 mg (39%) of 4-tert-butyl-2-chloro-N-[2-(3-trifluoromethyl-phenyl)-ethyl]-benzamide as a light yellow solid. $^{1H}$ NMR (DMSO-$d_6$, 300 MHz): δ 8.43 (t, 1H), 7.61-7.55 (m, 4H), 7.41 (s, 1H), 7.36 (d, 2H), 7.22 (d, 1H), 3.50 (q, 2H), 2.93 (t, 2H), 1.27 (s, 9H).

2.31 ml (2.31 mmol) of a 1M borane-THF complex solution in THF were added under nitrogen at rt to 295 mg (0.77 mmol) of 4-tert-butyl-2-chloro-N-[2-(3-trifluoromethyl-phenyl)-ethyl]-benzamide dissolved in 4 ml THF. The reaction mixture was heated to reflux over night. At rt 7 ml 2N aqueous HCl solution were added and the reaction mixture was heated to reflux for 3 h. The reaction mixture was basified with 7 ml 2N aqueous NaOH solution and extracted twice with diethyl ether. The combined organic layers were washed with saturated aqueous NaCl solution, dried over sodium sulfate, filtered and the solvent was evaporated. The residue was purified by column chromatography (45 g silica gel; DCM/methanol 19:1) to yield 256 mg (81%) (4-tert-butyl-2-chloro-benzyl)-[2-(3-trifluoromethyl-phenyl)-ethyl]-amine as a yellow oil. $^{1H}$ NMR (DMSO-$d_6$, 300 MHz): δ 7.58-7.52 (m, 5H), 7.6 (d, 1H), 7.34 (s, 1H), 7.30 (d, 1H), 3.75 (s, 2H), 2.81 (m, 4H), 1.26 (s, 1H).

Example S82

Preparation of (4-tert-butyl-2-chloro-benzyl)-[2-(3-trifluoromethoxy-phenyl)-ethyl]-amine 633 mg (2 mmol) of trifluoro-methanesulfonic acid 4-tert-butyl-2-chloro-phenyl ester (prepared as described in example S80), 532 mg (2.2 mmol) of 2-(3-trifluoromethoxy-phenyl) ethyl amine hydrochloride and 223 mg (2.2 mmol) of triethyl amine were dissolved in 10 ml DMF. Under argon at rt 13.4 mg (0.06 mmol) of palladium acetate and 24.8 mg (0.06 mmol) of dppp were added. The reaction mixture was evacuated and charged with carbon monoxide gas three times. The reaction mixture was heated to 70° C. under a carbon monoxide atmosphere for 1 h. Water was added and the reaction mixture was extracted twice with EtOAc. The combined organic layers were washed with 1N aqueous HCl solution, once with saturated aqueous NaCl solution, dried over sodium sulfate, filtered and the solvent was evaporated. The residue was purified by column chromatography (60 g silica gel; heptane/EtOAc 7:3) to yield 82 mg (10%) of 4-tert-butyl-2-chloro-N-[2-(3-trifluoromethoxy-phenyl)-ethyl]-benzamide as a light yellow solid. $^{1H}$ NMR (DMSO-d$_6$, 300 MHz): δ 8.43 (t, 1H), 7.44-7.41 (m, 2H), 7.37 (d, 1H), 7.31 (d, 1H), 7.26-7.21 (m, 3H), 3.48 (q, 2H), 2.88 (t, 2H), 1.27 (s, 9H).

0.60 ml (0.60 mmol) of a 1M borane-THF complex solution in THF were added under nitrogen at rt to 80 mg (0.20 mmol) of 4-tert-butyl-2-chloro-N-[2-(3-trifluoromethoxy-phenyl)-ethyl]-benzamide dissolved in 1 ml THF. The reaction mixture was heated to reflux over night. At rt 2 ml 2N aqueous HCl solution were added and the reaction mixture was heated to reflux for 3 h. The reaction mixture was basified with 3 ml 2N aqueous NaOH solution and extracted twice with diethyl ether. The combined organic layers were washed with saturated aqueous NaCl solution, dried over sodium sulfate, filtered and the solvent was evaporated. The residue was purified by column chromatography (25 g silica gel; DCM/methanol 19:1) to yield 60 mg (78%) (4-tert-butyl-2-chloro-benzyl)-[2-(3-trifluoromethoxy-phenyl)-ethyl]-amine as a colorless oil. $^{1H}$ NMR (DMSO-d$_6$, 300 MHz): δ 7.40-7.19 (m, 7H), 3.74 (s, 2H), 2.78 (s, 4H), 1.26 (s, 9H).

Example S83

Preparation of (4-tert-butyl-2-chloro-benzyl)-[2-(3,4-dichloro-phenyl)-ethyl]-amine 363 mg (1.15 mmol) of trifluoro-methanesulfonic acid 4-tert-butyl-2-chloro-phenyl ester (prepared as described in example S80) and 440 mg (2.29 mmol) of 2-(3,4-dichloro-phenyl) ethyl amine were dissolved in 5.8 ml DMF. Under argon at rt 7.7 mg (0.035 mmol) of palladium acetate and 14.1 mg (0.035 mmol) of dppp were added. The reaction mixture was evacuated and charged with carbon monoxide gas three times. The reaction mixture was heated to 70° C. under a carbon monoxide atmosphere for 1 h. Water was added and the reaction mixture was extracted twice with EtOAc. The combined organic layers were washed with 1N aqueous HCl solution, once with saturated aqueous NaCl solution, dried over sodium sulfate, filtered and the solvent was evaporated. The residue was purified by column chromatography (45 g silica gel; heptane/EtOAc 7:3) to yield 255 mg (58%) of 4-tert-butyl-2-chloro-N-[2-(3,4-dichloro-phenyl)-ethyl]-benzamide as a white solid. $^{1H}$ NMR (DMSO-d$_6$, 300 MHz): δ 8.41 (t, 1H), 7.55 (d, 1H), 7.54 (s, 1H), 7.42 (s, 1H), 7.38 (d, 1H), 7.28-7.23 (m, 2H), 3.46 (q, 2H), 2.83 (t, 2H), 1.27 (s, 9H).

1.95 ml (1.95 mmol) of a 1M borane-THF complex solution in THF were added under nitrogen at rt to 250 mg (0.65 mmol) of 4-tert-butyl-2-chloro-N-[2-(3,4-dichloro-phenyl)-ethyl]-benzamide dissolved in 3.2 ml THF. The reaction mixture was heated to reflux for 4 h. At rt 6 ml 2N aqueous HCl solution were added and the reaction mixture was heated to reflux for 3 h. The reaction mixture was basified with 7 ml 2N aqueous NaOH solution and extracted twice with diethyl ether. The combined organic layers were washed with saturated aqueous NaCl solution, dried over sodium sulfate, filtered and the solvent was evaporated. The residue was purified by column chromatography (45 g silica gel; DCM/methanol 19:1) to yield 215 mg (89%) of (4-tert-butyl-2-chloro-benzyl)-[2-(3,4-dichloro-phenyl)-ethyl]-amine as a light yellow oil. $^{1H}$ NMR (DMSO-d$_6$, 300 MHz): δ 7.46-7.43 (m, 2H), 7.30 (d, 1H), 7.28 (s, 1H), 7.23 (d, 1H), 7.15 (d, 1H), 3.67 (s, 2H), 2.67 (s, 4H), 1.19 (s, 9H).

Example S84

Preparation of (4-tert-butyl-2-fluoro-benzyl)-[2-(3-trifluoromethyl-phenyl)-ethyl]-amine Isobutylene was bubbled through a mixture of 1.12 g (10 mmol) of 2-fluorophenol in 3 ml benzene and 0.1 ml concentrated sulfuric acid for 20 min. The reaction mixture was stirred over night at rt. Then, isobutylene was again bubbled through for 15 min and the reaction mixture was heated in an autoclave to 60° C. over night. The reaction mixture was diluted with toluene, extracted twice with 1N aqueous NaOH solution. The aqueous layer was acidified with 2N aqueous HCl solution and extracted twice with diethyl ether. The combined organic layers were washed with saturated aqueous NaCl solution, dried over sodium sulfate, filtered and the solvent was evaporated to yield 889 mg of a colorless oil consisting of the product and starting material.

The crude product was dissolved in 8.8 ml DCM. At 0° C. under nitrogen 794 mg (7.85 mmol) of triethyl amine and 1.88 g (6.53 mmol) of trifluoro-methane-sulfonic acid anhydride dissolved in 1.1 ml DCM were added. The reaction mixture was stirred for 1 h at 0° C. and at rt over night, diluted with DCM and washed once with water and once with saturated aqueous NaCl solution, dried over sodium sulfate, filtered and the solvent was evaporated. The residue was purified twice by column chromatography (100 g silica gel; heptane/EtOAc 9:1) to yield 885 mg (30%) of trifluoro-methanesulfonic acid 4-tert-butyl-2-fluoro-phenyl ester as a yellow oil. $^{1H}$ NMR (DMSO-d$_6$, 300 MHz): δ 7.64-7.56 (m, 2H), 7.39 (d, 1H), 1.29 (s, 9H).

880 mg (2.93 mmol) of trifluoro-methanesulfonic acid 4-tert-butyl-2-fluoro-phenyl ester and 1.13 g (5.86 mmol) of 2-(3-trifluoromethyl-phenyl) ethyl amine were dissolved in 15 ml DMF. Under argon at rt 19.7 mg (0.0.88 mmol) of palladium acetate and 36.2 mg (0.088 mmol) of dppp were added. The reaction mixture was evacuated and charged with carbon monoxide gas three times. The reaction mixture was heated to 80° C. under a carbon monoxide atmosphere for 1 h. Water was added and the reaction mixture was extracted twice with EtOAc. The combined organic layers were washed with 1N aqueous HCl solution, once with saturated aqueous NaCl solution, dried over sodium sulfate, filtered and the solvent was evaporated. The residue was purified by column chromatography (60 g silica gel; heptane/EtOAc 7:3) to yield 676 mg (63%) of 4-tert-butyl-2-fluoro-N-[2-(3-trifluoromethyl-phenyl)-ethyl]-benzamide as a yellow viscous oil. $^{1H}$ NMR (DMSO-d$_6$, 300 MHz): δ 8.28 (t, 1H), 7.60-7.55 (m, 4H), 7.47 (t, 1H), 7.28-7.22 (m, 2H), 3.51 (q, 2H), 2.94 (t, 2H), 1.27 (s, 9H).

5.31 ml (5.31 mmol) of a 1M borane-THF complex solution in THF were added under nitrogen at rt to 650 mg (1.77 mmol) of 4-tert-butyl-2-fluoro-N-[2-(3-trifluoromethyl-phenyl)-ethyl]-benzamide dissolved in 8.9 ml THF. The reaction mixture was heated to reflux over night. At rt 15 ml 2N aqueous HCl solution were added and the reaction mixture was heated to reflux for 3 h. The reaction mixture was basified with 17 ml of 2N aqueous NaOH solution and extracted twice with diethyl ether. The combined organic layers were washed with saturated aqueous NaCl solution, dried over sodium sulfate, filtered and the solvent was evaporated. The residue was purified by column chromatography (60 g silica gel; DCM/methanol 19:1) to yield 562 mg (89%) of (4-tert-butyl-2-fluoro-benzyl)-[2-(3-trifluoromethyl-phenyl)-ethyl]-amine as a light yellow oil. $^{1}H$ NMR (DMSO-$d_6$, 300 MHz): δ 7.50-7.46 (m, 2H), 7.22 (t, 1H), 7.08-7.01 (m, 2H), 3.63 (s, 2H), 2.72 (m, 4H), 1.19 (s, 9H).

Example S85

Preparation of
5-chloro-2-methyl-1H-indole-7-carboxylic acid

Preparation of 2-amino-5-chlorobenzoic acid
methyl ester

To a suspension of 5-chloroisatoic anhydride (10 g, 50.61 mmol) in methanol (200 ml) was added DMAP (615 mg, 5.03 mmol) and the reaction mixture was heated to reflux for 3 h. The reaction mixture was cooled to rt and concentrated in vacuo. The residue was dissolved in EtOAc and washed with 0.1M HCl solution (3×), brine, dried over MgSO$_4$, filtered and concentrated in vacuo to give the desired product (9.25 g, 97%) as a white solid which did not require further purification. $^{1}H$ NMR (DMSO-$d_6$, 300 MHz): δ 7.64 (d, J=2.5 Hz, 1H), 7.30 (dd, J=2.5, 9.0 Hz, 1H), 6.82 (d, J=9.0 Hz, 1H), 6.78 (br s, 2H), 3.79 (s, 3H).

Preparation of 2-amino-5-chloro-3-iodo-benzoic
acid methyl ester

To a solution of 2-amino-5-chlorobenzoic acid methyl ester (1.10 g, 5.93 mmol) in acetic acid (20 ml) was added N-iodosuccinimide (1.47 g, 6.52 mmol) in small portions and the reaction mixture was stirred overnight at rt. The reaction mixture was diluted with ethyl acetate and washed with 1N NaOH solution, Na$_2$S$_2$O$_3$ solution, and brine, dried (MgSO$_4$), filtered and concentrated in vacuo to give a residue which was purified by flash column chromatography (EtOAc:cyclohexane 1:9-1:4) to give the desired iodide (1.64 g, 89%) as a cream colored solid. $^{1}H$ NMR (DMSO-$d_6$, 300 MHz): δ 7.93 (d, J=2.5 Hz, 1H), 7.76 (d, J=2.5 Hz, 1H), 6.73 (br s, 2H), 3.83 (s, 3H).

Preparation of
2-amino-5-chloro-3-prop-1-ynylbenzoic acid methyl
ester

Propyne (excess ca 3 ml) was condensed onto a cold (−78° C.) solution of 2-amino-5-chloro-3-iodobenzoic acid methyl ester (500 mg, 1.61 mmol) in triethylamine (10 ml) in a Parr pressure reaction vessel. To this solution was added copper (I) iodide and bis(triphenylphosphine)palladium (II) chloride and the pressure tube was then sealed and stirred at rt for 4 h. The solvent was then removed in vacuo and the residue was purified by flash column chromatography (9:1 cyclohexane:EtOAc) to give 2-amino-5-chloro-3-prop-1-ynylbenzoic acid methyl ester (340 mg, 95%) as an off white solid. $^{1}H$ NMR (CDCl$_3$, 300 MHz): δ 7.76 (d, J=2.5 Hz, 1H), 7.33 (d, J=2.5 Hz, 1H), 6.37 (br s, 2H), 3.87 (s, 3H), 2.13 (s, 3H).

Preparation of
5-chloro-2-methyl-1H-indole-7-carboxylic acid
methyl ester

To a cold (−10° C.) solution of t-BuOK (30 mg, 0.27 mmol) in 4 ml NMP was added a solution of 2-amino-5-chloro-3-prop-1-ynylbenzoic acid methyl ester (46 mg, 0.21 mmol) in NMP (2 ml). The reaction mixture was slowly warmed to rt and stirring was continued for 1 h. Water and EtOAc were added and organic phase was separated, washed with brine, dried (MgSO$_4$), filtered and concentrated in vacuo to give a residue which was purified by flash column chromatography (9:1 cyclohexane:EtOAc) to give 5-chloro-2-methyl-1H-indole-7-carboxylic acid methyl ester (25 mg, 54%) as a light yellow solid. MS (ISP) 222.3 (M+H)$^+$.

Preparation of
5-chloro-2-methyl-1H-indole-7-carboxylic acid

To a solution of 5-chloro-2-methyl-1H-indole-7-carboxylic acid methyl ester (30 mg, 0.13 mmol) in MeOH (5 ml) was added 1N NaOH$_{(aq)}$ (268 µl, 0.27 mmol) and the reaction mixture was refluxed for 2 h. The reaction mixture was concentrated in vacuo and water was added. The aqueous layer was acidified to pH3 using 1N HCl and the aqueous layer was extracted with EtOAc. The organic layer was dried (MgSO$_4$), filtered and concentrated in vacuo to give the desired product (20 mg, 71%) which did not require further purification. MS (ISP) 208.1 (M−H)$^-$.

Example S86

Preparation of
5-chloro-2-ethyl-1H-indole-7-carboxylic acid

Preparation of
2-amino-3-but-1-ynyl-5-chlorobenzoic acid methyl
ester

The title compound was synthesized in analogy to 2-amino-5-chloro-3-prop-1-ynylbenzoic acid methyl ester (described in example S85) using 1-butyne (excess ca 3 ml), 2-amino-5-chloro-3-iodo-benzoic acid methyl ester (prepared as described in example S85) (430 mg, 1.38 mmol), copper (I) iodide (19 mg, 0.10 mmol) and bis(triphenylphosphine) palladium (II) chloride (71 mg, 0.10 mmol) in triethylamine (10 ml). The final compound was purified by flash column chromatography (9:1 cyclohexane:EtOAc) to give 2-amino-3-but-1-ynyl-5-chlorobenzoic acid methyl ester (120 mg, 37%) as a yellow oil. $^{1}H$ NMR (CDCl$_3$, 300 MHz): δ 7.76 (d, J=2.5 Hz, 1H), 7.35 (d, J=2.5 Hz, 1H), 6.37 (br s, 2H), 3.87 (s, 3H), 2.49 (q, J=7.5 Hz, 2H), 1.27 (t, J=7.5 Hz, 3H).

Preparation of
5-chloro-2-ethyl-1H-indole-7-carboxylic acid
methyl ester

To a solution of 2-amino-3-but-1-ynyl-5-chlorobenzoic acid methyl ester (82 mg, 0.35 mmol) in MeCN was added palladium(II)chloride (3 mg, 0.02 mmol) and the reaction mixture was immersed into a preheated oil bath and refluxed for 20 min. The solvent was removed in vacuo and the residue was dissolved in ether and filtered through a short pad of silica. The resulting residue was purified by flash column chromatography (1:9 EtOAc:cyclohexane) to give the desired product (78 mg, 95%) as a light yellow solid. $^{1}H$ NMR (CDCl$_3$, 300 MHz): δ 9.56 (br s, 1H), 7.74 (s, 1H), 7.67 (s, 1H), 6.22 (s, 1H), 3.97 (s, 3H), 2.82 (q, J=7.5 Hz, 2H), 1.38 (t, J=7.5 Hz, 3H).

Preparation of
5-chloro-2-ethyl-1H-indole-7-carboxylic acid

The title compound was synthesized in analogy to 5-chloro-2-methyl-1H-indole-7-carboxylic acid (described in example S85) using 5-chloro-2-ethyl-1H-indole-7-carboxylic acid methyl ester (80 mg, 0.34 mmol) and 1N NaOH$_{(aq)}$ (505 μl, 0.51 mmol) in MeOH (5 ml). The desired product (74 mg, 98%) was isolated without further purification. MS (ISP) 222.3 (M−H)$^-$.

Example S87

Preparation of [4-(1-methylcyclopropyl)-benzyl]-[2-(3-trifluoromethylphenyl)-ethyl]-amine Preparation of 1-bromo-4-isopropenylbenzene To a solution of triphenylphosphonium bromide (17.94 g, 50.24 mmol) in DMSO (10 ml) was added n-BuLi (39.25 ml, 1.6M solution in hexane, 62.80 mmol). The solution was stirred at rt for 1 h and to this was added a solution of 4-bromoacetophenone (10.00 g, 50.24 mmol) in DMSO (4 ml). The reaction mixture was then stirred at rt overnight and then quenched with water and the product was extracted with pentane. The organic layers were combined washed with brine, dried (MgSO$_4$), filtered and concentrated in vacuo to give a residue which was purified by filtration through a short pad of silica using pentane as eluant to give 1-bromo-4-isopropenylbenzene (5.23 g, 53%) as a colorless oil. $^1H$ NMR (CDCl$_3$, 300 MHz): δ 7.45 (d, J=9.0 Hz, 2H), 7.32 (d, J=9.0 Hz, 2H), 5.36 (m, 1H), 5.10 (m, 1H), 2.12 (m, 3H).

Preparation of
1-bromo-4-(1-methylcyclopropyl)-benzene

To a solution of diethyl zinc (20.30 ml, 1M solution in hexane, 20.30 mmol) in DCM (25 ml) at 0° C. was added a solution of trifluoroacetic acid (1.56 ml, 20.30 mmol) in DCM (10 ml) dropwise. The mixture was stirred at 0° C. for 20 min and then a solution of CH$_2$I$_2$ (1.64 ml, 20.30 mmol) in DCM (10 ml) was added. After stirring for an additional 20 min a solution of 1-bromo-4-isopropenylbenzene (346 mg, 1.76 mmol) in DCM (10 ml) was added. The reaction mixture was slowly warmed to rt and stirring was continued for 16 h. Pentane was added and the mixture was washed with 1M HCl, sat. NaHCO$_3$, sat. Na$_2$SO$_3$ and brine. The organic layer was dried (MgSO$_4$), filtered, concentrated in vacuo to give a residue which was purified by flash column chromatography (100% pentane). The product (2.12 g, 86%) was isolated as a 4:1 mixture of product to methyleneiodide as a colorless oil. $^1H$ NMR (CDCl$_3$, 300 MHz): δ 7.38 (d, J=8.5 Hz, 2H), 7.12 (d, J=8.5 Hz, 2H), 1.37 (s, 3H), 0.84-0.79 (m, 2H), 0.76-0.71 (m, 2H).

Preparation of
4-(1-methylcyclopropyl)-benzaldehyde

The title compound was synthesized in analogy to 4-cyclopropyl benzaldehyde (described in example S53) using 1-bromo-4-(1-methylcyclopropyl)-benzene (2.10 g, 9.95 mmol), nBuLi (9.33 ml, 1.6M solution in hexane, 14.92 mmol) and DMF (3.87 ml, 49.74 mmol). The isolated residue was purified by flash column chromatography (1:9 ether:pentane) to give 4-(1-methylcyclopropyl)-benzaldehyde (1.28 g, 80%) as a colorless oil. $^1H$ NMR (CDCl$_3$, 300 MHz): 9.96 (s, 1H), 7.79 (d, J=8.5 Hz, 2H), 7.37 (d, J=8.5 Hz, 2H), 1.46 (s, 1H), 0.98-0.93 (m, 2H), 0.90-0.84 (m, 2H).

Preparation of [4-(1-methylcyclopropyl)-benzyl]-[2-(3-trifluoromethylphenyl)-ethyl]-amine The title compound was synthesized in analogy to (4-cyclopropylbenzyl)-[2-(4-fluoro-3-trifluoromethylphenyl)-ethyl]-amine (described in example S53) using 4-(1-methylcyclo-propyl)-benzaldehyde (150 mg, 0.94 mmol), 2-(3-trifluoromethylphenyl)-ethylamine (177 mg, 0.94 mmol) and sodium borohydride (53 mg, 1.40 mmol). The isolated residue was purified by flash column chromatography (2%-5% MeOH in EtOAc) to give the desired product (195 mg, 62%) as a colorless oil. MS (ISP) 334.3 (M+H)$^+$.

Example S88

Preparation of [1-(4-tert-butylphenyl)-ethyl]-[2-(3-trifluoromethylphenyl)-ethyl]-amine A mixture of 4-tert-butylbenzaldehyde (200 mg, 1.23 mmol), 3-(trifluoromethyl) phenethylamine (233 mg, 1.23 mmol) and molecular sieves (1 g, 4 Å) in diethyl ether (10 ml) was stirred at rt overnight. The mixture was filtered through celite® and concentrated in vacuo to give the corresponding imine which was dissolved in dry toluene. The solution was cooled to −78° C. and BF$_3$×OEt$_2$ (250 μl, 1.97 mmol) was added. The mixture was stirred at −78° C. for 10 min and then methyllithium (1.54 ml, 1.6 M solution in ether, 2.47 mmol) was added dropwise and stirring was continued at −78° C. for 6 h. The reaction mixture was then quenched with sat. NaHCO$_3$ and the mixture was diluted with EtOAc and washed with brine. The organic phase was dried (MgSO$_4$), filtered and concentrated in vacuo to give a residue which was purified by flash column chromatography to give the desired [1-(4-tert-butylphenyl)-ethyl]-[2-(3-trifluoromethylphenyl)-ethyl]-amine (412 mg, 95%) as a light yellow oil. MS (ISP) 350.5 (M+H)$^+$.

Example S89

Preparation of [4-(1-methoxycyclopropyl)-benzyl]-[2-(3-trifluoromethyl-phenyl)-ethyl]-amine Preparation of
1-bromo-4-(1-methoxycyclopropyl)-benzene Trimethyl orthoformate (2.75 ml, 25.12 mmol) was added to 4-bromoacetophenone (5.00 g, 25.12 mmol) followed by p-toluenesulfonic acid (239 mg, 1.26 mmol). The reaction mixture was stirred at rt for 30 h. The methyl formate and methanol formed in the reaction were distilled off slowly for at least 4 h at 85° C. until no further methanol was being formed. The reaction mixture was cooled to rt and a few drops of triethylamine were added. The crude residue was then purified by flash column chromatography (5% EtOAc, 1% Et$_3$N in cyclohexane) to give a mixture of 1-bromo-4-(1-methoxyvinyl)-benzene and 1-bromo-4-(1,1-dimethoxyethyl)-benzene in a 1:1 mixture. The products were not separated and reacted in the next step as a mixture.

To a solution of 2,4,6-trichlorophenol (1.90 g, 9.64 mmol) in methylene chloride (70 ml) at −40° C. was added diethyl zinc (9.64 ml, 1M solution in hexane, 9.64 mmol). The mixture was stirred at −40° C. for 20 min and then CH$_2$I$_2$ (778 μl, 9.64 mmol) was added. After stirring for an additional 20 min, 1-bromo-4-(1-methoxyvinyl)-benzene (1.37 g, 6.43 mmol) was added. The reaction mixture was slowly warmed to rt and stirring was continued for 16 h. Pentane was added and the mixture was washed with 1M HCl, sat. NaHCO$_3$, sat. Na$_2$SO$_3$ and brine. The organic layer was dried (MgSO$_4$), filtered, concentrated in vacuo to give a crude residue which was purified by flash column chromatography (2% ethylacetate in cyclohexane-10% ethylacetate in cyclohexane) to give 1-bromo-4-(1-methoxycyclopropyl)-benzene (880 mg, 60%) as a yellow oil. $^{1H}$ NMR (CDCl$_3$, 300 MHz): δ 7.46 (d, J=8.5 Hz, 2H), 7.18 (d, J=8.5 Hz, 2H), 3.21 (s, 3H), 1.21-1.17 (m, 2H), 0.95-0.91 (m, 2H).

Preparation of
4-(1-methoxycyclopropyl)-benzaldehyde

The title compound was synthesized in analogy to 4-cyclopropyl benzaldehyde (described in example S53) using 1-bromo-4-(1-methoxycyclopropyl)-benzene (250 mg, 1.10 mmol), n-BuLi (722 μl, 1.6M solution in hexane, 1.16 mmol) and DMF (171 μl, 2.20 mmol). The isolated residue was purified by flash column chromatography (1:9 ether:pentane) to give 4-(1-methoxycyclopropyl)-benzaldehyde (90 mg, 58%) as a colorless oil. $^{1H}$ NMR (CDCl$_3$, 300 MHz): δ 10.0 (s, 1H), 7.79 (d, J=8.5 Hz, 2H), 7.37 (d, J=8.5 Hz, 2H), 3.29 (s, 3H), 1.35-1.30 (m, 2H), 1.09-1.05 (m, 2H).

Preparation of [4-(1-methoxycyclopropyl)-benzyl]-[2-(3-trifluoromethylphenyl)-ethyl]-amine The title compound was synthesized in analogy to (4-cyclopropylbenzyl)-[2-(4-fluoro-3-trifluoromethylphenyl)-ethyl]-amine (described in example S53) using 4-(1-methoxy-cyclopropyl)-benzaldehyde (105 mg, 0.60 mmol), 2-(3-trifluoromethylphenyl)-ethylamine (113 mg, 0.60 mmol) and sodium borohydride (34 mg, 0.89 mmol). The desired product was isolated without further purification as a colorless oil. MS (ISP) 350.4 (M+H)$^+$.

Example S90

Preparation of [4-(1-ethylcyclopropyl)-benzyl]-[2-(3-trifluoromethylphenyl)-ethyl]-amine Preparation of
1-bromo-4-(1-methylenepropyl)-benzene To a solution of n-BuLi (2.79 ml, 1.6M solution in hexane, 4.46 mmol) in ether was added solid methyltriphenylphosphonium bromide (1.59 g, 4.46 mmol) in three portions. The mixture was stirred at rt for 4 h, and then a solution of 4-bromopropio-phenone (1.00 g, 4.69 mmol) in ether was added and the mixture was gently refluxed overnight. The mixture was filtered and the filtrate was washed with water and brine, dried (MgSO$_4$), filtered and concentrated in vacuo to give a residue which was purified by flash column chromatography to give 1-bromo-4-(1-methylenepropyl)-benzene (310 mg, 31%) as a colorless oil. $^{1H}$ NMR (CDCl$_3$, 300 MHz): δ 7.45 (d, J=9.0 Hz, 2H), 7.28 (d, J=9.0 Hz, 2H), 5.26 (m, 1H), 5.07 (m, 1H), 2.48 (q, J=7.5 Hz, 2H), 1.09 (t, J=7.5 Hz, 3H).

Preparation of
1-bromo-4-(1-ethylcyclopropyl)-benzene

The title compound was synthesized in analogy to 1-bromo-4-(1-methoxycyclopropyl)-benzene (described in example S89) using 2,4,6-trichlorophenol (580 mg, 2.94 mmol), diethyl zinc (2.94 ml, 1M solution in hexane, 2.94 mmol), CH$_2$I$_2$ (237 μl, 2.94 mmol) and 1-bromo-4-(1-methylenepropyl)-benzene (310 mg, 1.47 mmol). The isolated residue was purified by flash column chromatography (100% pentane) to give 1-bromo-4-(1-ethylcyclopropyl)-benzene (280 mg, 85%) as a colorless oil. $^{1H}$ NMR (CDCl$_3$, 300 MHz): δ 7.39 (d, J=8.5 Hz, 2H), 7.16 (d, J=8.5 Hz, 2H), 1.55 (q, J=7.5 Hz, 2H), 0.82 (t, J=7.5 Hz, 3H), 0.75-0.71(m, 2H), 0.68-0.64 (m, 2H).

Preparation of 4-(1-ethylcyclopropyl)-benzaldehyde

The title compound was synthesized in analogy to 4-cyclopropyl benzaldehyde (described in example S53) using 1-bromo-4-(1-ethylcyclopropyl)-benzene (208 mg, 0.92 mmol), n-BuLi (635 μl, 1.6M solution in hexane, 1.02 mmol) and DMF (144 μl, 1.85 mmol). The isolated residue was purified by flash column chromatography (1:9 ether: pentane) to give 4-(1-ethylcyclopropyl)-benzaldehyde (130 mg, 81%) as a colorless oil. $^{1H}$ NMR (CDCl$_3$, 300 MHz): δ 9.97 (s, 1H), 7.80 (d, J=8.5 Hz, 2H), 7.43 (d, J=8.5 Hz, 2H), 1.65 (q, J=7.5 Hz, 2H), 0.86 (t, J=7.5 Hz, 3H), 0.89-0.82 (m, 2H), 0.79-0.75 (m, 2H).

Preparation of [4-(1-ethylcyclopropyl)-benzyl]-[2-(3-trifluoromethylphenyl)-ethyl]-amine The title compound was synthesized in analogy to (4-cyclopropylbenzyl)-[2-(4-fluoro-3-trifluoromethylphenyl)-ethyl]-amine (described in example S53) using 4-(1-ethylcyclopropyl)-benzaldehyde (124 mg, 0.71 mmol), 2-(3-trifluoromethylphenyl)-ethylamine (135 mg, 0.71 mmol) and sodium borohydride (40 mg, 1.07 mmol). The desired product was isolated without further purification as a colorless oil. MS (ISP) 348.5 (M+H)$^+$.

Example S91

Preparation of 5-methyl-1H-indole-7-carboxylic acid 6.1 g of tert-butylnitrite (59 mmol) were added to a suspension of 10.57 g CuBr$_2$ (47 mmol) in 60 ml acetonitrile. The reaction mixture was heated to 65° C. and 6 g of 5-methyl-2-nitroaniline (39 mmol) were added in small portions during 15 min. After 4 h at 65° C. the mixture was cooled to rt and poured into 3N HCl solution. The product was extracted with EtOAc and the combined organic extracts were washed with brine, dried with magnesium sulfate, filtered and concentrated. Chromatography (silica gel; cyclohexane/EtOAc 4:1) yielded 3.95 g (46%) 2-bromo-4-methyl-1-nitro-benzene as an orange liquid. $^{1H}$ NMR (DMSO-d$_6$, 300 MHz): δ 2.40 (s, 3H), 7.43 (d, J=8 Hz, 1H), 7.77 (s, 1H), 7.94 (d, J=8 Hz, 1H).

3.3 g of 2-bromo-4-methyl-1-nitro-benzene (15 mmol) were dissolved in 200 ml THF and the solution was cooled to −65° C. Then 46 ml of a 1 molar solution of vinyl magnesium bromide in THF were added in a way, that the temperature of the reaction mixture stayed below −40° C. After 30 min at −40° C. the reaction was quenched with saturated ammonium chloride solution and was extracted with EtOAc. The combined organic phases were washed with brine and dried with magnesium sulfate. After filtration and evaporation of the solvent the crude product was purified by chromatography (silica gel; cyclohexane/EtOAc 4:1). 1.68 g (52%) of 7-bromo-5-methyl-indole were isolated as brown liquid. $^{1H}$ NMR (DMSO-d$_6$, 300 MHz): δ 2.36 (s, 3H), 6.45 (m, 1H), 7.14 (s, 1H), 7.34 (m, 2H), 11.16 (br s, 1H).

1.68 g of 7-bromo-5-methyl-indole (8 mmol) were dissolved in 30 ml THF and 15 ml of a 1.6 molar solution of n-BuLi in hexane were added at −78° C. The reaction mixture was then allowed to warm to 0-5° C. and was stirred at this temperature for 30 min. Then it was cooled again to −78° C., dry ice was added and the mixture was allowed to warm to rt. After 15 min at rt it was poured into water and extracted twice with ether. The aqueous phase was then acidified with 1 N HCl solution and extracted several times with DCM. The combined DCM extracts were then washed with brine, dried with magnesium sulfate, filtered and the solvent was evaporated. The remaining residue was triturated with n-hexane. Final filtration yielded 0.78 g (56%) of 5-methyl-1H-indole-7-carboxylic acid as light brown solid. $^{1H}$ NMR (DMSO-d, 300 MHz): δ 2.41 (s, 3H), 6.44 (m, 1H), 7.31 (m, 1H), 7.58 (s, 1H), 7.61 (s, 1H), 10.91 (br s, 1H), 12.92 (br s, 1H).

Example S92

Preparation of 5-trifluoromethyl-1H-indole-7-carboxylic acid 4.64 g of N-iodosuccinimide (21 mmol) were slowly added to a solution of 4.5 g 2-bromo-4-(trifluoromethyl)-aniline (19 mmol) in 18 ml acetic acid. After the reaction mixture had been stirred for 17 h at rt it was diluted with ether and washed with a 2 molar solution of Na$_2$S$_2$O$_3$ and with brine. The ether layer was then dried with magnesium sulfate, filtered and the solvent was evaporated. This yielded 6.96 g (100%) of crude 2-bromo-6-iodo-4-(trifluoromethyl)-aniline as a light red solid which was used for the following step without further purification. $^{1H}$NMR (CDCl$_3$, 300 MHz): δ 4.93 (br s, 2H), 7.66 (s, 1H), 7.82 (s, 1H).

To a solution of 7.54 g of 2-bromo-6-iodo-4-(trifluoromethyl)-aniline (21 mmol) in 70 ml triethylamine were added 723 mg of Pd(PPh$_3$)$_2$Cl$_2$ (1 mmol), 196 mg of CuI (1 mmol) and 3.14 ml of ethinyltrimethylsilane (23 mmol). The reaction mixture was stirred for 3 h at rt before the triethylamine was removed under reduced pressure. Then DCM was added and the resulting suspension was filtered. The filtrate was then concentrated and the residue purified by chromatography (silica gel; c-hexane/EtOAc 19:1) to yield 6.51 g (94%) of 2-bromo-4-trifluoromethyl-6-trimethylsilanylethynyl-phenylamine as a dark brown liquid. $^{1H}$ NMR (CDCl$_3$, 300 MHz): δ 0.28 (s, 9H), 4.99 (br s, 2H), 7.51 (s, 1H), 7.61 (s, 1H).

4.26 g of 2-bromo-4-trifluoromethyl-6-trimethylsilanylethynyl-phenylamine (13 mmol) were dissolved in 40 ml THF and the solution was cooled to 0° C. Then 15.2 ml of a 1 M solution of tetrabutylammonium fluoride in THF (15 mmol) were added and the reaction mixture was stirred for 20 min at 0° C. After addition of water, the mixture was extracted with EtOAc and the combined organic extracts were washed with brine, dried with magnesium sulfate, filtered and concentrated. 1.82 g (54%) of 2-bromo-6-ethynyl-4-trifluoromethyl-phenylamine were isolated as a brown solid after purification (silica gel; cyclohexane/EtOAc 9:1). $^{1H}$ NMR (CDCl$_3$, 300 MHz): δ 3.48 (s, 1H), 5.03 (br s, 2H), 7.54 (s, 1H), 7.65 (s, 1H).

A solution of 1.82 g of 2-bromo-6-ethynyl-4-trifluoromethyl-phenylamine (7 mmol) in 25 ml NMP was added dropwise to 1.62 g of potassium tert-butoxide (14 mmol) in 25 ml NMP at 0° C. The reaction mixture was stirred for 1 h at 0° C. and then for 3 h at rt, was then poured into water and extracted several times with ether. The combined extracts were washed with water and brine, dried with magnesium sulfate, filtered and concentrated. The remaining residue was purified by chromatography (silica gel; cyclohexane/EtOAc 9:1). This yielded 1.46 g (80%) of 7-bromo-5-trifluoromethyl-1H-indole as a light brown liquid. $^{1H}$ NMR (CDCl$_3$, 300 MHz): δ 6.73 (m, 1H), 7.37 (m, 1H), 7.60 (s, 1H), 7.89 (s, 1H), 8.51 (br s, 1H).

584 mg of 7-bromo-5-trifluoromethyl-indole (2.2 mmol) were dissolved in 15 ml THF and 4.1 ml of a 1.6 molar solution of n-BuLi in hexane were added at −78° C. The reaction mixture was then allowed to warm to 0-5° C. and was stirred at this temperature for 30 min. Then it was cooled again to −78° C., dry ice was added and the mixture was allowed to warm to rt. After 15 min at rt it was poured into water and extracted twice with ether. The aqueous phase was then acidified with 1 N HCl solution and extracted several times with DCM. The combined DCM extracts were then washed with brine, dried with magnesium sulfate, filtered and the solvent was evaporated. The remaining residue was triturated with n-hexane. Final filtration yielded 157 mg (31%) of 5-trifluoromethyl-1H-indole-7-carboxylic acid as an off-white solid. $^{1H}$ NMR (DMSO-d$_6$, 300 MHz): δ 6.66 (m, 1H), 7.48 (m, 1H), 7.89 (s, 1H), 8.18 (s, 1H), 11.46 (br s, 1H), 13.48 (br s, 1H).

Example S93

Preparation of (4-pentafluoro-sulphuranyl-benzyl)-[2-(4-fluoro-phenyl)-ethyl]-amine 200 mg of 4-pentafluoro-sulphuranyl-benzaldehyde (0.9 mmol) and 120 mg of 2-(4-fluoro-phenyl)-ethylamine (0.9 mmol) were dissolved in 5 ml methanol and the solution was refluxed for 5 h. The reaction mixture was then allowed to cool to rt and 49 mg of sodium borohydride (1.3 mmol) were added before it was again refluxed for 1 h. Then 0.1 N sodium hydroxide solution was added at rt and the mixture was extracted with EtOAc. The combined organic phases were dried with magnesium sulfate, filtered and concentrated in vacuo. The residue was purified by column chromatography (silica gel; DCM/methanol 95:5) to give 235 mg of a colorless oil (77%). MS (ISP) 356.0 (M+H)$^+$.

Example S94

Preparation of (4-pentafluoro-sulphuranyl-benzyl)-[2-(3,4-dichloro-phenyl)-ethyl]-amine 761 mg of 4-pentafluoro-sulphuranyl-benzaldehyde (3.3 mmol) and 623 mg of 2-(3,4-dichloro-phenyl)-ethylamine (3.3 mmol) were dissolved in 5 ml methanol and the solution was refluxed for 4 h. The reaction mixture was then allowed to cool to rt and 186 mg of sodium borohydride (4.9 mmol) were added before it was again refluxed for 1 h. Then 0.1 N sodium hydroxide solution was added at rt and the mixture was extracted with EtOAc. The combined organic phases were dried with magnesium sulfate, filtered and concentrated in vacuo. The residue was purified by column chromatography (silica gel; DCM/methanol 95:5) to give 1221 mg of a light yellow oil (92%). MS (ISP) 406.1 (M+H)$^+$.

Example S95

Preparation of 2-methyl-1H-indole-7-carboxylic acid 1000 mg of 7-bromo-2-methyl-indole (4.8 mmol) were dissolved in 15 ml THF and 8.9 ml of a 1.6 molar solution of n-BuLi in hexane were added at −78° C. The reaction mixture was then allowed to warm to 0-5° C. and was stirred at this temperature for 30 min. Then it was cooled again to −78° C., dry ice was added and the mixture was allowed to warm to rt. After 15 min at rt it was poured into water and extracted twice with ether. The aqueous phase was then acidified with 1 N HCl solution and extracted several times with DCM. The combined DCM extracts were then dried with magnesium sulfate, filtered and the solvent was evaporated. The remaining residue was triturated with pentane. Final filtration yielded 157 mg (31%) of 2-methyl-1H-indole-7-carboxylic acid as an off-white solid. MS (ISP) 174.3 (M−H)$^-$.

Example S96

Preparation of (4-tert-butyl-benzyl)-[2-(4-methyl-thiazol-2-yl)-ethyl]-amine 1.59 g of tert-butyl N-(3-amino-3-thioxopropyl) carbamate (7.8 mmol) were dissolved in 40 ml 1,2-dimethoxyethane. Then 3.12 g of KHCO$_3$ (31.1 mmol) and 2.48 ml of chloroacetone (31.1 mmol) were added and the mixture was heated to 50° C. over night. After the reaction mixture was cooled to ambient temperature it was filtered and then concentrated. The remaining residue was dissolved in 10 ml 1,2-dimethoxyethane and the solution was cooled to 0° C. Then 4.26 ml of pyridine (53 mmol) and 3.25 ml of trifluoroacetic acid anhydride (23.4 mmol) were added and the mixture was stirred for 1 h at 0° C. After evaporation, the residue was taken up in DCM, washed twice with water, dried with magnesium sulfate, filtrated and concentrated. Final purification (silica gel; c-hexane/EtOAc 4:1) gave 1.03 g (39%) of [2-(4-methyl-thiazol-2-yl)-ethyl]-(2,2,2-trifluoro-acetyl)-carbamic acid tert-butyl ester as a yellow liquid. $^{1H}$ NMR (CDCl$_3$, 300 MHz): δ 1.50 (s, 9H), 2.41 (d, J=1 Hz, 3H), 3.28 (t, J=7 Hz, 2H), 4.11 (t, J=7 Hz, 2H), 6.76 (m, 1H); MS (ISP) 339.1 (M+H)$^+$.

Trifluoroacetic acid (4 ml) was added to a solution of 680 mg of [2-(4-methyl-thiazol-2-yl)-ethyl]-(2,2,2-trifluoro-acetyl)-carbamic acid tert-butyl ester (2 mmol) in 4 ml DCM at 0° C. After 4 h at 0° C. the reaction mixture was neutralized by the addition of 1 N sodium hydroxide solution and extracted three times with DCM. The combined organic extracts were washed with brine, dried with magnesium sulfate, filtrated and the solvent was evaporated. The remaining 344 mg (72%) of 2,2,2-trifluoro-N-[2-(4-methyl-thiazol-2-yl)-ethyl]-acetamide were used in the following step without further purification. $^{1H}$ NMR (CDCl$_3$, 300 MHz): δ 2.42 (d, J=1 Hz, 3H), 3.19 (t, J=6 Hz, 2H), 3.79 (q, J=6 Hz, 2H), 6.78 (m, 1H), 8.06 (br s, 1H); MS (ISP) 239.1 (M+H)$^+$.

A solution of 224 mg of 2,2,2-trifluoro-N-[2-(4-methyl-thiazol-2-yl)-ethyl]-acetamide (0.94 mmol) in 4 ml DMF was added to a suspension of 45 mg of sodium hydride (60% in mineral oil) in 4 ml DMF at 0° C. After 30 min 0.173 ml 4-tert-butyl-benzylbromide were added and the reaction mixture was allowed to warm to rt. Stirring was continued for 3 h at ambient temperature, then water was added and the mixture was extracted with EtOAc. The organic layers were dried over magnesium sulfate, filtrated and the solvent was evaporated. Chromatography (silica gel; cyclohexane/EtOAc 4:1) yielded 265 mg (73%) of N-(4-tert-butyl-benzyl)-2,2,2-trifluoro-N-[2-(4-methyl-thiazol-2-yl)-ethyl]-acetamide as a light yellow liquid. $^{1H}$ NMR (CDCl$_3$, 300 MHz): δ 1.30 (s) and 1.31 (s, 9H), 2.42 (s, 3H), 3.23 (q, J=7 Hz, 2H), 3.70 (t, J=7 Hz) and 3.79 (t, J=7 Hz, 2H), 4.48(s) and 4.62 (s, 2H), 6.77 (m, 1H), 7.10 (d, J=8 Hz) and 7.17 (d, J=8 Hz, 2H), 7.36 (d, J=8 Hz) and 7.38 (d, J=8 Hz, 2H); MS (ISP) 385.4 (M+H)$^+$.

102 mg of sodium borohydride (2.7 mmol) were added to a solution of 260 mg of N-(4-tert-butyl-benzyl)-2,2,2-trifluoro-N-[2-(4-methyl-thiazol-2-yl)-ethyl]-acetamide (0.68 mmol) in ethanol at ambient temperature and the reaction mixture was stirred for 3 h. Then water was added and the mixture was extracted three times with EtOAc. The combined organic extracts were washed with brine, dried with magnesium sulfate, filtered and the solvent was evaporated. The remaining 195 mg (100%) of (4-tert-butyl-benzyl)-[2-(4-methyl-thiazol-2-yl)-ethyl]-amine were used in the following coupling step without further purification. $^{1H}$ NMR (CDCl$_3$, 300 MHz): δ 1.31 (s, 9H), 2.41 (s, 3H), 3.06 (m, 2H), 3.17 (m, 2H), 3.81 (s, 2H), 6.72 (s, 1H), 7.25 (d, J=8 Hz, 2H), 7.34 (d, J=8 Hz, 2H); MS (ISP) 289.1 (M+H)$^+$.

Example S97

Preparation of [4-(1-methoxycyclobutyl)-benzyl]-[2-(3-trifluoromethylphenyl)-ethyl]-amine Preparation of 1-(4-bromophenyl)-cyclobutanol To a solution of 1,4-dibromobenzene (1.00 g, 4.24 mmol) at −78° C. in ether (20 ml) was added n-BuLi (2.65 ml, 1.6 M solution in hexane, 4.24 mmol) and the reaction mixture was stirred at −78° C. for 30 min. Cyclobutanone (348 µl, 4.66 mmol) was then added and the reaction mixture was stirred at −78° C. for 15 min. The reaction mixture was then slowly (over 2 h) warmed to 0° C. and stirred for a further 1 h. Water was added followed by sat. NH$_4$Cl and the reaction mixture was extracted with ether. The organic layer was washed with brine, dried (MgSO$_4$), filtered and concentrated in vacuo to give a residue which was purified by flash column chromatography (1:4 ether:pentane) to give 1-(4-bromophenyl)-cyclobutanol (330 mg, 34%) as a colorless oil. $^{1H}$ NMR (CDCl$_3$, 300 MHz): δ 7.50 (d, J=8.5 Hz, 2H), 7.38 (d, J=8.5 Hz, 2H), 2.57-2.48 (m, 2H), 2.41-2.31 (m, 2H), 2.02 (m, 1H), 1.69 (m, 1H).

Preparation of 1-bromo-4-(1-methoxycyclobutyl)-benzene

To a suspension of NaH (24 mg, ~55% dispersion in oil, 0.53 mmol) in DMF (2 ml) at 0° C. was added a solution of 1-(4-bromophenyl)-cyclobutanol (100 mg, 0.44 mmol) in DMF (2 ml). The mixture was stirred at 0° C. for 30 min and then methyl iodide (41 µl, 0.66 mmol) was added. The reaction mixture was then warmed up to rt and stirring was continued overnight. The mixture was quenched with water and extracted with ether. The organic phase was washed with water and brine, dried (MgSO$_4$), filtered, and concentrated in vacuo to give a residue which was purified by flash column chromatography (1:9 ether:pentane) to give 1-bromo-4-(1-methoxycyclobutyl)-benzene (79 mg, 75%) as a colorless oil. $^{1H}$ NMR (CDCl$_3$, 300 MHz): δ 7.50 (d, J=8.5 Hz, 2H), 7.30 (d, J=8.5 Hz, 2H), 2.92 (s, 3H), 2.38-2.33 (m, 4H), 1.94 (m, 1H), 1.67 (m, 1H).

Preparation of 4-(1-methoxycyclobutyl)-benzaldehyde

The title compound was synthesized in analogy to 4-cyclopropyl benzaldehyde (described in example S53) using 1-bromo-4-(1-methoxycyclobutyl)-benzene (140 mg, 0.58 mmol), n-BuLi (363 μl, 1.6M solution in hexane, 0.58 mmol) and DMF (90 μl, 1.16 mmol). The isolated residue was purified by flash column chromatography (1:9 ether:pentane) to give 4-(1-methoxycyclobutyl)-benzaldehyde (76 mg, 69%) as a colorless oil. $^{1H}$ NMR (CDCl$_3$, 300 MHz): δ 10.03 (s, 1H), 7.91 (d, J=8.5 Hz, 2H), 7.61 (d, J=8.5 Hz, 2H), 2.96 (s, 3H), 2.45-2.39 (m, 4H), 1.99 (m, 1H), 1.73 (m, 1H).

Preparation of [4-(1-methoxycyclobutyl)-benzyl]-[2-(3-trifluoromethylphenyl)-ethyl]-amine The title compound was synthesized in analogy to (4-cyclopropylbenzyl)-[2-(4-fluoro-3-trifluoromethylphenyl)-ethyl]-amine (described in example S53) using 4-(1-methoxycyclobutyl)-benzaldehyde (76 mg, 0.40 mmol), 2-(3-trifluoromethylphenyl)-ethylamine (76 mg, 0.40 mmol) and sodium borohydride (17 mg, 0.44 mmol). The isolated residue was purified by flash column chromatography (2%-5% MeOH in EtOAc) to give the desired product (112 mg, 77%) as a colorless oil. MS (ISP) 364.3 (M+H)$^+$.

Example S98

Preparation of [2-(3,4-dichloro-phenyl)-ethyl]-[4-(2,2,2-trifluoro-1-hydroxy-1-trifluoromethyl-ethyl)-benzyl]-amine 557 mg of TBTU (1.74 mmol) and 330 mg of 3,4-dichlorophenylethylamine (1.74 mmol) were added to a stirred solution of 500 mg of 4-(2-hydroxyhexafluoroisopropyl)-benzoic acid (1.74 mmol) in 10 ml DMF. Then 1.48 ml of N,N-diisopropyl ethyl amine were added and stirring at ambient temperature was continued for 5 h. The reaction mixture was then poured into water and extracted with EtOAc. The combined extracts were washed with water and brine, dried over magnesium sulfate, filtered and the solvent was evaporated. The remaining residue was purified by silica gel filtration with EtOAc. This gave 689 mg (86%) of N-[2-(3,4-dichloro-phenyl)-ethyl]-4-(2,2,2-trifluoro-1-hydroxy-1-trifluoromethyl-ethyl)-benzamide as a white solid. MS (ISP) 460.1 (M+H)$^+$.

A solution of 680 mg N-[2-(3,4-dichloro-phenyl)-ethyl]-4-(2,2,2-trifluoro-1-hydroxy-1-trifluoromethyl-ethyl)-benzamide (1.48 mmol) in 10 ml of THF was added dropwise to 5.9 ml of a 1 molar solution of BH$_3$-THF complex in THF at 0° C. The reaction mixture was stirred for 1 h at rt and then heated to reflux over night. Then 2 ml of 6 N HCl solution were added very carefully at ambient temperature and the mixture was heated again to reflux for 1.5 h. After cooling to rt, the pH was adjusted to 8-9 by addition of 1 N sodium hydroxide solution and the mixture was extracted twice with EtOAc. The combined organic layers were washed with brine, dried with magnesium sulfate, filtered and concentrated. Final purification (silica gel; DCM/methanol 95:5) yielded 647 mg (98%) of [2-(3,4-dichloro-phenyl)-ethyl]-[4-(2,2,2-trifluoro-1-hydroxy-1-trifluoromethyl-ethyl)-benzyl]-amine as a white solid.

Example S99

Preparation of [2-(3,4-dichloro-phenyl)-ethyl]-[4-(1,2,2,2-tetrafluoro-1-trifluoromethyl-ethyl)-benzyl]-amine, [4-(1,2,2,2-tetrafluoro-1-trifluoromethyl-ethyl)-benzyl]-[2-(3-trifluoromethyl-phenyl)-ethyl]-amine, [2-(4-fluoro-3-trifluoromethyl-phenyl)-ethyl]-[4-(1,2,2,2-tetrafluoro-1-trifluoromethyl-ethyl)-benzyl]-amine, [4-(1,2,2,2-tetrafluoro-1-trifluoromethyl-ethyl)-benzyl]-[2-(3-trifluoromethoxy-phenyl)-ethyl]-amine and [2-(4-chloro-phenyl)-ethyl]-[4-(1,2,2,2-tetrafluoro-1-trifluoromethyl-ethyl)-benzyl]-amine A solution of 3.5 g of 4-(heptafluoroisopropyl)-toluene (13.4 mmol) in 100 ml tetra-chloromethane was heated to reflux. Then 2.63 g of N-bromosuccinimide (14.8 mmol) and 326 mg of dibenzoyl peroxide (1.34 mmol) were added in small portions. After 5 h the mixture was cooled to 0° C., filtered and the solvent was evaporated. The remaining residue was dissolved in 15 ml ethanol and was added to a suspension that had been prepared by addition of 2-nitropropane (1.4 ml, 15.5 mmol) to a solution of 340 mg sodium (14.8 mmol) in ethanol. This mixture was stirred for 3 days. Then it was filtered, the solvent was removed and the remaining residue was dissolved in EtOAc and washed with 1 N sodium hydroxide solution, 1 N HCl solution, saturated NaHCO$_3$ solution and with brine. The EtOAc layer was then dried with magnesium sulfate, filtered and concentrated. Purification of the residue (silica gel; c-hexane/EtOAc 10:1) gave 1.1 g (30%) of 4-(1,2,2,2-tetrafluoro-1-trifluoromethyl-ethyl)-benzaldehyde as a light yellow oil. $^{1H}$-NMR (CDCl$_3$, 300 MHz): δ 7.82 (d, J=8 Hz, 2H), 8.03 (d, J=8 Hz, 2H), 10.11 (s, 1H).

200 mg of 4-(1,2,2,2-tetrafluoro-1-trifluoromethyl-ethyl)-benzaldehyde (0.73 mmol) and 139 mg of 2-(3,4-dichloro-phenyl)-ethylamine (0.73 mmol) were dissolved in 10 ml methanol and the solution was refluxed for 3 h. The reaction mixture was then allowed to cool to rt and 41 mg of sodium borohydride (1.09 mmol) were added before it was again refluxed for 3 h. Then 0.1 N sodium hydroxide solution was added at rt and the mixture was extracted with EtOAc. The combined organic phases were dried with magnesium sulfate, filtered and concentrated in vacuo. The residue was purified by column chromatography (silica gel; DCM/methanol 96:4) to give 235 mg of a light yellow oil (72%). MS (ISP) 448.0 (M+H)$^+$.

[4-(1,2,2,2-tetrafluoro-1-trifluoromethyl-ethyl)-benzyl]-[2-(3-trifluoromethyl-phenyl)-ethyl]-amine was prepared in analogy to the above procedure starting from 200 mg of 4-(1,2,2,2-tetrafluoro-1-trifluoromethyl-ethyl)-benzaldehyde (0.73 mmol) and 138 mg of (3-trifluoromethyl-phenyl)-ethylamine (0.73 mmol). Final purification by column chromatography (silica gel; DCM/methanol 96:4) gave 285 mg of a light yellow oil (87%). MS (ISP) 448.1 (M+H)$^+$.

[2-(4-fluoro-3-trifluoromethyl-phenyl)-ethyl]-[4-(1,2,2,2-tetrafluoro-1-trifluoromethyl-ethyl)-benzyl]-amine was prepared in analogy to the above procedure starting from 200 mg of 4-(1,2,2,2-tetrafluoro-1-trifluoromethyl-ethyl)-benzaldehyde (0.73 mmol) and 151 mg of (4-fluoro-3-trifluoromethyl-phenyl)-ethylamine (0.73 mmol). Final purification by column chromatography (silica gel; DCM/methanol 96:4) gave 285 mg of a light yellow oil (87%). MS (ISP) 448.1 (M+H)$^+$.

[4-(1,2,2,2-tetrafluoro-1-trifluoromethyl-ethyl)-benzyl]-[2-(3-trifluoromethoxy-phenyl)-ethyl]-amine was prepared in analogy to the above procedure starting from 200 mg of 4-(1,2,2,2-tetrafluoro-1-trifluoromethyl-ethyl)-benzaldehyde (0.73 mmol) and 150 mg of (3-trifluoromethoxy-phenyl)-ethylamine (0.73 mmol). Final purification by column chromatography (silica gel; DCM/methanol 96:4) gave 276 mg of a light yellow oil (82%). MS (ISP) 464.2 (M+H)$^+$.

[2-(4-chloro-phenyl)-ethyl]-[4-(1,2,2,2-tetrafluoro-1-trifluoromethyl-ethyl)-benzyl]-amine was prepared in analogy to the above procedure starting from 200 mg of 4-(1,2,2,2-tetrafluoro-1-trifluoromethyl-ethyl)-benzaldehyde (0.73 mmol) and 114 mg of (4-chloro-phenyl)-ethylamine (0.73 mmol). Final purification by column chromatography (silica gel; DCM/methanol 96:4) gave 130 mg of a light yellow oil (43%). MS (ISP) 414.3 (M+H)$^+$.

Example S100

Preparation of (1,1-dimethylindan-5-ylmethyl)-[2-(3-trifluoromethylphenyl)-ethyl]-amine Preparation of 1,1-dimethylindan-5-carbaldehyde The title compound was synthesized in analogy to 4-cyclopropyl benzaldehyde (described in example S53) using 5-bromo-1,1-dimethylindan [synthesized in analogy to a procedure described in Org. Prep. Proc. Int. 10:123-131 (1978)] (270 mg, 1.20 mmol), nBuLi (833 µl, 1.6M solution in hexane, 1.33 mmol) and DMF (173 µl, 2.22 mmol). The isolated residue was purified by flash column chromatography (1:9 ether:pentane) to give 1,1-dimethylindan-5-carbaldehyde (195 mg, 93%) as a colorless oil. $^{1H}$ NMR (CDCl$_3$, 300 MHz): δ 9.96 (s, 1H), 7.71-7.69 (m, 2H), 7.28 (m, 1H), 2.95 (apt t, J=7.0 Hz, 2H), 1.98 (apt t, J=7.0 Hz, 2H), 1.95 (s, 6H).

Preparation of (1,1-dimethylindan-5-ylmethyl)-[2-(3-trifluoromethylphenyl)-ethyl]-amine The title compound was synthesized in analogy to (4-cyclopropylbenzyl)-[2-(4-fluoro-3-trifluoromethylphenyl)-ethyl]-amine (described in example S53) using 1,1-dimethylindan-5-carbaldehyde (100 mg, 0.57 mmol), 2-(3-trifluoromethylphenyl)-ethylamine (109 mg, 0.57 mmol) and sodium borohydride (33 mg, 0.86 mmol). The desired product (194 mg, 97%) was isolated without further purification as a colorless oil. MS (ISP) 348.4 (M+H)$^+$.

Example S101

Preparation of (1,1-dimethylindan-5-ylmethyl)-phenethylamine

The title compound was synthesized in analogy to (4-cyclopropylbenzyl)-[2-(4-fluoro-3-trifluoromethylphenyl)-ethyl]-amine (described in example S53) using 1,1-dimethylindan-5-carbaldehyde (prepared as described in example S100) (197 mg, 0.56 mmol), phenethylamine (67 mg, 0.56 mmol) and sodium borohydride (32 mg, 0.84 mmol). The desired product (129 mg, 83%) was isolated without further purification as a colorless oil. MS (ISP) 280.2 (M+H)$^+$.

Example S102

Preparation of [4-(1-methoxy-1-methyl-ethyl)-benzyl]-[2-(3-trifluoromethyl-phenyl)-ethyl]-amine and [4-(1-ethyl-1-methoxy-propyl)-benzyl]-[2-(3-trifluoromethyl-phenyl)-ethyl]-amine 6.3 ml of a 2 molar solution of isopropylmagnesium chloride in THF (12 mmol) were added dropwise to a solution of 3 g methyl 4-iodobenzoate (11.5 mmol) in 30 ml THF at a temperature of –20° C. The reaction mixture was stirred for 1.5 h at –20° C., then 1.26 ml acetone (17 mmol) were added and the mixture was allowed to warm to rt. After 30 min at ambient temperature the reaction was quenched with methanol, poured into water and extracted with EtOAc. The combined extracts were washed with brine, dried with magnesium sulfate, filtered and concentrated. Chromatographic purification (silica gel; c-hexane/EtOAc 2:1) of the remaining residue yielded 1.64 g (74%) of 4-(1-hydroxy-1-methyl-ethyl)-benzoic acid methyl ester as a colorless liquid. $^{1H}$-NMR (CDCl$_3$, 300 MHz): δ 1.60 (s, 6H), 3.91 (s, 3H), 7.56 (d, J=9 Hz, 1H), 8.01 (d, J=9 Hz, 1H).

439 mg of sodium hydride (60% in mineral oil) were suspended in 10 ml DMF and a solution of 1.64 g of 4-(1-hydroxy-1-methyl-ethyl)-benzoic acid methyl ester (8.4 mmol) in 10 ml DMF was added at 0° C. The mixture was allowed to warm to rt and was stirred for 1 h at this temperature before 0.79 ml of methyl iodide (12.7 mmol) were added. After 17 h additional 338 mg of sodium hydride (60% in mineral oil) and 0.53 ml methyl iodide (8.4 mmol) were added and stirring was continued for 20 h. Then saturated ammonium chloride solution was added and the mixture was extracted with EtOAc. The combined organic layers were washed with water and brine, dried with magnesium sulfate, filtered and the solvent was evaporated. Chromatographic purification (silica gel; c-hexane/EtOAc 9:1 to 4:1) of the remaining residue yielded 661 mg (38%) of 4-(1-methoxy-1-methyl-ethyl)-benzoic acid methyl ester as a colorless liquid. $^{1H}$ NMR (CDCl$_3$, 300 MHz): δ 1.54 (s, 6H), 3.09 (s, 3H), 3.92 (s, 3H), 7.48 (d, J=9 Hz, 1H), 8.02 (d, J=9 Hz, 1H).

660 mg of 4-(1-methoxy-1-methyl-ethyl)-benzoic acid methyl ester (3.2 mmol) were dissolved in 20 ml THF and 9.5 ml of a 1 N solution of lithium hydroxide were added. The reaction mixture was stirred for 4 days. Then the pH was adjusted to 2 by addition of 1 N HCl solution and the mixture was extracted with EtOAc. The combined organic layers were washed with water and brine, dried with magnesium sulfate, filtered and the solvent was evaporated. The remaining 600 mg (97%, white solid) of 4-(1-methoxy-1-methyl-ethyl)-benzoic acid were used in the following step without further purification. $^{1H}$ NMR (CDCl$_3$, 300 MHz): δ 1.56 (s, 6H), 3.11 (s, 3H), 7.53 (d, J=9 Hz, 1H), 8.10 (d, J=9 Hz, 1H).

992 mg of TBTU (3.09 mmol) and 584 mg of 2-(3-trifluoromethylphenyl)-ethylamine (3.09 mmol) were added to a stirred solution of 600 mg of 4-(1-methoxy-1-methyl-ethyl)-benzoic acid (3.09 mmol) in 10 ml DMF. Then 2.63 ml of N,N-diisopropyl ethyl amine were added and stirring at ambient temperature was continued for 17 h. The reaction mixture was then poured into water and extracted with EtOAc. The combined extracts were washed with water and brine, dried over magnesium sulfate, filtered and the solvent was evaporated. The remaining residue was purified by chromatography (silica gel; c-hexane/EtOAc 2:1). This gave 700 mg (62%) of 4-(1-methoxy-1-methyl-ethyl)-N-[2-(3-trifluoromethyl-phenyl)-ethyl]-benzamide as a white solid. MS (ISP) 366.0 (M+H)$^+$.

A solution of 183 mg of 4-(1-methoxy-1-methyl-ethyl)-N-[2-(3-trifluoromethyl-phenyl)-ethyl]-benzamide (0.5 mmol) in 3 ml of THF was added dropwise to 2 ml of a 1 molar solution of BH₃-THF complex in THF at 0° C. The reaction mixture was stirred for 1 h at rt and then heated to reflux over night. Upon cooling to rt 1 N sodium hydroxide solution was added and the mixture was extracted three times with EtOAc. The combined organic layers were washed with brine, dried with magnesium sulfate, filtered and concentrated. This gave 175 mg (100%) of [4-(1-methoxy-1-methyl-ethyl)-benzyl]-[2-(3-trifluoromethyl-phenyl)-ethyl]-amine as a light yellow oil which was used in the following coupling step without further purification. $^{1H}$ NMR (CDCl₃, 300 MHz): δ 1.52 (s, 6H), 2.91 (m, 4H), 3.06 (s, 3H), 3.80 (s, 2H), 7.15-7.51 (m, 8H).

[4-(1-ethyl-1-methoxy-propyl)-benzyl]-[2-(3-trifluoromethyl-phenyl)-ethyl]-amine was prepared in analogy to the above procedure starting from methyl 4-iodobenzoate and 3-pentanone instead of acetone.

Example S103

Preparation of [2-(3,4-dichlorophenyl)-ethyl]-[4-(1,1-dimethylpropyl)-benzyl]-amine Preparation of 4-(1,1-dimethylpropyl)-benzaldehyde The title compound was synthesized in analogy to 4-cyclopropyl benzaldehyde (described in example S53) using 1-bromo-4-(1,1-dimethylpropyl)-benzene [synthesized in analogy to a procedure described in J. Chem. Res. Miniprint. 12:2701-2733 (1997)] (250 mg, 1.10 mmol), n-BuLi (825 µl, 1.6M solution in hexane, 1.32 mmol) and DMF (427 µl, 5.50 mmol). The isolated residue was purified by flash column chromatography (1:9 ether:pentane) to give 4-(1,1-dimethylpropyl)-benzaldehyde (175 mg, 90%) as a colorless oil. $^{1H}$ NMR (CDCl₃, 300 MHz): δ 9.99 (s, 1H), 7.82 (d, J=8.5 Hz, 2H), 7.50 (d, J=8.5 Hz, 2H), 1.69 (q, J=7.5 Hz, 2H), 1.32 (s, 6H), 0.68 (t, J=7.5 Hz, 3H).

Preparation of [2-(3,4-dichlorophenyl)-ethyl]-[4-(1,1-dimethylpropyl)-benzyl]-amine The title compound was synthesized in analogy to (4-cyclopropylbenzyl)-[2-(4-fluoro-3-trifluoromethylphenyl)-ethyl]-amine (described in example S53) using 4-(1,1-dimethylpropyl)-benzaldehyde (87.5 mg, 0.50 mmol), 2-(3,4-dichlorophenyl)-ethylamine (94 mg, 0.50 mmol) and sodium borohydride (28 mg, 0.75 mmol). The desired product (169 mg, 97%) was isolated without further purification as a colorless oil. MS (ISP) 350.3 (M+H)⁺.

Example S104

Preparation of [4-(1,1-dimethylpropyl)-benzyl]-[2-(3-trifluoromethylphenyl)-ethyl]-amine The title compound was synthesized in analogy to (4-cyclopropylbenzyl)-[2-(4-fluoro-3-trifluoromethylphenyl)-ethyl]-amine (described in example S53) using 4-(1,1-dimethylpropyl)-benzaldehyde (prepared as described in example S103) (88 mg, 0.50 mmol), 2-(3-trifluoromethylphenyl)-ethylamine (94 mg, 0.50 mmol) and sodium borohydride (28 mg, 0.75 mmol). The desired product (163 mg, 94%) was isolated without further purification as a colorless oil. MS (ISP) 350.3 (M+H)⁺.

Example S105

Preparation of [3-chloro-4-(1-methylcyclopropyl)-benzyl]-[2-(3-trifluoromethylphenyl)-ethyl]-amine Preparation of 4-bromo-2-chloro-N-methoxy-N-methylbenzamide To a solution of 4-bromo-2-chlorobenzoic acid (2.00 g, 8.50 mmol) in DMF (20 ml) was added N,N-diisopropylethyl amine (3.18 ml, 18.69 mmol) followed by TBTU (3.00 g, 9.34 mmol) followed by dimethylhydroxylamine (829 mg, 8.50 mmol). The reaction mixture was stirred at rt overnight and then diluted with ether and the organic layer was washed with water, 1N HCl, sat. NaHCO₃, and brine. The organic layer was then dried (MgSO₄), filtered and concentrated in vacuo to give a residue which was purified by flash column chromatography to give 4-bromo-2-chloro-N-methoxy-N-methylbenzamide (2.27 g, 96%) as a colorless oil. $^{1H}$ NMR (CDCl₃, 300 MHz): δ 7.59 (d, J=1.5 Hz, 1H), 7.45 (dd, J=1.5, 8.0 Hz, 1H), 7.22 (d, J=8.0 Hz, 1H), 3.48 (br s, 3H), 3.38 (br s, 3H).

Preparation of 1-(4-bromo-2-chlorophenyl)-ethanone

To a solution of 4-bromo-2-chloro-N-methoxy-N-methylbenzamide (2.27 g, 8.15 mmol) in THF at −78° C. was added methylmagnesium chloride (4.07 ml, 3M solution in THF, 12.23 mmol) dropwise. The reaction mixture was stirred at −78° C. for 1 h and then warmed to rt slowly and stirring was continued at rt overnight. The reaction mixture was quenched with 1N HCl and extracted with ether. The organic layer was washed with water, and brine, dried (MgSO₄), filtered and concentrated in vacuo to give a residue which was purified by flash column chromatography (1:4 ether:pentane) to give 1-(4-bromo-2-chlorophenyl)-ethanone (1.52 g, 80%) as a yellow oil. $^{1H}$ NMR (CDCl₃, 300 MHz): δ 7.61 (m, 1H), 7.50-7.44 (m, 2H), 2.64 (s, 3H).

Preparation of 4-bromo-2-chloro-1-isopropenylbenzene

The title compound was synthesized in analogy to 1-bromo-4-isopropenylbenzene (described in example S87) using triphenylphosphonium bromide (2.32 g, 6.51 mmol), nBuLi (5.09 ml, 1.6M solution in hexane, 8.14 mmol) and 1-(4-bromo-2-chlorophenyl)-ethanone (1.52 g, 6.51 mmol) in DMSO (7 ml). The residue which was isolated was purified by filtration through a short pad of silica using pentane as eluant to give 4-bromo-2-chloro-1-isopropenylbenzene (750 mg, 50%) as a colorless oil. $^{1H}$ NMR (CDCl₃, 300 MHz): δ 7.51 (d, J=2.0 Hz, 1H), 7.34 (dd, J=2.0, 8.0 Hz, 1H), 7.07 (d, J=8.0 Hz, 1H), 5.24 (m, 1H), 4.96 (m, 1H), 2.07 (m, 3H).

Preparation of 4-bromo-2-chloro-1-(1-methylcyclopropyl)-benzene

The title compound was synthesized in analogy to 1-bromo-4-(1-methylcyclopropyl)-benzene (described in example S87) using diethyl zinc (2.59 ml, 1M solution in hexane, 2.59 mmol), trifluoroacetic acid (200 µl, 2.59 mmol), CH₂I₂ (209 µl, 2.59 mmol) and 4-bromo-2-chloro-1-isopropenylbenzene (300 mg, 1.30 mmol). The isolated residue was purified by flash column chromatography (100% pentane) to give 4-bromo-2-chloro-1-(1-methylcyclopropyl)-benzene (280 mg, 88%) as a colorless oil. $^{1H}$ NMR (CDCl$_3$, 300 MHz): δ 7.48 (d, J=2.0 Hz, 1H), 7.30 (dd, J=2.0, 8.5 Hz, 1H), 7.22 (d, J=8.5 Hz, 1H), 1.32 (s, 3H), 0.81-0.73(m, 4H).

Preparation of
3-chloro-4-(1-methylcyclopropyl)-benzaldehyde

The title compound was synthesized in analogy to 4-cyclopropyl benzaldehyde (described in example S53) using 4-bromo-2-chloro-1-(1-methylcyclopropyl)-benzene (350 mg, 1.43 mmol), n-BuLi (980 μl, 1.6M solution in hexane, 1.57 mmol) and DMF (443 μl, 5.70 mmol). The isolated residue was purified by flash column chromatography (1:9 ether:pentane) to give 3-chloro-4-(1-methylcyclopropyl)-benzaldehyde (176 mg, 63%) as a colorless oil. $^{1H}$ NMR (CDCl$_3$, 300 MHz): δ 9.94 (s, 1H), 7.84 (d, J=1.5 Hz, 1H), 7.69 (dd, J=1.5, 8.0 Hz, 1H), 7.52 (d, J=8.0 Hz, 1H), 1.38 (s, 3H), 0.90-0.80(m, 4H).

Preparation of [3-chloro-4-(1-methylcyclopropyl)-benzyl]-[2-(3-trifluoromethyl phenyl)-ethyl]-amine The title compound was synthesized in analogy to (4-cyclopropylbenzyl)-[2-(4-fluoro-3-trifluoromethylphenyl)-ethyl]-amine (described in example S53) using 3-chloro-4-(1-methylcyclopropyl)-benzaldehyde (86 mg, 0.44 mmol), 2-(3-trifluoromethylphenyl)-ethylamine (84 mg, 0.44 mmol) and sodium borohydride (25 mg, 0.66 mmol). The desired product (145 mg, 89%) was isolated without further purification as a colorless oil. MS (ISP) 368.3 (M+H)$^+$.

Example S106

Preparation of [3-chloro-4-(1-methylcyclopropyl)-benzyl]-[2-(3,4-dichlorophenyl)-ethyl]-amine The title compound was synthesized in analogy to (4-cyclopropylbenzyl)-[2-(4-fluoro-3-trifluoromethylphenyl)-ethyl]-amine (described in example S53) using 3-chloro-4-(1-methylcyclopropyl)-benzaldehyde (prepared as described in example S105) (90 mg, 0.46 mmol), 2-(3,4-dichlorophenyl)-ethylamine (88 mg, 0.46 mmol) and sodium borohydride (26 mg, 0.70 mmol). The desired product (168 mg, 99%) was isolated without further purification as a colorless oil. MS (ISP) 370.1 (M+H)$^+$.

Example S107

Preparation of
6-fluoro-5-trifluoromethyl-1H-indole-7-carboxylic acid 6.16 g of N-iodosuccinimide (27 mmol) were slowly added to a solution of 4.9 g of 3-fluoro-4-(trifluoromethyl)-aniline (27 mmol) in 20 ml acetic acid. After the reaction mixture had been stirred for 1.5 h at rt it was diluted with ether and washed with a 2 molar solution of Na$_2$S$_2$O$_3$ and with brine. The ether layer was then dried with magnesium sulfate, filtered and the solvent was evaporated. 5-Fluoro-2-iodo-4-trifluoromethyl-aniline was isolated from the remaining residue by chromatography (silica gel; cyclohexane/EtOAc 4:1). This yielded 3.27 g (39%) of 5-fluoro-2-iodo-4-trifluoromethyl-aniline as a dark red liquid. $^{1H}$-NMR (CDCl$_3$, 300 MHz): δ 4.52 (br s, 2H), 6.49 (d, J=12 Hz, 1H), 7.79 (d, J=8 Hz, 1H).

To a solution of 3.27 g of 5-fluoro-2-iodo-4-trifluoromethyl-aniline (10.7 mmol) in 20 ml triethylamine were added 3763 mg of Pd(PPh$_3$)$_2$Cl$_2$ (0.5 mmol), 102 mg of CuI (0.5 mmol) and 1.63 ml of ethinyltrimethylsilane (11.8 mmol). The reaction mixture was stirred over night at rt before most of the triethylamine was removed under reduced pressure. Then DCM was added and the resulting suspension was filtered. The filtrate was then concentrated and the residue purified by chromatography (silica gel; cyclohexane/EtOAc 9:1) to yield 2.83 g (96%) of 5-fluoro-4-trifluoromethyl-2-trimethylsilanylethynyl-phenylamine contaminated with triethylamine as a dark red liquid. $^{1H}$-NMR (CDCl$_3$, 300 MHz): δ 0.26 (s, 9H), 4.68 (br s, 2H), 6.44 (d, J=12 Hz, 1H), 7.51 (d, J=8 Hz, 1H).

A solution of 2.83 g of 5-fluoro-4-trifluoromethyl-2-trimethylsilanylethynyl-phenylamine (10.3 mmol) in 20 ml NMP was added dropwise to 2.42 g of potassium tert-butoxide (21.6 mmol) in 20 ml NMP at 0° C. The reaction mixture was stirred for 1 h at 0° C. and then for 3.5 h at rt, was then poured into water and extracted several times with ether. The combined extracts were washed with water and brine, dried with magnesium sulfate, filtered and concentrated. The remaining residue was purified by chromatography (silica gel; cyclohexane/EtOAc 4:1). This yielded 1.24 g of a mixture of 6-fluoro-5-trifluoromethyl-1H-indole and 2-ethynyl-5-fluoro-4-trifluoromethyl-phenylamine as a dark brown liquid. This mixture was again dissolved in 10 ml NMP and the solution was added dropwise to 1.44 g of potassium tert-butoxide (12.8 mmol) in 10 ml NMP at 0° C. The reaction mixture was stirred 6 days at rt, was then diluted with EtOAc and washed several times with water. The organic layer was then dried with magnesium sulfate, filtered and concentrated. The remaining residue was purified by silica gel filtration with EtOAc. This yielded 685 mg (33%) of 6-fluoro-5-trifluoromethyl-1H-indole as a yellow liquid. $^{1H}$-NMR (CDCl$_3$, 300 MHz): δ 6.62 (m, 1H), 7.19 (d, J=11 Hz, 1H), 7.28 (dd, J=2 and 3 Hz, 1H), 7.87 (d, J=7 Hz, 1H), 8.33 (br s, 1H).

A 1.6 molar solution of n-BuLi in hexane (1.38 ml, 2.2 mmol) was diluted with 3 ml THF and cooled to −78° C. Then, a solution of 203 mg of 6-fluoro-5-trifluoromethyl-1H-indole (1 mmol) in 1 ml THF was added dropwise, keeping the internal temperature below −70° C. After 5 min a solution of 269 mg potassium tert-butoxide (2.4 mmol) in 1 ml THF was added, again keeping the internal temperature below −70° C. The reaction mixture was then stirred for 2 h. Then dry ice was added and the mixture was allowed to warm to 10° C. Water was added and the phases were separated. The aqueous phase was washed twice with ether, then acidified with 1 N HCl solution and extracted several times with DCM. The combined DCM extracts were dried with magnesium sulfate, filtered and the solvent was evaporated. The remaining residue was triturated with pentane. Final filtration yielded 105 mg (42%) of 6-fluoro-5-trifluoromethyl-1H-indole-7-carboxylic acid as an off-white solid. $^{1H}$-NMR (DMSO-d$_6$, 300 MHz): δ 6.63 (m, 1H), 7.43 (t, J=3 Hz, 1H), 8.15 (d, J=7 Hz, 1H), 11.49 (br s, 1H), 13.70 (br s, 1H).

Example S108

Preparation of N-[2-(3,4-dichlorophenyl)ethyl]-2',3'-dihydro-spiro-[cyclopropane-1,1'-[1H]indene]-5'-methanamine

Preparation of 5-bromo-1-methylene-indan

The title compound was synthesized in analogy to example S87 using triphenyl-phospho-nium bromide (1.49 g, 4.17 mmol), n-BuLi (3.26 ml, 1.6M solution in hexane, 5.21 mmol) and 5-bromo-1-indanone (880 mg, 4.17 mmol) in DMSO (10 ml). The residue which was isolated was purified by filtration through a short pad of silica using pentane as eluant to give 5-bromo-1-methylene-indan (510 mg, 59%) as a colorless oil. $^{1H}$ NMR (CDCl$_3$, 300 MHz): δ 7.40-7.29 (m, 3H), 5.44 (m, 1H), 5.05 (m, 1H), 2.98-2.94 (m, 2H), 2.83-2.78 (m, 2H).

Preparation of 5'-bromo-2',3'dihydro-spiro[cyclopropane1,1'-[1H]indene]

The title compound was synthesized in analogy to example S87 using diethyl zinc (3.25 ml, 1M solution in hexane, 3.25 mmol), trifluoroacetic acid (251 µl, 3.25 mmol), CH$_2$I$_2$ (262 µl, 3.25 mmol) and 5-bromo-1-methyleneindan (340 mg, 1.63 mmol). The isolated residue was purified by flash column chromatography (100% pentane) to give 5'-bromo-2',3'dihydro-spiro[cyclopropane1,1'-[1H]indene](345 mg, 95%) as a colorless oil. $^{1H}$ NMR (CDCl$_3$, 300 MHz): δ 7.40-7.29 (m, 3H), 3.02 (apt t, J=7.5 Hz, 2H), 2.11 (apt t, J=7.5 Hz, 2H), 0.96-0.84 (m, 4H).

Preparation of 2',3'-dihydro-spiro[cyclopropane-1,1'-[1H]indene]-5'-carboxaldehyde The title compound was synthesized in analogy to 4-cyclopropyl benzaldehyde (described in example S53) using 5'-bromo-2',3'dihydro-spiro[cyclopropane1,1'-[1H]indene] (345 mg, 1.55 mmol), n-BuLi (1.16 ml, 1.6M solution in hexane, 1.86 mmol) and DMF (481 µl, 6.19 mmol). The isolated residue was purified by flash column chromatography (1:9 ether:pentane) to give 2',3'-dihydro-spiro[cyclopropane-1,1'-[1H]indene]-5'-carboxaldehyde (148 mg, 56%) as a colorless oil. $^{1H}$ NMR (CDCl$_3$, 300 MHz): δ 9.93 (s, 1H), 7.70 (m, 1H), 7.65 (m, 1H), 6.78 (d, J=8.0 Hz, 1H), 3.10 (apt t, J=8.0 Hz, 2H), 2.18 (apt t, J=8.0 Hz, 2H), 1.08-0.98 (m, 4H).

Preparation of N-[2-(3,4-dichlorophenyl)ethyl]-2',3'-dihydro-spiro [cyclopropane-1,1'-[1H]indene]-5'-methanamine The title compound was synthesized in analogy to (4-cyclopropylbenzyl)-[2-(4-fluoro-3-trifluoromethylphenyl)-ethyl]-amine (described in example S53) using 2',3'-dihydro-spiro-[cyclopropane-1,1'-[1H]indene]-5'-carboxaldehyde (62 mg, 0.36 mmol), 2-(3,4-dichlorophenyl)-ethylamine (68 mg, 0.36 mmol) and sodium borohydride (20 mg, 0.54 mmol). The desired product (115 mg, 92%) was isolated without further purification as a colorless oil. MS (ISP) 346.2 (M+H)$^+$.

Example S109

Preparation of 2',3'-dihydro-N-[2-[3-(trifluoromethyl)phenyl]ethyl]-spiro[cyclopropane-1,1'-[1H]indene]-5'-methanamine The title compound was synthesized in analogy to (4-cyclopropylbenzyl)-[2-(4-fluoro-3-trifluoromethylphenyl)-ethyl]-amine (described in example S53) using 2',3'-dihydro-spiro-[cyclopropane-1,1'-[1H]indene]-5'-carboxaldehyde (prepared as described in example S108) (68 mg, 0.40 mmol), 2-(3-trifluoromethylphenyl)-ethylamine (75 mg, 0.40 mmol) and sodium borohydride (22 mg, 0.59 mmol). The desired product (120 mg, 88%) was isolated without further purification as a colorless oil. MS (ISP) 346.3 (M+H)$^+$.

Example S110

Preparation of (4-tert-butyl-3-chloro-benzyl)-[2-(3-trifluoromethyl-phenyl)-ethyl]-amine

Preparation of 4-bromo-2-chloro-benzoyl chloride

Oxalylchloride (0.86 ml, 10.2 mmol) was added dropwise to a suspension of 4-bromo-2-chlorobenzoic acid (2.00 g, 8.5 mmol) in DCM (20 ml) at rt. After the addition of 5 drops of DMF, the reaction mixture was refluxed for 4 h, then cooled to rt and concentrated in vacuo to give 4-bromo-2-chloro-benzoyl chloride (2.15 g, 100%) which was used in the following step without further purification. $^{1H}$ NMR (CDCl$_3$, 300 MHz): δ 7.98 (d, J=8.5 Hz, 1H), 7.70 (d, J=2 Hz, 1H), 7.57 (dd, J=2 and 8 Hz 1H).

Preparation of 4-bromo-1-tert-butyl-2-chloro-benzene

To a solution of TiCl$_4$ (16.94 ml, 1M solution in DCM, 16.94 mmol) in DCM (5 ml) at −30° C. was added dimethyl zinc (10.58 ml, 2M solution in toluene, 21.17 mmol). The reaction mixture was stirred at −30° C. for 30 min and then a solution of 4-bromo-2-chloro-benzoyl chloride (2.15 g, 8.47 mmol) in DCM was added dropwise at −40° C. The reaction mixture was warmed to 0° C. over 2 h and then quenched by slowly pouring it into an ice/saturated NaHCO$_3$ solution. The aqueous phase was acidified with 1N HCl and then extracted with ether. The organic phases were combined, dried over MgSO4, filtered, and concentrated in vacuo. The title compound was isolated from the remaining residue by two sequential chromatographic purifications (silica gel; 100% pentane) as a colorless liquid (200 mg, 10%). $^{1H}$ NMR (CDCl$_3$, 300 MHz): δ 7.50 (d, J=2 Hz, 1H), 7.30 (d, J=2 Hz, 1H), 7.29 (s, 1H), 1.45 (s, 9H).

Preparation of 4-tert-butyl-3-chloro-benzaldehyde

The title compound was synthesized in analogy to 4-cyclopropyl benzaldehyde (described in example S53) using 4-bromo-1-tert-butyl-2-chloro-benzene (200 mg, 0.81 mmol), nBuLi (0.66 ml, 1.6M solution in hexane, 1.05 mmol) and DMF (251 µl, 3.23 mmol). The isolated residue was purified by flash column chromatography (1:9 ether:pentane) to give 4-tert-butyl-3-chloro-benzaldehyde (130 mg, 82%) as a colorless liquid. $^{1H}$ NMR (CDCl$_3$, 300 MHz): δ 9.94 (s, 1H), 7.85 (d, J=2 Hz, 1H), 7.70 (dd, J=2 and 8 Hz, 1H), 7.60 (d, J=8.0 Hz, 1H), 1.51 (s, 9H).

Preparation of (4-tert-butyl-3-chloro-benzyl)-[2-(3-trifluoromethyl-phenyl)-ethyl]-amine The title compound was synthesized in analogy to (4-cyclopropylbenzyl)-[2-(4-fluoro-3-trifluoromethylphenyl)-ethyl]-amine (described in example S53) using 4-tert-butyl-3-chloro-benzaldehyde (68 mg, 0.35 mmol), 2-(3-trifluoromethyl-phenyl)-ethylamine (65 mg, 0.35 mmol) and sodium borohydride (20 mg, 0.52 mmol). The desired product (123 mg, 96%) was isolated without further purification as a colorless oil. MS (ISP) 370.1 (M+H)+.

Example S111

Preparation of (4-tert-butyl-3-chloro-benzyl)-[2-(3,4-dichloro-phenyl)-ethyl]-amine The title compound was synthesized in analogy to (4-cyclopropylbenzyl)-[2-(4-fluoro-3-trifluoromethylphenyl)-ethyl]-amine (described in example S53) using 4-tert-butyl-3-chloro-benzaldehyde (prepared as described in example S110) (72 mg, 0.37 mmol), 2-(3,4-dichlorophenyl)-ethylamine (70 mg, 0.37 mmol) and sodium borohydride (21 mg, 0.55 mmol). The desired product (117 mg, 86%) was isolated without further purification as a colorless oil. MS (ISP) 370.1 (M+H)+.

Example S112

Preparation of [4-(1,1-dimethyl-butyl)-benzyl]-[2-(3-trifluoromethyl-phenyl)-ethyl]-amine 827 mg of 4-(1-methoxy-1-methyl-ethyl)-benzoic acid methyl ester (3.97 mmol) (prepared as described in example S102) and 1.26 ml allyltrimethylsilane (7.94 mmol) were dissolved in 10 ml DCM and the solution was cooled to −78° C. Then 4.77 ml of a 1 M solution of TiCl$_4$ in DCM were added dropwise. After 30 h the reaction was quenched at −78° C. by addition of methanol. Then water was added and the mixture was extracted 3 times with DCM. The combined extracts were washed with brine, dried with magnesium sulfate, filtered and concentrated. The remaining residue was purified by chromatography (silica gel; cyclohexane/EtOAc 95:5) to give 331 mg (38%) of 4-(1,1-dimethyl-but-3-enyl)-benzoic acid methyl ester as a colorless liquid. $^1H$ NMR (CDCl$_3$, 300 MHz): δ 1.33 (s, 6H), 2.38 (d, J=7 Hz, 2H), 3.90 (s, 3H), 4.91-5.00 (m, 3H), 5.51 (m, 1H), 7.41 (d, J=9 Hz, 1H), 7.97 (d, J=9 Hz, 1H).

365 mg of 4-(1,1-dimethyl-but-3-enyl)-benzoic acid methyl ester (1.67 mmol) were dissolved in 10 ml EtOAc and hydrogenated in the presence of 40 mg Pd/C (10%) at rt. After 1 h the catalyst was filtered off and the filtrate was concentrated. The remaining 323 mg (88%) of 4-(1,1-dimethyl-butyl)-benzoic acid methyl ester were used in the following reaction step without further purification. $^1H$ NMR (CDCl$_3$, 300 MHz): δ 0.81 (t, J=7 Hz, 3H), 1.05 (m, 2H), 1.31 (s, 6H), 1.59 (m, 2H), 3.90 (s, 3H), 7.39 (d, J=9 Hz, 1H), 7.96 (d, J=9 Hz, 1H).

320 mg of 4-(1,1-dimethyl-butyl)-benzoic acid methyl ester (1.45 mmol) were dissolved in 5 ml THF and 4.4 ml of a 1 N solution of lithium hydroxide and a few drops of methanol were added. The reaction mixture was stirred at rt overnight. Then the pH was adjusted to 2 by addition of 1 N HCl solution and the mixture was extracted with EtOAc. The combined organic layers were washed with water and brine, dried with magnesium sulfate, filtered and the solvent was evaporated. The remaining 290 mg (97%, white solid) of 4-(1,1-dimethyl-butyl)-benzoic acid were used in the following step without further purification. $^1H$ NMR (CDCl$_3$, 300 MHz): δ 0.82 (t, J=7 Hz, 3H), 1.06 (m, 2H), 1.32 (s, 6H), 1.61 (m, 2H), 7.43 (d, J=9 Hz, 1H), 8.04 (d, J=9 Hz, 1H).

451 mg of TBTU (1.41 mmol) and 266 mg of 2-(3-trifluoromethylphenyl)-ethylamine (1.41 mmol) were added to a stirred solution of 290 mg of 4-(1,1-dimethyl-butyl)-benzoic acid (3.09 mmol) in 6 ml DMF. Then 1.2 ml of N,N-diisopropyl ethyl amine (7.03 mmol) were added and stirring at ambient temperature was continued for 17 h. The reaction mixture was then poured into water and extracted with EtOAc. The combined extracts were washed with 10% aqueous KHCO$_3$, diluted aqueous HCl and brine, dried over magnesium sulfate, filtered and the solvent was evaporated. The remaining residue was purified by chromatography (silica gel; c-hexane/EtOAc 4:1). This gave 443 mg (83%) of 4-(1,1-dimethyl-butyl)-N-[2-(3-trifluoromethyl-phenyl)-ethyl]-benzamide as a colorless liquid. $^1H$ NMR (CDCl$_3$, 300 MHz): δ 0.80 (t, J=7 Hz, 3H), 1.04 (m, 2H), 1.29 (s, 6H), 1.57 (m, 2H), 3.00 (t, J=7 Hz, 2H), 3.73 (q, J=7 Hz, 2H), 6.11 (br s, 1H), 7.37 (d, J=9 Hz, 1H), 7.44 (m, 2H), 7.51 (m, 2H), 7.63 (d, J=9 Hz, 1H).

A solution of 440 mg of 4-(1,1-dimethyl-butyl)-N-[2-(3-trifluoromethyl-phenyl)-ethyl]-benzamide (1.17 mmol) in 10 ml of THF was added dropwise to 4.66 ml of a 1 molar solution of BH$_3$-THF complex in THF at 0° C. The reaction mixture was stirred for 1 h at rt and then heated to reflux overnight. Upon cooling to rt 2 ml of 6N HCl were added and the mixture was stirred for 1 h. Then the pH was adjusted to 9 by addition of 1 N sodium hydroxide solution and the mixture was extracted three times with EtOAc. The combined organic layers were washed with brine, dried with magnesium sulfate, filtered and concentrated. This gave 422 mg (100%) of [4-(1,1-dimethyl-butyl)-benzyl]-[2-(3-trifluoromethyl-phenyl)-ethyl]-amine as a light yellow oil which was used in the following coupling step without further purification. MS (ISP) 364.2 (M+H)+.

Example S113

Preparation of (4-cyclobutyl-benzyl)-[2-(3,4-dichloro-phenyl)-ethyl]-amine

Preparation of bromo-4-cyclobutyl-benzene

To a solution of 1.37 g of 1-(4-bromophenyl)-cyclobutanol (6 mmol) (prepared as described in example S97) in 15 ml DCM were added 1.15 ml of triethylsilane (7.2 mmol) and the mixture was cooled to −78° C. Then 1.15 ml of boron trifluoride diethyl etherate complex were added and the reaction mixture was warmed to −40° C. and stirred for 8 h. The reaction was then quenched by addition of 10% aqueous KHCO$_3$ and the mixture was extracted three times with DCM. The combined extracts were washed with brine, dried with magnesium sulfate and concentrated. The remaining residue was purified by column chromatography (silica gel; cyclohexane) to give 0.84 g (66%) of 1-bromo-4-cyclobutyl-benzene as a colorless liquid. $^1H$ NMR (CDCl$_3$, 300 MHz): δ 1.85 (m, 1H), 1.92-2.18 (m, 3H), 2.33 (m, 2H), 3.49 (quint, J=8.5 Hz, 1H), 7.08 (d, J=8.5 Hz, 2H), 7.40 (d, J=8.5 Hz, 2H).

Preparation of 4-cyclobutyl-benzaldehyde

The title compound was synthesized in analogy to 4-cyclopropyl benzaldehyde (described in example S53) using 830 mg of 1-bromo-4-cyclobutyl-benzene (3.93 mmol), 2.7 ml of a 1.6 molar solution of n-BuLi in hexane (4.32 mmol) and 605 µl of DMF (7.86 mmol). The isolated residue was purified by flash column chromatography (5:95 EtOAc/cyclohexane) to give 422 mg of 4-cyclobutyl-benzaldehyde (67%) as a colorless liquid. $^{1H}$ NMR (CDCl$_3$, 300 MHz): δ 1.89 (m, 1H), 1.97-2.26 (m, 3H), 2.40 (m, 2H), 3.63 (quint, J=8.5 Hz, 1H), 7.36 (d, J=8.0 Hz, 2H), 7.81 (d, J=8.0 Hz, 2H), 9.97 (s, 1H).

Preparation of (4-cyclobutyl-benzyl)-[2-(3,4-dichloro-phenyl)-ethyl]-amine

The title compound was synthesized in analogy to (4-cyclopropylbenzyl)-[2-(4-fluoro-3-trifluoromethylphenyl)-ethyl]-amine (described in example S53) using 200 mg of 4-cyclobutyl-benzaldehyde (1.25 mmol), 237 mg of 2-(3,4-dichloro-phenyl)-ethylamine (1.25 mmol) and 71 mg of sodium borohydride (1.87 mmol). The isolated yellow oil (416 mg, 100%) was used in the following step without further purification. $^{1H}$ NMR (CDCl$_3$, 300 MHz): δ 1.84 (m, 1H), 1.95-2.21 (m, 3H), 2.33 (m, 2H), 2.76 (m, 2H), 2.87 (m, 2H), 3.53 (quint, J=9 Hz, 1H), 3.76 (s, 2H), 7.03 (dd, J=8 and 2 Hz, 1H), 7.19 (m, 4H), 7.29 (d, J=2 Hz, 1H), 7.34 (d, J=8 Hz, 1H).

Example S114

Preparation of (4-cyclobutyl-benzyl)-[2-(3-trifluoromethyl-phenyl)-ethyl]-amine

The title compound was synthesized in analogy to (4-cyclopropylbenzyl)-[2-(4-fluoro-3-trifluoromethylphenyl)-ethyl]-amine (described in example S53) using 180 mg of 4-cyclobutyl-benzaldehyde (1.23 mmol) (described in example S113), 213 mg of 2-(3-trifluoromethylphenyl)-ethylamine (1.23 mmol) and 64 mg of sodium borohydride (1.69 mmol). The isolated yellow oil (343 mg, 92%) was used in the following step without further purification. $^{1H}$ NMR (CDCl$_3$, 300 MHz): δ 1.85 (m, 1H), 1.92-2.21 (m, 3H), 2.33 (m, 2H), 2.89 (m, 4H), 3.53 (quint, J=9 Hz, 1H), 3.78 (s, 2H), 7.19 (m, 4H), 7.39 (m, 2H), 7.46 (m, 2H).

Example S115

Preparation of (4-cyclopentyl-benzyl)-[2-(3,4-dichloro-phenyl)-ethyl]-amine

Preparation of 1-(4-bromo-phenyl)-cyclopentanol

The title compound was synthesized in analogy to 1-(4-bromo-phenyl)-cyclobutanol (described in example S97) using 3 g of 1,4-dibromobenzene (12.7 mmol), 7.95 ml of a 1.6 molar solution of n-BuLi in hexane (12.7 mmol) and 1.24 ml of cyclopentanone (14.0 mmol). The isolated residue was purified by flash column chromatography (1:4 diethyl ether/pentane) to give 1.2 g of 1-(4-bromo-phenyl)-cyclopentanol (39%) as a colorless liquid.

Preparation of bromo-4-cyclopentyl-benzene

The title compound was synthesized in analogy to bromo-4-cyclobutyl-benzene (described in example S113) using 823 mg of 1-(4-bromo-phenyl)-cyclopentanol (3.41 mmol), 652 µl of triethylsilane (4.10 mmol) and 649 µl of boron trifluoride diethyl etherate complex (5.12 mmol). The isolated residue was purified by flash column chromatography (1:9 EtOAc/-cyclohexane) to give 727 mg of a mixture of the desired 4-cyclopentyl-benzene and 1-bromo-4-cyclopent-1-enyl-benzene as a white semi-solid. This mixture was used in the following step without further purification.

Preparation of 4-cyclopentyl-benzaldehyde

The title compound was synthesized in analogy to 4-cyclopropyl benzaldehyde (described in example S53) using 720 mg of a mixture of 1-bromo-4-cyclopentyl-benzene and 1-bromo-4-cyclopent-1-enyl-benzene (~3.2 mmol), 2.2 ml of a 1.6 molar solution of n-BuLi in hexane (3.52 mmol) and 492 µl of DMF (6.40 mmol). 4-Cyclopentyl-benzaldehyde was isolated by flash column chromatography (5:95 EtOAc/c-hexane) as a yellow liquid (165 mg, 30%). $^{1H}$ NMR (CDCl$_3$, 300 MHz): δ 1.53-1.91 (m, 6H), 2.11 (m, 2H), 3.07 (quint, J=8.5 Hz, 1H), 7.40 (d, J=8 Hz, 2H), 7.80 (d, J=8 Hz, 2H), 9.97 (s, 1H).

Preparation of (4-cyclopentyl-benzyl)-[2-(3,4-dichloro-phenyl)-ethyl]-amine

The title compound was synthesized in analogy to (4-cyclopropylbenzyl)-[2-(4-fluoro-3-trifluoromethylphenyl)-ethyl]-amine (described in example S53) using 160 mg of 4-cyclopentyl-benzaldehyde (0.92 mmol), 175 mg of 2-(3,4-dichloro-phenyl)-ethylamine (0.92 mmol) and 52 mg of sodium borohydride (1.38 mmol). The isolated light yellow oil (183 mg, 57%) was used in the following step without further purification. MS (ISP) 348.2 (M+H)$^+$.

Example S116

Preparation of 4-fluoro-5-methyl-1H-indole-7-carboxylic acid ethyl ester

7-Bromo-4-fluoro-5-methyl-1H-indole: This compound was produced in accordance with the general method of example S91 from 5-bromo-2-fluoro-4-nitrotoluene (EP 0945435). Dark red liquid, MS (EI) 227.0/229.0 (87/100, M$^+$); $^1$H-NMR (300 MHz, CDCl$_3$): δ 8.28 (br. s, 1H), 7.20 (t, J=3.0 Hz, 1H), 7.14 (d, J=6.0 Hz, 1H), 6.65 (dd, J=3.0, 2.4 Hz, 1H), 2.34 (d, J=2.1 Hz, 3H).

4-Fluoro-5-methyl-1H-indole-7-carboxylic acid ethyl ester: A solution of 7-bromo-4-fluoro-5-methyl-1H-indole (1.79 g, 7.85 mmol), triethylamine (1.67 g, 16.5 mmol), and 1,1'-bis(diphenylphosphino)ferrocene-palladium(II)dichloride DCM complex (164 mg, 0.200 mmol) in ethanol (18 mL) and toluene (18 mL) was stirred for 24 h at 130° C. under a carbon monoxide atmosphere (50 bar). After cooling and evaporation of volatile material, the residue was chromatographed (SiO$_2$, heptane-EtOAc gradient), to afford the title compound (1.07 g, 61%). Light brown solid, MS (EI) 175.1 (100), 221.1 (98, M$^+$).

Example S117

Preparation of [3-chloro-4-(1-methoxy-1-methyl-ethyl)-benzyl]-[2-(3-trifluoromethyl-phenyl)-ethyl]-amine Preparation of 2-(4-bromo-2-chloro-phenyl)-propan-2-ol 1.88 ml of a 3 molar solution of methyl magnesium bromide in ether were added dropwise to a solution of 470 mg (1.88 mmol) of 4-bromo-2-chloro-benzoic acid methyl ester [CAS 185312-82-7] in 20 ml THF at −78° C. The reaction mixture was then warmed to rt and stirred overnight. The mixture was then poured into sat. ammonium chloride solution and extracted with ether. The combined organic layers were washed with brine, dried (MgSO$_4$), filtered and concentrated in vacuo to give a residue which was purified by flash column chromatography (0 to 20% ether in pentane). The title compound was obtained as a colorless liquid (415 mg, 82%). $^1H$ NMR (CDCl$_3$, 300 MHz): δ 1.71 (s, 6H), 2.39 (s, 1H), 7.38 (dd, J=8.5 and 2.1 Hz, 1H), 7.52 (d, J=2.1 Hz, 1H), 7.58 (d, J=8.5 Hz, 1H).

Preparation of 4-bromo-2-chloro-1-(1-methoxy-1-methyl-ethyl)-benzene

A solution of 370 mg (1.48 mmol) of 2-(4-bromo-2-chloro-phenyl)-propan-2-ol in 2 ml DMF was added to a suspension of sodium hydride (65 mg, ~60% dispersion in oil) in 2 ml DMF at 0° C. The mixture was stirred at 0° C. for 30 min and then 111 µl (1.78 mmol) of methyl iodide were added. The reaction mixture was then warmed to rt and stirring was continued overnight. Then water was added and the mixture was extracted with ether. The organic phase was washed with water and brine, dried (MgSO$_4$), filtered, and concentrated in vacuo to give a residue which was purified by flash column chromatography (1:9 ether/pentane). The title compound was obtained as a colorless liquid (310 mg, 79%). $^1H$ NMR (CDCl$_3$, 300 MHz): δ 1.64 (s, 6H), 3.13 (s, 3H), 7.35 (m, 2H), 7.54 (d, J=1.7 Hz, 1H).

Preparation of 3-chloro-4-(1-methoxy-1-methyl-ethyl)-benzaldehyde

The title compound was synthesized in analogy to 4-cyclopropyl benzaldehyde (described in example S53) using 310 mg of 4-bromo-2-chloro-1-(1-methoxy-1-methyl-ethyl)-benzene (1.18 mmol), 1.1 ml of a 1.6 molar solution of n-BuLi in hexane (1.76 mmol) and 457 µl of DMF (5.88 mmol). The isolated residue was purified by flash column chromatography (1:9 ether/pentane) to give 154 mg of 3-chloro-4-(1-methoxy-1-methyl-ethyl)-benzaldehyde (62%) as a colorless liquid. $^1H$ NMR (CDCl$_3$, 300 MHz): δ 1.69 (s, 6H), 3.18 (s, 3H), 7.69 (d, J=8.2 Hz, 1H), 7.75 (dd, J=8.2 and 1.7 Hz, 1H), 7.58 (d, J=1.7 Hz, 1H), 9.97 (s, 1H).

Preparation of [3-chloro-4-(1-methoxy-1-methyl-ethyl)-benzyl]-[2-(3-trifluoromethyl-phenyl)-ethyl]-amine The title compound was synthesized in analogy to (4-cyclopropylbenzyl)-[2-(4-fluoro-3-trifluoromethylphenyl)-ethyl]-amine (described in example S53) using 77 mg of 3-chloro-4-(1-methoxy-1-methyl-ethyl)-benzaldehyde (0.36 mmol), 68 mg of 2-(3-trifluoromethylphenyl)-ethylamine (0.36 mmol) and 21 mg of sodium borohydride (0.54 mmol). The isolated colorless liquid (113 mg, 81%) was used in the following step without further purification. MS (ISP) 386.2 (M+H)$^+$.

Example S118

Preparation of [3-chloro-4-(1-methoxy-1-methyl-ethyl)-benzyl]-[2-(3,4-dichloro-phenyl)-ethyl]-amine The title compound was synthesized in analogy to (4-cyclopropylbenzyl)-[2-(4-fluoro-3-trifluoromethylphenyl)-ethyl]-amine (described in example S53) using 77 mg of 3-chloro-4-(1-methoxy-1-methyl-ethyl)-benzaldehyde (0.36 mmol) (described in example S117), 69 mg of 2-(3,4-dichloro-phenyl)-ethylamine (0.36 mmol) and 21 mg of sodium borohydride (0.54 mmol). The isolated colorless liquid (126 mg, 90%) was used in the following step without further purification. MS (ISP) 386.1 (M+H)$^+$.

Example S119

Preparation of (2,2-dimethyl-benzo[1,3]dioxol-5-ylmethyl)-[2-(3-trifluoromethyl-phenyl)-ethyl]-amine Preparation of 2,2-dimethyl-benzo[1,3]dioxole-5-carbaldehyde The title compound was synthesized in analogy to 4-cyclopropyl benzaldehyde (described in example S53) using 420 mg of 5-bromo-2,2-dimethyl-benzo[1,3]dioxole [CAS 73790-19-9] (1.83 mmol), 1.38 ml of a 1.6 molar solution of n-BuLi in hexane (2.20 mmol) and 712 µl of DMF (9.17 mmol). The isolated residue was purified by flash column chromatography (1:9 ether/pentane) to give 270 mg of 2,2-dimethyl-benzo[1,3]dioxole-5-carbaldehyde (83%) as a light yellow liquid. $^1H$ NMR (CDCl$_3$, 300 MHz): δ 1.72 (s, 6H), 6.84 (d, J=7.8 Hz, 1H), 7.26 (s, 1H), 7.87 (dd, J=8.0 and 1.7 Hz, 1H), 9.97 (s, 1H).

Preparation of (2,2-dimethyl-benzo[1,3]dioxol-5-ylmethyl)-[2-(3-trifluoromethyl-phenyl)-ethyl]-amine The title compound was synthesized in analogy to (4-cyclopropylbenzyl)-[2-(4-fluoro-3-trifluoromethylphenyl)-ethyl]-amine (described in example S53) using 84 mg of 2,2-dimethyl-benzo[1,3]dioxole-5-carbaldehyde (0.47 mmol), 89 mg of 2-(3-trifluoromethylphenyl)-ethylamine (0.47 mmol) and 27 mg of sodium borohydride (0.71 mmol). The isolated colorless semisolid (137 mg, 83%) was used in the following step without further purification. $^1H$ NMR (CDCl$_3$, 300 MHz): δ 1.66 (s, 6H), 2.89 (m, 4H), 3.70 (s, 2H), 6.68 (m, 3H), 7.39 (m, 2H), 7.46 (m, 2H).

Example S120

Preparation of [2-(3,4-dichloro-phenyl)-ethyl]-(2,2-dimethyl-benzo[1,3]dioxol-5-ylmethyl)-amine The title compound was synthesized in analogy to (4-cyclopropylbenzyl)-[2-(4-fluoro-3-trifluoromethylphenyl)-ethyl]-amine (described in example S53) using 83 mg of 2,2-dimethyl-benzo[1,3]dioxole-5-carbaldehyde (0.47 mmol) (described in example S119), 89 mg of 2-(3,4-dichloro-phenyl)-ethylamine (0.47 mmol) and 26 mg of sodium borohydride (0.70 mmol). The isolated colorless liquid (133 mg, 81%) was used in the following step without further purification. $^1H$ NMR (CDCl$_3$, 300 MHz): δ 1.66 (s, 6H), 2.76 (m, 2H), 2.86 (m, 2H), 3.68 (s, 2H), 6.66 (s, 1H), 6.68 (d, J=7.4 Hz, 2H), 7.04 (dd, J=8.2 and 2.1 Hz, 1H), 7.29 (d, J=2.1 Hz, 1H), 7.34 (d, J=8.2 Hz, 1H).

Example S121

Preparation of (3-chloro-4-trifluoromethyl-benzyl)-[2-(3-trifluoromethyl-phenyl)-ethyl]-amine

Preparation of 3-chloro-4-trifluoromethyl-N-[2-(3-trifluoromethyl-phenyl)-ethyl]-benzamide The title compound was synthesized in analogy to N-[2-(3,4-dichloro-phenyl)-ethyl]-4-(2,2,2-trifluoro-1-hydroxy-1-trifluoromethyl-ethyl)-benzamide (described in example S98) using 250 mg of 3-chloro-4-trifluoromethyl-benzoic acid (1.11 mmol) and 221 mg (1.17 mmol) of 2-(3-trifluoromethylphenyl)-ethylamine. The isolated residue was purified by flash column chromatography to give 360 mg of 3-chloro-4-trifluoromethyl-N-[2-(3-trifluoromethyl-phenyl)-ethyl]-benzamide (82%) as a yellow solid.

Preparation of (3-chloro-4-trifluoromethyl-benzyl)-[2-(3-trifluoromethyl-phenyl)-ethyl]-amine The title compound was synthesized in analogy to [2-(3,4-dichloro-phenyl)-ethyl]-[4-(2,2,2-trifluoro-1-hydroxy-1-trifluoromethyl-ethyl)-benzyl]-amine (described in example S98) using 200 mg of 3-chloro-4-trifluoromethyl-N-[2-(3-trifluoromethyl-phenyl)-ethyl]-benzamide (0.51 mmol) and 2.02 ml of a 1 molar solution of $BH_3$-THF complex in THF. The isolated residue was purified by flash column chromatography to give 180 mg of (3-chloro-4-trifluoromethyl-benzyl)-[2-(3-trifluoromethyl-phenyl)-ethyl]-amine (93%) as a colorless oil. MS (ISP) 382.1 $(M+H)^+$.

Example S122

Preparation of (2-chloro-4-cyclopropyl-benzyl)-[2-(3-trifluoromethyl-phenyl)-ethyl]-amine 3.0 g of 4-bromo-2-chloro-benzoic acid (12.74 mmol) were dissolved in 60 ml methanol and treated with 0.6 ml concentrated HCl. After 17 h at reflux the reaction mixture was concentrated in vacuo, diluted with DCM and washed with a saturated aqueous $NaHCO_3$ solution and brine, dried with magnesium sulfate, filtered and concentrated in vacuo leading to 2.7 g of 4-bromo-2-chloro-benzoic acid methyl ester as a light yellow oil. MS (+cEI) 250.0 (M).

2.1 g crude 4-bromo-2-chloro-benzoic acid methyl ester were dissolved in 38 ml toluene and treated with 0.94 g cyclopropylboronic acid (10.94 mmol), 6.25 g potassium phosphate (29.46 mmol), 236 mg triphenylphosphine (0.84 mmol), 94 mg palladium acetate (0.42 mmol) and 1.9 ml water. The reaction mixture was stirred 17 h at 100° C. under Argon. After cooling down to rt, the reaction mixture was treated with 80 ml water, extracted with 2×80 ml EtOAc, washed with brine, dried over magnesium sulfate, filtered and concentrated in vacuo. The residue was purified by silicagel chromatography (100 g silicagel, heptane/AcOEt 95:5) leading to 1.17 g 2-chloro-4-cyclopropyl-benzoic acid methyl ester (66%) as a yellow oil. MS (+cEI): 210.1 (M).

To a solution of 7.01 ml Red-Al 3.5 M (24.54 mmol) in toluene was added at 0° C. a solution of 3.0 ml 1-methylpiperazine (26.89 mmol) in 16 ml toluene over 30 min. The resulting solution was then added dropwise over 40 min to 1.1 g 2-chloro-4-cyclopropyl-benzoic acid methyl ester (5.2 mmol) in 32 ml toluene between −5° C. and 0° C. After 30 min stirring at this temperature, the reaction mixture was cooled to −10° C. and treated dropwise with 30 ml water. The mixture was then filtered, diluted with ethylacetate, washed with 1N-HCl, brine, dried over magnesium sulfate, filtered and concentrated in vacuo, leading to 0.98 g of 2-chloro-4-cyclopropyl-benzaldehyde as a brown oil (100%). MS (+cEI): 180.1 (M).

0.927 g of 2-chloro-4-cyclopropyl-benzaldehyde (5.37 mmol) and 1.52 g 2-(3-trifluoromethyl-phenyl)-ethylamine (8.05 mmol) were dissolved in 15 ml methanol and refluxed for 2 h. After cooling down to rt, the reaction mixture was treated in portions with 305 mg $NaBH_4$, stirred at rt for 10 min and 12 h under reflux. The reaction mixture was then cooled to rt, treated with 1 ml 1N HCl and concentrated in vacuo. The resulting oil was then diluted with EtOAc, washed with water and brine, dried over magnesium sulfate, filtered and concentrated in vacuo. The residue was purified by chromatography (40 g silicagel, heltane/AcOEt 2:1) leading to 1.41 g (2-chloro-4-cyclopropyl-benzyl)-[2-(3-trifluoromethyl-phenyl)-ethyl]-amine (74%) as a yellow oil. MS: 354 $(M+H)^+$.

The following compounds were prepared in analogy to the above procedure starting from the appropriate acid:

| Ex. | acid | amine |
| --- | --- | --- |
| S123 | 4-Bromo-2-fluoro-benzoic-acid | (4-cyclopropyl-2-fluoro-benzyl)-[2-(3-trifluoromethyl-phenyl)-ethyl]-amine |
| S124 | 4-Bromo-3-fluoro-benzoic-acid | (4-cyclopropyl-3-fluoro-benzyl)-[2-(3-trifluoromethyl-phenyl)-ethyl]-amine |

Preparation of Compounds of Formula I

Example 1

Preparation of 1H-Indole-7-carboxylic acid (4-tert-butyl-benzyl)-(3-methyl-butyl)-amide 1 and other compounds of formula I To a solution of 48 mg of 1H-indole-7-carboxylic acid (0.3 mmol) and 96 mg of TBTU (0.3 mmol) in 4 ml DMF, were added 0.26 ml (1.5 mmol) of N,N-diisopropylethyl amine. After stirring for 5 min at rt, 70 mg (0.3 mmol) of (4-tert-butyl-benzyl)-(3-methyl-butyl)-amine in 1 ml DMF were added. After stirring for 2 h at rt, the reaction mixture was diluted with 50 ml water and extracted with 2×50 ml EtOAc. The combined organic phases were washed with water and brine, dried with magnesium sulfate, filtered and concentrated in vacuo. The resulting orange oil was purified by column chromatography (8 g silica gel; heptane/EtOAc 4:1) to give 101 mg (86%) of a light yellow solid. MS (ISP) 377.5 $(M+H)^+$.

The following compounds were prepared according to the above procedure:

5-Chloro-1H-indole-7-carboxylic acid (4-cyclopropyl-benzyl)-[2-(4-fluoro-3-trifluoromethylphenyl)-ethyl]-amide 61 using 5-chloro-1H-indole-7-carboxylic acid (50 mg, 0.26 mmol), N,N-diisopropylethyl amine (65 µl, 0.38 mmol), TBTU (90 mg, 0.28 mmol) and (4-cyclopropylbenzyl)-[2-(4-fluoro-3-trifluoromethylphenyl)-ethyl]-amine (95 mg, 0.28 mmol) in DMF. Flash column chromatography (1:9-1:4 EtOAc:cyclohexane): 108 mg, 82%; off white foam. MS (ISP) 515.3 $(M+H)^+$.

5-Chloro-1H-indole-7-carboxylic acid (4-cyclopropyl-benzyl)-[2-(3-trifluoromethoxy-phenyl)-ethyl]-amide 63 using 5-chloro-1H-indole-7-carboxylic acid (50 mg, 0.26 mmol), N,N-diisopropylethyl amine (65 µl, 0.38 mmol), TBTU (90 mg, 0.28 mmol) and (4-cyclopropylbenzyl)-[2-

(3-trifluoromethoxyphenyl)-ethyl]-amine (94 mg, 0.28 mmol) in DMF. Flash column chromatography (1:9-1:4 EtOAc:cyclohexane): 92 mg, 70%; light yellow foam. MS (ISP) 513.3 (M+H)$^+$.

5-Chloro-1H-indole-7-carboxylic acid (4-cyclopropyl-benzyl)-[2-(3,4-dichlorophenyl)-ethyl]-amide 65 using 5-chloro-1H-indole-7-carboxylic acid (50 mg, 0.26 mmol), N,N-diisopropylethyl amine (65 µl, 0.38 mmol), TBTU (90 mg, 0.28 mmol) and (4-cyclopropylbenzyl)-[2-(3,4-dichlorophenyl)-ethyl]-amine (90 mg, 0.28 mmol) in DMF. Flash column chromatography (1:9-1:4 EtOAc:cyclohexane): 95 mg, 75%, white foam. MS (ISP) 499.1 (M+H)$^+$.

5-Chloro-1H-indole-7-carboxylic acid [2-(4-chlorophenyl)-ethyl]-(4-cyclopropylbenzyl)-amide 67 using 5-chloro-1H-indole-7-carboxylic acid (50 mg, 0.26 mmol), N,N-diisopropylethyl amine (65 µl, 0.38 mmol), TBTU (90 mg, 0.28 mmol) and [2-(4-chlorophenyl)-ethyl]-(4-cyclopropylbenzyl)-amine (80 mg, 0.28 mmol) in DMF. Flash column chromatography (1:9-1:4 EtOAc:cyclohexane): 103 mg, 87%, white foam. MS (ISP) 465.2 (M+H)$^+$.

5-Chloro-2-methyl-1H-indole-7-carboxylic acid (4-tert-butylbenzyl)-[2-(4-fluorophenyl)-ethyl]-amide 143 using 5-chloro-2-methyl-1H-indole-7-carboxylic acid (22 mg, 0.11 mmol), N,N-diisopropylethyl amine (29 µl, 0.17 mmol), TBTU (37 mg, 0.12 mmol) and (4-tert-butylbenzyl)-[2-(4-fluorophenyl)-ethyl]-amine (25 mg, 0.01 mmol) in DMF. Flash column chromatography (1:9-1:4 EtOAc:cyclohexane): 44 mg, 88%, white foam. MS (ISP) 477.1 (M+H)$^+$.

5-Chloro-2-ethyl-1H-indole-7-carboxylic acid (4-tert-butylbenzyl)-[2-(4-fluorophenyl)-ethyl]-amide 144 using 5-chloro-2-ethyl-1H-indole-7-carboxylic acid (38 mg, 0.17 mmol), N,N-diisopropylethyl amine (57.8 µl, 0.34 mmol), TBTU (60 mg, 0.19 mmol) and (4-tert-butylbenzyl)-[2-(4-fluorophenyl)-ethyl]-amine (48.5 mg, 0.17 mmol) in DMF. Flash column chromatography (1:9-1:4 EtOAc:cyclohexane): 69 mg, 83%, light yellow foam. MS (ISP) 491.3 (M+H)$^+$.

5-Chloro-2-ethyl-1H-indole-7-carboxylic acid (4-tert-butylbenzyl)-[2-(3,4-dichlorophenyl)-ethyl]-amide 145 using 5-chloro-2-ethyl-1H-indole-7-carboxylic acid (36 mg, 0.16 mmol), N,N-diisopropylethyl amine (54.81 µl, 0.32 mmol), TBTU (57 mg, 0.18 mmol) and (4-tert-butylbenzyl)-[2-(3,4-dichlorophenyl)ethyl]amine (54 mg, 0.16 mmol) in DMF. Flash column chromatography (1:9-1:4 EtOAc:cyclohexane): 80 mg, 92%, light yellow foam. MS (ISP) 543.3 (M+H)$^+$.

5-Chloro-1H-indole-7-carboxylic acid (4-cyclopropylbenzyl)-[2-(3-trifluoromethyl-phenyl)-ethyl]-amide 146 using 5-chloro-1H-indole-7-carboxylic acid (40 mg, 0.20 mmol), N,N-diisopropylethyl amine (87 µl, 0.51 mmol), TBTU (72 mg, 0.23 mmol) and (4-cyclopropylbenzyl)-[2-(3-trifluoromethylphenyl)-ethyl]-amine (72 mg, 0.23 mmol) in DMF. Flash column chromatography (1:9-1:4 EtOAc:cyclohexane): 69 mg, 68%, light yellow foam. MS (ISP) 497.1 (M+H)$^+$.

5-Chloro-1H-indole-7-carboxylic acid [4-(1-methylcyclopropyl)-benzyl]-[2-(3-trifluoromethylphenyl)-ethyl]-amide 147 using 5-chloro-1H-indole-7-carboxylic acid (50 mg, 0.26 mmol), N,N-diisopropylethyl amine (52.2 µl, 0.31 mmol), TBTU (90 mg, 0.28 mmol) and [4-(1-methylcyclopropyl)-benzyl]-[2-(3-trifluoro-methylphenyl)-ethyl]-amine (85 mg, 0.26 mmol) in DMF. Flash column chromatography (1:9-1:4 EtOAc:cyclohexane): 94 mg, 72%, white foam. MS (ISP) 511.3 (M+H)$^+$.

5-Chloro-1H-indole-7-carboxylic acid [1-(4-tert-butylphenyl)-ethyl]-[2-(3-trifluoro-methylphenyl)-ethyl]-amide 148 using 5-chloro-1H-indole-7-carboxylic acid (50 mg, 0.26 mmol), N,N-diisopropylethyl amine (52.2 µl, 0.31 mmol), TBTU (90 mg, 0.28 mmol) and [1-(4-tert-butylphenyl)-ethyl]-[2-(3-trifluoromethyl-phenyl)-ethyl]-amine (89 mg, 0.26 mmol) in DMF. Flash column chromatography (1:9-1:4 EtOAc:cyclohexane): 87 mg, 65%, white foam. MS (ISP) 527.5 (M+H)$^+$.

5-Chloro-1H-indole-7-carboxylic acid [4-(1-methoxycyclopropyl)-benzyl]-[2-(3-trifluoromethylphenyl)-ethyl]-amide 149 using 5-chloro-1H-indole-7-carboxylic acid (50 mg, 0.26 mmol), N,N-diisopropylethyl amine (52.2 µl, 0.31 mmol), TBTU (90 mg, 0.28 mmol) and [4-(1-methoxycyclopropyl)-benzyl]-[2-(3-trifluoromethylphenyl)-ethyl]-amine (89 mg, 0.26 mmol) in DMF. Flash column chromatography (1:9-1:4 EtOAc:cyclohexane): 98 mg, 73%, white foam. MS (ISP) 527.0 (M+H)$^+$.

5-Chloro-1H-indole-7-carboxylic acid [4-(1-ethylcyclopropyl)-benzyl]-[2-(3-trifluoro-methylphenyl)-ethyl]-amide 150 using 5-chloro-1H-indole-7-carboxylic acid (60 mg, 0.31 mmol), N,N-diisopropylethyl amine (78 µl, 0.46 mmol), TBTU (108 mg, 0.34 mmol) and [4-(1-ethylcyclopropyl)-benzyl]-[2-(3-trifluoromethylphenyl)-ethyl]-amine (107 mg, 0.31 mmol) in DMF. Flash column chromatography (1:9-1:4 EtOAc:cyclohexane): 102 mg, 63%, white foam. MS (ISP) 525.5 (M+H)$^+$.

5-Methyl-1H-indole-7-carboxylic acid (4-tert-butyl-benzyl)-[2-(4-chloro-phenyl)-ethyl]-amide 151 from 50 mg of 5-methyl-1H-indole-7-carboxylic acid (0.29 mmol) and 86 mg (0.29 mmol) of (4-tert-butyl-benzyl)-[2-(4-chloro-phenyl)-ethyl]-amine. After final purification (silica gel; c-hexane/EtOAc 4:1) 82 mg (63%) of an off-white solid were isolated. MS (ISP) 459.4 (M+H)$^+$.

5-Methyl-1H-indole-7-carboxylic acid (4-tert-butyl-benzyl)-[2-(3-trifluoromethyl-phenyl)-ethyl]-amide 152 from 50 mg of 5-methyl-1H-indole-7-carboxylic acid (0.29 mmol) and 96 mg (0.29 mmol) of (4-tert-butyl-benzyl)-[2-(3-trifluoromethyl-phenyl)-ethyl]-amine. After final purification (silica gel; c-hexane/EtOAc 4:1) 79 mg (56%) of an off-white solid were isolated. MS (ISP) 493.3 (M+H)$^+$.

5-Methyl-1H-indole-7-carboxylic acid (4-tert-butyl-benzyl)-[2-(4-fluoro-phenyl)-ethyl]-amide 153 from 50 mg of 5-methyl-1H-indole-7-carboxylic acid (0.29 mmol) and 81 mg (0.29 mmol) of (4-tert-butyl-benzyl)-[2-(4-fluoro-phenyl)-ethyl]-amine. After final purification (silica gel; c-hexane/EtOAc 4:1) 73 mg (58%) of an off-white solid were isolated. MS (ISP) 443.5 (M+H)$^+$.

5-Trifluoromethyl-1H-indole-7-carboxylic acid (4-tert-butyl-benzyl)-[2-(3,4-dichloro-phenyl)-ethyl]-amide 154 from 50 mg of 5-trifluoromethyl-1H-indole-7-carboxylic acid (0.22 mmol) and 73 mg (0.22 mmol) of (4-tert-butyl-benzyl)-[2-(3,4-dichloro-phenyl)-ethyl]-amine. After final purification (silica gel; cyclohexane/EtOAc 4:1) 60 mg (50%) of an off-white solid were isolated. MS (ISP) 547.3 (M+H)$^+$.

5-Methyl-1H-indole-7-carboxylic acid (4-pentafluoro-sulphuranyl-benzyl)-[2-(4-fluoro-phenyl)-ethyl]-amide 155 from 59 mg of 5-methyl-1H-indole-7-carboxylic acid (0.28 mmol) and 100 mg (0.28 mmol) of (4-pentafluoro-sulphuranyl-benzyl)-[2-(4-fluoro-phenyl)-ethyl]-amine. After final purification (silica gel; cyclohexane/EtOAc 2:1) 100 mg (63%) of an off-white solid were isolated. MS (ISP) 513.2 (M+H)$^+$.

2-Methyl-1H-indole-7-carboxylic acid (4-pentafluoro-sulphuranyl-benzyl)-[2-(3,4-dichloro-phenyl)-ethyl]-amide 156 from of 50 mg of 2-methyl-1H-indole-7-carboxylic acid (0.29 mmol) and 116 mg (0.29 mmol) of (4-pentafluoro-sulphuranyl-benzyl)-[2-(3,4-dichloro-phenyl)-ethyl]-amine.

After final purification (silica gel; cyclohexane/EtOAc 2:1) 93 mg (58%) of an off-white solid were isolated. MS (ISP) 563.2 (M+H)+.

2-Methyl-1H-indole-7-carboxylic acid (4-tert-butyl-benzyl)-[2-(3-trifluoromethoxy-phenyl)-ethyl]-amide 157 from 50 mg of 2-methyl-1H-indole-7-carboxylic acid (0.29 mmol) and 100 mg (0.29 mmol) of (4-tert-butyl-benzyl)-[2-(3-trifluoromethoxy-phenyl)-ethyl]-amine. After final purification (silica gel; cyclohexane/EtOAc 2:1) 77 mg (53%) of an off-white solid were isolated. MS (ISP) 509.4 (M+H)+.

2-Methyl-1H-indole-7-carboxylic acid (4-tert-butyl-benzyl)-[2-(4-fluoro-3-trifluoromethyl-phenyl)-ethyl]-amide 158 from 50 mg of 2-methyl-1H-indole-7-carboxylic acid (0.29 mmol) and 101 mg (0.29 mmol) of (4-tert-butyl-benzyl)-[2-(4-fluoro-3-trifluoromethyl-phenyl)-ethyl]-amine. After final purification (silica gel; cyclohexane/EtOAc 2:1) 77 mg (53%) of an off-white solid were isolated. MS (ISP) 511.3 (M+H)+.

5-Methyl-1H-indole-7-carboxylic acid (4-tert-butyl-benzyl)-[2-(3-trifluoromethoxy-phenyl)-ethyl]-amide 159 from 50 mg of 5-methyl-1H-indole-7-carboxylic acid (0.29 mmol) and 100 mg (0.29 mmol) of (4-tert-butyl-benzyl)-[2-(3-trifluoromethoxy-phenyl)-ethyl]-amine. After final purification (silica gel; cyclohexane/EtOAc 2:1) 123 mg (85%) of a light brown solid were isolated. MS (ISP) 509.4 (M+H)+.

5-Methyl-1H-indole-7-carboxylic acid (4-tert-butyl-benzyl)-[2-(4-fluoro-3-trifluoromethyl-phenyl)-ethyl]-amide 160 from 50 mg of 5-methyl-1H-indole-7-carboxylic acid (0.29 mmol) and 101 mg (0.29 mmol) of (4-tert-butyl-benzyl)-[2-(4-fluoro-3-trifluoromethyl-phenyl)-ethyl]-amine. After final purification (silica gel; c-hexane/EtOAc 2:1) 125 mg (86%) of a light brown solid were isolated. MS (ISP) 511.2 (M+H)+.

5,6-Difluoro-1H-indole-7-carboxylic acid (4-tert-butyl-benzyl)-[2-(4-methyl-thiazol-2-yl)-ethyl]-amide 161 from 34 mg of 5,6-difluoro-1H-indole-7-carboxylic acid (0.17 mmol) and 50 mg (0.17 mmol) of (4-tert-butyl-benzyl)-[2-(4-methyl-thiazol-2-yl)-ethyl]-amine. After final purification (silica gel; c-hexane/EtOAc 2:1) 42 mg (52%) of an off-white solid were isolated. MS (ISP) 468.3 (M+H)+.

5-Chloro-1H-indole-7-carboxylic acid (4-tert-butyl-benzyl)-[2-(4-methyl-thiazol-2-yl)-ethyl]-amide 162 from 54 mg of 5-chloro-1H-indole-7-carboxylic acid (0.28 mmol) and 80 mg (0.28 mmol) of (4-tert-butyl-benzyl)-[2-(4-methyl-thiazol-2-yl)-ethyl]-amine. After final purification (silica gel; cyclohexane/EtOAc 2:1) 82 mg (52%) of an off-white solid were isolated. MS (ISP) 466.3 (M+H)+.

5-Trifluoromethyl-1H-indole-7-carboxylic acid (4-tert-butyl-benzyl)-[2-(3-trifluoro-methyl-phenyl)-ethyl]-amide 163 from 90 mg of 5-trifluoromethyl-1H-indole-7-carboxylic acid (0.39 mmol) and 132 mg (0.39 mmol) of (4-tert-butyl-benzyl)-[2-(3-trifluoromethyl-phenyl)-ethyl]-amine. After final purification (silica gel; cyclohexane/EtOAc 4:1) 115 mg (54%) of an off-white solid were isolated. MS (ISP) 547.3 (M+H)+.

5-Trifluoromethyl-1H-indole-7-carboxylic acid (4-tert-butyl-benzyl)-[2-(4-fluoro-3-trifluoromethyl-phenyl)-ethyl]-amide 164 from 90 mg of 5-trifluoromethyl-1H-indole-7-carboxylic acid (0.39 mmol) and 139 mg (0.39 mmol) of (4-tert-butyl-benzyl)-[2-(4-fluoro-3-trifluoromethyl-phenyl)-ethyl]-amine. After final purification (silica gel; cyclohexane/EtOAc 4:1) 121 mg (55%) of an off-white solid were isolated. MS (ISP) 565.3 (M+H)+.

5-Trifluoromethyl-1H-indole-7-carboxylic acid (4-tert-butyl-benzyl)-[2-(3-trifluoromethoxy-phenyl)-ethyl]-amide 165 from 90 mg of 5-trifluoromethyl-1H-indole-7-carboxylic acid (0.39 mmol) and 138 mg (0.39 mmol) of (4-tert-butyl-benzyl)-[2-(3-trifluoromethoxy-phenyl)-ethyl]-amine. After final purification (silica gel; c-hexane/EtOAc 4:1) 109 mg (49%) of an off-white solid were isolated. MS (ISP) 563.4 (M+H)+.

5-Trifluoromethyl-1H-indole-7-carboxylic acid (4-tert-butyl-benzyl)-[2-(4-chloro-phenyl)-ethyl]-amide 166 from 90 mg of 5-trifluoromethyl-1H-indole-7-carboxylic acid (0.39 mmol) and 119 mg (0.39 mmol) of (4-tert-butyl-benzyl)-[2-(4-chloro-phenyl)-ethyl]-amine. After final purification (silica gel; cyclohexane/EtOAc 4:1) 92 mg (46%) of an off-white solid were isolated. MS (ISP) 513.4 (M+H)+.

5-Trifluoromethyl-1H-indole-7-carboxylic acid (4-cyclopropyl-benzyl)-[2-(3-trifluoromethyl-phenyl)-ethyl]-amide 167 from 90 mg of 5-trifluoromethyl-1H-indole-7-carboxylic acid (0.39 mmol) and 125 mg (0.39 mmol) of (4-cyclopropyl-benzyl)-[2-(3-trifluoromethyl-phenyl)-ethyl]-amine. After final purification (silica gel; c-hexane/EtOAc 4:1) 75 mg (36%) of an off-white solid were isolated. MS (ISP) 531.2 (M+H)+.

5-Chloro-1H-indole-7-carboxylic acid [4-(1-methoxycyclobutyl)-benzyl]-[2-(3-trifluoromethylphenyl)-ethyl]-amide 168 using 5-chloro-1H-indole-7-carboxylic acid (56 mg, 0.29 mmol), N,N-diisopropylethyl amine (73 μl, 0.43 mmol), TBTU (101 mg, 0.32 mmol) and [4-(1-methoxycyclobutyl)-benzyl]-[2-(3-trifluoromethylphenyl)-ethyl]-amine (109 mg, 0.30 mmol) in DMF. Flash column chromatography (1:9-1:4 EtOAc:cyclohexane): 120 mg, 75%, white foam. MS (ISP) 541.2 (M+H)+.

2-Methyl-1H-indole-7-carboxylic acid (4-tert-butyl-benzyl)-[2-(3,4-dichloro-phenyl)-ethyl]-amide 169 from 50 mg of 2-methyl-1H-indole-7-carboxylic acid (0.29 mmol) and 96 mg (0.29 mmol) of (4-tert-butyl-benzyl)-[2-(3,4-dichloro-phenyl)-ethyl]-amine. After final purification (silica gel; cyclohexane/EtOAc 2:1) 82 mg (58%) of an off-white solid were isolated. MS (ISP) 493.4 (M+H)+.

2- Methyl-1H-indole-7-carboxylic acid (4-tert-butyl-benzyl)-[2-(4-chloro-phenyl)-ethyl]-amide 170 from 50 mg of 2-methyl-1H-indole-7-carboxylic acid (0.29 mmol) and 86 mg (0.29 mmol) of (4-tert-butyl-benzyl)-[2-(4-chloro-phenyl)-ethyl]-amine. After final purification (silica gel; c-hexane/EtOAc 2:1) 94 mg (72%) of an off-white solid were isolated. MS (ISP) 459.3 (M+H)+.

2-Methyl-1H-indole-7-carboxylic acid (4-tert-butyl-benzyl)-(2-p-tolyl-ethyl)-amide 171 from 50 mg of 2-methyl-1H-indole-7-carboxylic acid (0.29 mmol) and 80 mg (0.29 mmol) of (4-tert-butyl-benzyl)-(2-p-tolyl-ethyl)-amine. After final purification (silica gel; cyclohexane/EtOAc 2:1) 77 mg (61%) of an off-white solid were isolated. MS (ISP) 439.3 (M+H)+.

2-Methyl-1H-indole-7-carboxylic acid (4-tert-butyl-benzyl)-[2-(3-trifluoromethyl-phenyl)-ethyl]-amide 172 from 50 mg of 2-methyl-1H-indole-7-carboxylic acid (0.29 mmol) and 96 mg (0.29 mmol) of (4-tert-butyl-benzyl)-[2-(3-trifluoromethyl-phenyl)-ethyl]-amine. After final purification (silica gel; c-hexane/EtOAc 2:1) 76 mg (54%) of an off-white solid were isolated. MS (ISP) 493.4 (M+H)+.

5-Methyl-1H-indole-7-carboxylic acid (4-tert-butyl-benzyl)-[2-(3,4-dichloro-phenyl)-ethyl]-amide 173 from 50 mg of 5-methyl-1H-indole-7-carboxylic acid (0.29 mmol) and 96 mg (0.29 mmol) of (4-tert-butyl-benzyl)-[2-(3,4-dichloro-phenyl)-ethyl]-amine. After final purification (silica gel; c-hexane/EtOAc 4:1) 88 mg (62%) of an off-white solid were isolated. MS (ISP) 493.3 (M+H)+.

1H-Indole-7-carboxylic acid (4-pentafluoro-sulphuranyl-benzyl)-[2-(4-fluoro-phenyl)-ethyl]-amide 174 from 44 mg of 1H-indole-7-carboxylic acid (0.28 mmol) and 98 mg (0.28 mmol) of (4-pentafluoro-sulphuranyl-benzyl)-[2-(4-fluoro-phenyl)-ethyl]-amine. After final purification (silica gel; c-hexane/EtOAc 2:1) 121 mg (88%) of a colorless viscous oil were isolated. MS (ISP) 499.0 (M+H)$^+$.

2-Methyl-1H-indole-7-carboxylic acid (4-tert-butyl-benzyl)-[2-(4-fluoro-phenyl)-ethyl]-amide 175 from 50 mg of 2-methyl-1H-indole-7-carboxylic acid (0.29 mmol) and 81 mg (0.29 mmol) of (4-tert-butyl-benzyl)-[2-(4-fluoro-phenyl)-ethyl]-amine. After final purification (silica gel; heptane/EtOAc 70:30 to 50:50) 78 mg (62%) of a white solid were isolated. MS (ISP) 443.2 (M+H)$^+$.

2-Methyl-1H-indole-7-carboxylic acid (4-tert-butyl-benzyl)-[2-(3,4-difluoro-phenyl)-ethyl]-amide 176 from 50 mg of 2-methyl-1H-indole-7-carboxylic acid (0.29 mmol) and 87 mg (0.29 mmol) of (4-tert-butyl-benzyl)-[2-(3,4-difluoro-phenyl)-ethyl]-amine. After final purification (silica gel; heptane/EtOAc 70:30 to 50:50) 88 mg (67%) of a white solid were isolated. MS (ISP) 461.3 (M+H)$^+$.

5-Methyl-1H-indole-7-carboxylic acid (4-pentafluoro-sulphuranyl-benzyl)-[2-(3,4-dichloro-phenyl)-ethyl]-amide 177 from 50 mg of 5-methyl-1H-indole-7-carboxylic acid (0.29 mmol) and 116 mg (0.29 mmol) of (4-pentafluoro-sulphuranyl-benzyl)-[2-(3,4-dichloro-phenyl)-ethyl]-amine. After final purification (silica gel; heptane/EtOAc 70:30 to 50:50) 117 mg (73%) of a white foam were isolated. MS (ISP) 563.2 (M+H)$^+$.

5-Chloro-1H-indole-7-carboxylic acid [2-(3,4-dichloro-phenyl)-ethyl]-[4-(1,2,2,2-tetra-fluoro-1-trifluoromethyl-ethyl)-benzyl]-amide 179 from 70 mg of 5-chloro-1H-indole-7-carboxylic acid (0.36 mmol) and 160 mg (0.36 mmol) of [2-(3,4-dichloro-phenyl)-ethyl]-[4-(1,2,2,2-tetrafluoro-1-trifluoromethyl-ethyl)-benzyl]-amine. After final purification (silica gel; heptane/EtOAc 70:30 to 50:50) 186 mg (83%) of a light yellow foam were isolated. MS (ISP) 625.0 (M+H)$^+$.

5-Chloro-1H-indole-7-carboxylic acid [4-(1,2,2,2-tetrafluoro-1-trifluoromethyl-ethyl)-benzyl]-[2-(3-trifluoromethyl-phenyl)-ethyl]-amide 180 from 122 mg of 5-chloro-1H-indole-7-carboxylic acid (0.63 mmol) and 280 mg (0.63 mmol) of [4-(1,2,2,2-tetrafluoro-1-trifluoromethyl-ethyl)-benzyl]-[2-(3-trifluoromethyl-phenyl)-ethyl]-amine. After final purification (silica gel; heptane/EtOAc 70:30 to 50:50) 330 mg (83%) of a light brown foam were isolated. MS (ISP) 625.2 (M+H)$^+$.

5-Chloro-1H-indole-7-carboxylic acid [2-(4-fluoro-3-trifluoromethyl-phenyl)-ethyl]-[4-(1,2,2,2-tetrafluoro-1-trifluoromethyl-ethyl)-benzyl]-amide 181 from 115 mg of 5-chloro-1H-indole-7-carboxylic acid (0.59 mmol) and 275 mg (0.59 mmol) of [2-(4-fluoro-3-trifluoromethyl-phenyl)-ethyl]-[4-(1,2,2,2-tetrafluoro-1-trifluoromethyl-ethyl)-benzyl]-amine. After final purification (silica gel; heptane/EtOAc 70:30 to 50:50) 343 mg (90%) of a light brown foam were isolated. MS (ISP) 643.2 (M+H)$^+$.

5-Chloro-1H-indole-7-carboxylic acid [4-(1,2,2,2-tetrafluoro-1-trifluoromethyl-ethyl)-benzyl]-[2-(3-trifluoromethoxy-phenyl)-ethyl]-amide 182 from 114 mg of 5-chloro-1H-indole-7-carboxylic acid (0.58 mmol) and 270 mg (0.58 mmol) of [4-(1,2,2,2-tetrafluoro-1-trifluoromethyl-ethyl)-benzyl]-[2-(3-trifluoromethoxy-phenyl)-ethyl]-amine. After final purification (silica gel; heptane/EtOAc 70:30 to 50:50) 301 mg (81%) of a light brown foam were isolated. MS (ISP) 641.2 (M+H)$^+$.

5-Chloro-1H-indole-7-carboxylic acid [2-(4-chloro-phenyl)-ethyl]-[4-(1,2,2,2-tetrafluoro-1-trifluoromethyl-ethyl)-benzyl]-amide 183 from 59 mg of 5-chloro-1H-indole-7-carboxylic acid (0.30 mmol) and 125 mg (0.30 mmol) of [2-(4-chloro-phenyl)-ethyl]-[4-(1,2,2,2-tetrafluoro-1-trifluoromethyl-ethyl)-benzyl]-amine. After final purification (silica gel; heptane/EtOAc 70:30 to 50:50) 159 mg (89%) of a light brown foam were isolated. MS (ISP) 591.2 (M+H)$^+$.

1H-Indole-7-carboxylic acid (4-tert-butyl-benzyl)-(2-thiophen-2-yl-ethyl)-amide 184 from 48 mg of 1H-indole-7-carboxylic acid (0.30 mmol) and 81 mg (0.30 mmol) of (4-tert-butyl-benzyl)-(2-thiophen-2-yl-ethyl)-amine. After final purification (silica gel; toluene/EtOAc 9:1) 50 mg (89%) of a colorless oil were isolated. MS (ISP) 417.4 (M+H)$^+$.

5-Chloro-1H-indole-7-carboxylic acid (1,1-dimethylindan-5-ylmethyl)-[2-(3-trifluoromethylphenyl)-ethyl]-amide 185 using 5-chloro-1H-indole-7-carboxylic acid (110 mg, 0.56 mmol), N,N-diisopropylethyl amine (143 μl, 0.84 mmol), TBTU (199 mg, 0.62 mmol) and (1,1-dimethylindan-5-ylmethyl)-[2-(3-trifluoromethyl-phenyl)-ethyl]-amine (195 mg, 0.56 mmol) in DMF. Flash column chromatography (1:9-1:4 EtOAc:cyclohexane): 248 mg, 84%, white foam. MS (ISP) 525.3 (M+H)$^+$.

5-Chloro-1H-indole-7-carboxylic acid (1,1-dimethylindan-5-ylmethyl)-phenethylamide 186 using 5-chloro-1H-indole-7-carboxylic acid (85 mg, 0.44 mmol), N,N-diisopropylethyl amine (111 μl, 0.65 mmol), TBTU (153 mg, 0.49 mmol) and (1,1-dimethylindan-5-ylmethyl)-phenethylamine (121 mg, 0.44 mmol) in DMF. Flash column chromatography (1:9-1:4 EtOAc:cyclohexane): 125 mg, 63%, white foam. MS (ISP) 457.3 (M+H)$^+$.

5-Chloro-1H-indole-7-carboxylic acid [4-(1-methoxy-1-methyl-ethyl)-benzyl]-[2-(3-trifluoromethyl-phenyl)-ethyl]-amide 187 from 97 mg of 5-chloro-1H-indole-7-carboxylic acid (0.50 mmol) and 175 mg (0.50 mmol) of [4-(1-methoxy-1-methyl-ethyl)-benzyl]-[2-(3-trifluoromethyl-phenyl)-ethyl]-amine. After final purification (silica gel; cyclohexane/EtOAc 2:1) 90 mg (34%) of an off-white semisolid were isolated. MS (ISP) 529.2 (M+H)$^+$.

5-Chloro-1H-indole-7-carboxylic acid [2-(3,4-dichlorophenyl)-ethyl]-[4-(1,1-dimethyl-propyl)-benzyl]-amide 188 using 5-chloro-1H-indole-7-carboxylic acid (94 mg, 0.48 mmol), N,N-diisopropylethyl amine (122 μl, 0.72 mmol), TBTU (170 mg, 0.53 mmol) and [2-(3,4-dichlorophenyl)-ethyl]-[4-(1,1-dimethylpropyl)-benzyl]-amine (168 mg, 0.48 mmol) in DMF. Flash column chromatography (1:9-1:4 EtOAc:cyclohexane): 205 mg, 81%, white foam. MS (ISP) 529.2 (M+H)$^+$.

5-Chloro-1H-indole-7-carboxylic acid [4-(1,1-dimethylpropyl)-benzyl]-[2-(3-trifluoromethylphenyl)-ethyl]-amide 189 using 5-chloro-1H-indole-7-carboxylic acid (92 mg, 0.47 mmol), N,N-diisopropylethyl amine (120 μl, 0.71 mmol), TBTU (166 mg, 0.52 mmol) and [4-(1,1-dimethylpropyl)-benzyl]-[2-(3-trifluoromethylphenyl)-ethyl]-amine (164 mg, 0.47 mmol) in DMF. Flash column chromatography (1:9-1:4 EtOAc:cyclohexane): 202 mg, 82%, white foam. MS (ISP) 527.2 (M+H)$^+$.

5-Chloro-1H-indole-7-carboxylic acid [3-chloro-4-(1-methylcyclopropyl)-benzyl]-[2-(3-trifluoromethylphenyl)-ethyl]-amide 190 using 5-chloro-1H-indole-7-carboxylic acid (78 mg, 0.40 mmol), N,N-diisopropylethyl amine (102 μl, 0.60 mmol), TBTU (141 mg, 0.44 mmol) and [3-chloro-4-(1-methylcyclopropyl)-benzyl]-[2-(3-trifluoromethyl phenyl)-ethyl]-amine (147 mg, 0.47 mmol) in DMF. Flash column chromatography (1:9-1:4 EtOAc:cyclohexane): 169 mg, 78% white foam. MS (ISP) 545.1 (M+H)$^+$.

5-Chloro-1H-indole-7-carboxylic acid [3-chloro-4-(1-methylcyclopropyl)-benzyl]-[2-(3,4-dichlorophenyl)-ethyl]-amide 191 using 5-chloro-1H-indole-7-carboxylic acid (85 mg, 0.44 mmol), N,N-diisopropylethyl amine (111 μl, 0.65 mmol), TBTU (153 mg, 0.48 mmol) and [3-chloro- 4-(1-methylcyclopropyl)-benzyl]-[2-(3,4-dichlorophenyl)-ethyl]-amine (160 mg, 0.44 mmol) in DMF. Flash column chromatography (1:9-1:4 EtOAc:cyclohexane): 170 mg, 72%, white foam. MS (ISP) 547.1 (M+H)⁺.

6-Fluoro-5-trifluoromethyl-1H-indole-7-carboxylic acid (4-tert-butyl-benzyl)-[2-(3-trifluoromethyl-phenyl)-ethyl]-amide 192 from 50 mg of 6-fluoro-5-trifluoromethyl-1H-indole-7-carboxylic acid (0.2 mmol) and 68 mg (0.2 mmol) of (4-tert-butyl-benzyl)-[2-(3-trifluoromethyl-phenyl)-ethyl]-amine. After final purification (silica gel; cyclohexane/EtOAc 4:1) 79 mg (69%) of a gray oil were isolated. MS (ISP) 565.2 (M+H)⁺.

6-Fluoro-5-trifluoromethyl-1H-indole-7-carboxylic acid (4-tert-butyl-benzyl)-[2-(3,4-dichloro-phenyl)-ethyl]-amide 193 from 50 mg of 6-fluoro-5-trifluoromethyl-1H-indole-7-carboxylic acid (0.2 mmol) and 68 mg (0.2 mmol) of (4-tert-butyl-benzyl)-[2-(3,4-dichloro-phenyl)-ethyl]-amine. After final purification (silica gel; c-hexane/EtOAc 4:1) 55 mg (48%) of a gray oil were isolated. MS (ISP) 565.2 (M+H)⁺.

6-Fluoro-5-trifluoromethyl-1H-indole-7-carboxylic acid (4-tert-butyl-benzyl)-[2-(4-fluoro-3-trifluoromethyl-phenyl)-ethyl]-amide 194 from 50 mg of 6-fluoro-5-trifluoromethyl-1H-indole-7-carboxylic acid (0.2 mmol) and 72 mg (0.2 mmol) of (4-tert-butyl-benzyl)-[2-(4-fluoro-3-trifluoromethyl-phenyl)-ethyl]-amine. After final purification (silica gel; cyclohexane/EtOAc 4:1) 80 mg (68%) of a light brown oil were isolated. MS (ISP) 583.2 (M+H)⁺.

6-Fluoro-5-trifluoromethyl-1H-indole-7-carboxylic acid (4-tert-butyl-benzyl)-[2-(3-chloro-4-fluoro-phenyl)-ethyl]-amide 195 from 50 mg of 6-fluoro-5-trifluoromethyl-1H-indole-7-carboxylic acid (0.2 mmol) and 65 mg (0.2 mmol) of (4-tert-butyl-benzyl)-[2-(3-chloro-4-fluoro-phenyl)-ethyl]-amine. After final purification (silica gel; cyclohexane/EtOAc 4:1) 75 mg (68%) of a gray oil were isolated. MS (ISP) 547.2 (M–H)⁻.

5-Chloro-1H-indole-7-carboxylic acid (2,2-dimethyl-chroman-6-ylmethyl)-[2-(3-trifluoromethylphenyl)-ethyl]-amide 196 using 5-chloro-1H-indole-7-carboxylic acid (100 mg, 0.51 mmol), N,N-diisopropylethyl amine (130 µl, 0.77 mmol), TBTU (180 mg, 0.56 mmol) and (2,2-dimethylchroman-6-ylmethyl)-[2-(3-trifluoromethylphenyl)-ethyl]-amine (186 mg, 0.51 mmol) in DMF. Flash column chromatography (1:9-1:4 EtOAc:cyclohexane): 150 mg, 54%, white foam. MS (ISP) 541.1 (M+H)⁺.

5-Chloro-1H-indole-7-carboxylic acid (2,2-dimethyl-chroman-6-ylmethyl)-phenethyl-amide 197 using 5-chloro-1H-indole-7-carboxylic acid (100 mg, 0.51 mmol), N,N-diisopropylethyl amine (130 µl, 0.77 mmol), TBTU (180 mg, 0.56 mmol) and (2,2-dimethyl-chroman-6-ylmethyl)-phenethylamine (151 mg, 0.51 mmol) in DMF. Flash column chromatography (1:9-1:4 EtOAc:cyclohexane): 150 mg, 54%, white foam. MS (ISP) 473.2 (M+H)⁺.

5-Chloro-1H-indole-7-carboxylic acid [4-(1-ethyl-1-methoxy-propyl)-benzyl]-[2-(3-trifluoromethyl-phenyl)-ethyl]-amide 198 from 57 mg 5-chloro-1H-indole-7-carboxylic acid (0.29 mmol) and 110 mg (0.29 mmol) of [4-(1-ethyl-1-methoxy-propyl)-benzyl]-[2-(3-trifluoromethyl-phenyl)-ethyl]]-amine. After final purification (silica gel; c-hexane/EtOAc 2:1) 128 mg (79%) of a gray oil were isolated. MS (ISP) 565.2 (M+H)⁺.

5-Chloro-N-[2-(3,4-dichlorophenyl)ethyl]-N-[(2',3'-dihydrospiro[cyclopropane-1,1'-[1H]inden]-5'-yl)methyl]-1H-indole-7-carboxamide 199 using 5-chloro-1H-indole-7-carboxylic acid (75 mg, 0.38 mmol), N,N-diisopropylethyl amine (98 µl, 0.58 mmol), TBTU (135 mg, 0.42 mmol) and N-[2-(3,4-dichlorophenyl)ethyl]-2',3'-dihydro-spiro [cyclopropane-1,1'-[1H]indene]-5'-methanamine (133 mg, 0.38 mmol) in DMF. Flash column chromatography (1:9-1:4 EtOAc:cyclohexane): 153 mg, 76%, white foam. MS (ISP) 525.3 (M+H)⁺.

5-Chloro-N-[(2',3'-dihydrospiro[cyclopropane-1,1'-[1H]inden]-5'-yl)methyl]-N-[2-[3-(trifluoromethyl)phenyl]ethyl]-1H-indole-7-carboxamide 200 using 5-chloro-1H-indole-7-carboxylic acid (70 mg, 0.36 mmol), N,N-diisopropylethyl amine (91 µl, 0.54 mmol), TBTU (126 mg, 0.39 mmol) and 2',3'-dihydro-N-[2-[3-(trifluoromethyl)phenyl]ethyl]-spiro [cyclopropane-1,1'-[1H]indene]-5'-methanamine (124 mg, 0.36 mmol) in DMF. Flash column chromatography (1:9-1:4 EtOAc:cyclohexane): 115 mg, 61%, white foam. MS (ISP) 523.5 (M+H)⁺.

5-Chloro-1H-indole-7-carboxylic acid (4-tert-butyl-3-chloro-benzyl)-[2-(3-trifluoromethyl-phenyl)-ethyl]-amide 201 using 5-chloro-1H-indole-7-carboxylic acid (65 mg, 0.33 mmol), N,N-diisopropylethyl amine (66 µl, 0.50 mmol), TBTU (117 mg, 0.37 mmol) and (4-tert-butyl-3-chloro-benzyl)-[2-(3-trifluoromethyl-phenyl)-ethyl]-amine (117 mg, 0.33 mmol) in DMF. Flash column chromatography (1:4-3:7 EtOAc:cyclohexane): 127 mg, 70%, white foam. MS (ISP) 547.3 (M+H)⁺.

5-Chloro-1H-indole-7-carboxylic acid (4-tert-butyl-3-chloro-benzyl)-[2-(3,4-dichloro-phenyl)-ethyl]-amide 202 using 5-chloro-1H-indole-7-carboxylic acid (63 mg, 0.32 mmol), N,N-diisopropylethyl amine (64 µl, 0.48 mmol), TBTU (114 mg, 0.34 mmol) and (4-tert-butyl-3-chloro-benzyl)-[2-(3,4-dichloro-phenyl)-ethyl]-amine (119 mg, 0.32 mmol) in DMF. Flash column chromatography (1:4-3:7 EtOAc:cyclohexane): 122 mg, 69%, white foam. MS (ISP) 549.4 (M+H)⁺.

5-Chloro-1H-indole-7-carboxylic acid [4-(1,1-dimethyl-butyl)-benzyl]-[2-(3-trifluoromethyl-phenyl)-ethyl]-amide 203 from 65 mg of 5-chloro-1H-indole-7-carboxylic acid (0.33 mmol) and 120 mg (0.33 mmol) of [4-(1,1-dimethyl-butyl)-benzyl]-[2-(3-trifluoromethyl-phenyl)-ethyl]-amine. After final purification (silica gel; c-hexane/EtOAc 4:1) 132 mg (74%) of a light yellow oil were isolated. MS (ISP) 541.4 (M+H)⁺.

5-Chloro-6-fluoro-1H-indole-7-carboxylic acid [4-(1,1-dimethyl-butyl)-benzyl]-[2-(3-trifluoromethyl-phenyl)-ethyl]-amide 204 from 59 mg of 5-chloro-6-fluoro-1H-indole-7-carboxylic acid (0.28 mmol) and 100 mg (0.28 mmol) of [4-(1,1-dimethyl-butyl)-benzyl]-[2-(3-trifluoromethyl-phenyl)-ethyl]-amine. After final purification (silica gel; cyclohexane/AcOEt 4:1) 105 mg (68%) of a yellow oil were isolated. MS (ISP) 557.3 (M–H)⁻.

5-Chloro-1H-indole-7-carboxylic acid (4-cyclobutyl-benzyl)-[2-(3,4-dichloro-phenyl)-ethyl]-amide 205 from 59 mg of 5-chloro-1H-indole-7-carboxylic acid (0.30 mmol) and 100 mg (0.30 mmol) of (4-cyclobutyl-benzyl)-[2-(3,4-dichloro-phenyl)-ethyl]-amine. After final purification (silica gel; cyclohexane/AcOEt 4:1) 144 mg (94%) of a yellow oil were isolated. MS (ISP) 511.4 (M+H)⁺.

5-Chloro-6-fluoro-1H-indole-7-carboxylic acid (4-cyclobutyl-benzyl)-[2-(3,4-dichloro-phenyl)-ethyl]-amide 206 from 64 mg of 5-chloro-6-fluoro-1H-indole-7-carboxylic acid (0.30 mmol) and 100 mg (0.30 mmol) of (4-cyclobutyl-benzyl)-[2-(3,4-dichloro-phenyl)-ethyl]-amine. After final purification (silica gel; cyclohexane/AcOEt 4:1) 65 mg (41%) of a white solid were isolated. MS (ISP) 529.2 (M+H)⁺.

5-Chloro-6-fluoro-1H-indole-7-carboxylic acid (4-cyclobutyl-benzyl)-[2-(3-trifluoromethyl-phenyl)-ethyl]-amide 207 from 64 mg of 5-chloro-6-fluoro-1H-indole-7-carboxylic acid (0.30 mmol) and 100 mg (0.30 mmol) of (4-cyclobutyl-benzyl)-[2-(3-trifluoromethyl-phenyl)-ethyl]-amine. After final purification (silica gel; cyclohexane/AcOEt 4:1) 111 mg (70%) of a yellow oil were isolated. MS (ISP) 429.3 (M+H)$^+$.

5-Chloro-1H-indole-7-carboxylic acid (4-cyclobutyl-benzyl)-[2-(3-trifluoromethyl-phenyl)-ethyl]-amide 208 from 59 mg of 5-chloro-1H-indole-7-carboxylic acid (0.30 mmol) and 100 mg (0.30 mmol) of (4-cyclobutyl-benzyl)-[2-(3-trifluoromethyl-phenyl)-ethyl]-amine. After final purification (silica gel; cyclohexane/AcOEt 4:1) 124 mg (81%) of a yellow oil were isolated. MS (ISP) 509.3 (M–H)$^-$.

5-Chloro-1H-indole-7-carboxylic acid (4-cyclopentyl-benzyl)-[2-(3,4-dichloro-phenyl)-ethyl]-amide 209 from 51 mg of 5-chloro-1H-indole-7-carboxylic acid (0.26 mmol) and 90 mg (0.26 mmol) of (4-cyclopentyl-benzyl)-[2-(3,4-dichloro-phenyl)-ethyl]-amine. After final purification (silica gel; cyclohexane/AcOEt 4:1) 109 mg (80%) of a light yellow oil were isolated. MS (ISP) 525.3 (M+H)$^+$.

5-Chloro-1H-indole-7-carboxylic acid [3-chloro-4-(1-methoxy-1-methyl-ethyl)-benzyl]-[2-(3-trifluoromethyl-phenyl)-ethyl]-amide 214 from 60 mg of 5-chloro-1H-indole-7-carboxylic acid (0.31 mmol) and 118 mg (0.31 mmol) of [3-chloro-4-(1-methoxy-1-methyl-ethyl)-benzyl]-[2-(3-trifluoromethyl-phenyl)-ethyl]-amine. After final purification (silica gel; c-hexane/AcOEt 4:1 to 7:3) 126 mg (73%) of a white foam were isolated. MS (ISP) 563.4 (M+H)$^+$.

5-Chloro-1H-indole-7-carboxylic acid [3-chloro-4-(1-methoxy-1-methyl-ethyl)-benzyl]-[2-(3,4-dichloro-phenyl)-ethyl]-amide 215 from 65 mg of 5-chloro-1H-indole-7-carboxylic acid (0.33 mmol) and 129 mg (0.33 mmol) of [3-chloro-4-(1-methoxy-1-methyl-ethyl)-benzyl]-[2-(3,4-dichloro-phenyl)-ethyl]-amine. After final purification (silica gel; c-hexane/AcOEt 4:1 to 7:3) 113 mg (60%) of a white foam were isolated. MS (ISP) 565.3 (M+H)$^+$.

5-Chloro-1H-indole-7-carboxylic acid (2,2-dimethyl-benzo[1,3]dioxol-5-ylmethyl)-[2-(3-trifluoromethyl-phenyl)-ethyl]-amide 216 from 76 mg of 5-chloro-1H-indole-7-carboxylic acid (0.39 mmol) and 137 mg (0.39 mmol) of (2,2-dimethyl-benzo[1,3]dioxol-5-ylmethyl)-[2-(3-trifluoromethyl-phenyl)-ethyl]-amine. After final purification (silica gel; c-hexane/AcOEt 4:1 to 7:3) 161 mg (78%) of a white foam were isolated. MS (ISP) 529.3 (M+H)$^+$.

5-Chloro-1H-indole-7-carboxylic acid [2-(3,4-dichloro-phenyl)-ethyl]-(2,2-dimethyl-benzo[1,3]dioxol-5-ylmethyl)-amide 217 from 74 mg of 5-chloro-1H-indole-7-carboxylic acid (0.38 mmol) and 133 mg (0.38 mmol) of [2-(3,4-dichloro-phenyl)-ethyl]-(2,2-dimethyl-benzo[1,3]dioxol-5-ylmethyl)-amine. After final purification (silica gel; c-hexane/AcOEt 4:1 to 7:3) 152 mg (76%) of a white foam were isolated. MS (ISP) 529.2 (M+H)$^+$.

5-Chloro-1H-indole-7-carboxylic acid (3-chloro-4-trifluoromethyl-benzyl)-[2-(3-trifluoromethyl-phenyl)-ethyl]-amide 218 from 85 mg of 5-chloro-1H-indole-7-carboxylic acid (0.44 mmol) and 166 mg (0.44 mmol) of (3-chloro-4-trifluoromethyl-benzyl)-[2-(3-trifluoromethyl-phenyl)-ethyl]-amine. After final purification (silica gel; c-hexane/AcOEt 4:1 to 7:3) 171 mg (70%) of a light yellow gum were isolated. MS (ISP) 559.2 (M+H)$^+$.

5-Chloro-1H-indole-7-carboxylic acid (2,2-difluoro-benzo[1,3]dioxol-5-ylmethyl)-[2-(3-trifluoromethyl-phenyl)-ethyl]-amide 219 from 60 mg of 5-chloro-1H-indole-7-carboxylic acid (0.31 mmol) and 110 mg (0.31 mmol) of (2,2-difluoro-benzo[1,3]dioxol-5-ylmethyl)-[2-(3-trifluoromethyl-phenyl)-ethyl]-amine. After final purification (silica gel; c-hexane/AcOEt 4:1 to 7:3) 108 mg (66%) of an off-white solid were isolated. MS (ISP) 537.4 (M+H)$^+$.

5-Chloro-1H-indole-7-carboxylic acid [2-(3,4-dichloro-phenyl)-ethyl]-(2,2-difluoro-benzo[1,3]dioxol-5-ylmethyl)-amide 220 from 53 mg of 5-chloro-1H-indole-7-carboxylic acid (0.27 mmol) and 98 mg (0.27 mmol) of [2-(3,4-dichloro-phenyl)-ethyl]-(2,2-difluoro-benzo[1,3]dioxol-5-ylmethyl)-amine. After final purification (silica gel; c-hexane/AcOEt 4:1 to 7:3) 105 mg (72%) of an off-white solid were isolated. MS (ISP) 537.3 (M+H)$^+$.

Example 2

Preparation of 1H-Indole-7-carboxylic acid (4-tert-butyl-benzyl)-pent-4-enyl-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 69 mg (0.3 mmol) of (4-tert-butyl-benzyl)-pent-4-enyl-amine in 1 ml DMF was added. After stirring for 2 h at rt, the reaction mixture was diluted with 50 ml water and extracted with 2×50 ml EtOAc. The combined organic phases were washed with water and brine, dried with magnesium sulfate, filtered and concentrated in vacuo. The resulting oil was purified by column chromatography (8 g silica gel; heptane/EtOAc 6:1) to give 62 mg (53%) of a light yellow viscous oil. MS (ISP) 375.5 (M+H)$^+$.

Example 3

Preparation of 1H-Indole-7-carboxylic acid (4-tert-butyl-benzyl)-(4,4,4-trifluoro-butyl)-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 82 mg (0.3 mmol) of (4-tert-butyl-benzyl)-(4,4,4-trifluoro-butyl)-amine in 1 ml DMF were added. After stirring for 19 h at rt, the reaction mixture was diluted with 50 ml water and extracted with 2×50 ml EtOAc. The combined organic phases were washed with water and brine, dried with magnesium sulfate, filtered and concentrated in vacuo to give 130 mg (99%) of an orange solid. MS (ISP) 416.2 (M+H)$^+$.

Example 4

Preparation of 1H-Indole-7-carboxylic acid (4-tert-butyl-benzyl)-[2-(tetrahydro-thiopyran-4-yl)-ethyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 78 mg (0.3 mmol) of (4-tert-butyl-benzyl)-[2-(tetrahydro-thiopyran-4-yl)-ethyl]-amine in 1 ml DMF were added. After stirring for 24 h at rt, the reaction mixture was diluted with 50 ml water and extracted with 2×50 ml EtOAc. The combined organic phases were washed with water and brine, dried with magnesium sulfate, filtered and concentrated in vacuo to give 134 mg (99%) of a yellow solid. MS (ISP) 435.5 (M+H)$^+$.

Example 5

Preparation of [rac]-1H-Indole-7-carboxylic acid (4-tert-butyl-benzyl)-[3-(5-methyl-furan-2-yl)-butyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 90 mg (0.3 mmol) of [rac]-(4-tert-butyl-benzyl)-[3-(5-methyl-furan-2-yl)-butyl]-amine in 1 ml DMF were added. After stirring for 2 h at rt, the reaction mixture was diluted with 50 ml water and extracted with 2×50 ml EtOAc. The combined organic phases were washed with water and brine, dried with magnesium sulfate, filtered and concentrated in vacuo. The orange residue was purified by column chromatography (8 g silica gel; heptane/EtOAc 6:1) to give 87 mg (63%) of a colorless viscous oil. MS (ISP) 443.5 (M+H)$^+$.

Example 6

Preparation of 1H-Indole-7-carboxylic acid (4-tert-butyl-benzyl)-[2-(4-fluoro-phenyl)-ethyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 86 mg (0.3 mmol) of (4-tert-butyl-benzyl)-[2-(4-fluoro-phenyl)-ethyl]-amine in 1 ml DMF were added. After stirring for 4 h at rt, the reaction mixture was diluted with 50 ml water and extracted with 2×50 ml EtOAc. The combined organic phases were washed with water and brine, dried with magnesium sulfate, filtered and concentrated in vacuo. The orange residue was purified by column chromatography (8 g silica gel; heptane/EtOAc 6:1) to give 107 mg (82%) of a white solid. MS (ISP) 429.6 (M+H)$^+$.

Example 7

Preparation of 1H-Indole-7-carboxylic acid (4-tert-butyl-benzyl)-[2-(4-methoxy-phenyl)-ethyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 89 mg (0.3 mmol) (4-tert-butyl-benzyl)-[2-(4-methoxy-phenyl)-ethyl]-amine in 1 ml DMF was added. After 2.5 h stirring at rt, the reaction mixture was diluted with 50 ml water and extracted with 2×50 ml EtOAc. The combined organic phases were washed with water and brine, dried with magnesium sulfate, filtered and concentrated in vacuo. The yellow solid foam was purified by column chromatography (8 g silica gel; heptane/EtOAc 6:1) to give 107 mg (80%) of a white solid. MS (ISP) 441.4 (M+H)$^+$.

Example 8

Preparation of 1H-Indole-7-carboxylic acid (4-tert-butyl-benzyl)-(2-p-tolyl-ethyl)-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 89 mg (0.3 mmol) (4-tert-butyl-benzyl)-(2-p-tolyl-ethyl)-amine in 1 ml DMF was added. After stirring for 3 h at rt, the reaction mixture was diluted with 50 ml water and extracted with 2×50 ml EtOAc. The combined organic phases were washed with water and brine, dried with magnesium sulfate, filtered and concentrated in vacuo. The yellow residue was purified by column chromatography (8 g silica gel; heptane/EtOAc 9:1) to give 111 mg (86%) of a white solid. MS (ISP) 425.3 (M+H)$^+$.

Example 9

Preparation of 5-Bromo-1H-indole-7-carboxylic acid (4-tert-butyl-benzyl)-[2-(3-trifluoromethyl-phenyl)-ethyl]-amide To a solution of 80 mg (0.3 mmol) 5-bromo-1H-indole-7-carboxylic acid and 112 mg (0.33 mmol) (4-tert-butyl-benzyl)-[2-(3-trifluoromethyl-phenyl)-ethyl]-amine in 3 ml DMF, were added 0.1 ml (0.91 mmol) of N-methylmorpholine and 173 mg of TBTU (0.45 mmol) at rt. After stirring for 17 h at rt, the reaction mixture was diluted with 33 ml water and extracted with EtOAc (2×). The combined organic phases were washed with water and brine, dried with magnesium sulfate, filtered and concentrated in vacuo. The residue was purified by column chromatography (8 g silica gel; DCM/heptane 50:50 to 70:30) to give 152 mg white powder (90%). MS (ISP) 574.3 (M+H)$^+$.

Example 10

Preparation of 1H-Indole-7-carboxylic acid (4-tert-butyl-benzyl)-[2-(3-fluoro-phenyl)-ethyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 86 mg (0.3 mmol) (4-tert-butyl-benzyl)-[2-(3-fluoro-phenyl)-ethyl]-amine in 1 ml DMF was added. After stirring for 3 h at rt, the reaction mixture was diluted with 50 ml water and extracted with 2×50 ml EtOAc. The combined organic phases were washed with water and brine, dried with magnesium sulfate, filtered and concentrated in vacuo. The orange residue was purified by column chromatography (8 g silica gel; heptane/EtOAc 9:1) to give 112 mg (86%) of a yellow solid. MS (EI) 428.2 (M)$^+$.

Example 11

Preparation of 5-Chloro-1H-indole-7-carboxylic acid (4-tert-butyl-benzyl)-[2-(3-cyclopropyl-methoxy-phenyl)-ethyl]-amide 5-Chloro-1H-indole-7-carboxylic acid [2-(3-benzyloxy-phenyl)-ethyl]-(4-tert-butyl-benzyl)-amide To a solution of 951 mg (4.86 mmol) of 5-chloro-1H-indole-7-carboxylic acid and 1.997 g (5.35 mmol) [2-(3-benzyloxy-phenyl)-ethyl]-(4-tert-butyl-benzyl)-amine in 50 ml DMF, were added 1.6 ml (14.58 mmol) N-methylmorpholine and 2.77 g TBTU (7.29 mmol) at rt. After stirring for 16 h at rt, the reaction mixture was diluted with 300 ml water and extracted with EtOAc (2×). The combined organic phases were washed with twice 200 ml water and 100 ml brine, dried with magnesium sulfate, filtered and concentrated in vacuo. The residue was purified by column chromatography (90 g silica gel; heptane/EtOAc 9:1 then 4:1) to give 2.41 g of 5-chloro-1H-indole-7-carboxylic acid [2-(3-benzyloxy-phenyl)-ethyl]-(4-tert-butyl-benzyl)-amide as a light yellow solid (88%). MS (ISP) 551.3 (M+H)+.

5-Chloro-1H-indole-7-carboxylic acid (4-tert-butyl-benzyl)-[2-(3-hydroxy-phenyl)-ethyl]-amide 200 mg of 5-chloro-1H-indole-7-carboxylic acid [2-(3-benzyloxy-phenyl)-ethyl]-(4-tert-butyl-benzyl)-amide (0.36 mmol) were dissolved in 20 ml EtOAc and hydrogenated for 5 h over 20 mg Pd/C 10%. After removal of the catalyst by filtration, the solution was concentrated in vacuo and the residue purified by column chromatography (8 g silicagel, heptane/EtOAc 2:1) leading to 136 mg of 5-chloro-1H-indole-7-carboxylic acid (4-tert-butyl-benzyl)-[2-(3-hydroxy-phenyl)-ethyl]-amide (79%) as a light yellow solid. MS (ISP) 461.4 (M+H)+.

5-Chloro-1H-indole-7-carboxylic acid (4-tert-butyl-benzyl)-[2-(3-cyclopropylmethoxy-phenyl)-ethyl]-amide 122 mg of 5-chloro-1H-indole-7-carboxylic acid (4-tert-butyl-benzyl)-[2-(3-hydroxy-phenyl)-ethyl]-amide (0.25 mmol) and 52 mg potassium carbonate (0.375 mmol) were suspended in 5 ml acetonitrile and treated with 0.027 ml bromomethyl-cyclopropane (0.275 mmol). The mixture was stirred for 24 h in an oil-bath heated to 80° C. After cooling down, the mixture was poured on water/EtOAc, and after separation the aqueous phase was extracted with EtOAc. The combined organic phases were then washed with water and brine, dried over magnesium sulfate, filtered and concentrated in vacuo. The residue was purified by column chromatography (8 g silicagel, heptane/EtOAc 9:1) leading to 66 mg of 5-chloro-1H-indole-7-carboxylic acid (4-tert-butyl-benzyl)-[2-(3-cyclopropylmethoxy-phenyl)-ethyl]-amide as a colorless viscous oil. MS (ISP) 515.5 (M+H)+.

Example 12

Preparation of 1H-Indole-7-carboxylic acid (4-tert-butyl-benzyl)-[2-(2-fluoro-phenyl)-ethyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 86 mg (0.3 mmol) (4-tert-butyl-benzyl)-[2-(2-fluoro-phenyl)-ethyl]-amine in 1 ml DMF was added. After stirring for 3 h at rt, the reaction mixture was diluted with 50 ml water and extracted with 2×50 ml EtOAc. The combined organic phases were washed with water and brine, dried with magnesium sulfate, filtered and concentrated in vacuo. The yellow residue was purified by column chromatography (8 g silica gel; heptane/EtOAc 9:1) to give 111 mg (83%) of a white solid. MS (ISP) 429.6 (M+H)+.

Example 13

Preparation of 1H-Indole-7-carboxylic acid (4-tert-butyl-benzyl)-[2-(4-chloro-phenyl)-ethyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 91 mg (0.3 mmol) (4-tert-butyl-benzyl)-[2-(4-chloro-phenyl)-ethyl]-amine in 1 ml DMF was added. After stirring for 3 h at rt, the reaction mixture was diluted with 50 ml water and extracted with 2×50 ml EtOAc. The combined organic phases were washed with water and brine, dried with magnesium sulfate, filtered and concentrated in vacuo. The yellow solid foam was purified by column chromatography (8 g silica gel; heptane/EtOAc 9:1) to give 128 mg (86%) of a white solid. MS (ISP) 445.4 (M+H)+.

Example 14

Preparation of 5-Chloro-6-fluoro-1H-indole-7-carboxylic acid [4-(1-cyano-cyclopropyl)-benzyl]-[2-(3-trifluoromethyl-phenyl)-ethyl]-amide 69 mg (0.7 mmol) of N-methyl morpholine and then 129 mg (0.34 mmol) of TBTU were added to 48 mg (0.23 mol) of 5-chloro-6-fluoro-1H-indol-7-carboxylic acid and 78 mg (0.27 mmol) of 1-(4-{[2-(3-trifluoromethyl-phenyl)-ethylamino]-methyl}-phenyl)-cyclo-propanecarbonitrile dissolved in 2.3 ml DMF at rt under nitrogen. The reaction mixture was stirred at rt over night. Water was added and the reaction mixture was extracted twice with EtOAc. The combined organic layers were washed once with 1N aqueous HCl solution, once with saturated aqueous NaHCO$_3$ solution and once with saturated aqueous NaCl solution, dried over sodium sulfate, filtered and the solvent was evaporated. The residue was purified by column chromatography (20 g silica gel; methylene chloride/methanol 19:1) to yield 107 mg (87%) product as a yellow viscous oil. MS (ISP) 540.3 (100), 541.3 (30), 542.3 (32) (M+H)+, 562.3 (39), 563.4 (11), 564.4 (12) (M+Na)+.

Example 15

Preparation of 1H-Indole-7-carboxylic acid (4-tert-butyl-benzyl)-[2-(3-chloro-phenyl)-ethyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 91 mg (0.3 mmol) (4-tert-butyl-benzyl)-[2-(3-chloro-phenyl)-ethyl]-amine in 1 ml DMF was added. After 2.5 h stirring at rt, the reaction mixture was diluted with 50 ml water and extracted with 2×50 ml EtOAc. The combined organic phases were washed with water and brine, dried with magnesium sulfate, filtered and concentrated in vacuo. The yellow solid foam was purified by column chromatography (8 g silica gel; heptane/EtOAc 9:1) to give 122 mg (90%) of a white semisolid. MS (EI) 444.2 (M)+.

Example 16

Preparation of 1H-Indole-7-carboxylic acid (4-tert-butyl-benzyl)-[2-(3-trifluoromethyl-phenyl)-ethyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 101 mg (0.3 mmol) of (4-tert-butyl-benzyl)-[2-(3-trifluoromethyl-phenyl)-ethyl]-amine in 1 ml DMF were added. After 2.5 h stirring at rt, the reaction mixture was diluted with 50 ml water and extracted with 2×50 ml EtOAc. The combined organic phases were washed with water and brine, dried with magnesium sulfate, filtered and concentrated in vacuo. The yellow solid foam was purified by column chromatography (8 g silica gel; heptane/EtOAc 9:1) to give 124 mg (84%) of a colorless gum. MS (ISP) 479.5 (M+H)+.

Example 17

Preparation of 1H-Indole-7-carboxylic acid (4-tert-butyl-benzyl)-[2-(2-chloro-phenyl)-ethyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 95 mg (0.3 mmol) (4-tert-butyl-benzyl)-[2-(2-chloro-phenyl)-ethyl]-amine in 1 ml DMF was added. After stirring for 2 h at rt, the reaction mixture was diluted with 50 ml water and extracted with 2×50 ml EtOAc. The combined organic phases were washed with water and brine, dried with magnesium sulfate, filtered and concentrated in vacuo. The yellow solid foam was purified by column chromatography (8 g silica gel; heptane/EtOAc 9:1) to give 127 mg (90%) of a white solid. MS (ISP) 445.4 (M+H)+.

Example 18

Preparation of 1H-Indole-7-carboxylic acid (4-tert-butyl-benzyl)-[2-(3,4-dichloro-phenyl)-ethyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 95 mg (0.3 mmol) (4-tert-butyl-benzyl)-[2-(3,4-dichloro-phenyl)-ethyl]-amine in 1 ml DMF was added. After 1.5 h stirring at rt, the reaction mixture was diluted with 50 ml water and extracted with 2×50 ml EtOAc. The combined organic phases were washed with water and brine, dried with magnesium sulfate, filtered and concentrated in vacuo. The yellow solid foam was purified by column chromatography (8 g silica gel; heptane/EtOAc 9:1) to give 137 mg (94%) of a white solid. MS (ISP) 479.5 (M+H)+.

Example 19

Preparation of 1H-Indole-7-carboxylic acid (4-tert-butyl-benzyl)-[2-(2,6-dichloro-phenyl)-ethyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 106 mg (0.3 mmol) (4-tert-butyl-benzyl)-[2-(2,6-dichloro-phenyl)-ethyl]-amine in 1 ml DMF was added. After stirring for 2 h at rt, the reaction mixture was diluted with 50 ml water and extracted with 2×50 ml EtOAc. The combined organic phases were washed with water and brine, dried with magnesium sulfate, filtered and concentrated in vacuo. The residue was crystallized from diethylether, leading to 123 mg white solid (85%). MS (ISP) 479.5 (M+H)+.

Example 20

Preparation of 1H-Indole-7-carboxylic acid (4-tert-butyl-benzyl)-[2-(3,5-difluoro-phenyl)-ethyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 91 mg (0.3 mmol) (4-tert-butyl-benzyl)-[2-(3,5-difluoro-phenyl)-ethyl]-amine in 1 ml DMF was added. After stirring for 4 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:6) to give 97 mg off-white solid (71%). MS (ISP) 447.3 (M+H)+.

Example 21

Preparation of 1H-Indole-7-carboxylic acid (4-tert-butyl-benzyl)-[2-(4-trifluoromethyl-phenyl)-ethyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 101 mg (0.3 mmol) (4-tert-butyl-benzyl)-[2-(4-trifluoromethyl-phenyl)-ethyl]-amine in 1 ml DMF was added. After stirring for 17 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:9) to give 110 mg colorless viscous oil (71%). MS (ISP) 479.5 (M+H)+.

Example 22

Preparation of 1H-Indole-7-carboxylic acid (4-tert-butyl-benzyl)-[2-(3,4-difluoro-phenyl)-ethyl]-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 91 mg (0.3 mmol) (4-tert-butyl-benzyl)-[2-(3,4-difluoro-phenyl)-ethyl]-amine in 2 ml DMF was added. After stirring for 18 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:6) to give 95 mg light yellow viscous oil (66%). MS (ISP) 447.2 (M+H)+.

Example 23

Preparation of 1H-Indole-7-carboxylic acid (4-tert-butyl-benzyl)-phenethyl-amide To a solution of 48 mg (0.3 mmol) of 1H-indole-7-carboxylic acid and 96 mg of TBTU (0.3 mmol) in 4 ml DMF, were added 0.26 ml (1.5 mmol) of N,N-diisopropylethyl amine. After stirring for 5 min at rt, 80 mg (0.3 mmol)

of (4-tert-butyl-benzyl)-phenethyl-amine in 1 ml DMF were added. After stirring for 5 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:6) to give 100 mg white solid (80%). MS (ISP) 411.5 (M+H)+.

Example 24

Preparation of 1H-Indole-7-carboxylic acid (4-tert-butyl-benzyl)-[2-(3-fluoro-4-trifluoromethyl-phenyl)-ethyl]-amide To a solution of 48 mg (0.3 mmol) of 1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 106 mg (0.3 mmol) of (4-tert-butyl-benzyl)-[2-(3-fluoro-4-trifluoromethyl-phenyl)-ethyl]-amine in 2 ml DMF were added. After stirring for 16 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:6) to give 138 mg light yellow solid (91%). MS (ISP) 497.4 (M+H)+.

Example 25

Preparation of 1H-Indole-7-carboxylic acid (4-tert-butyl-benzyl)-[2-(3-trifluoromethoxy-phenyl)-ethyl]-amide To a solution of 48 mg (0.3 mmol) of 1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 105 mg (0.3 mmol) of (4-tert-butyl-benzyl)-[2-(3-trifluoromethoxy-phenyl)-ethyl]-amine in 2 ml DMF were added. After stirring for 3 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:6) to give 99 mg light yellow viscous oil (66%). MS (ISP) 495.5 (M+H)+.

Example 26

Preparation of 1H-Indole-7-carboxylic acid (4-tert-butyl-benzyl)-[2-(4-fluoro-3-trifluoromethyl-phenyl)-ethyl]-amide To a solution of 48 mg (0.3 mmol) of 1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 106 mg (0.3 mmol) of (4-tert-butyl-benzyl)-[2-(4-fluoro-3-trifluoromethyl-phenyl)-ethyl]-amine in 2 ml DMF were added. After stirring for 3 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:9) to give 113 mg light yellow viscous oil (72%). MS (ISP) 497.4 (M+H)+.

Example 27

Preparation of 1H-Indole-7-carboxylic acid (4-tert-butyl-benzyl)-[2-(2-fluoro-3-trifluoromethyl-phenyl)-ethyl]-amide To a solution of 48 mg (0.3 mmol) of 1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 106 mg (0.3 mmol) of (4-tert-butyl-benzyl)-[2-(2-fluoro-3-trifluoromethyl-phenyl)-ethyl]-amine in 2 ml DMF were added. After stirring for 4 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:6) to give 112 mg light yellow solid (73%). MS (ISP) 497.4 (M+H)+.

Example 28

Preparation of 1H-Indole-7-carboxylic acid (4-tert-butyl-benzyl)-[2-(4-difluoromethoxy-phenyl)-ethyl]-amide To a solution of 48 mg (0.3 mmol) of 1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 105 mg (0.3 mmol) of (4-tert-butyl-benzyl)-[2-(4-difluoromethoxy-phenyl)-ethyl]-amine in 2 ml DMF were added. After 2.5 h stirring at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:6) to give 114 mg white solid (68%). MS (ISP) 477.4 (M+H)+.

Example 29

Preparation of 5,6-Difluoro-1H-indole-7-carboxylic acid (4-tert-butyl-benzyl)-[2-(4-fluoro-3-trifluoromethyl-phenyl)-ethyl]-amide To a solution of 59 mg (0.3 mmol) of 5,6-difluoro-1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 106 mg (0.3 mmol) of (4-tert-butyl-benzyl)-[2-(4-fluoro-3-trifluoromethyl-phenyl)-ethyl]-amine in 2 ml DMF were added. After stirring for 3 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by two successive column chromatographies (8 g silica gel; EtOAc/heptane 1:4; second column eluted with n-hexane/EtOAc 9:1) to give 62 mg yellow viscous oil (35%). MS (ISP) 533.2 (M+H)+.

Example 30

Preparation of 5-Chloro-1H-indole-7-carboxylic acid (4-tert-butyl-benzyl)-[2-(4-chloro-phenyl)-ethyl]-amide To a solution of 59 mg (0.3 mmol) of 5-chloro-1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 91 mg (0.3 mmol) of (4-tert-butyl-benzyl)-[2-(4-chloro-phenyl)-ethyl]-amine in 2 ml DMF were added. After stirring for 2 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:9) to give 65 mg white solid (42%). MS (ISP) 479.4 $(M+H)^+$.

Example 31

Preparation of 1H-Indole-7-carboxylic acid (4-tert-butyl-benzyl)-[(R)-2-(4-chloro-phenyl)-2-hydroxy-ethyl]-amide To a solution of 48 mg (0.3 mmol) of 1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 95 mg (0.3 mmol) of (4-tert-butyl-benzyl)-[(R)-2-(4-chloro-phenyl)-2-hydroxy-ethyl]-amine were added. After stirring for 24 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:6) to give 72 mg light yellow solid (50%). MS (ISP) 461.4 $(M+H)^+$.

Example 32

Preparation of 5-Chloro-1H-indole-7-carboxylic acid (4-tert-butyl-benzyl)-[(R)-2-(4-chloro-phenyl)-2-hydroxy-ethyl]-amide To a solution of 59 mg (0.3 mmol) of 5-chloro-1H-indole-7-carboxylic acid and 96 mg of TBTU (0.3 mmol) in 5 ml DMF, were added 0.26 ml (1.5 mmol) of N,N-diisopropylethyl amine. After stirring for 5 min at rt, 95 mg (0.3 mmol) of (4-tert-butyl-benzyl)-[(R)-2-(4-chloro-phenyl)-2-hydroxy-ethyl]-amine were added. After stirring for 24 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:6) to give 80 mg light yellow solid (43%). MS (ISP) 495.4 $(M+H)^+$.

Example 33

Preparation of 1H-Indole-7-carboxylic acid (4-tert-butyl-benzyl)-(3-phenyl-propyl)-amide To a solution of 120 mg (0.74 mmol) of 1H-indole-7-carboxylic acid and 240 mg of TBTU (0.74 mmol) in 8 ml DMF, were added 0.64 ml (3.72 mmol) of N,N-diisopropylethyl amine. After stirring for 5 min at rt, 280 mg (0.74 mmol) of (4-tert-butyl-benzyl)-(3-phenyl-propyl)-amine were added. After stirring for 4 h at rt, the reaction mixture was diluted with 80 ml water and extracted with EtOAc (2×). The combined organic phases were washed with brine, dried with magnesium sulfate, filtered and concentrated in vacuo. The residue was purified by column chromatography (40 g silica gel; EtOAc/heptane 1:4) to give 205 mg white solid (63%). MS (ISP) 425.5 $(M+H)^+$.

Example 34

Preparation of 1H-Indole-7-carboxylic acid (4-tert-butyl-benzyl)-[2-(3-ethoxy-phenyl)-ethyl]-amide To a solution of 120 mg (0.74 mmol) of 1H-indole-7-carboxylic acid and 240 mg of TBTU (0.74 mmol) in 8 ml DMF, were added 0.64 ml (3.72 mmol) of N,N-diisopropylethyl amine. After stirring for 5 min at rt, 309 mg (0.94 mmol) of (4-tert-butyl-benzyl)-[2-(3-ethoxy-phenyl)-ethyl]-amine were added. After stirring for 4 h at rt, the reaction mixture was diluted with 80 ml water and extracted with EtOAc (2×). The combined organic phases were washed with brine, dried with magnesium sulfate, filtered and concentrated in vacuo. The residue was purified by column chromatography (40 g silica gel; EtOAc/heptane 1:4) to give 110 mg off-white foam (31%). MS (ISP) 455.7 $(M+H)^+$.

Example 35

Preparation of [rac]-1H-Indole-7-carboxylic acid (4-tert-butyl-benzyl)-(2-hydroxy-2-phenyl-ethyl)-amide To a solution of 100 mg (0.62 mmol) of 1H-indole-7-carboxylic acid and 200 mg of TBTU (0.62 mmol) in 8 ml DMF, were added 0.53 ml (3.1 mmol) of N,N-diisopropylethyl amine. After stirring for 5 min at rt, 176 mg (0.62 mmol) of [rac]-(4-tert-butyl-benzyl)-(2-hydroxy-2-phenyl-ethyl)-amide were added. After stirring for 17 h at rt, the reaction mixture was diluted with 80 ml water and extracted with EtOAc (2×). The combined organic phases were washed with brine, dried with magnesium sulfate, filtered and concentrated in vacuo. The residue was purified by column chromatography (40 g silica gel; EtOAc/heptane 1:4) to give 181 mg white solid (66%). MS (ISP) 427.4 $(M+H)^+$.

Example 36

Preparation of 6-Fluoro-1H-indole-7-carboxylic acid (4-tert-butyl-benzyl)-[2-(3,5-difluoro-phenyl)-ethyl]-amide To a solution of 80 mg (0.45 mmol) of 6-fluoro-1H-indole-7-carboxylic acid and 143 mg of TBTU (0.45 mmol) in 5 ml DMF, were added 0.38 ml (2.23 mmol) of N,N-diisopropylethyl amine. After stirring for 5 min at rt, 176 mg (0.58 mmol) of (4-tert-butyl-benzyl)-[2-(3,5-difluoro-phenyl)-ethyl]-amine were added. After stirring for 17 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (40 g silica gel; EtOAc/heptane 1:4) to give 166 mg light brown foam (78%). MS 464.1 (M)

Example 37

Preparation of 6-Fluoro-1H-indole-7-carboxylic acid (4-tert-butyl-benzyl)-[2-(3,4-difluoro-phenyl)-ethyl]-amide To a solution of 50 mg (0.28 mmol) of 6-fluoro-1H-indole-7-carboxylic acid and 90 mg of TBTU (0.28 mmol) in 4 ml DMF, were added 0.24 ml (1.4 mmol) of N,N-diisopropylethyl amine. After stirring for 5 min at rt, 180 mg (0.28 mmol) acid of (4-tert-butyl-benzyl)-[2-(3,4-difluoro-phenyl)-ethyl]-amine were added. After stirring for 17 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (9 g silica gel; EtOAc/heptane 1:4) to give 85 mg light yellow foam (85%). MS 464.1 (M)

Example 38

Preparation of 5-Chloro-1H-indole-7-carboxylic acid (4-tert-butyl-benzyl)-[2-(3-trifluoromethoxy-phenyl)-ethyl]-amide To a solution of 50 mg (0.26 mmol) of 5-chloro-1H-indole-7-carboxylic acid and 82 mg of TBTU (0.26 mmol) in 4 ml DMF, were added 0.22 ml (1.28 mmol) of N,N-diisopropyl-ethyl amine. After stirring for 5 min at rt, 101 mg (0.33 mmol) of (4-tert-butyl-benzyl)-[2-(3-trifluoromethoxy-phenyl)-ethyl]-amine were added. After stirring for 4 h at rt, the reaction mixture was diluted with 40 ml water and extracted with EtOAc (2×). The combined organic phases were washed with water and brine, dried with magnesium sulfate, filtered and concentrated in vacuo. The residue was purified by column chromatography (8 g silica gel; EtOAc/heptane 1:4) to give 106 mg light brown foam (43%). MS (ISP) 529.4 (M+H)$^+$.

Example 39

Preparation of 5-Chloro-1H-indole-7-carboxylic acid (4-tert-butyl-benzyl)-[2-(4-fluoro-3-trifluoromethyl-phenyl)-ethyl]-amide To a solution of 50 mg (0.26 mmol) of 5-chloro-1H-indole-7-carboxylic acid and 82 mg of TBTU (0.26 mmol) in 4 ml DMF, were added 0.22 ml (1.28 mmol) of N,N-diisopropylethyl amine. After stirring for 5 min at rt, 99 mg (0.28 mmol) of (4-tert-butyl-benzyl)-[2-(4-fluoro-3-trifluoromethyl-phenyl)-ethyl]-amine were added. After stirring for 17 h at rt, the reaction mixture was diluted with 20 ml water and extracted with EtOAc (2×). The combined organic phases were washed with water and brine, dried with magnesium sulfate, filtered and concentrated in vacuo. The residue was purified by column chromatography (8 g silica gel; EtOAc/heptane 1:2) to give 81 mg off-white foam (55%). MS (ISP) 531.3 (M+H)$^+$.

Example 40

Preparation of [rac]-1H-Indole-7-carboxylic acid (4-tert-butyl-benzyl)-[2-(3,4-dichloro-phenyl)-2-hydroxy-ethyl]-amide To a solution of 36 mg (0.22 mmol) of 1H-indole-7-carboxylic acid and 72 mg of TBTU (0.22 mmol) in 3 ml DMF, were added 0.19 ml (1.12 mmol) of N,N-diisopropylethyl amine. After stirring for 5 min at rt, 79 mg (0.22 mmol) of [rac]-(4-tert-butyl-benzyl)-[2-(3,4-dichloro-phenyl)-2-hydroxy-ethyl]-amine was added. After stirring for 17 h at rt, the reaction mixture was diluted with 30 ml water and extracted with EtOAc (2×). The combined organic phases were washed with water and brine, dried with magnesium sulfate, filtered and concentrated in vacuo. The residue was purified by column chromatography (8 g silica gel; heptane/EtOAc 2:1) to give 68 mg (59%) of an off-white solid. MS (ISP) 495.4 (M+H)$^+$.

Example 41

Preparation of 5,6-Difluoro-1H-indole-7-carboxylic acid (4-tert-butyl-benzyl)-[2-(3-trifluoromethoxy-phenyl)-ethyl]-amide To a solution of 50 mg (0.25 mmol) of 5,6-difluoro-1H-indole-7-carboxylic acid and 81 mg of TBTU (0.25 mmol) in 4 ml DMF, were added 0.22 ml (1.28 mmol) of N,N-diisopropylethyl amine. After stirring for 5 min at rt, 89 mg (0.25 mmol) of (4-tert-butyl-benzyl)-[2-(3-trifluoromethoxy-phenyl)-ethyl]-amine were added. After stirring for 17 h at rt, the reaction mixture was diluted with 40 ml water and extracted with EtOAc (2×). The combined organic phases were washed with water and brine, dried with magnesium sulfate, filtered and concentrated in vacuo. The residue was purified by column chromatography (8 g silica gel; EtOAc/heptane 1:2) to give 56 mg light yellow amorphous material (38%). MS: 530.1 (M).

Example 42

Preparation of [rac]-1H-Indole-7-carboxylic acid (4-tert-butyl-benzyl)-[2-(4-fluoro-phenyl)-2-hydroxy-ethyl]-amide To a solution of 80 mg (0.5 mmol) of 1H-indole-7-carboxylic acid and 159 mg of TBTU (0.5 mmol) in 6 ml DMF, were added 0.43 ml (2.48 mmol) of N,N-diisopropylethyl amine. After stirring for 5 min at rt, 150 mg (0.5 mmol) of [rac]-(4-tert-butyl-benzyl)-[2-(4-fluoro-phenyl)-2-hydroxy-ethyl]-amine were added. After stirring for 17 h at rt, the reaction mixture was diluted with 60 ml water and extracted with EtOAc (2×). The combined organic phases were washed with water and brine, dried with magnesium sulfate, filtered and concentrated in vacuo. The residue was purified by column chromatography (40 g silica gel; heptane/EtOAc 2:1) to give 150 mg (66%) of an white solid. MS (ISP) 445.4 (M+H)$^+$.

Example 43

Preparation of [rac]-5-Chloro-1H-indole-7-carboxylic acid (4-tert-butyl-benzyl)-[2-(3,4-dichloro-phenyl)-2-hydroxy-ethyl]-amide To a solution of 31 mg (0.16 mmol) of 5-chloro-1H-indole-7-carboxylic acid and 51 mg of TBTU (0.16 mmol) in 2 ml DMF, were added 0.14 ml (0.79 mmol) of N,N-diisopropyl-ethyl amine. After stirring for 5 min at rt, 81 mg (0.16 mmol) of [rac]-(4-tert-butyl-benzyl)-[2-(3,4-dichloro-phenyl)-2-hydroxy-ethyl]-amine were added. After stirring for 17 h at rt, the reaction mixture was diluted with 20 ml water and extracted with EtOAc (2×). The combined organic phases were washed with water and brine, dried with mag-

Example 44

Preparation of [rac]-5-Chloro-1H-indole-7-carboxylic acid (4-tert-butyl-benzyl)-[2-(4-fluoro-phenyl)-2-hydroxy-ethyl]-amide To a solution of 43 mg (0.22 mmol) of 5-chloro-1H-indole-7-carboxylic acid and 70 mg of TBTU (0.22 mmol) in 3 ml DMF, were added 0.19 ml (1.1 mmol) of N,N-diisopropylethyl amine. After stirring for 5 min at rt, 81 mg (0.22 mmol) of [rac]-(4-tert-butyl-benzyl)-[2-(4-fluoro-phenyl)-2-hydroxy-ethyl]-amine were added. After stirring for 17 h at rt, the reaction mixture was diluted with 30 ml water and extracted with EtOAc (2×). The combined organic phases were washed with water and brine, dried with magnesium sulfate, filtered and concentrated in vacuo. The residue was purified by column chromatography (8 g silica gel; heptane/EtOAc 2:1) to give 63 mg (55%) of a light yellow foam. MS (ISP) 479.4 (M+H)$^+$.

Example 45

Preparation of [rac]-5,6-Difluoro-1H-indole-7-carboxylic acid (4-tert-butyl-benzyl)-[2-(4-fluoro-phenyl)-2-hydroxy-ethyl]-amide To a solution of 43 mg (0.22 mmol) of 5,6-difluoro-1H-indole-7-carboxylic acid and 68 mg of TBTU (0.22 mmol) in 2 ml DMF, were added 0.19 ml (1.09 mmol) of N,N-diisopropylethyl amine. After stirring for 5 min at rt, 66 mg (0.22 mmol) of [rac]-(4-tert-butyl-benzyl)-[2-(4-fluoro-phenyl)-2-hydroxy-ethyl]-amine were added. After stirring for 17 h at rt, the reaction mixture was diluted with 20 ml water and extracted with EtOAc (2×). The combined organic phases were washed with water and brine, dried with magnesium sulfate, filtered and concentrated in vacuo. The residue was purified by column chromatography (8 g silica gel; EtOAc/heptane 1:2) to give 56 mg light yellow foam (47%). MS(ISP): 481.4 (M+H)$^+$.

Example 46

Preparation of [rac]-1H-Indole-7-carboxylic acid (4-tert-butyl-benzyl)-[2-(4-chloro-phenyl)-2-hydroxy-ethyl]-amide To a solution of 50 mg (0.31 mmol) of 1H-indole-7-carboxylic acid and 97 mg of TBTU (0.31 mmol) in 4 ml DMF, were added 0.27 ml (1.55 mmol) of N,N-diisopropylethyl amine. After stirring for 5 min at rt, 99 mg (0.31 mmol) of [rac]-(4-tert-butyl-benzyl)-[2-(4-chloro-phenyl)-2-hydroxy-ethyl]-amine were added. After stirring for 17 h at rt, the reaction mixture was diluted with 40 ml water and extracted with EtOAc (2×). The combined organic phases were washed with water and brine, dried with magnesium sulfate, filtered and concentrated in vacuo. The residue was purified by column chromatography (8 g silica gel; heptane/EtOAc 2:1) to give 89 mg (61%) of a white solid. MS (ISP) 461.4 (M+H)$^+$.

Example 47

Preparation of [rac]-5-Chloro-1H-indole-7-carboxylic acid (4-tert-butyl-benzyl)-[2-(4-chloro-phenyl)-2-hydroxy-ethyl]-amide To a solution of 50 mg (0.26 mmol) of 5-chloro-1H-indole-7-carboxylic acid and 80 mg of TBTU (0.26 mmol) in 4 ml DMF, were added 0.22 ml (1.28 mmol) of N,N-diisopropyl-ethyl amine. After stirring for 5 min at rt, 81 mg (0.26 mmol) of [rac]-(4-tert-butyl-benzyl)-[2-(4-chloro-phenyl)-2-hydroxy-ethyl]-amine were added. After stirring for 17 h at rt, the reaction mixture was diluted with 30 ml water and extracted with EtOAc (2×). The combined organic phases were washed with water and brine, dried with magnesium sulfate, filtered and concentrated in vacuo. The residue was purified by column chromatography (8 g silica gel; heptane/EtOAc 2:1) to give 60 mg (42%) of a light yellow solid. MS (ISP): 495.4 (M+H)$^+$.

Example 48

Preparation of [rac]-5-Chloro-1H-indole-7-carboxylic acid (4-tert-butyl-benzyl)-[2-(4-chloro-phenyl)-2-fluoro-ethyl]-amide To a solution of 15 mg (0.08 mmol) of 5-chloro-1H-indole-7-carboxylic acid and 24 mg of TBTU (0.08 mmol) in 1.5 ml DMF, were added 0.066 ml (0.38 mmol) of N,N-diisopropylethyl amine in 1 ml DMF. After stirring for 5 min at rt, 25 mg (0.08 mmol) of [rac]-(4-tert-butyl-benzyl)-[2-(4-chloro-phenyl)-2-fluoro-ethyl]-amine were added. After stirring for 17 h at rt, the reaction mixture was diluted with 40 ml water and extracted with EtOAc (2×). The combined organic phases were washed with water and brine, dried with magnesium sulfate, filtered and concentrated in vacuo. The residue was purified by column chromatography (8 g silica gel; heptane/EtOAc 4:1) to give 9 mg (21%) of a light yellow solid. MS (ISP): 497.3 (M+H)$^+$.

Example 49

Preparation of 5-Chloro-6-fluoro-1H-indole-7-carboxylic acid (4-tert-butyl-benzyl)-[2-(3-trifluoromethoxy-phenyl)-ethyl]-amide To a solution of 200 mg (0.94 mmol) 5-chloro-6-fluoro-1H-indole-7-carboxylic acid and 300 mg of TBTU (0.94 mmol) in 15 ml DMF, were added 0.8 ml (4.68 mmol) of N,N-diisopropylethyl amine. After stirring for 5 min at rt, 329 mg (0.94 mmol) (4-tert-butyl-benzyl)-[2-(3-trifluoromethoxy-phenyl)-ethyl]-amine in 1 ml DMF was added. After stirring for 17 h at rt, the reaction mixture was diluted with 160 ml water and extracted with EtOAc (2×). The combined organic phases were washed with water and brine, dried with magnesium sulfate, filtered and concentrated in vacuo. The residue was purified by column chromatography (90 g silica gel; diethylether/heptane 1:1) to give 130 mg off-white foam (23%). MS (ISP) 547.4 (M+H)$^+$.

Previous page: nesium sulfate, filtered and concentrated in vacuo. The residue was purified by column chromatography (8 g silica gel; heptane/EtOAc 2:1) to give 38 mg (44%) of a light yellow foam. MS: 528 (M).

Example 50

Preparation of 5-Chloro-6-fluoro-1H-indole-7-carboxylic acid (4-tert-butyl-benzyl)-[2-(3-trifluoromethyl-phenyl)-ethyl]-amide and other compounds of formula I To a solution of 185 mg (0.87 mmol) 5-chloro-6-fluoro-1H-indole-7-carboxylic acid and 278 mg of TBTU (0.87 mmol) in 13 ml DMF, were added 0.74 ml (4.33 mmol) of N,N-diisopropylethyl amine. After stirring for 5 min at rt, 290 mg (0.87 mmol) (4-tert-butyl-benzyl)-[2-(3-trifluoromethyl-phenyl)-ethyl]-amine in 1 ml DMF was added. After stirring for 17 h at rt, the reaction mixture was diluted with 140 ml water and extracted with EtOAc (2×). The combined organic phases were washed with water and brine, dried with magnesium sulfate, filtered and concentrated in vacuo. The residue was purified by two successive column chromatographies (90 g silica gel; diethylether/heptane 1:1; then 8 g silica gel; DCM/heptane 70:30 to 90:10) to give 125 mg white foam (27%). M (EI) 530.2 (M)$^+$.

Alternatively, better yields are obtained when using HBTU instead of TBTU as coupling reagent:

A solution of 0.52 g 5-chloro-6-fluoro-1H-indole-7-carboxylic acid (2.43 mmol) in 28 ml DMF and 0.946 g (4-tert-butyl-benzyl)-[2-(3-trifluoromethyl-phenyl)-ethyl]-amine (2.68 mmol) was stirred at rt and treated with 0.89 ml N-methyl-morpholine (7.3 mmol) followed by 1.385 g HBTU. The brown solution was stirred 17 h at rt, then poured into 280 ml water and extracted twice with EtOAc. The combined organic phases were washed with brine, dried over magnesium sulfate, filtered and concentrated in vacuo. The residue was purified by column chromatography (80 g silica gel; DCM/heptane 70:30 to 90:10) to give 1.04 g of a light yellow foam, which was crystallized from ethanol, leading to 0.909 g white solid (68%).

The following compounds were prepared according to the above procedure (HBTU method):

5-Chloro-6-fluoro-1-indole-7-carboxylic acid (4-tert-butyl-benzyl)-[2-(4-trifluoromethyl-phenyl)-ethyl]-amide 221 from 520 mg of 5-Chloro-6-fluoro-1H-indole-7-carboxylic acid (2.43 mmol) and 0.946 mg (2.68 mmol) of (4-tert-butyl-benzyl)-[2-(3-trifluoromethyl-phenyl)-ethyl]-amine, containing few % of (4-tert-butyl-benzyl)-[2-(4-trifluoromethyl-phenyl)-ethyl]-amine. After final purification (silica gel; DCM/heptane 70:30 to 90:10) and crystallization from EtOH 41 mg (3.2%) of white crystals were isolated. MS: 530.3 (M).

5-Chloro-6-fluoro-1-indole-7-carboxylic acid (4-tert-butyl-benzyl)-[2-(2-trifluoromethyl-phenyl)-ethyl]-amide 222 from 2.3 g of 5-Chloro-6-fluoro-1H-indole-7-carboxylic acid (10.66 mmol) and 4.43 g (11.73 mmol) of (4-tert-butyl-benzyl)-[2-(2-trifluoromethyl-phenyl)-ethyl]-amine; hydrochloride. After crystallization from heptane 4.7 g (79%) of white crystals were isolated. MS: 530.3 (M).

5-Chloro-6-fluoro-1H-indole-7-carboxylic acid [(R)-2-(4-chloro-phenyl)-2-hydroxy-ethyl]-(4-cyclopropyl-benzyl)-amide 223 from 60 mg of 5-chloro-6-fluoro-1H-indole-7-carboxylic acid (0.28 mmol) and 93 mg (0.31 mmol) of [(R)-2-(4-chloro-phenyl)-2-hydroxy-ethyl]-(4-cyclopropyl-benzyl)-amine. After final purification (8 g silica gel chromatography; heptane/AcOEt 6:1) 70 mg (47%) of an off-white solid were isolated. MS (ISP) 497.0 (M+H)$^+$.

5-Chloro-1H-indole-7-carboxylic acid [(R)-2-(4-chloro-phenyl)-2-hydroxy-ethyl]-(4-cyclopropyl-benzyl)-amide 224 from 59 mg of 5-chloro-1H-indole-7-carboxylic acid (0.3 mmol) and 100 mg (0.33 mmol) of [(R)-2-(4-chloro-phenyl)-2-hydroxy-ethyl]-(4-cyclopropyl-benzyl)-amine. After final purification (8 g silica gel chromatography; heptane/AcOEt 6:1) 107 mg (64%) of an off-white solid were isolated. MS (ISP) 479.2 (M+H)$^+$.

5-Chloro-6-fluoro-1H-indole-7-carboxylic acid (4-cyclopropyl-benzyl)-[2-(3-trifluoromethoxy-phenyl)-ethyl]-amide 225 from 43 mg of 5-chloro-6-fluoro-1H-indole-7-carboxylic acid (0.2 mmol) and 74 mg (0.22 mmol) of (4-cyclopropyl-benzyl)-[2-(3-trifluoromethoxy-phenyl)-ethyl]-amine. After final purification (8 g silica gel chromatography; heptane/AcOEt 4:1) 60 mg (47%) of an light yellow viscous oil were isolated. MS: 530.1 (M).

5-Chloro-6-fluoro-1H-indole-7-carboxylic acid (2-chloro-4-cyclopropyl-benzyl)-[2-(3-trifluoromethyl-phenyl)-ethyl]-amide 226 from 80 mg of 5-chloro-6-fluoro-1H-indole-7-carboxylic acid (0.4 mmol) and 146 mg (0.41 mmol) of (2-chloro-4-cyclopropyl-benzyl)-[2-(3-trifluoromethyl-phenyl)-ethyl]-amine. After final purification (8 g silica gel chromatography; heptane/DCM 1:4) 115 mg (54%) of an off-white foam were isolated. MS (+cEI): 550.2 (M).

5-Chloro-1H-indole-7-carboxylic acid (2-chloro-4-cyclopropyl-benzyl)-[2-(3-trifluoromethyl-phenyl)-ethyl]-amide 227 from 80 mg of 5-chloro-1H-indole-7-carboxylic acid (0.41 mmol) and 159 mg (0.45 mmol) of (2-chloro-4-cyclopropyl-benzyl)-[2-(3-trifluoromethyl-phenyl)-ethyl]-amine. After final purification (8 g silica gel chromatography; heptane/AcOEt 9:1) 186 mg (83%) of a light yellow viscous oil were isolated. MS: 531.0 (M+H)$^+$.

5-Chloro-6-fluoro-1H-indole-7-carboxylic acid (4-cyclopropyl-2-fluoro-benzyl)-[2-(3-trifluoromethyl-phenyl)-ethyl]-amide 228 from 33 mg of 5-chloro-6-fluoro-1H-indole-7-carboxylic acid (0.15 mmol) and 56 mg (0.17 mmol) of (4-cyclopropyl-2-fluoro-benzyl)-[2-(3-trifluoromethyl-phenyl)-ethyl]-amine. After final purification (8 g silica gel chromatography; heptane/AcOEt 9:1) 68 mg (79%) of a colorless viscous oil were isolated. MS: 532.2 (M).

5-Chloro-1H-indole-7-carboxylic acid (4-cyclopropyl-2-fluoro-benzyl)-[2-(3-trifluoromethyl-phenyl)-ethyl]-amide 229 from 29 mg of 5-chloro-1H-indole-7-carboxylic acid (0.15 mmol) and 56 mg (0.17 mmol) of (4-cyclopropyl-2-fluoro-benzyl)-[2-(3-trifluoromethyl-phenyl)-ethyl]-amine. After final purification (8 g silica gel chromatography; heptane/AcOEt 9:1) 71 mg (90%) of a colorless viscous oil were isolated. MS: 514.2 (M).

5-Chloro-6-fluoro-1H-indole-7-carboxylic acid (4-cyclopropyl-3-fluoro-benzyl)-[2-(3-trifluoromethyl-phenyl)-ethyl]-amide 230 from 33 mg of 5-chloro-6-fluoro-1H-indole-7-carboxylic acid (0.15 mmol) and 56 mg (0.17 mmol) of (4-cyclopropyl-3-fluoro-benzyl)-[2-(3-trifluoromethyl-phenyl)-ethyl]-amine. After final purification (8 g silica gel chromatography; heptane/AcOEt 9:1) 60 mg (68%) of a light yellow solid were isolated. MS: 533.2 (M+H)$^+$.

5-Chloro-6-fluoro-1H-indole-7-carboxylic acid (4-trifluoromethoxy-benzyl)-[2-(3-trifluoromethyl-phenyl)-ethyl]-amide 231 from 50 mg of 5-chloro-6-fluoro-1H-indole-7-carboxylic acid (0.23 mmol) and 94 mg (0.26 mmol) of (4-trifluoromethoxy-benzyl)-[2-(3-trifluoromethyl-phenyl)-ethyl]-amine. After final purification (8 g silica gel chromatography; heptane/AcOEt 8:2) 80 mg (61%) of a light yellow oil were isolated. MS: 559 (M+H)$^+$.

5-Chloro-1H-indole-7-carboxylic acid (4-trifluoromethoxy-benzyl)-[2-(3-trifluoromethyl-phenyl)-ethyl]-amide 232 from 50 mg of 5-chloro-1H-indole-7-carboxylic acid (0.26 mmol) and 102 mg (0.28 mmol) of (4-trifluoromethoxy-benzyl)-[2-(3-trifluoromethyl-phenyl)-ethyl]-amine. After final purification (8 g silica gel chromatography; heptane/AcOEt 8:2) 102 mg (74%) of a purple oil were isolated. MS: 541 (M+H)$^+$.

Example 51

Preparation of 5-Chloro-6-fluoro-1H-indole-7-carboxylic acid (4-tert-butyl-benzyl)-[2-(3-chloro-4-fluoro-phenyl)-ethyl]-amide To a solution of 100 mg (0.47 mmol) 5-chloro-6-fluoro-1H-indole-7-carboxylic acid and 150 mg of TBTU (0.47 mmol) in 7 ml DMF, were added 0.4 ml (2.34 mmol) of N,N-diisopropylethyl amine. After stirring for 5 min at rt, 150 mg (0.47 mmol) (4-tert-butyl-benzyl)-[2-(3-chloro-4-fluoro-phenyl)-ethyl]-amine in 1 ml DMF was added. After stirring for 17 h at rt, the reaction mixture was diluted with 80 ml water and extracted with EtOAc (2×). The combined organic phases were washed with water and brine, dried with magnesium sulfate, filtered and concentrated in vacuo. The residue was purified by column chromatography (8 g silica gel; diethylether/heptane 1:1; then 8 g silicagel DCM/heptane 70:30 to 90:10) to give 130 mg light yellow foam (52%). MS (EI) 514.1 (M)$^+$.

Example 52

Preparation of 5-Chloro-6-fluoro-1H-indole-7-carboxylic acid (4-tert-butyl-benzyl)-[2-(4-chloro-phenyl)-ethyl]-amide To a solution of 100 mg (0.47 mmol) 5-chloro-6-fluoro-1H-indole-7-carboxylic acid and 150 mg of TBTU (0.47 mmol) in 7 ml DMF, were added 0.4 ml (2.34 mmol) of N,N-diisopropylethyl amine. After stirring for 5 min at rt, 141 mg (0.47 mmol) (4-tert-butyl-benzyl)-[2-(4-chloro-phenyl)-ethyl]-amine in 1 ml DMF was added. After stirring for 17 h at rt, the reaction mixture was diluted with 80 ml water and extracted with EtOAc (2×). The combined organic phases were washed with water and brine, dried with magnesium sulfate, filtered and concentrated in vacuo. The residue was purified by column chromatography (8 g silica gel; diethylether/heptane 1:1; then 8 g silicagel DCM/heptane 70:30 to 90:10) to give 112 mg off-white foam (47%). MS (EI) 496.1 (M)$^+$.

Example 53

Preparation of 5-Chloro-6-fluoro-1H-indole-7-carboxylic acid (4-cyclopropyl-benzyl)-[2-(3-trifluoromethyl-phenyl)-ethyl]-amide To a solution of 37 mg (0.17 mmol) 5-chloro-6-fluoro-1H-indole-7-carboxylic acid and 54 mg of TBTU (0.17 mmol) in 2 ml DMF, were added 0.148 ml (0.87 mmol) of N,N-diisopropylethyl amine. After stirring for 5 min at rt, 51 mg (0.17 mmol) (4-cyclopropyl-benzyl)-[2-(3-trifluoromethyl-phenyl)-ethyl]-amine in 1 ml DMF was added. After stirring for 17 h at rt, the reaction mixture was diluted with 30 ml water and extracted with EtOAc (2×). The combined organic phases were washed with water and brine, dried with magnesium sulfate, filtered and concentrated in vacuo. The residue was purified by column chromatography (8 g silica gel; diethylether/heptane 1:1; then 8 g silicagel DCM/heptane 70:30 to 90:10) to give 43 mg white foam (48%). MS (EI) 514.1 (M)$^+$.

Example 54

Preparation of 5-Chloro-1H-indole-7-carboxylic acid (4-tert-butyl-benzyl)-(4,4,4-trifluoro-3-trifluoromethyl-butyl)-amide To a solution of 80 mg (0.41 mmol) 5-chloro-1H-indole-7-carboxylic acid and 128 mg of TBTU (0.41 mmol) in 6 ml DMF, were added 0.42 ml (2.45 mmol) of N,N-diisopropylethyl amine. After stirring for 5 min at rt, 155 mg (0.41 mmol) (4-tert-butyl-benzyl)-(4,4,4-trifluoro-3-trifluoromethyl-butyl)-amine hydrochloride was added. After stirring for 17 h at rt, the reaction mixture was diluted with 60 ml water and extracted with EtOAc (2×). The combined organic phases were washed with water and brine, dried with magnesium sulfate, filtered and concentrated in vacuo. The residue was purified by column chromatography (8 g silica gel; diethylether/heptane 1:1; then 8 g silicagel DCM/heptane 70:30 to 90:10) to give 144 mg white foam (66%). MS (EI) 518.1 (M)$^+$.

Example 55

Preparation of 1H-Indole-7-carboxylic acid (4-tert-butyl-benzyl)-[2-(3-chloro-4-fluoro-phenyl)-ethyl]-amide To a solution of 48 mg (0.3 mmol) 1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 96 mg (0.3 mmol) of (4-tert-butyl-benzyl)-[2-(3-chloro-4-fluoro-phenyl)-ethyl]-amine in 2 ml DMF were added. After stirring for 3 h at rt, the reaction mixture was diluted with 50 ml water and extracted with 2×50 ml EtOAc. The combined organic phases were washed with water and brine, dried with magnesium sulfate, filtered and concentrated in vacuo to give 141 mg white solid (99%). MS (ISP) 463.4 (M+H)$^+$.

Example 56

Preparation of 5-Chloro-1H-indole-7-carboxylic acid (4-tert-butyl-benzyl)-[2-(3-chloro-4-fluoro-phenyl)-ethyl]-amide To a solution of 59 mg (0.3 mmol) of 5-chloro-1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 96 mg (0.3 mmol) (4-tert-butyl-benzyl)-[2-(3-chloro-4-fluoro-phenyl)-ethyl]-amine in 2 ml DMF was added. After 3.5 h stirring at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:9) to give to give 110 mg light yellow solid (68%). MS (EI) 496.1 (M)$^+$.

Example 57

Preparation of 1H-Indole-7-carboxylic acid (4-tert-butyl-benzyl)-[2-(2-fluoro-5-trifluoromethyl-phenyl)-ethyl]-amide To a solution of 48 mg (0.3 mmol) of 1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 118 mg (0.3 mmol) (4-tert-butyl-benzyl)-[2-(2-fluoro-5-trifluoromethyl-phenyl)-ethyl]-amine in 2 ml DMF was added. After 3¾ h stirring at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:9) to give 120 mg light yellow viscous oil (77%). MS (EI) 496.3 (M)$^+$.

Example 58

Preparation of 5-Chloro-1H-indole-7-carboxylic acid (4-tert-butyl-benzyl)-[2-(2-fluoro-5-trifluoromethyl-phenyl)-ethyl]-amide To a solution of 59 mg (0.3 mmol) of 5-chloro-1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 118 mg (0.3 mmol) of (4-tert-butyl-benzyl)-[2-(2-fluoro-5-trifluoromethyl-phenyl)-ethyl]-amine in 2 ml DMF were added. After 3.5 h stirring at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:9) to give 90 mg light yellow viscous oil (53%). MS (EI) 530.2 (M)$^+$.

Example 59

Preparation of 5-Chloro-6-fluoro-1H-indole-7-carboxylic acid (4-tert-butyl-benzyl)-[2-(4-fluoro-3-trifluoromethyl-phenyl)-ethyl]-amide To a solution of 60 mg (0.28 mmol) of 5-chloro-6-fluoro-1H-indole-7-carboxylic acid and 90 mg of TBTU (0.3 mmol) in 3 ml DMF, were added 0.24 ml (1.4 mmol) of N,N-diisopropylethyl amine. After stirring for 5 min at rt, 99 mg (0.28 mmol) of (4-tert-butyl-benzyl)-[2-(4-fluoro-3-trifluoromethyl-phenyl)-ethyl]-amine in 2 ml DMF were added. After stirring for 15 h at rt, the reaction mixture was diluted with 50 ml water and extracted with 2×50 ml EtOAc. The combined organic phases were washed with water and brine, dried with magnesium sulfate, filtered and concentrated in vacuo. The residue was purified by column chromatography (8 g silica gel; EtOAc/heptane 1:19 then 1:9) followed by a second column chromatography (8 g silica gel; gradient DCM/heptane from 70% to 90% DCM) to give 69 mg white solid (44%). MS (ISP) 549.3 (M+H)$^+$.

Example 60

Preparation of 5-Chloro-1H-indole-7-carboxylic acid (4-tert-butyl-benzyl)-[2-(4-chloro-3-trifluoromethyl-phenyl)-ethyl]-amide To a solution of 98 mg (0.5 mmol) of 5-chloro-1H-indole-7-carboxylic acid and 161 mg of TBTU (0.5 mmol) in 6 ml DMF, were added 0.43 ml (2.51 mmol) of N,N-diisopropylethyl amine. After stirring for 5 min at rt, 200 mg (0.54 mmol) of (4-tert-butyl-benzyl)-[2-(4-chloro-3-trifluoromethyl-phenyl)-ethyl]-amine in 2 ml DMF were added. After stirring for 3 h at rt, the reaction mixture was diluted with 80 ml water and extracted with EtOAc (2×). The combined organic phases were washed with water and brine, dried with magnesium sulfate, filtered and concentrated in vacuo. The residue was purified by column chromatography (40 g silica gel; DCM/heptane 9:1) to give 206 mg white solid (69%). MS (EI) 546.2 (M)$^+$.

Example 61

Preparation of 5-Chloro-6-fluoro-1H-indole-7-carboxylic acid (4-tert-butyl-benzyl)-[2-(4-chloro-3-trifluoromethyl-phenyl)-ethyl]-amide 62

To a solution of 107 mg (0.5 mmol) of 5-chloro-6-fluoro-1H-indole-7-carboxylic acid and 161 mg of TBTU (0.5 mmol) in 6 ml DMF, were added 0.43 ml (2.51 mmol) of N,N-diisopropylethyl amine. After stirring for 5 min at rt, 200 mg (0.54 mmol) of (4-tert-butyl-benzyl)-[2-(4-chloro-3-trifluoromethyl-phenyl)-ethyl]-amine in 2 ml DMF were added. After stirring for 22 h at rt, the reaction mixture was diluted with 80 ml water and extracted with EtOAc (2×). The combined organic phases were washed with water and brine, dried with magnesium sulfate, filtered and concentrated in vacuo. The residue was purified by column chromatography (40 g silica gel; DCM/heptane 9:1) to give 182 mg off-white solid (54%). MS (EI) 564.2 (M)$^+$.

Example 62

Preparation of 5-Chloro-1H-indole-7-carboxylic acid (4-tert-butyl-benzyl)-[2-(3-fluoro-5-trifluoromethyl-phenyl)-ethyl]-amide 64

To a solution of 103 mg (0.53 mmol) of 5-chloro-1H-indole-7-carboxylic acid and 169 mg of TBTU (0.53 mmol) in 6 ml DMF, were added 0.45 ml (2.63 mmol) of N,N-diisopropylethyl amine. After stirring for 5 min at rt, 200 mg (0.57 mmol) of (4-tert-butyl-benzyl)-[2-(3-fluoro-5-trifluoromethyl-phenyl)-ethyl]-amine in 2 ml DMF were added. After stirring for 3 h at rt, the reaction mixture was diluted with 80 ml water and extracted with EtOAc (2×). The combined organic phases were washed with water and brine, dried with magnesium sulfate, filtered and concentrated in vacuo. The residue was purified by column chromatography (40 g silica gel; DCM/heptane 9:1) to give 211 mg white solid (70%). MS (EI) 530.2 (M)$^+$.

Example 63

Preparation of 5-Chloro-6-fluoro-1H-indole-7-carboxylic acid (4-tert-butyl-benzyl)-[2-(3-fluoro-5-trifluoromethyl-phenyl)-ethyl]-amide 66

To a solution of 112 mg (0.53 mmol) of 5-chloro-6-fluoro-1H-indole-7-carboxylic acid and 169 mg of TBTU (0.53 mmol) in 6 ml DMF, were added 0.45 ml (2.63 mmol) of N,N-diisopropylethyl amine. After stirring for 5 min at rt, 200 mg (0.57 mmol) of (4-tert-butyl-benzyl)-[2-(3-fluoro-5-trifluoromethyl-phenyl)-ethyl]-amine in 2 ml DMF were added. After stirring for 21 h at rt, the reaction mixture was diluted with 80 ml water and extracted with EtOAc (2×). The combined organic phases were washed with water and brine, dried with magnesium sulfate, filtered and concentrated in vacuo. The residue was purified by column chromatography (40 g silica gel; DCM/heptane 9:1) to give 158 mg off-white solid (48%). MS (EI) 548.2 (M)$^+$.

Example 64

Preparation of 1H-Indole-7-carboxylic acid (4-tert-butyl-benzyl)-[2-(3-difluoromethoxy-phenyl)-ethyl]-amide 68

To a solution of 48 mg (0.3 mmol) of 1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 100 mg (0.3 mmol) of (4-tert-butyl-benzyl)-[2-(3-difluoromethoxy-phenyl)-ethyl]-amine in 2 ml DMF was added. After 2.5 h stirring at rt, the reaction mixture was diluted with 50 ml water and extracted with EtOAc (2×). The combined organic phases were washed with water and brine, dried with magnesium sulfate, filtered and concentrated in vacuo. The residue was purified by column chromatography (8 g silica gel; EtOAc/heptane 1:6) to give 105 mg colorless viscous oil (73%). MS (EI) 477.4 (M)$^+$.

Example 65

Preparation of 1H-Indole-7-carboxylic acid (4-tert-butyl-benzyl)-[2-(3-chloro-2-fluoro-phenyl)-ethyl]-amide 69

To a solution of 48 mg (0.3 mmol) of 1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 96 mg (0.3 mmol) of (4-tert-butyl-benzyl)-[2-(3-chloro-2-fluoro-phenyl)-ethyl]-amine in 2 ml DMF were added. After stirring for 4 h at rt, the reaction mixture was diluted with 50 ml water and extracted with EtOAc (2×). The combined organic phases were washed with water and brine, dried with magnesium sulfate, filtered and concentrated in vacuo. The residue was purified by column chromatography (8 g silica gel; EtOAc/heptane 1:6) to give 103 mg white solid (73%). MS (EI) 464.1 (M)$^+$.

Example 66

Preparation of 5-Chloro-1H-indole-7-carboxylic acid (4-tert-butyl-benzyl)-[2-(3-chloro-2-fluoro-phenyl)-ethyl]-amide 70

To a solution of 59 mg (0.3 mmol) of 5-chloro-1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 96 mg (0.3 mmol) of (4-tert-butyl-benzyl)-[2-(3-chloro-2-fluoro-phenyl)-ethyl]-amine in 2 ml DMF were added. After stirring for 4.5 h at rt, the reaction mixture was diluted with 50 ml water and extracted with EtOAc (2×). The combined organic phases were washed with water and brine, dried with magnesium sulfate, filtered and concentrated in vacuo. The residue was purified by column chromatography (8 g silica gel; EtOAc/heptane 1:6) to give 107 mg white solid (68%). MS (ISP) 498.0 (M+H)$^+$.

Example 67

Preparation of 5,6-Difluoro-1H-indole-7-carboxylic acid (4-tert-butyl-benzyl)-[2-(3-chloro-2-fluoro-phenyl)-ethyl]-amide 71

To a solution of 59 mg (0.3 mmol) of 5,6-difluoro-1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 96 mg (0.3 mmol) of (4-tert-butyl-benzyl)-[2-(3-chloro-2-fluoro-phenyl)-ethyl]-amine in 2 ml DMF were added. After stirring for 23 h at rt, the reaction mixture was diluted with 50 ml water and extracted with EtOAc (2×). The combined organic phases were washed with water and brine, dried with magnesium sulfate, filtered and concentrated in vacuo. The residue was purified by column chromatography (8 g silica gel; EtOAc/heptane 1:6) to give 78 mg white solid (46%). MS (ISP) 499.2 (M+H)$^+$.

Example 68

Preparation of 5-Chloro-1H-indole-7-carboxylic acid (4-tert-butyl-benzyl)-[2-(3-difluoromethoxy-phenyl)-ethyl]-amide 72

To a solution of 59 mg (0.3 mmol) of 5-chloro-1H-indole-7-carboxylic acid and 96 mg of TBTU (0.3 mmol) in 3 ml DMF, were added 0.26 ml (1.5 mmol) of N,N-diisopropylethyl amine. After stirring for 5 min at rt, 100 mg (0.3 mmol) of (4-tert-butyl-benzyl)-[2-(3-difluoromethoxy-phenyl)-ethyl]-amine in 2 ml DMF were added. After stirring for 4 h at rt, the reaction mixture was diluted with 50 ml water and extracted with EtOAc (2×). The combined organic phases were washed with water and brine, dried with magnesium sulfate, filtered and concentrated in vacuo. The residue was purified by column chromatography (8 g silica gel; EtOAc/heptane 1:6) to give 114 mg white solid (67%). MS(ISP) 512.2 (M+H)$^+$.

Example 69

Preparation of 5-Chloro-6-fluoro-1H-indole-7-carboxylic acid (4-tert-butyl-benzyl)-[2-(3-difluoromethoxy-phenyl)-ethyl]-amide 73

To a solution of 100 mg (0.47 mmol) of 5-chloro-6-fluoro-1H-indole-7-carboxylic acid and 150 mg of TBTU (0.47 mmol) in 10 ml DMF, were added 0.4 ml (2.34 mmol) of N,N-diisopropylethyl amine. After stirring for 5 min at rt, 156 mg (0.47 mmol) of (4-tert-butyl-benzyl)-[2-(3-difluoromethoxy-phenyl)-ethyl]-amine were added. After stirring for 22 h at rt, the reaction mixture was diluted with 10 ml water and extracted with EtOAc (2×). The combined organic phases were washed with water and brine, dried with magnesium sulfate, filtered and concentrated in vacuo. The residue was purified by two successive column chromatographies (8 g silica gel; EtOAc/heptane 1:3; then again 8 g silica gel; and DCM/heptane 70:30 to 90:10) to give 91 mg white solid (27%). MS(ISP) 528.3 (M+H)$^+$.

Example 70

Preparation of 5-Chloro-6-fluoro-1H-indole-7-carboxylic acid (4-tert-butyl-benzyl)-[2-(2-fluoro-5-trifluoromethyl-phenyl)-ethyl]-amide 74

To a solution of 100 mg (0.47 mmol) of 5-chloro-6-fluoro-1H-indole-7-carboxylic acid and 150 mg of TBTU (0.47 mmol) in 10 ml DMF, were added 0.4 ml (2.34 mmol) of N,N-diisopropylethyl amine. After stirring for 5 min at rt, 184 mg (0.47 mmol) of (4-tert-butyl-benzyl)-[2-(2-fluoro-5-trifluoromethyl-phenyl)-ethyl]-amine were added. After stirring for 22 h at rt, the reaction mixture was diluted with 10 ml water and extracted with EtOAc (2×). The combined organic phases were washed with water and brine, dried with magnesium sulfate, filtered and concentrated in vacuo. The residue was purified by two successive column chromatographies (8 g silica gel; EtOAc/heptane 1:3; then again 8 g silicagel and DCM/heptane 70:30 to 90:10) to give 77 mg white solid (30%). MS(ISP) 548.2 (M+H)$^+$.

Example 71

Preparation of [rac]-1H-Indole-7-carboxylic acid (4-tert-butyl-benzyl)-(3,3,3-trifluoro-2-hydroxy-propyl)-amide 75

To a solution of 30 mg (0.19 mmol) of 1H-indole-7-carboxylic acid and 60 mg of TBTU (0.19 mmol) in 6 ml DMF, were added 0.16 ml (0.93 mmol) of N,N-diisopropylethyl amine. After stirring for 5 min at rt, 85 mg (0.19 mmol) of [rac]-(4-tert-butyl-benzyl)-(3,3,3-trifluoro-2-hydroxy-propyl)-amine were added. After stirring for 4 h at rt, the reaction mixture was diluted with 60 ml water and extracted with EtOAc (2×). The combined organic phases were washed with water and brine, dried with magnesium sulfate, filtered and concentrated in vacuo. The residue was purified by column chromatography (9 g silica gel; EtOAc/heptane 1:4) to give 17 mg white solid (17%). MS (EI) 418.2 (M)$^+$.

Example 72

Preparation of 2,3-Dihydro-1H-indole-7-carboxylic acid (4-tert-butyl-benzyl)-[2-(4-fluoro-phenyl)-ethyl]-amide 76

To a solution of 95 mg (0.22 mmol) of 1H-indole-7-carboxylic acid (4-tert-butyl-benzyl)-[2-(4-fluoro-phenyl)-ethyl]-amide in 2 ml conc. acetic acid 46 mg of sodium borohydride (0.67 mmol) were added in three portions (ice bath cooling). The reaction mixture was stirred for 3 h at rt, then treated with 2N NaOH to adjust the pH to 12, extracted twice with diethylether and the combined organic phases were washed with brine, dried with magnesium sulfate, filtered and concentrated in vacuo. The residue was purified by column chromatography (8 g silica gel; EtOAc/heptane 1:4) to give 45 mg white foam (45%). MS(ISP) 431.5 (M+H)$^+$.

Example 73

Preparation of 1H-Indole-7-carboxylic acid butyl-(4-tert-butyl-benzyl)-amide 77

To a solution of 110 mg of 1H-indole-7-carboxylic acid (0.68 mmol) and 220 mg of TBTU (0.68 mmol) in 10 ml DMF, were added 0.59 ml (3.42 mmol) of N,N-diisopropylethyl amine. After stirring for 5 min at rt, 150 mg (0.68 mmol) of butyl-(4-tert-butyl-benzyl)-amine were added. After stirring for 2 h at rt, the reaction mixture was diluted with 100 ml water and extracted twice with EtOAc. The combined organic phases were washed with water and brine, dried with magnesium sulfate, filtered and concentrated in vacuo. The residue was purified by column chromatography (8 g silica gel; heptane/EtOAc 2:1) to give 209 mg (82%) of a light yellow viscous oil. MS (EI) 362.2 (M)$^+$.

Example 74

Preparation of 1H-Indole-7-carboxylic acid (4-tert-butyl-benzyl)-[2-(3-methoxy-phenyl)-ethyl]-amide 78

To a solution of 80 mg of 1H-indole-7-carboxylic acid (0.5 mmol) and 159 mg of TBTU (0.5 mmol) in 10 ml DMF, were added 0.425 ml (2.48 mmol) of N,N-diisopropylethyl amine. After stirring for 5 min at rt, 174 mg (0.68 mmol) of (4-tert-butyl-benzyl)-[2-(3-methoxy-phenyl)-ethyl]-amine were added. After stirring for 3 h at rt, the reaction mixture was diluted with 50 ml water and extracted twice with EtOAc. The combined organic phases were washed with water and brine, dried with magnesium sulfate, filtered and concentrated in vacuo. The residue was purified by column chromatography (40 g silica gel; heptane/EtOAc 2:1) to give 168 mg (75%) of a white solid. MS (ISP) 441.4 (M+H)$^+$.

Example 75

Preparation of [rac]-1H-Indole-7-carboxylic acid (4-tert-butyl-benzyl)-[2-(4-chloro-phenyl)-propyl]-amide 79

To a solution of 81 mg of 1H-indole-7-carboxylic acid (0.5 mmol) and 161 mg of TBTU (0.5 mmol) in 2 ml DMF, were added 0.43 ml (2.5 mmol) of N,N-diisopropylethyl amine. After stirring for 5 min at rt, 158 mg (0.5 mmol) [rac]-(4-tert-butyl-benzyl)-[2-(4-chloro-phenyl)-propyl]-amine in 3.5 ml DMF was added. After stirring for 22 h at rt, the reaction mixture was diluted with 50 ml water and extracted twice with EtOAc. The combined organic phases were washed with water and brine, dried with magnesium sulfate, filtered and concentrated in vacuo. The residue was purified by column chromatography (40 g silica gel; heptane/EtOAc 2:1) to give 203 mg (86%) of a off-white solid. MS(ISP) 459.4 (M+H)$^+$.

Example 76

Preparation of 1H-Indole-7-carboxylic acid (4-tert-butyl-benzyl)-[2-(2,4-dichloro-phenyl)-ethyl]-amide 80

To a solution of 81 mg of 1H-indole-7-carboxylic acid (0.5 mmol) and 161 mg of TBTU (0.5 mmol) in 10 ml DMF, were added 0.43 ml (2.5 mmol) of N,N-diisopropylethyl amine. After stirring for 5 min at rt, 168 mg (0.5 mmol) of (4-tert-butyl-benzyl)-[2-(2,4-dichloro-phenyl)-ethyl]-amine were added. After stirring for 3 h at rt, the reaction mixture was diluted with 50 ml water and extracted twice with EtOAc. The combined organic phases were washed with water and brine, dried with magnesium sulfate, filtered and concentrated in vacuo. The residue was purified by column chromatography (40 g silica gel; heptane/EtOAc 2:1) to give 213 mg (87%) of a light yellow oil. MS(ISP) 479.4 (M+H)$^+$.

Example 77

Preparation of 4-Chloro-1H-indole-7-carboxylic acid (4-tert-butyl-benzyl)-[2-(4-fluoro-phenyl)-ethyl]-amide 81

To a solution of 64 mg (0.33 mmol) of 4-chloro-1H-indole-7-carboxylic acid in 2 ml DCM 50 mg of HOBT (0.33 mmol) were added and the reaction mixture was stirred for 15 min at rt under nitrogen. 85 mg (0.3 mmol) of (4-tert-butyl-benzyl)-[2-(4-fluoro-phenyl)-ethyl]-amine in 1 ml DCM were added and then 63 mg (0.33 mmol) of EDC.HCl. The reaction mixture was stirred over night at rt to yield a slight turbid yellow solution. The solvent was evaporated and the residue was dissolved in 1,2-dichloro ethane. The reaction mixture was stirred at reflux for 3 h. The solvent was evaporated and the residue was purified by column chromatography (25 g silica gel, heptane/EtOAc 7:3) to yield 90 mg (65%) product as a light yellow viscous oil. MS (ISP) 463.4 (M+H)$^+$.

Example 78

Preparation of 4-Chloro-1H-indole-7-carboxylic acid (4-tert-butyl-benzyl)-[2-(4-chloro-phenyl)-ethyl]-amide 82

To a solution of 64 mg (0.33 mmol) of 4-chloro-1H-indole-7-carboxylic acid and 91 mg (0.3 mmol) of (4-tert-butyl-benzyl)-[2-(4-chloro-phenyl)-ethyl]-amine in 3 ml DCM 63 mg (0.33 mmol) of EDC.HCl were added and the reaction mixture was stirred over night at rt. The product was purified by column chromatography (25 g silica gel; heptane/EtOAc 7:3) to yield 104 mg (72%) product as a light yellow foam. MS (ISP) 479.1 (M+H)$^+$.

Example 79

Preparation of 4-Fluoro-1H-indole-7-carboxylic acid (4-tert-butyl-benzyl)-phenethyl-amide 83

To a solution of 59 mg (0.33 mmol) of 4-fluoro-1H-indole-7-carboxylic acid and 80 mg (0.3 mmol) of (4-tert-butyl-benzyl)-2-phenyl-ethyl-amine in 3 ml DCM 63 mg (0.33 mmol) of EDC.HCl were added and the reaction mixture was stirred over night at rt. The product was purified by column chromatography (20 g silica gel; heptane/EtOAc 4:1) to yield 105 mg (72%) product as a white solid. MS (ISP) 429.6 (M+H)$^+$.

Example 80

Preparation of 4-Fluoro-1H-indole-7-carboxylic acid (4-tert-butyl-benzyl)-[2-(4-fluoro-phenyl)-ethyl]-amide 84

To a solution of 59 mg (0.33 mmol) of 4-fluoro-1H-indole-7-carboxylic acid and 86 mg (0.3 mmol) of (4-tert-butyl-benzyl)-[2-(4-fluoro-phenyl)-ethyl]-amine in 3 ml DCM 63 mg (0.33 mmol) of EDC.HCl were added and the reaction mixture was stirred over night at rt. The product was purified by column chromatography (20 g silica gel; heptane/EtOAc 4:1) to yield 96 mg (72%) product as a colorless viscous oil. MS (ISP) 447.4 (M+H)$^+$.

Example 81

Preparation of 4-Fluoro-1H-indole-7-carboxylic acid (4-tert-butyl-benzyl)-[2-(4-chloro-phenyl)-ethyl]-amide 85

To a solution of 59 mg (0.33 mmol) of 4-fluoro-1H-indole-7-carboxylic acid and 91 mg (0.3 mmol) of (4-tert-butyl-benzyl)-[2-(4-chloro-phenyl)-ethyl]-amine in 3 ml DCM 63 mg (0.33 mmol) of EDC.HCl were added and the reaction mixture was stirred over night at rt. The product was purified by column chromatography (20 g silica gel; heptane/EtOAc 4:1) to yield 113 mg (81%) product as a colorless viscous oil. MS (ISP) 463.4 (M+H)$^+$.

Example 82

Preparation of 6-Fluoro-1H-indole-7-carboxylic acid (4-tert-butyl-benzyl)-[2-(4-chloro-phenyl)-ethyl]-amide 86

To a solution of 59 mg (0.33 mmol) of 6-fluoro-1H-indole-7-carboxylic acid and 91 mg (0.3 mmol) of (4-tert-butyl-benzyl)-[2-(4-chloro-phenyl)-ethyl]-amine in 3 ml DCM 63 mg (0.33 mmol) of EDC.HCl were added and the reaction mixture was stirred over night at rt. The product was purified by column chromatography (20 g silica gel; heptane/EtOAc 4:1) to yield 55 mg (40%) product as a white solid. MS (ISP) 463.4 (M+H)$^+$.

Example 83

Preparation of 6-Fluoro-1H-indole-7-carboxylic acid (4-tert-butyl-benzyl)-[2-(4-fluoro-phenyl)-ethyl]-amide 87

To a solution of 59 mg (0.33 mmol) of 6-fluoro-1H-indole-7-carboxylic acid and 86 mg (0.3 mmol) of (4-tert-butyl-benzyl)-[2-(4-fluoro-phenyl)-ethyl]-amine in 3 ml DCM 63 mg (0.33 mmol) of EDC.HCl were added and the reaction mixture was stirred over night at rt. The product was purified by column chromatography (20 g silica gel; heptane/EtOAc 4:1) to yield 51 mg (38%) product as a colorless viscous oil. MS (ISP) 447.4 (M+H)$^+$.

Example 84

Preparation of 2,3-Dihydro-1H-indole-7-carboxylic acid (4-tert-butyl-benzyl)-phenethyl-amide 88

To a solution of 310 mg (0.76 mmol) of 1H-indole-7-carboxylic acid (4-tert-butyl-benzyl)-phenethyl-amide in 5 ml acetic acid cooled to 0° C. were added in portions 142 mg (2.26 mmol) of sodium cyano borohydride. The reaction mixture was stirred for 2 h at 0° C. and 2N aqueous sodium hydroxide solution was added until the reaction mixture was basic. The reaction mixture was extracted with diethyl ether. The combined organic layers were washed with saturated aqueous sodium chloride solution, dried over sodium sulfate, filtered and the solvent was evaporated to yield 310 mg (100%) of product as a colorless oil. MS (ISP) 413.5 (M+H)$^+$.

Example 85

Preparation of 6-Fluoro-1H-indole-7-carboxylic acid (4-tert-butyl-benzyl)-phenethyl-amide 89

To a solution of 89 mg (0.5 mmol) of 6-fluoro-1H-indole-7-carboxylic acid and 134 mg (0.3 mmol) of (4-tert-butyl-benzyl)-phenethyl-amine in 5 ml DCM 105 mg (0.55 mmol) of EDC.HCl were added and the reaction mixture was stirred over night at rt. The solvent was evaporated and the residue was partitioned between diethyl ether/EtOAc and 1N aqueous HCl solution. A white solid precipitated. The reaction mixture was filtered and the organic layer was washed twice with 1N aqueous HCl solution, once with 2N aqueous NaOH solution and once with saturated aqueous NaCl solution,

Example 86

Preparation of 1H-Indole-7-carboxylic acid (4-tert-butyl-benzyl)-[2-(4-fluoro-phenoxy)-ethyl]-amide 90

To a solution of 175 mg (0.5 mmol) of 1H-indole-7-carboxylic acid (4-tert-butyl-benzyl)-(2-hydroxy-ethyl)-amide, 62 mg (0.55 mmol) of 4-fluorophenol and 144 mg (0.55 mmol) of triphenyl phosphine in 5 ml THF were added dropwise 88 μl (0.55 mmol) of azodicarboxylic acid diethyl ester at 0° C. The reaction mixture was stirred at rt over night. The solvent was evaporated and the residue was dissolved in diethyl ether. The organic layer was washed twice with 2N aqueous NaOH solution, once with saturated aqueous NaCl solution, dried over sodium sulfate, filtered and the solvent was evaporated. The residue was purified by column chromatography (silica gel; diethyl ether/heptane 1:1) to yield 100 mg (45%) product as a white solid. MS (ISP) 445.4 (M+H)$^+$.

Example 87

Preparation of 1H-Indole-7-carboxylic acid (4-tert-butyl-benzyl)-[2-(2-chloro-phenoxy)-ethyl]-amide 91

To a solution of 175 mg (0.5 mmol) of 1H-indole-7-carboxylic acid (4-tert-butyl-benzyl)-(2-hydroxy-ethyl)-amide, 71 mg (0.55 mmol) of 2-chlorophenol and 144 mg (0.55 mmol) of triphenyl phosphine in 5 ml THF were added dropwise 88 μl (0.55 mmol) of azodicarboxylic acid diethyl ester at 0° C. The reaction mixture was stirred at rt over night. The solvent was evaporated and the residue was dissolved in diethyl ether. The organic layer was washed twice with 2N aqueous NaOH solution, once with saturated aqueous NaCl solution, dried over sodium sulfate, filtered and the solvent was evaporated. The residue was purified by column chromatography (silica gel, diethyl ether/heptane 1:1) to yield 160 mg (69%) product as a white solid. MS (ISP) 461.0 (M+H)$^+$.

Example 88

Preparation of 1H-Indole-7-carboxylic acid [2-(3-bromo-phenoxy)-ethyl]-(4-tert-butyl-benzyl)-amide 92

To a solution of 175 mg (0.5 mmol) of 1H-indole-7-carboxylic acid (4-tert-butyl-benzyl)-(2-hydroxy-ethyl)-amide, 95 mg (0.55 mmol) of 3-bromophenol and 144 mg (0.55 mmol) of triphenyl phosphine in 5 ml THF were added dropwise 88 μl (0.55 mmol) of azodicarboxylic acid diethyl ester at 0° C. The reaction mixture was stirred at rt over night. The solvent was evaporated and the residue was dissolved in diethyl ether. The organic layer was washed twice with 2N aqueous NaOH solution, once with saturated aqueous NaCl solution, dried over sodium sulfate, filtered and the solvent was evaporated. The residue was purified by column chromatography (silica gel, diethyl ether/heptane 1:1) to yield 160 mg (63%) product as a white solid. MS (ISP) 505.1 (100), 507.1 (82) (M+H)$^+$.

Example 89

Preparation of 1H-Indole-7-carboxylic acid (4-tert-butyl-benzyl)-[2-(3-fluoro-phenoxy)-ethyl]-amide 93

To a solution of 175 mg (0.5 mmol) of 1H-indole-7-carboxylic acid (4-tert-butyl-benzyl)-(2-hydroxy-ethyl)-amide, 62 mg (0.55 mmol) of 3-fluorophenol and 144 mg (0.55 mmol) of triphenyl phosphine in 5 ml THF were added dropwise 88 μl (0.55 mmol) of azodicarboxylic acid diethyl ester at 0° C. The reaction mixture was stirred at rt over night. The solvent was evaporated and the residue was dissolved in diethyl ether. The organic layer was washed twice with 2N aqueous NaOH solution, once with saturated aqueous NaCl solution, dried over sodium sulfate, filtered and the solvent was evaporated. The residue was purified by column chromatography (silica gel; diethyl ether/heptane 1:1) to yield 90 mg (40%) product as a white solid. MS (ISP) 445.0 (M+H)$^+$.

Example 90

Preparation of 1H-Indole-7-carboxylic acid (4-tert-butyl-benzyl)-{2-[(4-chloro-phenyl)-methyl-amino]-ethyl}-amide 94

81 mg (0.5 mmol) of 4-tert-butyl benzaldehyde and 92 mg (0.5 mmol) of N-(4-chloro-phenyl)-N-methyl-ethane-1,2-diamine were dissolved in 2 ml methanol and the solution was stirred for 2 h at rt. 18.5 mg (0.5 mmol) of sodium borohydride were added in portions under nitrogen. The reaction mixture was stirred at rt for 30 min, the solvent was evaporated and the residue was suspended in 4 ml DCM. 88 mg (0.55 mol) of 1H-indole-7-carboxylic acid and 105 mg (0.55 mmol) of EDC.HCl were added and the mixture was stirred at rt over night. The product was purified by column chromatography (silica gel, diethyl ether) to yield 140 mg (59%) product as a colorless oil. MS (ISP) 474.4 (M+H)$^+$.

Example 91

Preparation of 1H-Indole-7-carboxylic acid (4-tert-butyl-benzyl)-(2-phenylamino-ethyl)-amide 85

81 mg (0.5 mmol) of 4-tert-butyl benzaldehyde and 68 mg (0.5 mmol) of N-phenyl ethylene diamine were dissolved in 2 ml methanol and the solution was stirred for 2 h at rt. 18.5 mg (0.5 mmol) of sodium borohydride were added in portions under nitrogen. The reaction mixture was stirred at rt for 30 min, the solvent was evaporated and the residue was suspended in 4 ml DCM. 88 mg (0.55 mol) of 1H-indole-7-carboxylic acid and 105 mg (0.55 mmol) of EDC.HCl were added and the mixture was stirred at rt over night. The product was purified by column chromatography (silica gel; diethyl ether) to yield 80 mg (37%) product as a colorless oil. MS (ISP) 426.5 (M+H)$^+$.

Example 92

Preparation of 1H-Indole-7-carboxylic acid (4-tert-butyl-benzyl)-(2-pyridin-3-yl-ethyl)-amide 96

81 mg (0.5 mmol) of 4-tert-butyl benzaldehyde and 61 mg (0.5 mmol) of 2-(3-pyridyl)-ethyl amine were dissolved in 2 ml methanol and the solution was stirred for 2 h at rt. 18.5 mg (0.5 mmol) of sodium borohydride were added in portions under nitrogen. The reaction mixture was stirred at

--- dried over sodium sulfate, filtered and the solvent was evaporated to leave 70 mg (33%) product as a colorless oil. MS (ISP) 429.4 (M+H)$^+$.

rt for 30 min, the solvent was evaporated and the residue was suspended in 4 ml DCM. 88 mg (0.55 mol) of 1H-indole-7-carboxylic acid and 105 mg (0.55 mmol) of EDC.HCl were added and the mixture was stirred at rt over night. The product was purified by column chromatography (silica gel; diethyl ether) to yield 70 mg (34%) product as a colorless oil. MS (ISP) 412.4 (M+H)$^+$.

Example 93

Preparation of 1H-Indole-7-carboxylic acid (4-tert-butyl-benzyl)-(2-pyridin-4-yl-ethyl)-amide 97

81 mg (0.5 mmol) of 4-tert-butyl benzaldehyde and 61 mg (0.5 mmol) of 2-(4-pyridyl)-ethyl amine were dissolved in 2 ml methanol and the solution was stirred for 2 h at rt. 18.5 mg (0.5 mmol) of sodium borohydride were added in portions under nitrogen. The reaction mixture was stirred at rt for 30 min, the solvent was evaporated and the residue was suspended in 4 ml DCM. 88 mg (0.55 mol) of 1H-indole-7-carboxylic acid and 105 mg (0.55 mmol) of EDC.HCl were added and the mixture was stirred at rt over night. The product was purified by column chromatography (silica gel; diethyl ether) to yield 120 mg (58%) product as a colorless oil. MS (ISP) 412.4 (M+H)$^+$.

Example 94

Preparation of 3-[(4-tert-Butyl-benzyl)-(1H-indole-7-carbonyl)-amino]-propionic acid tert-butyl ester 98

4.37 g (15 mmol) of 3-(4-tert-butyl-benzylamino)-propionic acid tert-butyl ester, 2.42 g (15 mmol) of 1H-indole-7-carboxylic acid and 3.25 g (16.5 mmol) of EDC.HCl were dissolved in 50 ml DCM. The reaction mixture was stirred at rt over night, washed twice with 1N aqueous HCl solution, once with 2N aqueous NaOH solution and once with saturated aqueous NaCl solution, dried over sodium sulfate, filtered and the solvent was evaporated to leave 6.25 g (97%) product as a white solid. MS (ISP) 435.4 (M+H)$^+$.

Example 95

Preparation of 5-Chloro-1H-indole-7-carboxylic acid (4-tert-butyl-benzyl)-(2-pyridin-4-yl-ethyl)-amide 99

268 mg (1 mmol) of (4-tert-butyl-benzyl)-(2-pyridin-4-yl-ethyl)-amine, 196 mg (1 mmol) of 5-chloro-1H-indole-7-carboxylic acid and 217 mg (1.1 mmol) of EDC.HCl were stirred over night at rt in 20 ml DCM. The product was purified by column chromatography (silica gel; EtOAc) to yield 210 mg (47%) product as a colorless oil. MS (ISP) 446.0 (M+H)$^+$.

Example 96

Preparation of 5-Chloro-1H-indole-7-carboxylic acid (4-tert-butyl-benzyl)-{2-[(4-chloro-phenyl)-methyl-amino]-ethyl}-amide 100

98 mg (0.50 mol) of 5-chloro-1H-indole-7-carboxylic acid, 165 mg (0.5 mmol) of N'-(4-tert-butyl-benzyl)-N-(4-chloro-phenyl)-N-methyl-ethane-1,2-diamine and 108 mg (0.55 mmol) of EDC.HCl were dissolved in 5 ml DCM. The reaction mixture was stirred at rt over night. The solvent was evaporated and the residue was dissolved in diethyl ether. The organic layer was washed with 1N aqueous HCl solution, once with 1N aqueous NaOH solution and once with saturated aqueous NaCl solution, dried over sodium sulfate, filtered and the solvent was evaporated to leave 140 mg (55%) product as a colorless oil. MS (ISP) 508.4 (M+H)$^+$.

Example 97

Preparation of 1H-Indole-7-carboxylic acid (4-tert-butyl-benzyl)-[2-(ethyl-m-tolyl-amino)-ethyl]-amide 101

81 mg (0.50 mol) of 1H-indole-7-carboxylic acid, 162 mg (0.5 mmol) of N'-(4-tert-butyl-benzyl)-N-ethyl-N-m-tolyl-ethane-1,2-diamine and 108 mg (0.55 mmol) of EDC.HCl were dissolved in 5 ml DCM. The reaction mixture was stirred at rt over night. The solvent was evaporated and the residue was dissolved in diethyl ether. The organic layer was washed with 1N aqueous HCl solution, once with 1N aqueous NaOH solution and once with saturated aqueous NaCl solution, dried over sodium sulfate, filtered and the solvent was evaporated to leave 140 mg (55%) product as a colorless oil. MS (ISP) 468.4 (M+H)$^+$.

Example 98

Preparation of 5-Chloro-1H-indole-7-carboxylic acid (4-tert-butyl-benzyl)-[2-(ethyl-m-tolyl-amino)-ethyl]-amide 102

97 mg (0.50 mol) of 5-chloro-1H-indole-7-carboxylic acid, 162 mg (0.5 mmol) of N'-(4-tert-butyl-benzyl)-N-ethyl-N-m-tolyl-ethane-1,2-diamine and 108 mg (0.55 mmol) of EDC.HCl were dissolved in 5 ml DCM. The reaction mixture was stirred at rt over night. The solvent was evaporated and the residue was dissolved in diethyl ether. The organic layer was washed with 1N aqueous HCl solution, once with 1N aqueous NaOH solution and once with saturated aqueous NaCl solution, dried over sodium sulfate, filtered and the solvent was evaporated to leave 150 mg (60%) product as a colorless oil. MS (ISP) 502.3 (M+H)$^+$.

Example 99

Preparation of 5-Chloro-1H-indole-7-carboxylic acid (4-tert-butyl-benzyl)-(2-phenylamino-ethyl)-amide 103

489 mg (2.5 mol) of 5-chloro-1H-indole-7-carboxylic acid, 706 mg (2.5 mmol) of N-(4-tert-butyl-benzyl)-N'-phenyl-ethane-1,2-diamine and 541 mg (2.75 mmol) of EDC.HCl were dissolved in 20 ml DCM. The reaction mixture was stirred at rt over night. The solvent was evaporated and the residue was dissolved in diethyl ether. The organic layer was washed with 1N aqueous HCl solution, once with 1N aqueous NaOH solution and once with saturated aqueous NaCl solution, dried over sodium sulfate, filtered and the solvent was evaporated. The residue was purified by column chromatography (silica gel; diethyl ether/heptane 1:1) to yield 460 mg (40%) product as a white solid. MS (ISP) 460.3 (M+H)$^+$.

Example 100

Preparation of 5-Chloro-1H-indazole-7-carboxylic acid (4-tert-butyl-benzyl)-[2-(3,4-dichloro-phenyl)-ethyl]-amide 104

130 mg (0.66 mol) of 5-chloro-1H-indazole-7-carboxylic acid, 244 mg (0.73 mmol) of (4-tert-butyl-benzyl)-[2-(3,4-dichloro-phenyl)-ethyl]-amine and 143 mg (0.73 mmol) of EDC.HCl were dissolved in 20 ml DCM. The reaction mixture was stirred at rt over night. The solvent was evaporated and the residue was dissolved in EtOAc. The organic layer was washed with 1N aqueous HCl solution, once with 1N aqueous NaOH solution and once with saturated aqueous NaCl solution, dried over sodium sulfate, filtered and the solvent was evaporated to yield 150 mg (44%) product as a white solid. MS (ISP) 516.2 (100), 514.1 (100), 518.2 (48) $(M+H)^+$.

Example 101

Preparation of 5-Fluoro-1H-indole-7-carboxylic acid (4-tert-butyl-benzyl)-phenethyl-amide 105

66 mg (0.33 mol) of 5-fluoro-1H-indol-7-carboxylic acid, 80 mg (0.30 mmol) of (4-tert-butyl-benzyl)-2-phenyl-ethyl-amine and 63 mg (0.33 mmol) of EDC.HCl were dissolved in 3 ml DCM. The reaction mixture was stirred at rt over night. The solvent was evaporated and the residue was purified by column chromatography (20 g silica gel; heptane/EtOAc 7:3) to yield 85 mg (66%) product as a light yellow viscous oil. MS (ISP) 429.4 $(M+H)^+$.

Example 102

Preparation of 5-Fluoro-1H-indole-7-carboxylic acid (4-tert-butyl-benzyl)-[2-(4-fluoro-phenyl)-ethyl]-amide 106

66 mg (0.33 mol) of 5-fluoro-1H-indol-7-carboxylic acid, 86 mg (0.30 mmol) of (4-tert-butyl-benzyl)-[2-(4-fluoro-phenyl)-ethyl]-amine and 63 mg (0.33 mmol) of EDC.HCl were dissolved in 3 ml DCM. The reaction mixture was stirred at rt over night. The solvent was evaporated and the residue was purified by column chromatography (20 g silica gel; heptane/EtOAc 7:3) to yield 98 mg (73%) product as a light yellow viscous oil. MS (ISP) 447.2 $(M+H)^+$.

Example 103

Preparation of 5-Fluoro-1H-indole-7-carboxylic acid (4-tert-butyl-benzyl)-[2-(4-chloro-phenyl)-ethyl]-amide 107

66 mg (0.33 mol) of 5-fluoro-1H-indol-7-carboxylic acid, 91 mg (0.30 mmol) of (4-tert-butyl-benzyl)-[2-(4-chloro-phenyl)-ethyl]-amine and 63 mg (0.33 mmol) of EDC.HCl were dissolved in 3 ml DCM. The reaction mixture was stirred at rt over night. The solvent was evaporated and the residue was purified by column chromatography (20 g silica gel; heptane/EtOAc 7:3) to yield 100 mg (72%) product as a light yellow viscous oil. MS (ISP) 463.3 $(M+H)^+$.

Example 104

Preparation of 5-Fluoro-1H-indole-7-carboxylic acid (4-tert-butyl-benzyl)-[2-(3-trifluoromethyl-phenyl)-ethyl]-amide 108

66 mg (0.33 mol) of 5-fluoro-1H-indol-7-carboxylic acid, 101 mg (0.30 mmol) of (4-tert-butyl-benzyl)-[2-(3-trifluoromethyl-phenyl)-ethyl]-amine and 63 mg (0.33 mmol) of EDC.HCl were dissolved in 3 ml DCM. The reaction mixture was stirred at rt over night. The solvent was evaporated and the residue was purified by column chromatography (20 g silica gel, heptane/EtOAc 7:3) to yield 118 mg (79%) product as a light yellow viscous oil. MS (ISP) 497.4 $(M+H)^+$.

Example 105

Preparation of [rac]-5-Chloro-1H-indole-7-carboxylic acid (4-tert-butyl-benzyl)-[3-(5-methyl-furan-2-yl)-butyl]-amide 109

65 mg (0.33 mol) of 5-chloro-1H-indol-7-carboxylic acid, 89 mg (0.30 mmol) of [rac]-(4-tert-butyl-benzyl)-(3-furan-2-yl-butyl)-amine and 63 mg (0.33 mmol) of EDC.HCl were dissolved in 3 ml DCM. The reaction mixture was stirred at rt over night. The solvent was evaporated and the residue was purified by column chromatography (20 g silica gel, heptane/EtOAc 4:1) to yield 94 mg (66%) product as a colorless viscous oil. MS (ISP) 477.2 $(M+H)^+$.

Example 106

Preparation of 6-Fluoro-1H-indole-7-carboxylic acid (4-tert-butyl-benzyl)-[2-(3,4-dichloro-phenyl)-ethyl]-amide 110

98 mg (0.55 mol) of 6-fluoro-1H-indol-7-carboxylic acid, 168 mg (0.50 mmol) of (4-tert-butyl-benzyl)-[2-(3,4-dichloro-phenyl)-ethyl]-amine and 105 mg (0.55 mmol) of EDC.HCl were dissolved in 5 ml 1,2-dichloro-ethane. The reaction mixture was stirred at rt over night and heated to 80° C. for 3 h. The solvent was evaporated and the residue was purified by column chromatography (20 g silica gel; heptane/EtOAc 4:1) to yield 108 mg (43%) product as a colorless viscous oil. MS (ISP) 497.2 $(M+H)^+$.

Example 107

Preparation of 4-Fluoro-1H-indole-7-carboxylic acid (4-tert-butyl-benzyl)-[2-(3-trifluoromethyl-phenyl)-ethyl]-amide 111

59 mg (0.33 mol) 4-fluoro-1H-indol-7-carboxylic acid, 101 mg (0.30 mmol) of (4-tert-butyl-benzyl)-[2-(3-trifluoromethyl-phenyl)-ethyl]-amine and 63 mg (0.33 mmol) of EDC.HCl were dissolved in 3 ml DCM. The reaction mixture was stirred at rt over night. The solvent was evaporated and the residue was purified by column chromatography (20 g silica gel; heptane/EtOAc 4:1) to yield 120 mg (81%) product as a colorless viscous oil. MS (ISP) 497.3 $(M+H)^+$.

Example 108

Preparation of 4-Fluoro-1H-indole-7-carboxylic acid (4-tert-butyl-benzyl)-[2-(3,4-dichloro-phenyl)-ethyl]-amide 112

59 mg (0.33 mol) of 4-fluoro-1H-indol-7-carboxylic acid, 101 mg (0.30 mmol) of (4-tert-butyl-benzyl)-[2-(3,4-dichloro-phenyl)-ethyl]-amine and 63 mg (0.33 mmol) of EDC.HCl were dissolved in 3 ml DCM. The reaction mixture was stirred at rt over night. The solvent was evaporated and the residue was purified by column chromatography (20 g silica gel; heptane/EtOAc 4:1) to yield 120 mg (81%) product as a colorless viscous oil. MS (ISP) 497.2 (81) 499.1 (49) $(M+H)^+$.

Example 109

Preparation of 1H-Indole-7-carboxylic acid (4-tert-butyl-benzyl)-[2-(3-trifluoromethyl-phenoxy)-ethyl]-amide 113

To a solution of 175 mg (0.5 mmol) of 1H-indole-7-carboxylic acid (4-tert-butyl-benzyl)-(2-hydroxy-ethyl)-amide, 91 mg (0.55 mmol) of 3-hydroxy-benzotrifluoride and 144 mg (0.55 mmol) of triphenyl phosphine in 5 ml THF were added dropwise 88 µl (0.55 mmol) azodicarboxylic acid diethyl ester at 0° C. The reaction mixture was stirred at rt over night. The solvent was evaporated and the residue purified by column chromatography (20 g silica gel, diethyl ether/heptane 1:1) to yield 182 mg (74%) product as a white solid. MS (ISP) 495.5 $(M+H)^+$.

Example 110

Preparation of 5-Fluoro-1H-indole-7-carboxylic acid (4-tert-butyl-benzyl)-[2-(3,4-dichloro-phenyl)-ethyl]-amide 114

66 mg (0.33 mol) of 5-fluoro-1H-indol-7-carboxylic acid, 101 mg (0.30 mmol) of (4-tert-butyl-benzyl)-[2-(3,4-dichloro-phenyl)-ethyl]-amine and 63 mg (0.33 mmol) of EDC.HCl were dissolved in 3 ml DCM. The reaction mixture was stirred at rt over night. The solvent was evaporated and the residue was purified by column chromatography (20 g silica gel; heptane/EtOAc 7:3) to yield 95 mg (64%) product as a white solid. MS (ISP) 497.3 (100), 499.4 (55) $(M+H)^+$.

Example 111

Preparation of 1H-Indole-7-carboxylic acid (4-tert-butyl-benzyl)-[2-(2-trifluoromethyl-phenoxy)-ethyl]-amide 115

To a solution of 175 mg (0.5 mmol) of 1H-indole-7-carboxylic acid (4-tert-butyl-benzyl)-(2-hydroxy-ethyl)-amide, 91 mg (0.55 mmol) of 2-hydroxy-benzotrifluoride and 144 mg (0.55 mmol) of triphenyl phosphine in 5 ml THF were added dropwise 88 µl (0.55 mmol) azodicarboxylic acid diethyl ester at 0° C. The reaction mixture was stirred at rt over night. The solvent was evaporated and the residue purified by column chromatography (50 g silica gel; diethyl ether/heptane 1:1) to yield 172 mg (70%) product as a white solid. MS (ISP) 495.5 $(M+H)^+$.

Example 112

Preparation of 5,6-Difluoro-1H-indole-7-carboxylic acid (4-tert-butyl-benzyl)-[2-(4-chloro-phenyl)-ethyl]-amide 116

87 mg (0.44 mol) of 5,6-difluoro-1H-indol-7-carboxylic acid, 121 mg (0.40 mmol) of (4-tert-butyl-benzyl)-[2-(4-chloro-phenyl)-ethyl]-amine and 84 mg (0.44 mmol) of EDC.HCl were dissolved in 4 ml DCM. The reaction mixture was stirred at rt over night. The solvent was evaporated and the residue was purified by column chromatography (20 g silica gel; heptane/EtOAc 4:1) to yield 65 mg (34%) product as a white solid. MS (ISP) 481.2 (100), 483.2 (30) $(M+H)^+$.

Example 113

Preparation of 5,6-Difluoro-1H-indole-7-carboxylic acid (4-tert-butyl-benzyl)-[2-(3,4-dichloro-phenyl)-ethyl]-amide 117

87 mg (0.44 mol) of 5,6-difluoro-1H-indol-7-carboxylic acid, 134 mg (0.40 mmol) of (4-tert-butyl-benzyl)-[2-(3,4-dichloro-phenyl)-ethyl]-amine and 84 mg (0.44 mmol) of EDC.HCl were dissolved in 4 ml DCM. The reaction mixture was stirred at rt over night. The solvent was evaporated and the residue was purified by column chromatography (20 g silica gel; heptane/EtOAc 4:1) to yield 73 mg (35%) product as a light yellow viscous oil. MS (ISP) 515.2 (100), 517.3 (55) $(M+H)^+$.

Example 114

Preparation of 5,6-Difluoro-1H-indole-7-carboxylic acid (4-tert-butyl-benzyl)-phenethyl-amide 118

87 mg (0.44 mol) of 5,6-difluoro-1H-indol-7-carboxylic acid, 106 mg (0.40 mmol) of (4-tert-butyl-benzyl)-[2-phenyl-ethyl]-amine and 84 mg (0.44 mmol) of EDC.HCl were dissolved in 4 ml DCM. The reaction mixture was stirred at rt over night. The solvent was evaporated and the residue was purified by column chromatography (20 g silica gel; heptane/EtOAc 4:1) to yield 59 mg (33%) product as a colorless viscous oil. MS (ISP) 447.2 $(M+H)^+$.

Example 115

Preparation of 5,6-Difluoro-1H-indole-7-carboxylic acid (4-tert-butyl-benzyl)-[2-(3-trifluoromethyl-phenyl)-ethyl]-amide 119

87 mg (0.44 mol) of 5,6-difluoro-1H-indol-7-carboxylic acid, 134 mg (0.40 mmol) of (4-tert-butyl-benzyl)-[2-(3-trifluoromethyl-phenyl)-ethyl]-amine and 84 mg (0.44 mmol) of EDC.HCl were dissolved in 4 ml DCM. The reaction mixture was stirred at rt over night. The solvent was evaporated and the residue was purified by column chromatography (20 g silica gel; heptane/EtOAc 4:1) to yield 78 mg (38%) product as a colorless viscous oil. MS (ISP) 515.3 $(M+H)^+$.

Example 116

Preparation of 5,6-Difluoro-1H-indole-7-carboxylic acid (4-tert-butyl-benzyl)-(2-p-tolyl-ethyl)-amide 120

87 mg (0.44 mol) of 5,6-difluoro-1H-indol-7-carboxylic acid, 113 mg (0.40 mmol) of (4-tert-butyl-benzyl)-[2-(4-methyl-phenyl)-ethyl]-amine and 84 mg (0.44 mmol) of EDC.HCl were dissolved in 4 ml DCM. The reaction mixture was stirred at rt over night. The solvent was evaporated and the residue was purified by column chromatography (20 g silica gel; heptane/EtOAc 4:1) to yield 69 mg (38%) product as a colorless viscous oil. MS (ISP) 461.3 $(M+H)^+$.

Example 117

Preparation of 5,6-Difluoro-1H-indole-7-carboxylic acid (4-tert-butyl-benzyl)-[2-(3-chloro-phenyl)-ethyl]-amide 121

87 mg (0.44 mol) of 5,6-difluoro-1H-indol-7-carboxylic acid, 121 mg (0.40 mmol) of (4-tert-butyl-benzyl)-[2-(3-chloro-phenyl)-ethyl]-amine and 84 mg (0.44 mmol) of EDC.HCl were dissolved in 4 ml DCM. The reaction mixture was stirred at rt over night. The solvent was evaporated and the residue was purified by column chromatography (20 g silica gel; heptane/EtOAc 4:1) to yield 74 mg (39%) of the product as a colorless viscous oil. MS (ISP) 481.2 (100), 483.2 (50) $(M+H)^+$.

Example 118

Preparation of 5-Chloro-6-fluoro-1H-indole-7-carboxylic acid (4-tert-butyl-benzyl)-[2-(3,4-dichloro-phenyl)-ethyl]-amide 122

121 mg (0.566 mol) of 5-chloro-6-fluoro-1H-indol-7-carboxylic acid and 86 mg (0.57 mmol) of HOBT were stirred in 3 ml 1,2-dichloroethane for 30 min at rt. 168 mg (0.57 mmol) of (4-tert-butyl-benzyl)-[2-(3,4-dichloro-phenyl)-ethyl]-amine dissolved in 2 ml 1,2-dichloroethane and 108 mg (0.57 mmol) of EDC.HCl were added and the reaction mixture was stirred at rt over night. The solvent was evaporated and the residue was purified by column chromatography (45 g silica gel; heptane/EtOAc 4:1) to yield 227 mg (85%) product as a colorless foam. MS (ISP) 531.3 (90), 533.4 (100), 536.4 (30) $(M+H)^+$.

Example 119

Preparation of 1H-Indole-7-carboxylic acid (4-tert-butyl-2-methoxy-benzyl)-[2-(4-fluoro-phenyl)-ethyl]-amide 123

133 mg (0.3 mmol) of 1H-indole-7-carboxylic acid (4-tert-butyl-2-hydroxy-benzyl)-[2-(4-fluoro-phenyl)-ethyl]-amide, 64 mg (0.45 mmol) of methyl iodide and 83 mg (0.6 mmol) of potassium carbonate were heated in 3 ml acetonitrile for 2 h to 60° C. Additional 32 mg (0.22 mmol) of methyl iodide were added and the reaction mixture was heated to 60° C. over night. The reaction mixture was filtered and the solvent was evaporated. The residue was purified by column chromatography (20 g silica gel; DCM/diethyl ether 10:1) to yield 54 mg (39%) product as a colorless gum. MS (ISP) 459.6 $(M+H)^+$.

Example 120

Preparation of 5-Chloro-1H-indole-7-carboxylic acid [2-(4-fluoro-phenyl)-ethyl]-(4-trifluoromethyl-benzyl)-amide 124

121 mg (1.2 mmol) of N-methyl morpholine and then 227 mg (0.6 mmol) of HBTU were added to 78 mg (0.40 mmol) of 5-chloro-1H-indol-7-carboxylic acid and 142 mg (0.48 mmol) of [2-(4-fluoro-phenyl)-ethyl]-(4-trifluoromethyl-benzyl)-amine dissolved in 4 ml DMF at rt under nitrogen. The reaction mixture was stirred at rt over night. Water was added and the reaction mixture was extracted twice with EtOAc. The combined organic layers were washed once with 1N aqueous HCl solution, once with saturated aqueous $NaHCO_3$ solution and once with saturated aqueous NaCl. Solution, dried over sodium sulfate, filtered and the solvent was evaporated. The residue was purified by column chromatography (20 g silica gel; heptane/EtOAc 7:3) to yield 178 mg (94%) product as a yellow viscous oil. MS (ISP) 475.1 $(M+H)^+$.

Example 121

Preparation of 5-Chloro-1H-indole-7-carboxylic acid (4-tert-butyl-2-chloro-benzyl)-[2-(4-fluoro-phenyl)-ethyl]-amide 125

106 mg (1.05 mmol) of N-methyl morpholine and then 199 mg (0.53 mmol) of HBTU were added to 68 mg (0.35 mol) of 5-chloro-1H-indol-7-carboxylic acid and 136 mg (0.39 mmol) of (4-tert-butyl-2-chloro-benzyl)-[2-(4-fluoro-phenyl)-ethyl]-amine dissolved in 3.5 ml DMF at rt under nitrogen. The reaction mixture was stirred at rt for 3 h. Water was added and the reaction mixture was extracted twice with EtOAc. The combined organic layers were washed once with 1N aqueous HCl solution, once with saturated aqueous $NaHCO_3$ solution and once with saturated aqueous NaCl solution, dried over sodium sulfate, filtered and the solvent was evaporated. The residue was purified by column chromatography (20 g silica gel, heptane/EtOAc 7:3) to yield 160 mg (92%) product as a light yellow foam. MS (EI) 496.1 $(M)^+$.

Example 122

Preparation of 5-Chloro-1H-indole-7-carboxylic acid (4-tert-butyl-2-chloro-benzyl)-[2-(3-trifluoromethyl-phenyl)-ethyl]-amide 126

91 mg (0.9 mmol) of N-methyl morpholine and then 170 mg (0.45 mmol) of HBTU were added to 59 mg (0.30 mol) of 5-chloro-1H-indol-7-carboxylic acid and 122 mg (0.33 mmol) of (4-tert-butyl-2-chloro-benzyl)-[2-(3-trifluoromethyl-phenyl)-ethyl]-amine dissolved in 3 ml DMF at rt under nitrogen. The reaction mixture was stirred at rt over night. Water was added and the reaction mixture was extracted twice with EtOAc. The combined organic layers were washed once with 1N aqueous HCl solution, once with saturated aqueous $NaHCO_3$ solution and once with saturated aqueous NaCl solution, dried over sodium sulfate, filtered and the solvent was evaporated. The residue was purified by column chromatography (20 g silica gel; heptane/EtOAc 4:1) to yield 150 mg (91%) product as a yellow viscous oil. MS (ISP) 547.3 $(M+H)^+$.

Example 123

Preparation of 5-Chloro-6-fluoro-1H-indole-7-carboxylic acid (4-tert-butyl-2-chloro-benzyl)-[2-(3-trifluoromethyl-phenyl)-ethyl]-amide 127

91 mg (0.9 mmol) of N-methyl morpholine and then 170 mg (0.45 mmol) of HBTU were added to 64 mg (0.30 mol) of 5-chloro-6-fluoro-1H-indol-7-carboxylic acid and 122 mg (0.33 mmol) of (4-tert-butyl-2-chloro-benzyl)-[2-(3-trifluoromethyl-phenyl)-ethyl]-amine dissolved in 3 ml DMF at rt under nitrogen. The reaction mixture was stirred at rt over night. Water was added and the reaction mixture was extracted twice with EtOAc. The combined organic layers were washed once with 1N aqueous HCl solution, once with saturated aqueous NaHCO$_3$ solution and once with saturated aqueous NaCl solution, dried over sodium sulfate, filtered and the solvent was evaporated. The residue was purified by column chromatography (20 g silica gel; heptane/EtOAc 4:1) to yield 146 mg (86%) product as a yellow viscous oil. MS (ISP) 565.4 (80), 567.3 (50) (M+H)$^+$, 582.2 (100), 584.3 (80) (M+NH$_4$)$^+$.

Example 124

Preparation of 5-Chloro-1H-indole-7-carboxylic acid (4-tert-butyl-2-chloro-benzyl)-[2-(3-trifluoromethoxy-phenyl)-ethyl]-amide 128

47 mg (0.47 mmol) of N-methyl morpholine and then 88 mg (0.23 mmol) of HBTU were added to 30 mg (0.16 mol) of 5-chloro-1H-indol-7-carboxylic acid and 60 mg (0.16 mmol) of (4-tert-butyl-2-chloro-benzyl)-[2-(3-trifluoromethoxy-phenyl)-ethyl]-amine dissolved in 1.6 ml DMF at rt under nitrogen. The reaction mixture was stirred at rt over night. Water was added and the reaction mixture was extracted twice with EtOAc. The combined organic layers were washed once with 1N aqueous HCl solution, once with saturated aqueous NaHCO$_3$ solution and once with saturated aqueous NaCl solution, dried over sodium sulfate, filtered and the solvent was evaporated. The residue was purified by column chromatography (20 g silica gel, heptane/EtOAc 7:3) to yield 75 mg (86%) product as a colorless viscous oil. MS (ISP) 563.0 (100), 565.1 (71) (M+H)$^+$.

Example 125

Preparation of 5-Chloro-6-fluoro-1H-indole-7-carboxylic acid (4-tert-butyl-2-chloro-benzyl)-[2-(3,4-dichloro-phenyl)-ethyl]-amide 129

91 mg (0.9 mmol) of N-methyl morpholine and then 170 mg (0.45 mmol) of HBTU were added to 64 mg (0.30 mol) of 5-chloro-6-fluoro-1H-indol-7-carboxylic acid and 111 mg (0.30 mmol) of (4-tert-butyl-2-chloro-benzyl)-[2-(3,4-dichloro-phenyl)-ethyl]-amine dissolved in 3 ml DMF at rt under nitrogen. The reaction mixture was stirred at rt over night. Water was added and the reaction mixture was extracted twice with EtOAc. The combined organic layers were washed once with 1N aqueous HCl solution, once with saturated aqueous NaHCO$_3$ solution and once with saturated aqueous NaCl solution, dried over sodium sulfate, filtered and the solvent was evaporated. The residue was purified by column chromatography (20 g silica gel; heptane/EtOAc 7:3) to yield 120 mg (71%) product as a yellow viscous oil. MS (ISP) 567.1 (100), 565.2 (96), 569.1 (66) (M+H)$^+$, 584.1 (64), 582.1 (43), 586.2 (31) (M+NH4)$^+$.

Example 126

Preparation of 5-Chloro-1H-indole-7-carboxylic acid (4-tert-butyl-2-chloro-benzyl)-[2-(3,4-dichloro-phenyl)-ethyl]-amide 130

91 mg (0.9 mmol) of N-methyl morpholine and then 170 mg (0.45 mmol) of HBTU were added to 59 mg (0.30 mol) of 5-chloro-1H-indol-7-carboxylic acid and 111 mg (0.30 mmol) of (4-tert-butyl-2-chloro-benzyl)-[2-(3,4-dichloro-phenyl)-ethyl]-amine dissolved in 3 ml DMF at rt under nitrogen. The reaction mixture was stirred at rt over night. Water was added and the reaction mixture was extracted twice with EtOAc. The combined organic layers were washed once with 1N aqueous HCl solution, once with saturated aqueous NaHCO$_3$ solution and once with saturated aqueous NaCl solution, dried over sodium sulfate, filtered and the solvent was evaporated. The residue was purified by column chromatography (20 g silica gel; heptane/EtOAc 7:3) to yield 120 mg (73%) product as a light yellow viscous oil. MS (ISP) 549.1 (100), 547.2 (100), 551.0 (47) (M+H)$^+$, 566.2 (31), 564.2 (29), 568.1 (19) (M+NH$_4$)$^+$.

Example 127

5-Chloro-1H-indole-7-carboxylic acid (4-tert-butyl-2-fluoro-benzyl)-[2-(3-trifluoromethyl-phenyl)-ethyl]-amide 131

152 mg (1.5 mmol) of N-methyl morpholine and then 284 mg (0.75 mmol) of HBTU were added to 98 mg (0.50 mol) of 5-chloro-1H-indol-7-carboxylic acid and 194 mg (0.55 mmol) of (4-tert-butyl-2-fluoro-benzyl)-[2-(3-trifluoromethyl-phenyl)-ethyl]-amine dissolved in 5 ml DMF at rt under nitrogen. The reaction mixture was stirred at rt over night. Water was added and the reaction mixture was extracted twice with EtOAc. The combined organic layers were washed once with 1N aqueous HCl solution, once with saturated aqueous NaHCO$_3$ solution and once with saturated aqueous NaCl solution, dried over sodium sulfate, filtered and the solvent was evaporated. The residue was purified by column chromatography (20 g silica gel, heptane/EtOAc 7:3) to yield 196 mg (74%) product as a light yellow viscous oil. MS (ISP) 531.0 (100), 532.9 (33) (M+H)$^+$.

Example 128

5-Chloro-6-fluoro-1H-indole-7-carboxylic acid (4-tert-butyl-2-fluoro-benzyl)-[2-(3-trifluoromethyl-phenyl)-ethyl]-amide 132

152 mg (1.5 mmol) of N-methyl morpholine and then 284 mg (0.75 mmol) of HBTU were added to 107 mg (0.50 mol) of 5-chloro-6-fluoro-1H-indol-7-carboxylic acid and 194 mg (0.55 mmol) of (4-tert-butyl-2-fluoro-benzyl)-[2-(3-trifluoromethyl-phenyl)-ethyl]-amine dissolved in 5 ml DMF at rt under nitrogen. The reaction mixture was stirred at rt over night. Water was added and the reaction mixture was extracted twice with EtOAc. The combined organic layers were washed once with 1N aqueous HCl solution, once with saturated aqueous NaHCO$_3$ solution and once with saturated aqueous NaCl solution, dried over sodium sulfate, filtered and the solvent was evaporated. The residue was purified by column chromatography (20 g silica gel; heptane/EtOAc 7:3) to yield 228 mg (83%) product as a yellow viscous oil. MS (ISP) 549.1 (100), 550.2 (40), 551.2 (38) (M+H)$^+$.

Example 129

5-Chloro-1H-indole-7-carboxylic acid (4-tert-butyl-benzyl)-phenethyl-amide 133

130 mg (0.5 mmol) of (4-tert-butyl-benzyl)-phenethyl-amine, 97 mg (0.5 mmol) of 5-chloro-1H-indole-7-carboxylic acid and 115 mg (0.6 mmol) of EDC.HCl were stirred over night at rt in 10 ml DCM. The product was purified by column chromatography (20 silica gel; DCM) to yield 130 mg (62%) product as a colorless oil. MS (ISP) 445.4 (100), 447.4 (30) (M+H)$^+$.

Example 130

5-Chloro-1H-indole-7-carboxylic acid (4-tert-butyl-benzyl)-[2-(4-fluoro-phenyl)-ethyl]-amide 134

140 mg (0.5 mmol) of (4-tert-butyl-benzyl)-[2-(4-fluoro-phenyl)-ethyl]-amine, 97 mg (0.5 mmol) of 5-chloro-1H-indole-7-carboxylic acid and 115 mg (0.6 mmol) of EDC.HCl were stirred over night at rt in 10 ml DCM. The product was purified by column chromatography (20 silica gel; DCM) to yield 140 mg (64%) product as a colorless oil. MS (EI) 462.2 (27), 463.2 (14), 464.2 (12) (M)$^+$.

Example 131

5-Chloro-1H-indole-7-carboxylic acid (4-tert-butyl-benzyl)-[2-(3,4-dichloro-phenyl)-ethyl]-amide 135

168 mg (0.5 mmol) of (4-tert-butyl-benzyl)-[2-(3,4-dichloro-phenyl)-ethyl]-amine, 97 mg (0.5 mmol) of 5-chloro-1H-indole-7-carboxylic acid and 115 mg (0.6 mmol) of EDC.HCl were stirred over night at rt in 10 ml DCM. The product was purified by column chromatography (20 silica gel; DCM) to yield 190 mg (76%) product as a colorless oil. MS (ISP) 513.4 (100), 515.4 (90), 517.3 (25) (M+H)$^+$, 530.4 (30), 532.4 (28) 534.4 (5) (M+NH$_4$)$^+$.

Example 132

5-Chloro-1H-indole-7-carboxylic acid (4-tert-butyl-benzyl)-[2-(3-trifluoromethyl-phenyl)-ethyl]-amide 136

167 mg (0.5 mmol) of (4-tert-butyl-benzyl)-[2-(3-trifluoromethyl-phenyl)-ethyl]-amine, 97 mg (0.5 mmol) of 5-chloro-1H-indole-7-carboxylic acid and 115 mg (0.6 mmol) of EDC.HCl were stirred over night at rt in 10 ml DCM. The product was purified by column chromatography (20 silica gel; DCM) to yield 160 mg (64%) product as a white solid. MS (EI) 512.2 (60), 514.2 (25) (M)$^+$.

Example 133

5-Chloro-1H-indole-7-carboxylic acid (4-tert-butyl-benzyl)-(2-p-tolyl-ethyl)-amide 137

140 mg (0.5 mmol) of (4-tert-butyl-benzyl)-[2-(4-methyl-phenyl)-ethyl]-amine, 97 mg (0.5 mmol) of 5-chloro-1H-indole-7-carboxylic acid and 115 mg (0.6 mmol) of EDC.HCl were stirred over night at rt in 10 ml DCM. The product was purified by column chromatography (20 silica gel; DCM) to yield 160 mg (73%) product as a colorless oil. MS (ISP) 459.6 (100), 460.5 (30), 461.5 (28), 462.5 (15) (M+H)$^+$.

Example 134

5-Chloro-1H-indole-7-carboxylic acid (4-tert-butyl-benzyl)-[2-(3-chloro-phenyl)-ethyl]-amide 138

150 mg (0.5 mmol) of (4-tert-butyl-benzyl)-[2-(3-chloro-phenyl)-ethyl]-amine, 97 mg (0.5 mmol) of 5-chloro-1H-indole-7-carboxylic acid and 115 mg (0.6 mmol) of EDC.HCl were stirred over night at rt in 10 ml DCM. The product was purified by column chromatography (20 silica gel; DCM) to yield 160 mg (70%) product as a colorless oil. MS (ISP) 479.5 (100), 480.5 (40), 481.4 (50), 482.5 (15) (M+H)$^+$.

Example 135

5-Chloro-1H-indazole-7-carboxylic acid (4-tert-butyl-benzyl)-[2-(4-fluoro-phenyl)-ethyl]-amide 139

142 mg (0.5 mmol) of (4-tert-butyl-benzyl)-[2-(4-fluoro-phenyl)-ethyl]-amine, 97 mg (0.5 mmol) of 5-chloro-1H-indazole-7-carboxylic acid and 115 mg (0.6 mmol) of EDC.HCl were stirred for 4 h at rt in 5 ml DCM and 4 ml THF. The product was purified by column chromatography (20 silica gel; DCM/EtOAc 1:1) to yield 170 mg (74%) product as an orange oil. MS (ISP) 462.2 (100), 464.2 (35) (M+H)$^+$.

Example 136

5-Chloro-1H-indazole-7-carboxylic acid (4-tert-butyl-benzyl)-[2-(3-trifluoromethyl-phenyl)-ethyl]-amide 140

167 mg (0.5 mmol) of (4-tert-butyl-benzyl)-[2-(3-trifluoromethyl-phenyl)-ethyl]-amine, 97 mg (0.5 mmol) of 5-chloro-1H-indazole-7-carboxylic acid and 115 mg (0.6 mmol) of EDC.HCl were stirred for 4 h at rt in 5 ml DCM and 4 ml THF. The product was purified by column chromatography (20 silica gel; EtOAc) to yield 200 mg (80%) product as an orange oil. MS (ISP) 514.5 (100), 515.4 (28), 516.4 (30), 517.3 (10) (M+H)$^+$, 536.5 (20), 538.4 (10) (M+Na)$^+$.

Example 137

5-Chloro-1H-indazole-7-carboxylic acid (4-tert-butyl-benzyl)-(2-p-tolyl-ethyl)-amide 141

140 mg (0.5 mmol) of (4-tert-butyl-benzyl)-[2-(4-methyl-phenyl)-ethyl]-amine, 97 mg (0.5 mmol) of 5-chloro-1H-indazole-7-carboxylic acid and 115 mg (0.6 mmol) of EDC.HCl were stirred for 4 h at rt in 5 ml DCM and 4 ml THF. The product was purified by column chromatography (20 silica gel; EtOAc) to yield 170 mg (77%) product as an orange oil. MS (ISP) 460.5 (100), 461.4 (20), 462.3 (40), 463.5 (10) (M+H)$^+$.

Example 138

5-Chloro-1H-indazole-7-carboxylic acid (4-tert-butyl-benzyl)-(2-p-tolyl-ethyl)-amide 142

150 mg (0.5 mmol) of (4-tert-butyl-benzyl)-[2-(4-chloro-phenyl)-ethyl]-amine, 97 mg (0.5 mmol) of 5-chloro-1H-indazole-7-carboxylic acid and 115 mg (0.6 mmol) of EDC.HCl were stirred for 4 h at rt in 5 ml DCM and 4 ml THF. The product was purified by column chromatography (20 silica gel; EtOAc) to yield 170 mg (74%) product as an orange oil. MS (ISP) 480.2 (100), 482.3 (55), 481.4 (37), 483.3 (10) (M+H)$^+$.

Example 139

5-Methyl-1H-indole-7-carboxylic acid [2-(3,4-dichloro-phenyl)-ethyl]-[4-(2,2,2-trifluoro-1-methoxy-1-trifluoromethyl-ethyl)-benzyl]-amide 178

This compound was prepared in analogy to example 1 from 50 mg of 5-methyl-1H-indole-7-carboxylic acid (0.29 mmol) and 127 mg (0.29 mmol) of [2-(3,4-dichloro-phenyl)-ethyl]-[4-(2,2,2-trifluoro-1-hydroxy-1-trifluoromethyl-ethyl)-benzyl]-amine. After final purification (silica gel; heptane/EtOAc 70:30 to 50:50) 152 mg (88%) of the intermediate 5-methyl-1H-indole-7-carboxylic acid [2-(3,4-dichloro-phenyl)-ethyl]-[4-(2,2,2-trifluoro-1-hydroxy-1-trifluoromethyl-ethyl)-benzyl]-amide were isolated as a white foam. MS (ISP) 603.1 (M+H)$^+$.

20 mg of 5-methyl-1H-indole-7-carboxylic acid [2-(3,4-dichloro-phenyl)-ethyl]-[4-(2,2,2-trifluoro-1-hydroxy-1-trifluoromethyl-ethyl)-benzyl]-amide (0.03 mmol) were dissolved in 5 ml DMF and potassium carbonate (9 mg, 0.07 mmol) and methyl iodide (3 µl, 0.05 mmol) were added. The reaction mixture was stirred over night at rt, then saturated ammonium chloride solution was added and the mixture was extracted twice with EtOAc. The combined organic extracts were washed with water and brine, dried with magnesium sulfate, filtrated and concentrated. The remaining residue was purified by silica gel filtration (hexane/EtOAc 1:1). This gave 20 mg (98%) of the title compound as a white foam. MS (ISP) 617.2 (M+H)$^+$.

Example 140

Preparation of 4-Fluoro-5-methyl-1H-indole-7-carboxylic acid (4-tert-butyl-benzyl)-[2-(4-fluoro-phenyl)-ethyl]-amide 210 and Other Compounds of Formula I A solution of 4-fluoro-5-methyl-1H-indole-7-carboxylic acid ethyl ester (50 mg, 0.23 mmol) in THF (0.7 mL) was treated with 2 M aq. potassium hydroxide solution (0.23 mL, 0.46 mmol), and the reaction mixture was heated under reflux. After 64 h, the solution was evaporated, the residue dissolved in DMF (3.2 mL) and treated with (4-tert-butyl-benzyl)-[2-(4-fluoro-phenyl)-ethyl]-amine (71 mg, 0.25 mmol), N-methylmorpholine (69 mg, 0.68 mmol), and HBTU (129 mg, 0.34 mmol). After 16 h, the reaction mixture was partitioned between water and EtOAc, the organic layer was washed with brine, dried (MgSO$_4$), and evaporated. Chromatography of the residue (SiO$_2$, heptane-EtOAc gradient) afforded the title compound (71 mg, 68%). Yellow oil, MS (EI) 176.1 (100), 351.2 (19), 460.2 (14, M$^+$).

The following compounds were prepared in accordance with the above procedure:

4-Fluoro-5-methyl-1H-indole-7-carboxylic acid (4-tert-butyl-benzyl)-[2-(3,4-dichloro-phenyl)-ethyl]-amide 211 from 4-fluoro-5-methyl-1H-indole-7-carboxylic acid ethyl ester and (4-tert-butyl-benzyl)-[2-(3,4-dichloro-phenyl)-ethyl]-amine (example S18). Light yellow gum, MS (EI) 176.1 (100), 351.2 (13), 510.2 (10, M$^+$).

4-Fluoro-5-methyl-1H-indole-7-carboxylic acid (4-tert-butyl-benzyl)-[2-(3-trifluoromethyl-phenyl)-ethyl]-amide 212 from 4-fluoro-5-methyl-1H-indole-7-carboxylic acid ethyl ester and (4-tert-butyl-benzyl)-[2-(3-trifluoromethyl-phenyl)-ethyl]-amine. Light yellow oil, MS (EI) 176.1 (100), 351.2 (12), 510.2 (32, M$^+$).

4-Fluoro-5-methyl-1H-indole-7-carboxylic acid (4-tert-butyl-benzyl)-[2-(3-trifluoromethoxy-phenyl)-ethyl]-amide 213 from 4-fluoro-5-methyl-1H-indole-7-carboxylic acid ethyl ester and (4-tert-butyl-benzyl)-[2-(3-trifluoromethoxy-phenyl)-ethyl]-amine. Yellow oil, MS (EI) 176.1 (100), 351.2 (15), 526.2 (32, M$^+$).

Example 141

Film Coated Tablets

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example 142

Capsules

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 143

Injection Solutions

| | |
|---|---|
| Compound of formula (I) | 3.0 mg |
| Gelatine | 150.0 mg |
| Phenol | 4.7 mg |

-continued

| | |
|---|---|
| Sodium carbonate | to obtain a final pH of 7 |
| Water for injection solutions | ad 1.0 ml |

Example 144

Soft Gelatin Capsules

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85 % | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 145

The following tests were carried out in order to determine the activity of the compounds of formula I.

Activity of CETP inhibitors was determined using a buffer assay system. Partially purified CETP transferred radiolabeled cholesteryl ester from HDL donor particles to biotin-labeled LDL acceptor particles. The reaction was stopped by addition of streptavidin-coupled scintillation proximity assay (SPA) beads. These beads captured the biotinylated acceptor particles and transferred radioactivity was measured. The assay system was purchased and performed according to manufacturer's recommendations (Amersham Biosciences). Inhibitory activity of compounds was determined as percentage of positive control activity containing CETP together with donor and acceptor particles. Serial dilution of compounds was performed in order to determine the $IC_{50}$ values.

The compounds of the present invention exhibit $IC_{50}$ values within the range of about 1 nM to about 10 µM, preferably of about 1 nM to about 1 µM, and more preferably of about 1 nM to about 100 nM. The following table shows measured values for some selected compounds of the present invention.

| | $IC_{50}$ (nM) |
|---|---|
| Compound 1 | 539 |
| Compound 76 | 58 |
| Compound 90 | 202 |

Activity of the compounds was subsequently measured in the presence of plasma using the same assay as described above except that the source of CETP was human lipoprotein-deprived serum (LPDS). Inhibitory activity of compounds was determined as percentage of positive control activity containing all the assay components except compound. Serial dilution of compounds was performed in order to determine the $IC_{50}$ values.

In vivo activity of the compounds of formula I were determined in hamster using the following protocol:

Male golden Syrian hamsters (6-week-old, 100-130 g) under standard chow diet received compounds in the morning by oral gavage using appropriate vehicle, blood was taken 2 h later by retro-orbital bleeding under isofluran anaesthesia and 7 h later on sacrificed animals. Plasma was separated from blood using low speed centrifugation and CETP activity was measured in plasma using the radioactive CETP activity assay as described above except that diluted plasma replaced LPDS. In vivo CETP inhibition was expressed as CETP activity remaining in the plasma of treated animals as compared to plasma CETP activity of placebo treated animals.

Efficacy of compounds in modulating plasma lipid levels was determined in hamsters after 7 days of daily administration of compounds. Male hamsters were acclimated for 3-4 days to receive food as a paste made of 10 g chow and 10 g water per day. Compounds were then mixed within this paste and a portion containing the proper amount of compounds was given every morning for 7 days. Alternatively compounds could be given by oral gavage using the proper vehicle. Blood was taken before compound treatment by retro-orbital bleeding and at the end of the treatment on sacrificed animals. Plasma was separated from blood by low speed centrifugation and selected organs were taken (e.g liver, fat, brain, etc.). Effects of compounds on plasma lipid levels were determined by measuring total cholesterol, HDL-cholesterol, LDL-cholesterol and triglyceride using colorimetric enzymatic assays (Roche Diagnostic GmbH, Mannheim, Germany). HDL-C, LDL-C and VLDL-C were preferably quantified using size exclusion chromatography on superpose-6 column using SMART™ system (Pharmacia). Lipoprotein distribution was calculated assuming a Gaussian distribution for each peak, using a non-linear, least-squares curve-fitting procedure to calculate the area under the curve. Plasma samples were also used to quantify CETP activity as described above. Compound concentration was also determined in plasma and selected tissues as liver, fat, heart, muscle and brain.

Efficacy of compounds in modulating plasma lipid levels was also determined in cholesterol/fat fed hamsters. The protocol is identical as described above except that animals are fed with chow diet enriched with 10% (w/w) saturated fat and 0.05% (w/w) cholesterol. Animals received this high fat diet 2 weeks before starting compound administration and continued this diet throughout the study. The 2 weeks pre-treatment induced an increase in plasma cholesterol and triglyceride levels allowing a better assessment of LDL-C and triglyceride lowering.

Efficacy of compounds in its ability to acutely raise HDL-C was assessed in cynomolgus monkeys. Animals were fed with standard primate maintenance diet. Compounds was formulated with appropriate vehicle and administered to animals by oral gavage. Blood was taken before and at several time-points after compound administration (usually 30 min, 1 h, 2 h, 4 h, 7 h and 24 h). Plasma was separated from blood by low speed centrifugation and CETP activity and plasma lipids were quantified. Compound potency and efficacy could be assessed by measuring the HDL-C increase after this single-dose administration. In such pharmacodynamic model the extent together with the kinetics of the pharmacologic effect could be assessed.

It is to be understood that the invention is not limited to the particular embodiments of the invention described above, as variations of the particular embodiments may be made and still fall within the scope of the appended claims.

What is claimed is:

1. A compound of the formula (I):

wherein:
—X—Y— is —$CR^a$=$CR^c$— or —$CR^a$=N— or —$CR^aR^b$—$CR^cR^d$—, $R^a$, $R^b$, $R^c$ and $R^d$ are independently from each other selected from the group consisting of hydrogen and lower alkyl;

$R^1$, $R^2$, $R^4$ and $R^5$ are independently from each other selected from the group consisting of hydrogen, lower alkyl, lower alkoxy, halogen and lower halogenalkyl;

$R^3$ is selected from the group consisting of lower alkyl, cycloalkyl being unsubstituted or substituted by lower alkyl, cyano or lower alkoxy, lower halogenalkyl, lower alkoxyalkyl, lower alkoxy-halogenalkyl, halogenalkoxy and pentafluorosulphuranyl; or $R^2$ and $R^3$ taken together with the carbon atoms to which they are attached form a 5- or 6-membered carbocyclic ring or a 5- or 6-membered heterocyclic ring containing one or two heteroatoms selected from the group consisting of N, O and S, said carbocyclic or heterocyclic ring being unsubstituted or substituted by one, two, three or four groups independently selected from lower alkyl, cycloalkyl, lower alkoxy, halogen, and lower halogenalkyl;

$R^6$ is selected from the group consisting of hydrogen and lower alkyl;

$R^7$ is selected from the group consisting of hydrogen, lower alkyl hydroxy and halogen;

$R^8$ is selected from the group consisting of lower alkyl, lower alkenyl, lower halogenalkyl, heterocyclyl, heteroaryl which is unsubstituted or substituted by one or two groups independently selected from lower alkyl, lower alkoxy, lower halogenalkyl, lower halogenalkoxy and halogen, phenyl which is unsubstituted or substituted by one or two groups independently selected from lower alkyl, lower alkoxy, lower halogenalkyl, lower halogenalkoxy and halogen, —$OR^{12}$, wherein $R^{12}$ is lower alkyl or phenyl which is unsubstituted or substituted by one or two groups independently selected from lower alkyl, lower alkoxy, lower halogenalkyl, lower halogenalkoxy and halogen, —$NR^{13}R^{14}$, wherein $R^{13}$ and $R^{14}$ independently from each other are selected from hydrogen, lower alkyl, and phenyl which is unsubstituted or substituted by one or two groups independently selected from lower alkyl, lower alkoxy, lower halogenalkyl, lower halogenalkoxy and halogen, and —C(O)—$OR^{15}$, wherein $R^{15}$ is hydrogen or lower alkyl;

$R^9$, $R^{10}$ and $R^{11}$ independently from each other are selected from the group consisting of hydrogen, lower alkyl, cycloalkyl, lower alkoxy, lower halogenalkyl, and halogen;

n is 1 or 2;

and all pharmaceutically acceptable salts thereof.

2. The compound according to claim 1, wherein —X—Y— signifies —$CR^a$=$CR^c$— and $R^a$ and $R^c$ are independently from each other selected from the group consisting of hydrogen and lower alkyl.

3. The compound according to claim 1, selected from the group consisting of:
5-chloro-1H-indole-7-carboxylic acid (4-tert-butyl-benzyl)-[2-(3-trifluoromethoxy-phenyl)-ethyl]-amide,
5-chloro-6-fluoro-1H-indole-7-carboxylic acid (4-tert-butyl-benzyl)-[2-(3-trifluoromethoxy-phenyl)-ethyl]-amide,
5-chloro-6-fluoro-1H-indole-7-carboxylic acid (4-tert-butyl-benzyl)-[2-(3-trifluoromethyl-phenyl)-ethyl]-amide,
5-chloro-6-fluoro-1H-indole-7-carboxylic acid (4-tert-butyl-benzyl)-[2-(3-difluoromethoxy-phenyl)-ethyl]-amide,
5-chloro-6-fluoro-1H-indole-7-carboxylic acid (4-tert-butyl-benzyl)-[2-(3-chloro-4-fluoro-phenyl)-ethyl]-amide,
5-chloro-6-fluoro-1H-indole-7-carboxylic acid (4-tert-butyl-benzyl)-[2-(4-fluoro-3-trifluoromethyl-phenyl)-ethyl]-amide,
5-chloro-6-fluoro-1H-indole-7-carboxylic acid (4-tert-butyl-benzyl)-[2-(4-chloro-3-trifluoromethyl-phenyl)-ethyl]-amide,
5-chloro-6-fluoro-1H-indole-7-carboxylic acid (4-tert-butyl-benzyl)-[2-(3,4-dichloro-phenyl)-ethyl]-amide,
5-chloro-6-fluoro-1H-indole-7-carboxylic acid (4-tert-butyl-2-chloro-benzyl)-[2-(3,4-dichloro-phenyl)-ethyl]-amide,
5-chloro-6-fluoro-1H-indole-7-carboxylic acid (4-tert-butyl-2-fluoro-benzyl)-[2-(3-trifluoromethyl-phenyl)-ethyl]-amide,
5-chloro-1H-indole-7-carboxylic acid (4-tert-butyl-benzyl)-[2-(3,4-dichloro-phenyl)-ethyl]-amide,
5-chloro-1H-indole-7-carboxylic acid (4-tert-butyl-benzyl)-[2-(3-trifluoromethyl-phenyl)-ethyl]-amide;
5-chloro-1H-indole-7-carboxylic acid [4-(1-methyl-cyclopropyl)-benzyl]-[2-(3-trifluoromethyl-phenyl)-ethyl]-amide, and
5-chloro-1H-indole-7-carboxylic acid [2-(3,4-dichloro-phenyl)-ethyl]-[4-(1,2,2,2-tetrafluoro-1-trifluoromethyl-ethyl)-benzyl]-amide, and pharmaceutically acceptable salts thereof.

4. A process for the manufacture of a compound of formula I according to claim 1, comprising the steps of:

a) reacting an acid of the formula II

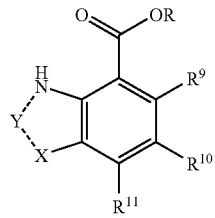

(II)

wherein —X—Y—, $R^9$, $R^{10}$ and $R^{11}$ are as defined in claim 1 and R is hydrogen or lower alkyl, with an amine of formula III

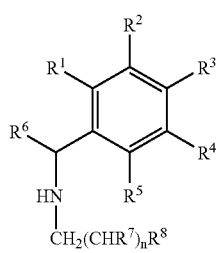

(III)

wherein $R^1$ to $R^8$ and n are as defined in claim 1, in the presence of a coupling agent; or, alternatively, b) reacting a halogen derivative of formula IV

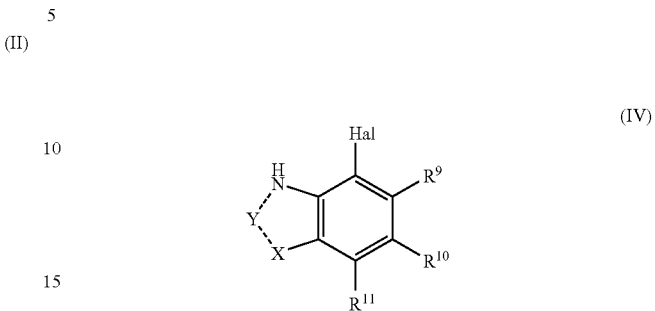

(IV)

wherein —X—Y—, $R^9$, $R^{10}$ and $R^{11}$ are as defined in claim 1 and Hal means halogen, with an amine of formula III in the presence of a suitable catalyst and carbon monoxide, and if desired, converting the compound obtained into a pharmaceutically acceptable acid addition salt.

5. A pharmaceutical composition comprising a therapeutically effective amount of a compound of claim 1 as well as a pharmaceutically acceptable carrier and/or adjuvant.

* * * * *